United States Patent
Huddart et al.

(10) Patent No.: US 11,813,384 B2
(45) Date of Patent: Nov. 14, 2023

(54) INTRAMOLD HEADGEAR

(71) Applicant: FISHER & PAYKEL HEALTHCARE LIMITED, Auckland (NZ)

(72) Inventors: Brett John Huddart, Auckland (NZ); Callum Ross Gordon, Auckland (NZ); Bruce Michael Walls, Auckland (NZ); Vitaly Kapelevich, Auckland (NZ); Jeroen Hammer, Auckland (NZ); David Monroy Felix, Auckland (NZ); Melissa Catherine Bornholdt, Auckland (NZ); Matthew Roger Stephenson, Auckland (NZ); Paul Mathew Freestone, Auckland (NZ); Ryan Anthony Graham, Auckland (NZ); Mark Arvind McLaren, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 508 days.

(21) Appl. No.: 17/061,493

(22) Filed: Oct. 1, 2020

(65) Prior Publication Data
US 2021/0016041 A1    Jan. 21, 2021

Related U.S. Application Data

(63) Continuation of application No. 14/856,502, filed on Sep. 16, 2015, now Pat. No. 10,828,452.
(Continued)

(51) Int. Cl.
*A61M 16/00* (2006.01)
*A61M 16/06* (2006.01)
(Continued)

(52) U.S. Cl.
CPC .... *A61M 16/0683* (2013.01); *A61M 16/0666* (2013.01); *A61M 16/0825* (2014.02);
(Continued)

(58) Field of Classification Search
CPC .......... A61M 16/0683; A61M 16/0666; A61M 2205/0216; B32B 7/12; B32B 27/08;
(Continued)

(56) References Cited

U.S. PATENT DOCUMENTS

| 301,111 A | 7/1884 | Genese |
|---|---|---|
| 472,238 A | 4/1892 | Van Orden |

(Continued)

FOREIGN PATENT DOCUMENTS

| CA | 996301 | 9/1976 |
|---|---|---|
| CA | 1311662 | 12/1992 |

(Continued)

OTHER PUBLICATIONS

Bravo Innomed Mask (http://web.archive.org/web/*/https://www.cpap.com/productpage/bravo-nasal-interface/).
(Continued)

*Primary Examiner* — Philip R Wiest
*Assistant Examiner* — Sarah B Lederer
(74) *Attorney, Agent, or Firm* — Knobbe Martens Olson and Bear, LLP

(57) ABSTRACT

A headgear portion or assembly for use in combination with a breathing apparatus in some configurations is at least substantially inelastic and is three dimensional in shape. The headgear portion or assembly can comprise a plastic core and a textile casing. The headgear, or part thereof, may also have integrally moulded labels, connectors, adjustment mechanisms and/or grips.

19 Claims, 71 Drawing Sheets

Related U.S. Application Data

(60) Provisional application No. 62/198,104, filed on Jul. 28, 2015, provisional application No. 62/159,857, filed on May 11, 2015, provisional application No. 62/050,925, filed on Sep. 16, 2014.

(51) Int. Cl.
*A61M 16/08* (2006.01)
*A61M 16/20* (2006.01)

(52) U.S. Cl.
CPC ...... *A61M 16/0866* (2014.02); *A61M 16/208* (2013.01); *A61M 16/06* (2013.01); *A61M 16/0875* (2013.01); *A61M 2205/0216* (2013.01); *A61M 2207/00* (2013.01); *A61M 2210/0618* (2013.01)

(58) Field of Classification Search
CPC .... B32B 3/08; B32B 3/20; B32B 3/06; B32B 3/26; B23B 25/00; B23B 5/00
See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 4,051,556 A | 10/1977 | Davenport et al. |
| 4,062,068 A | 12/1977 | Davenport et al. |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchison et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |
| 5,724,965 A | 3/1998 | Handke et al. |
| 5,752,510 A | 5/1998 | Goldstein |
| 5,755,578 A | 5/1998 | Contant et al. |
| 5,774,901 A | 7/1998 | Minami |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |

(56) References Cited

U.S. PATENT DOCUMENTS

| | | |
|---|---|---|
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,581,594 B1 | 6/2003 | Drew et al. |
| 6,581,601 B2 | 6/2003 | Ziaee |
| 6,588,424 B2 | 7/2003 | Bardel |
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B2 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,517,025 B2 | 8/2013 | Ho et al. |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,839,789 B2 | 9/2014 | Guney et al. |
| 8,856,975 B2 | 10/2014 | Lang et al. |
| 8,857,435 B2 | 10/2014 | Matula, Jr. et al. |
| 8,915,251 B2 | 12/2014 | Lubke et al. |
| 8,950,404 B2 | 2/2015 | Formica et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 19,138,555 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,592,336 B2 | 3/2017 | Nielsen et al. |
| 9,629,974 B2 | 4/2017 | Gibson |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica et al. |
| D810,277 S | 2/2018 | Amarasinghe et al. |
| 9,884,160 B2 | 2/2018 | McAuley et al. |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow et al. |
| 10,080,856 B2 | 9/2018 | McLaren et al. |
| 10,207,072 B2 | 2/2019 | Dunn et al. |
| 10,279,138 B2 | 5/2019 | Ovzinsky et al. |
| 10,456,546 B2 | 10/2019 | Mclaren et al. |
| 10,646,680 B2 | 5/2020 | Huddart et al. |
| 10,668,242 B2 | 6/2020 | Bearne |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |

(56) References Cited

U.S. PATENT DOCUMENTS

| | | |
|---|---|---|
| 2005/0205096 A1 | 9/2005 | Matula |
| 2005/0235999 A1 | 10/2005 | Wood et al. |
| 2005/0262619 A1 | 12/2005 | Musal et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0191938 A1 | 8/2011 | Elliott |
| 2011/0197341 A1* | 8/2011 | Formica .................. B32B 5/18 |
| | | 2/209.3 |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0247490 A1 | 10/2012 | Matthews |
| 2012/0304999 A1 | 12/2012 | Swift et al. |
| 2013/0000648 A1 | 1/2013 | Madaus et al. |
| 2013/0008449 A1 | 1/2013 | Busch et al. |
| 2013/0139822 A1* | 6/2013 | Gibson ............. A61M 16/0605 |
| | | 128/205.25 |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1* | 8/2013 | Barlow ............. A61M 16/0605 |
| | | 128/205.25 |
| 2013/0228173 A1 | 9/2013 | Busch |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0102456 A1* | 4/2014 | Ovizinsky ......... A61M 16/0683 |
| | | 128/205.25 |
| 2014/0137870 A1 | 5/2014 | Barlow et al. |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn et al. |
| 2014/0216452 A1 | 8/2014 | Miller et al. |
| 2014/0305439 A1 | 10/2014 | Chodkowski et al. |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe et al. |
| 2016/0082214 A1 | 3/2016 | Barlow et al. |
| 2016/0166793 A1 | 6/2016 | McLaren et al. |
| 2016/0178027 A1 | 6/2016 | Wetzel |
| 2016/0256655 A1 | 9/2016 | Mah |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer et al. |
| 2017/0189636 A1 | 7/2017 | Gibson et al. |
| 2017/0216548 A1 | 8/2017 | Gerhardt et al. |
| 2017/0274167 A1 | 9/2017 | Huddart et al. |
| 2018/0209618 A1 | 7/2018 | Pontano |
| 2018/0214655 A1 | 8/2018 | Kooij et al. |
| 2018/0264218 A1 | 9/2018 | Chodkowski |
| 2018/0339123 A1 | 11/2018 | Smith et al. |
| 2019/0083734 A1 | 3/2019 | Hammer et al. |
| 2019/0111227 A1 | 4/2019 | Veliss et al. |
| 2019/0117026 A1 | 4/2019 | Felix et al. |
| 2019/0118009 A1 | 4/2019 | Vogus |
| 2019/0151592 A1 | 5/2019 | Bornholdt et al. |

(56) References Cited

U.S. PATENT DOCUMENTS

| | | |
|---|---|---|
| 2020/0129720 A1 | 4/2020 | McLaren et al. |
| 2020/0171260 A1 | 6/2020 | McLaren et al. |
| 2020/0230343 A1 | 7/2020 | Sims et al. |
| 2020/0230344 A1 | 7/2020 | Huddart et al. |
| 2020/0338294 A1 | 10/2020 | McLaren et al. |
| 2021/0008316 A1 | 1/2021 | McLaren et al. |
| 2021/0170134 A1 | 6/2021 | Freestone |
| 2021/0220598 A1 | 7/2021 | Felix et al. |
| 2022/0126049 A1 | 4/2022 | Amarasinghe |
| 2022/0331542 A1 | 10/2022 | McLaren et al. |

FOREIGN PATENT DOCUMENTS

| | | |
|---|---|---|
| CA | 2995960 | 2/2017 |
| CN | 2172538 | 7/1994 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 102753230 A | 10/2012 |
| CN | 202822396 U | 3/2013 |
| CN | 103930168 | 7/2014 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0401307 B1 | 8/1995 |
| EP | 0879565 A2 | 11/1998 |
| EP | 0982049 | 3/2000 |
| EP | 1187650 | 3/2002 |
| EP | 2 130 563 | 12/2009 |
| EP | 2 327 443 | 6/2011 |
| EP | 2 517 757 | 10/2012 |
| EP | 2529781 A1 | 12/2012 |
| EP | 2 022 528 | 3/2016 |
| FR | 825960 | 3/1938 |
| FR | 2390116 | 12/1978 |
| FR | 2618340 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1211268 | 11/1970 |
| GB | 1467828 | 3/1977 |
| GB | 2133275 | 7/1984 |
| GB | 2188236 | 9/1987 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2000-102624 | 4/2000 |
| JP | 368861 U | 5/2000 |
| JP | 2004-016488 | 1/2004 |
| JP | 2003-53874 | 9/2004 |
| JP | 2009-125306 | 6/2009 |
| JP | 2010-090973 | 4/2010 |
| JP | 2012-511341 | 5/2012 |
| JP | 2013-515536 | 5/2013 |
| JP | 2014-205066 | 10/2014 |
| JP | 2018-127729 | 8/2018 |
| KR | 10-2011-0028950 | 3/2011 |
| NZ | 585295 | 12/2011 |
| TW | 201340900 | 1/2013 |
| WO | WO 95/12432 | 5/1995 |
| WO | WO 97/32494. | 9/1997 |
| WO | WO 1998/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 2005/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/038918 | 3/2009 |
| WO | WO 2009/026627 | 3/2009 |
| WO | WO 09/052560 | 4/2009 |
| WO | WO 09/059353 | 5/2009 |
| WO | WO 2009/059353 A1 | 5/2009 |
| WO | WO 09/092057 | 7/2009 |
| WO | WO 09/108995 | 9/2009 |
| WO | WO 09/139647 | 11/2009 |
| WO | WO 2009/148956 | 12/2009 |
| WO | WO 2010/066004 | 6/2010 |
| WO | WO 10/131189 | 11/2010 |
| WO | WO 2010/139014 | 12/2010 |
| WO | WO 11/077254 | 6/2011 |
| WO | WO 2011/072739 | 6/2011 |
| WO | WO 11/112401 | 9/2011 |
| WO | WO 12/07300 | 1/2012 |
| WO | WO 2012/045127 | 4/2012 |
| WO | WO 12/069951 | 5/2012 |
| WO | WO 2012/071300 | 5/2012 |
| WO | WO 2012/0143822 | 10/2012 |
| WO | WO 12/177152 | 12/2012 |
| WO | WO 13/006913 | 1/2013 |
| WO | WO 2013/026091 | 2/2013 |
| WO | WO 2013/026092 | 2/2013 |
| WO | WO 13/064930 | 5/2013 |
| WO | WO 14/020469 | 2/2014 |
| WO | WO 14/031673 | 2/2014 |
| WO | WO 2014/025267 | 2/2014 |
| WO | WO 14/077708 | 5/2014 |
| WO | WO 2014/075141 | 5/2014 |
| WO | WO 14/110622 | 7/2014 |
| WO | WO 14/110626 | 7/2014 |
| WO | WO 14/129913 | 8/2014 |
| WO | WO 14/175753 | 10/2014 |
| WO | WO 2014/175752 | 10/2014 |
| WO | WO 15/033287 | 3/2015 |
| WO | WO 15/043229 | 4/2015 |
| WO | WO 15/070289 | 5/2015 |
| WO | WO 15/079396 | 6/2015 |
| WO | WO 2015/083060 | 6/2015 |
| WO | WO 2015/151019 | 10/2015 |
| WO | WO 15/187986 | 12/2015 |
| WO | WO 16/043603 | 3/2016 |
| WO | WO 17/030447 | 2/2017 |
| WO | WO 17/150990 | 9/2017 |

(56) References Cited

FOREIGN PATENT DOCUMENTS

| WO | WO 17/158474 | 9/2017 |
|----|--------------|--------|
| WO | WO 17/158544 | 9/2017 |
| WO | WO 17/160166 | 9/2017 |
| WO | WO 17/216708 | 12/2017 |
| WO | WO 19/003094 | 1/2019 |

OTHER PUBLICATIONS

Brazil National Institute of Industrial Property, Search Report, Application No. BR112017004877-9, dated Apr. 1, 2020, in 9 pages.
Chinese Office Action, Application No. 201580049820.0, dated Jan. 17, 2020.
Combined Search and Examination Report for GB Patent Application No. GB2016297.0, dated Oct. 26, 2020 in 7 pages.
First Examination Report for Australian Application No. 2015318728; dated Oct. 9, 2019; 4 pages.
International Search Report and Written Opinion in application No. PCT/NZ2015/050149 dated Dec. 24, 2015 in 18 pages.
Japanese Patent Application No. 2017-514904 Office Action dated Jun. 1, 2020, in 5 pages.
Notification of the First Office Action, Application No. 201580049820.2, China National Intellectual Property Administration, dated Apr. 4, 2019, in 16 pages.
Office Action dated Aug. 9, 2019; U.S. Appl. No. 15/511,192, filed Mar. 14, 2017; 29 pages.
Pad-a-cheek (http://web.archive.org/web/20070701000000*/http://www.padacheek.com/;Waybak Machine): 2pages.
Pad-a-cheek (http://www.padacheek.com/).
Taiwanese Search Report; Application No. 104130628, dated Dec. 19, 2019 in 1 page.
Taiwanese Office Action; Application No. 104130628, dated Dec. 19, 2019 in 5 pages including English Translation.
Japanese Office Action for Japanese Patent Application No. 2017-514904, dated Dec. 10, 2020 in 2 pages.
Indian Examination Report for Indian Patent Application No. 201737006344, dated Dec. 4, 2020 in 9 pages.
Examination Report for United Kingdom Patent Application No. GB2016297.0, dated Dec. 10, 2020 in 2 pages.
European Examination Report for European Patent Application No. 15 842 007.5, dated Feb. 2, 2021 in 5 pages.
Office Action for Chinese Patent Application No. 201810366796.0, dated Feb. 9, 2021 in 7 pages.
Combined Search and Examination Report for United Kingdom Patent Application No. GB2103410.3, dated Mar. 26, 2021 in 6 pages.
Philips Respironics 'System One Heated Humidifier-User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.

* cited by examiner

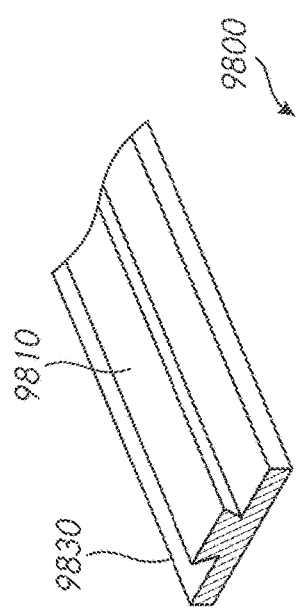
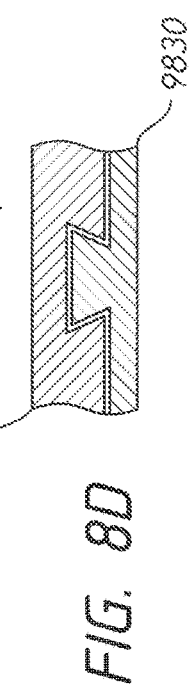
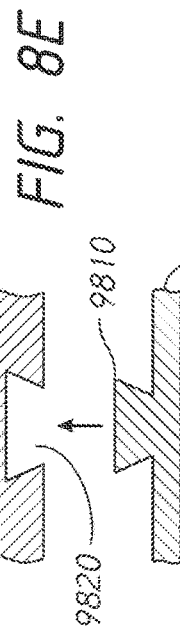
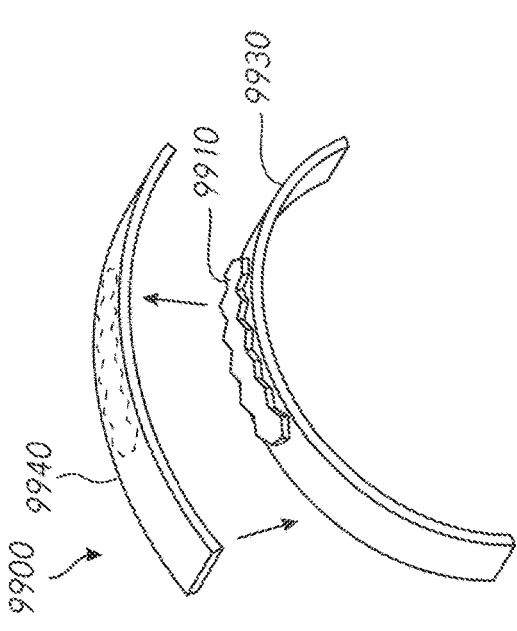
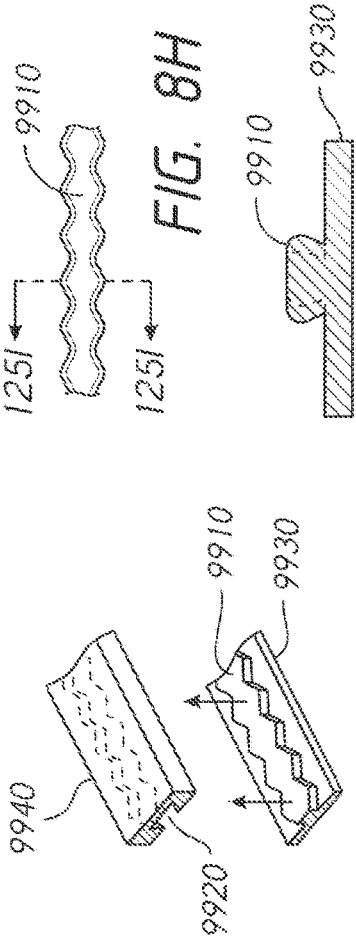
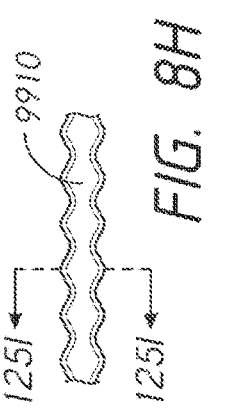

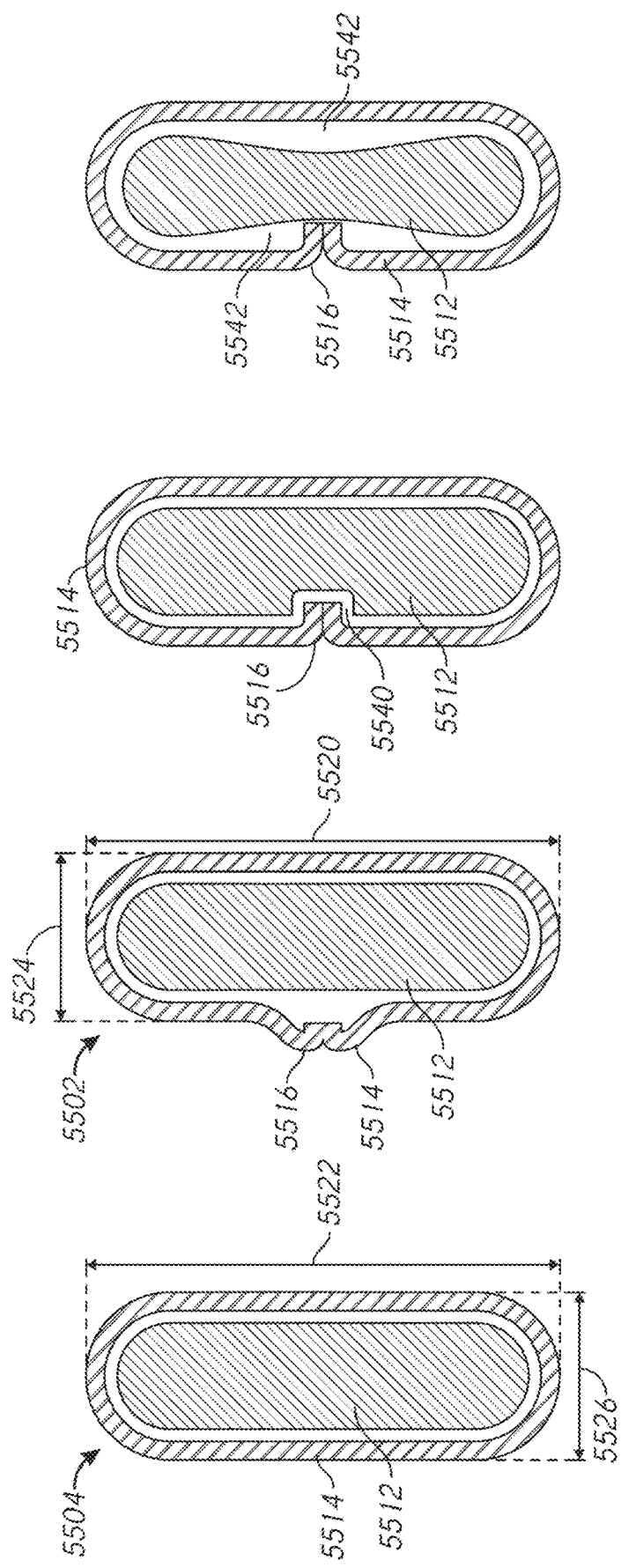

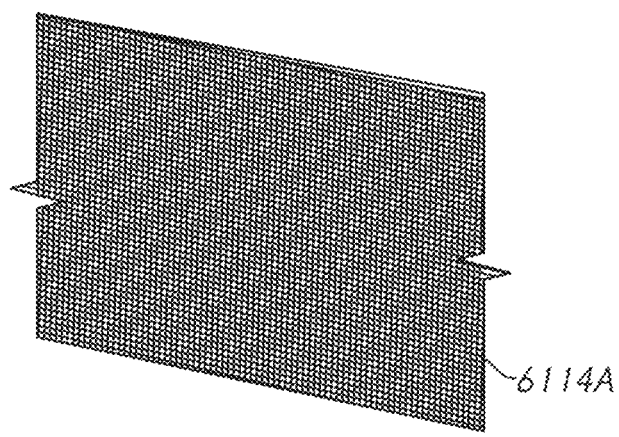
FIG. 40A
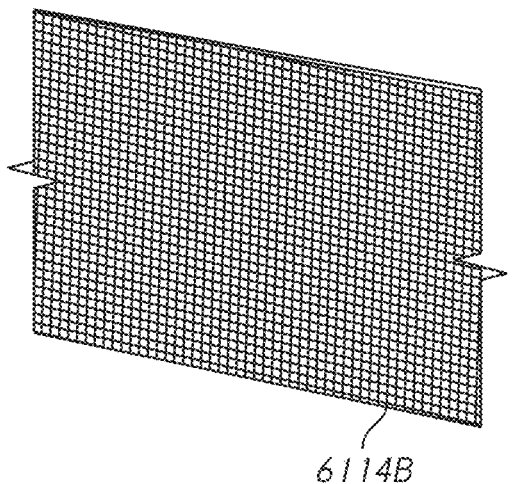
FIG. 40B
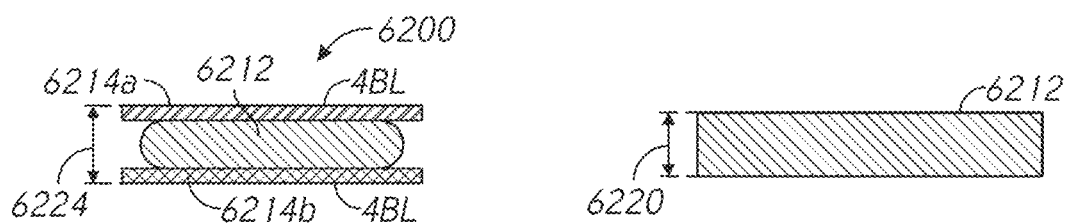
FIG. 41
FIG. 42

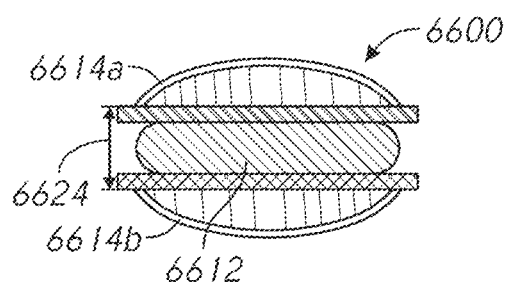
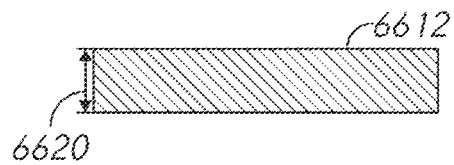
FIG. 49  FIG. 50
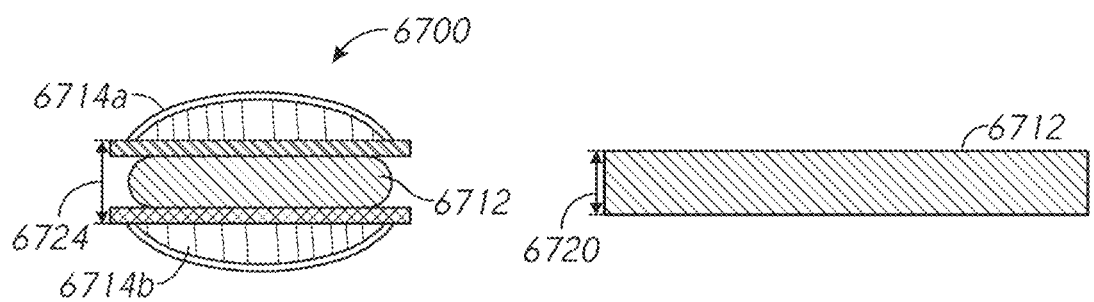
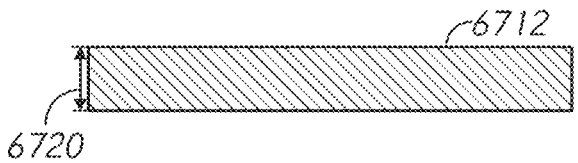
FIG. 51  FIG. 52

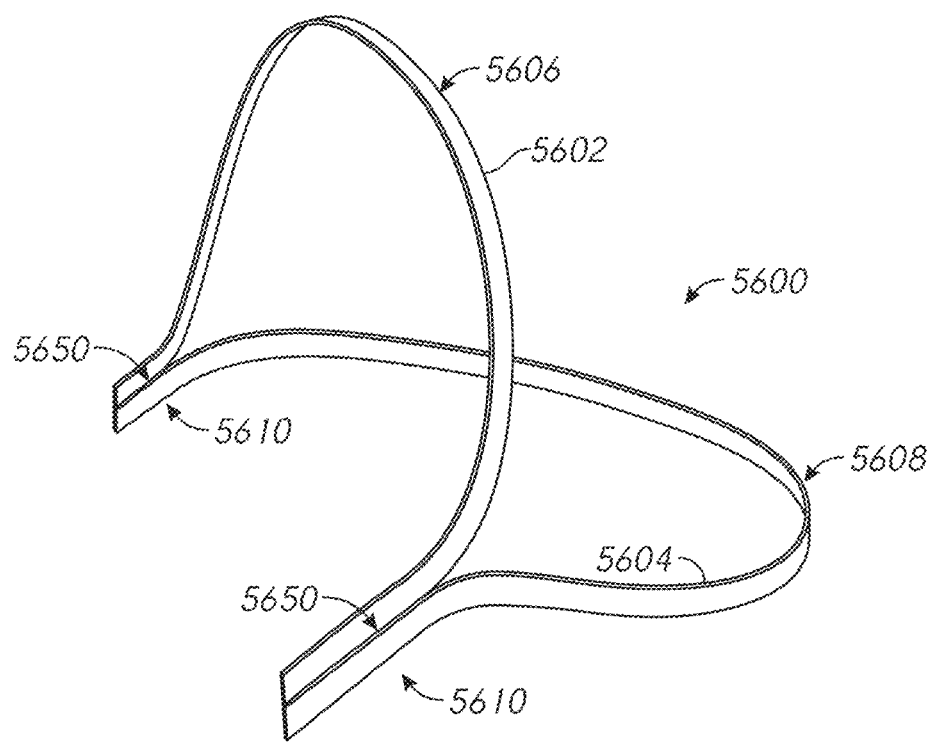
FIG. 71
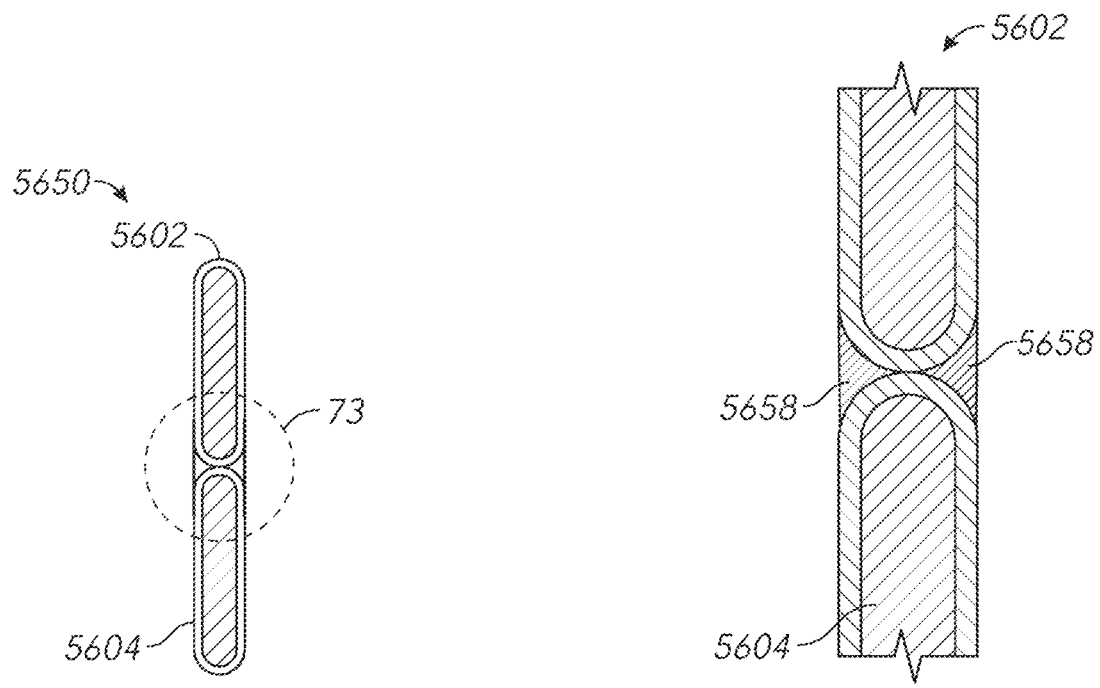
FIG. 72
FIG. 73

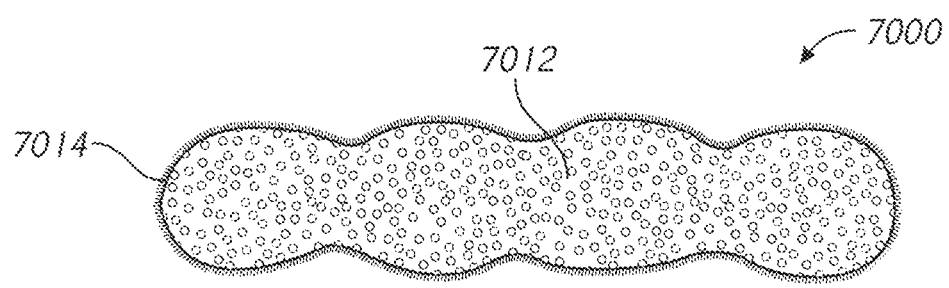
FIG. 104
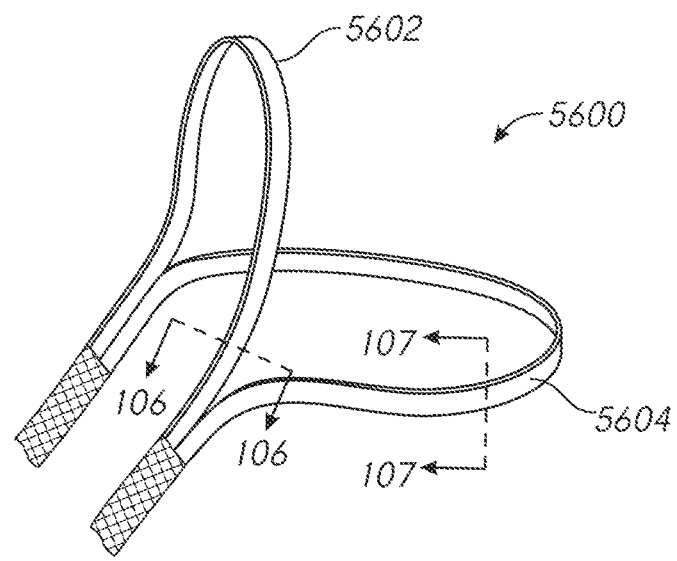
FIG. 105
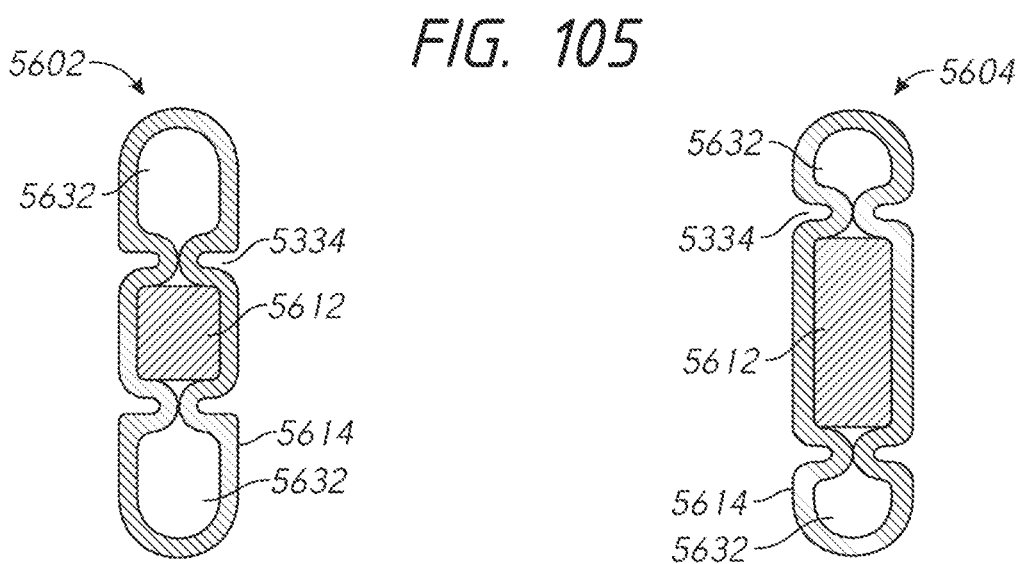
FIG. 106
FIG. 107

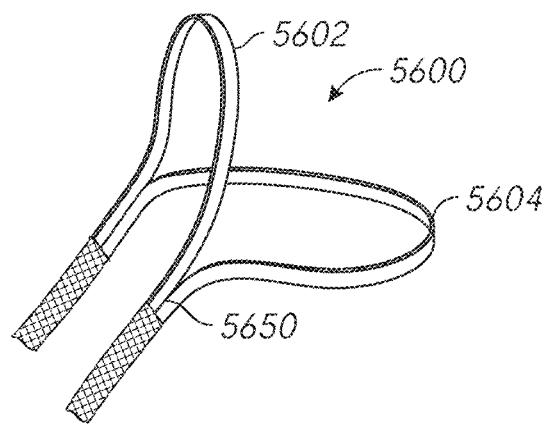
FIG. 111
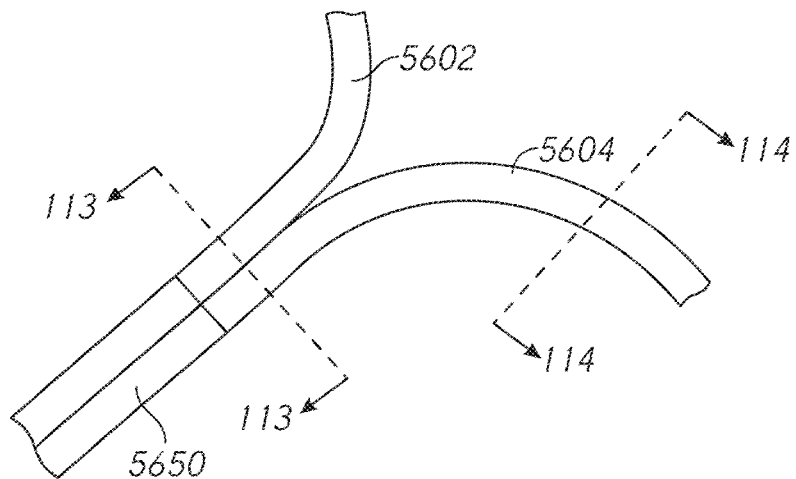
FIG. 112
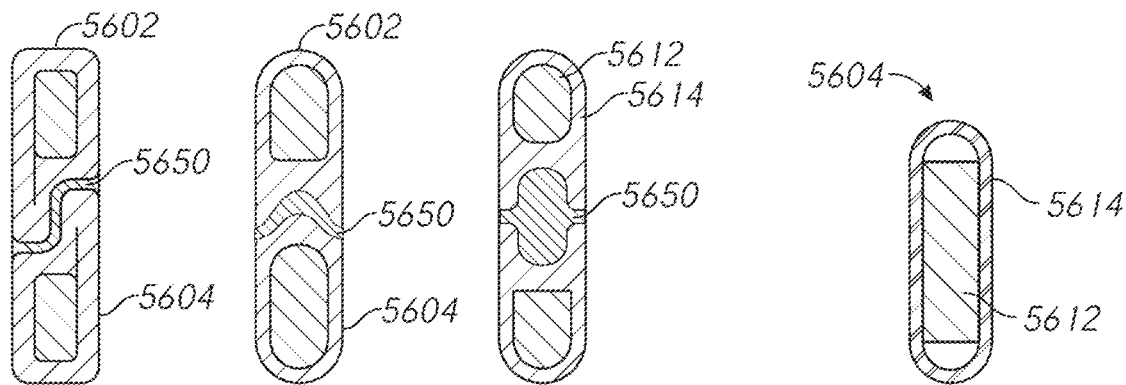
FIG. 113
FIG. 114

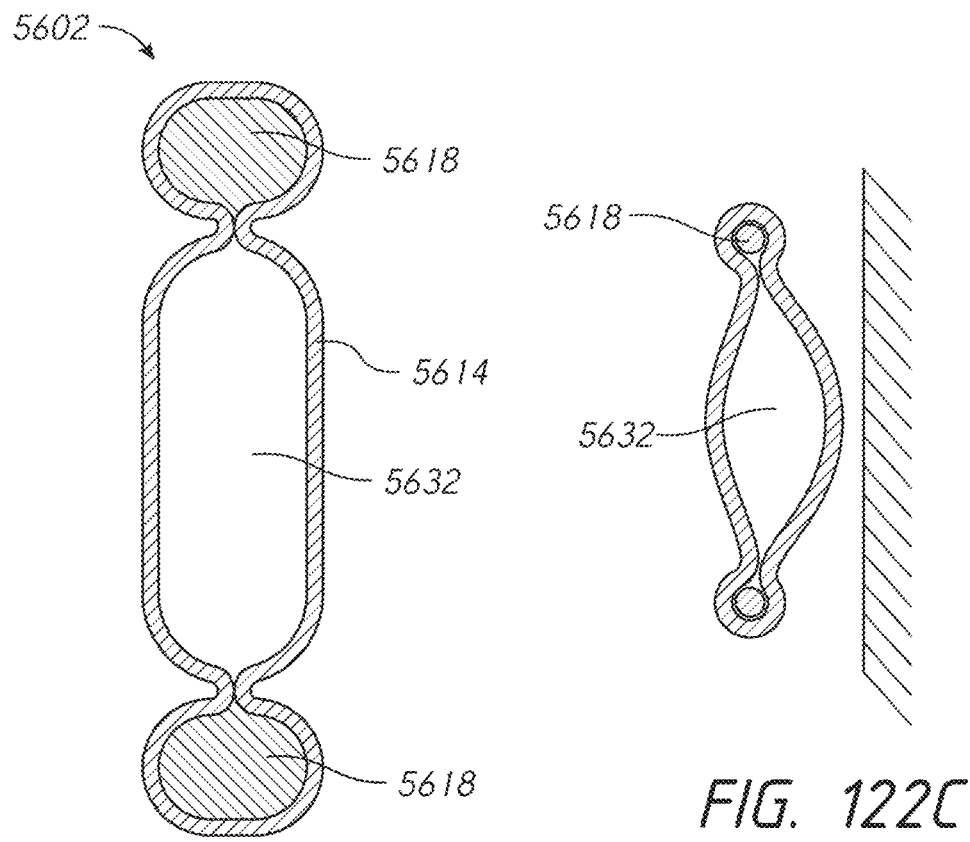
FIG. 122A
FIG. 122C
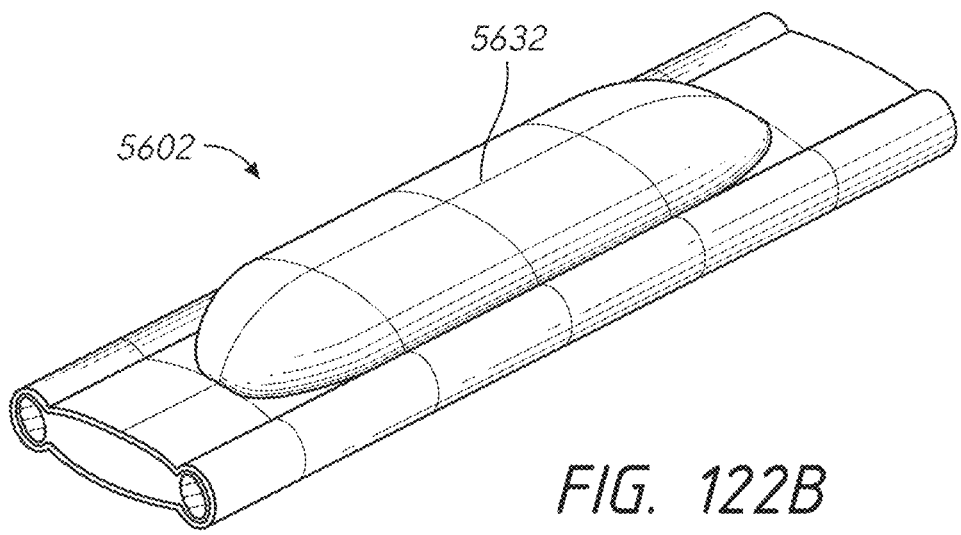
FIG. 122B

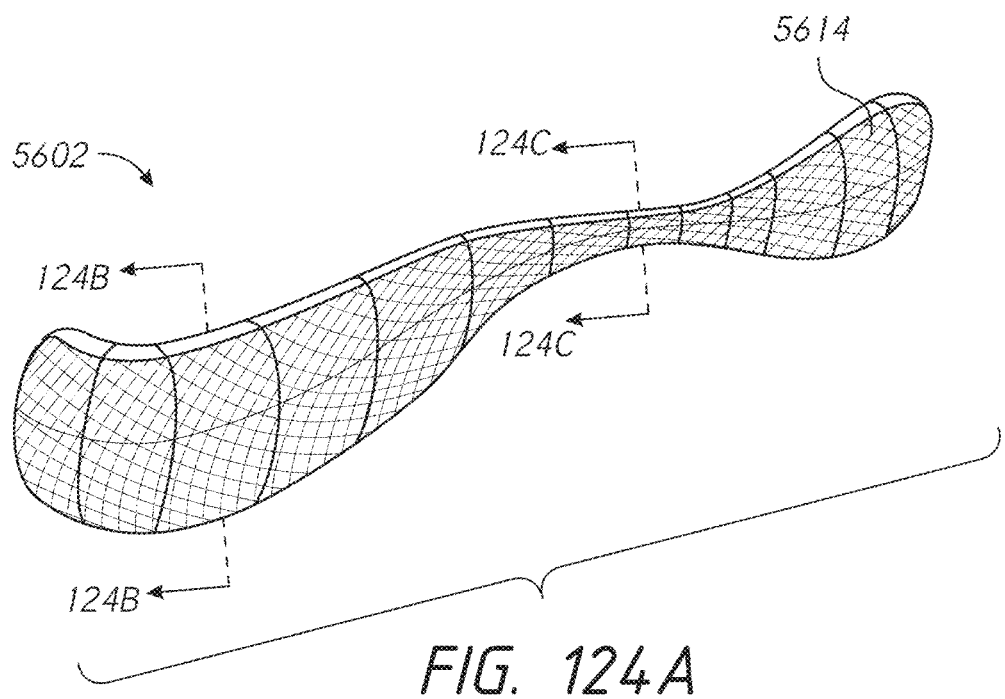
FIG. 124A
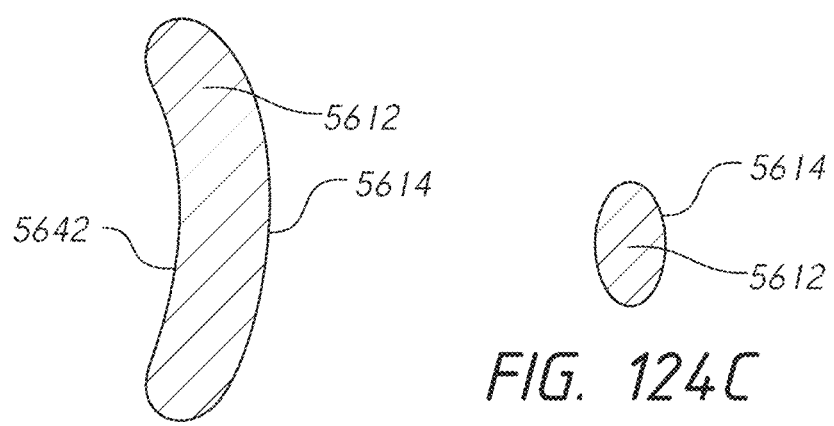
FIG. 124B
FIG. 124C

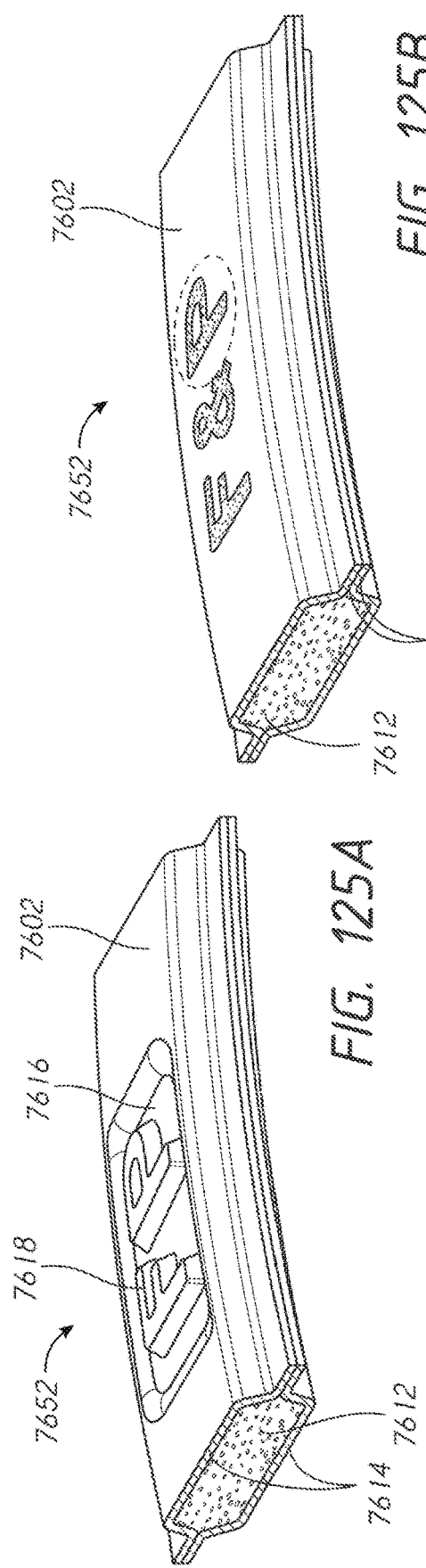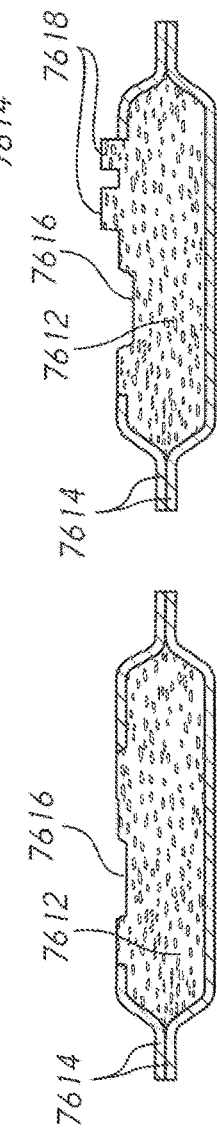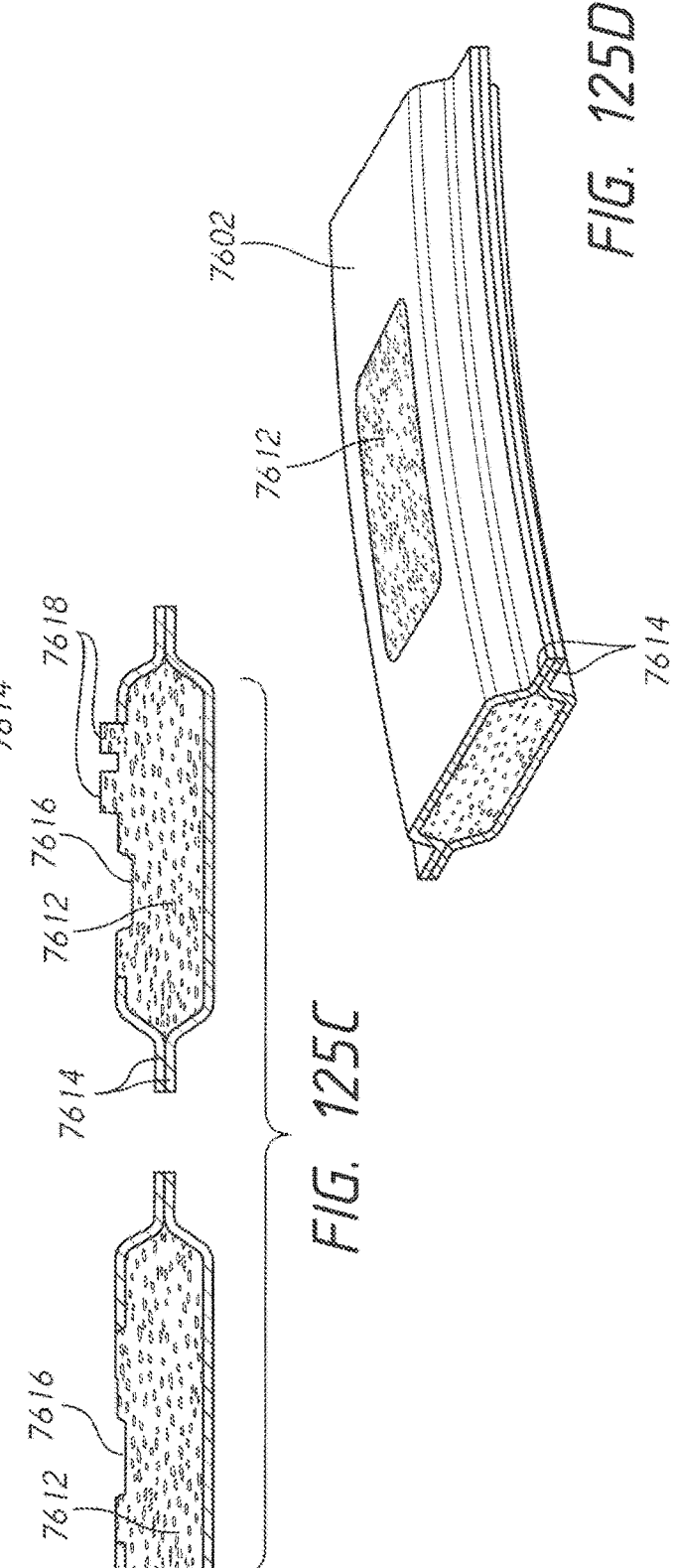

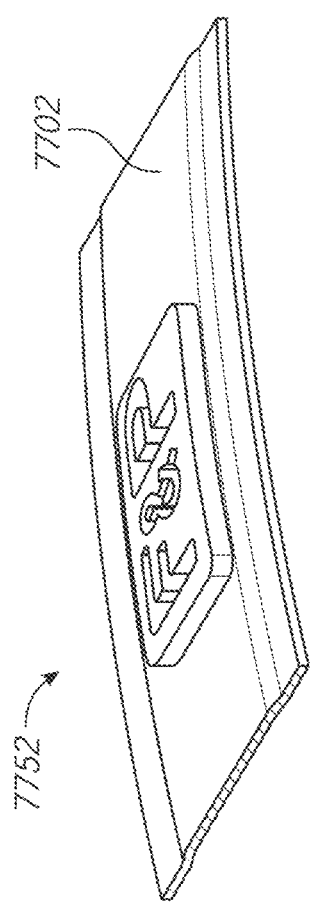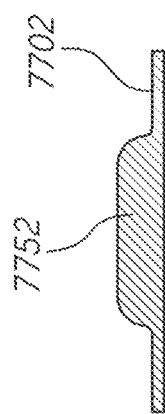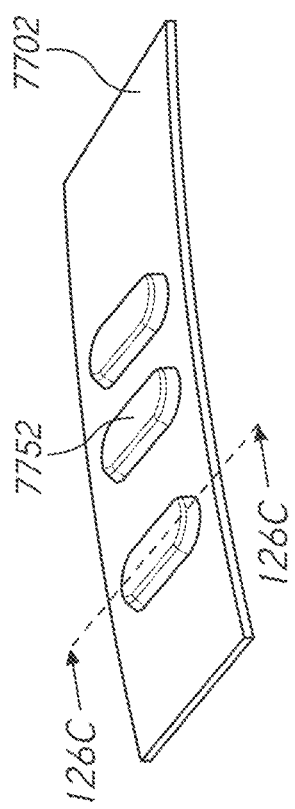

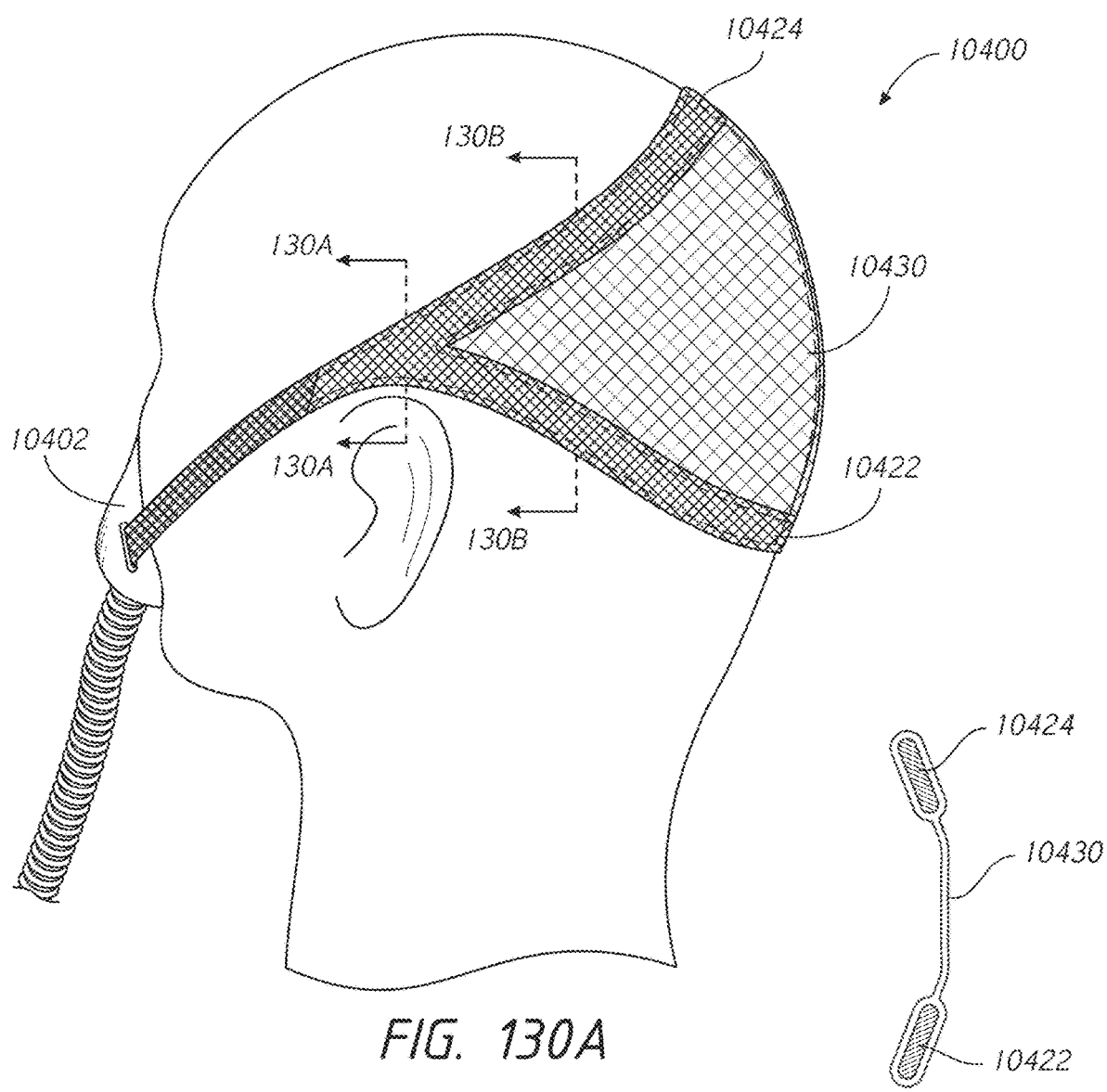
FIG. 130A
FIG. 130B
FIG. 130C
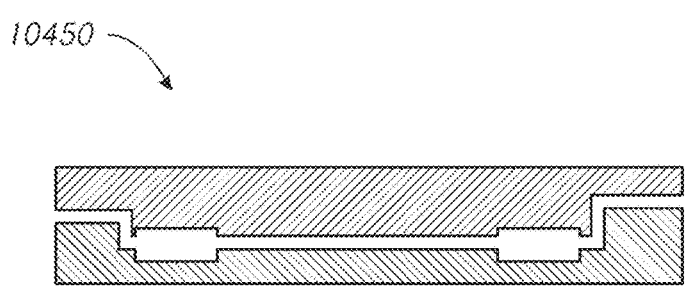
FIG. 130D

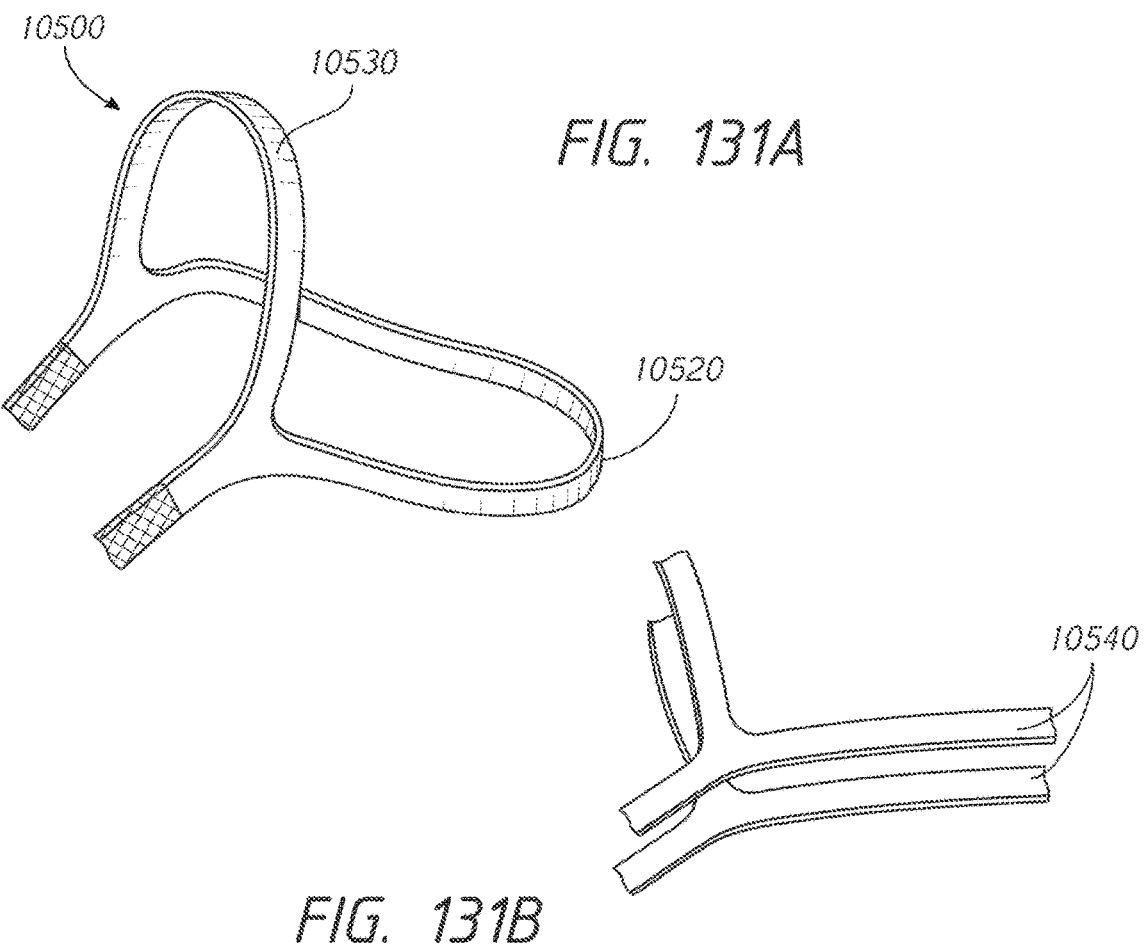
FIG. 131A
FIG. 131B
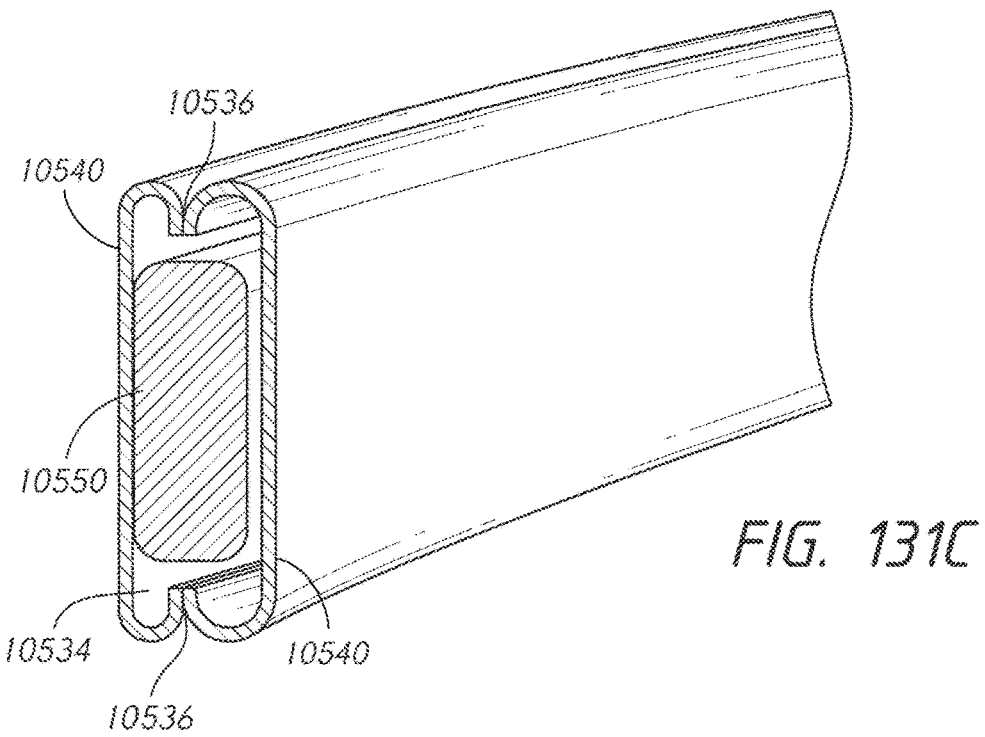
FIG. 131C

INTRAMOLD HEADGEAR

INCORPORATION BY REFERENCE TO ANY PRIORITY APPLICATIONS

The present application is a continuation application of U.S. patent application Ser. No. 14/856,502, filed on Sep. 16, 2015, which claims priority benefit of U.S. Provisional Application Ser. No. 62/198,104, filed on Jul. 28, 2015, U.S. Provisional Application Ser. No. 62/159,857, filed on May 11, 2015, and U.S. Provisional Application Ser. No. 62/050,925, filed on Sep. 16, 2014, the disclosures of each of which are hereby incorporated by reference in its entirety.

BACKGROUND

Field

The present disclosure generally relates to headgear for use in combination with a breathing apparatus. More particularly, the present disclosure relates to a substantially inelastic three dimensional headgear, portions thereof and a process for moulding such headgear. Further applications of the moulding process are also disclosed.

Description of Related Art

The treatment of respiratory ailments or conditions with therapies, such as NIV, Bi-level or CPAP, involves the delivery of pressurized air to the airways of a human via a conduit and a breathing apparatus (e.g., a mask or cannula). Typically, a mask creates at least a substantial "seal" on or around the nose and/or the mouth of a user while a cannula does not provide a seal but provides a delivery pathway for supplemental respiratory gas delivery.

A result of creating this "seal" is that the combination of the enclosure area of the breathing apparatus and its internal pressure creates a resulting force that attempts to push the breathing apparatus off of the face. To counteract this force, it is normal to use a headgear comprising a series of straps that pass around the back and/or top of a user's head. Headgear such as this are typically made from a compliant material, such as Breath-o-Prene™. The use of such a material results in the headgear having relatively little structure when not being worn. This lack of structure can give rise to the straps of the headgear becoming tangled, which in turn can make it difficult for a user to don the headgear and breathing apparatus.

These traditional headgear are usually configured to have some elasticity. This can result in the headgear stretching over, and applying pinching forces to, the user's head, which can be uncomfortable. It is desirable to make headgear and breathing apparatus that are easy to use and comfortable to wear because this may improve a user's compliance with therapy being provided.

SUMMARY

The present disclosure relates to headgear for use in combination with a breathing apparatus, wherein the headgear may at least go some way towards improving on the above or that may at least provide the public with a useful choice. The present inventors have discovered that applying molten plastic onto a textile component placed within a moulding tool results in a satisfactory bond between the moulded plastic and the textile component. Such methods can be utilized to create headgear assemblies or portions thereof that can be substantially inelastic in at least one direction, such as a lengthwise direction of a strap of the headgear, while having a softer material positioned on at least one surface of the headgear or headgear portion without requiring a post-forming step of attaching the softer material and without the need for adhesives, sleeves or other methods of attaching the softer material to the moulded material. The systems, methods and devices described herein have innovative aspects, no single one of which is indispensable or solely responsible for their desirable attributes. Without limiting the scope of the claims, some of the advantageous features will now be summarized.

In accordance with at least one of the embodiments disclosed herein, a headgear assembly for a respiratory interface is provided comprising a top strap, a rear strap, a front strap, a yoke and a connector. The headgear is configured to be substantially inelastic and three dimensional in structure.

According to a further aspect, the headgear assembly is constructed from a composite material, wherein a textile casing is integrally formed about a plastic core.

According to a further aspect, the headgear assembly comprises integrally moulded labels, connections, and/or adjustment features.

According to a further aspect, a headgear assembly component comprises a grip that is moulded to a textile strap.

According to a further aspect, the textile casing comprises a first portion that covers an inwardly-facing surface of the headgear.

According to a further aspect, the textile casing comprises a second portion that covers an outwardly-facing surface of the headgear.

According to a further aspect, the first portion and the second portion of the textile casing meet at first and second edges.

According to a further aspect, the first portion and the second portion are not connected to one another at the first and second edges.

According to a further aspect, the textile casing comprises one or more retainer holes configured to engage a retaining pin of a moulding tool.

According to a further aspect, the headgear assembly comprises at least one flexible joint that permits the strap to bend.

According to a further aspect, the at least one flexible joint comprises a gap between portions of the plastic core and wherein the textile casing extends within the gap to connect the portion of the plastic core.

According to a further aspect, the headgear assembly comprises at least one bridge portion extending within the flexible joint between the portions of the plastic core.

According to a further aspect, the at least one bridge portion is unitarily formed with the portions of the plastic core.

According to a further aspect, the headgear assembly comprises a top strap, a rear strap connected to the top strap at an upper connection point located on a side of a user's forehead, and a lower side strap connected to the top and rear straps at the upper connection point. The headgear assembly also comprises a first length adjusting portion adjusting the distance between the upper connection point and a frame of the respiratory interface, and a second length adjusting portion connected to the lower side strap at a lower connection point located forward of the user's ear and approximately in line with the user's mouth, wherein the second adjustment mechanism adjusts the distance between the lower connection point and the frame of the respiratory interface.

According to a further aspect, the top strap and the rear strap are formed unitarily as an integral structure.

According to a further aspect, the top strap, the rear strap and the lower side strap are formed unitarily as an integral structure.

According to a further aspect, the first length adjusting portion includes a fabric strap having a hook and loop fastener mechanism.

According to a further aspect, the second length adjusting portion includes a plurality of length adjusting mechanisms.

According to a further aspect, the headgear assembly comprises a top strap and a rear strap connected to the top strap at an upper connection point located on a side of a user's forehead. The headgear assembly also comprises an upper side strap connected to the top and rear straps at the upper connection point and connected to a frame of the respiratory interface. The upper side strap extends between the user's ear and eye and across the user's cheek towards the frame of the respiratory interface. The headgear assembly further comprises a lower side strap connected to the rear strap at a rear connection point located behind the user's ear. The lower side strap extends below the user's ear and across the user's cheek towards the frame of the respiratory interface. The headgear assembly additionally comprises a first length adjusting portion connected to the lower side strap and the frame of the respiratory interface. The first length adjusting portion adjusts the distance between the lower side strap and the frame of the respiratory interface.

According to a further aspect, the top strap and the rear strap are formed unitarily as an integral structure.

According to a further aspect, the top strap, the rear strap, the upper side strap and the lower side strap are formed unitarily as an integral structure.

According to a further aspect, the first length adjusting portion includes a one-way adjusting mechanism.

According to a further aspect, the headgear assembly further comprises a second length adjusting portion connected between the upper side strap and the frame of the respiratory interface, wherein the second length adjusting portion adjusts the distance between the upper side strap and the frame of the respiratory interface.

According to a further aspect, the headgear assembly comprises a top strap, a rear strap connected to the top strap at an upper connection point located on a side of a user's forehead, and a front strap connected to the top and rear straps at the upper connection point and connected to the respiratory interface. The front strap extends between the user's ear and eye and towards a bottom of the user's nose.

According to a further aspect, the top strap and the rear strap are formed unitarily as an integral structure.

According to a further aspect, the top strap, the rear strap and the front strap are formed unitarily as an integral structure.

According to a further aspect, the front strap extends across the front of the respiratory interface and forms a portion of a frame of the respiratory interface.

According to a further aspect, the headgear assembly further comprises a length adjusting portion connected between the front strap and the respiratory interface, wherein the length adjusting portion adjusts the distance between the front strap and the respiratory interface.

According to a further aspect, the headgear assembly comprises a top strap, a rear strap connected to the top strap at an upper connection point located on a side of a user's forehead, and a lower side strap connected to the top and rear straps at the upper connection point and extends away from the upper connection point in a substantially vertical direction. The lower strap is positioned in front of the user's ear. The headgear assembly also comprises a first length adjusting portion connected to the lower strap at a first lower connection point, the first length adjusting portion adjusting the distance between the first lower connection point and a frame of the respiratory interface. The first lower connection point is positioned in line with the user's eye and the first length adjusting portion extends across the user's cheeks just below the eyes. The headgear assembly further comprises a second length adjusting portion connected to the lower strap at a second lower connection point, the second length adjusting portion adjusting the distance between the second lower connection point and the frame of the respiratory interface. The second lower connection point is positioned approximately in line with a bottom of the user's nose and the second length adjusting portion extends substantially horizontally across the users cheek.

According to a further aspect, the top strap and the rear strap are formed unitarily as an integral structure.

According to a further aspect, the top strap, the rear strap and the lower side strap are formed unitarily as an integral structure.

According to a further aspect, at least one of the first or second length adjusting portions include a one-way adjusting mechanism.

In accordance with at least one of the embodiments disclosed herein, a headgear comprises a plastic core and a textile casing. The plastic core and the textile casing are formed as an integral structure by the application of a molten plastic material onto the textile casing.

According to a further aspect, the textile casing comprises a first portion that covers an inwardly-facing surface of the headgear.

According to a further aspect, the textile casing comprises a second portion that covers an outwardly-facing surface of the headgear.

According to a further aspect, the first portion and the second portion of the textile casing meet at first and second edges.

According to a further aspect, the first portion and the second portion are not connected to one another at the first and second edges.

According to a further aspect, the textile casing comprises one or more retainer holes configured to engage a retaining pin of a moulding tool.

According to a further aspect, the headgear comprises at least one flexible joint that permits the headgear to bend.

According to a further aspect, the at least one flexible joint comprises a gap between portions of the plastic core and the textile casing extends within the gap to connect the portion of the plastic core.

According to a further aspect, the headgear comprises at least one bridge portion extending within the flexible joint between the portions of the plastic core.

According to a further aspect, the at least one bridge portion is unitarily formed with the portions of the plastic core.

In accordance with at least one of the embodiments disclosed herein, a method of making a headgear comprises placing a textile casing within a moulding tool, introducing a molten plastic material into the moulding tool and into contact with the textile casing, and allowing the molten plastic material to solidify on the textile casing to form a plastic core.

According to a further aspect, the placing of the textile casing into the moulding tool comprises placing a first textile portion and a second textile portion into the moulding tool, and the introducing the molten plastic material into the moulding tool comprises introducing the molten plastic material between the first and second textile portions.

According to a further aspect, the method further comprises retaining an end of each of the first and second textile portions at which the molten plastic material is introduced within a retaining feature of the moulding tool.

According to a further aspect, the method further comprises capturing at least one edge of the textile casing between first and second separable portions of a moulding tool.

According to a further aspect, the method further comprises engaging an opening of the textile casing with a retention pin of the moulding tool.

According to a further aspect, the method further comprises securing the textile casing within the moulding tool prior to the introduction of the molten plastic material.

According to a further aspect, the securing of the textile casing comprises securing the textile casing by one or more of a static electrical charge, air pressure, retaining the textile casing with another component inserted into the moulding tool, or supporting a strip of material that forms the textile casing extending through the moulding tool on each side of the moulding tool.

According to a further aspect, the supporting the strip of material comprises supporting one end on a roll and securing a free end relative to the moulding tool.

According to a further aspect, the method further comprises forming a flexible joint by providing a gap in plastic core along a length of the headgear, and extending the textile casing along the gap.

According to a further aspect, the method further comprises extending a flexible bridge portion of plastic material through the flexible joint from a portion of the plastic core on one side of the gap to a portion of the plastic core on the opposite side of the gap.

In accordance with at least one of the embodiments disclosed herein, a method of making a headgear comprises placing a textile casing within a moulding tool, introducing a molten plastic material into the moulding tool and into contact with an inside of the textile casing, and allowing the molten plastic material to solidify in the textile casing to form a plastic core.

In accordance with at least one embodiment disclosed herein, a headgear comprises a first strap and a second strap, wherein the first strap and the second strap cooperate to form at least one of a top strap, a rear strap and a front strap of the headgear.

According to a further aspect, the first strap and the second strap cooperate to form the rear strap, wherein the first strap and the second strap overlap one another within the rear strap, and wherein only one of the first strap and the second strap defines the top strap.

According to a further aspect, the first strap and the second strap cooperate to form the front strap, wherein the first strap and the second strap are stacked within the front strap, and wherein the first strap and the second strap alone defines a respective one of the top strap and the rear strap.

According to a further aspect, one or both of the straps are constructed from a plastic core and a textile casing formed as an integral structure by the application of a molten plastic material onto the textile casing.

In accordance with at least one embodiment disclosed herein, a headgear includes an inner core, a first outer layer defining an inner surface of the headgear that faces the user in use, and a second outer layer defining an outer surface of the headgear that faces away from the user in use. The first layer and the second layer have different colors, textures or other indicia that permit tactile or visual differentiation of the inner surface and the outer surface.

According to a further aspect, the first outer layer or the second outer layer comprises one of a polyurethane (imitation leather), patterned polyester, wool with mesh knit, unbroken loop, nylon, a composite of spacer fabric and unbroken loop or a composite of foam an unbroken loop.

According to a further aspect, edges of one or both of the first and second outer layers extend beyond the inner core.

According to a further aspect, the inner core comprises an interior cut-out.

In accordance with at least one embodiment disclosed herein, a headgear comprises a first strap, a second strap, and a connector that couples the first strap to the second strap, wherein the connector is formed by over-moulding onto the first strap and the second strap.

According to a further aspect, the first strap and the second strap are stacked in a vertical direction within the connector.

According to a further aspect, the connector includes a portion extending between and separating the first strap from the second strap.

According to a further aspect, the connector includes a front band portion and a rear band portion separated by a bridge portion, wherein the bridge portion does not surround an entirety of both the first strap and the second strap.

According to a further aspect, the connector includes a front band portion and a rear gusset.

According to a further aspect, the front band portion and the rear gusset are separated by a bridge portion, wherein the bridge portion does not surround an entirety of both the first strap and the second strap.

In accordance with at least one embodiment disclosed herein, a strap of a headgear comprises an inner core, at least one outer layer that at least partially surrounds the inner core, and at least one air gap within the outer layer.

According to a further aspect, the at least one air gap comprises a first air gap at one lateral edge of the strap and a second air gap at the opposite lateral edge of the strap.

According to a further aspect, a portion of the inner core is externally exposed.

According to a further aspect, a conduit is positioned within the air gap.

According to a further aspect, the air gap is defined by the inner core.

In accordance with at least one embodiment disclosed herein, a strap of a headgear comprises an inner core, at least one outer layer, and at least one conduit extending lengthwise along the strap and within the outer layer.

According to a further aspect, the conduit is at least partially received within a recess of the inner core.

According to a further aspect, the conduit is completely encapsulated within the inner core.

According to a further aspect, the at least one conduit comprises a first conduit and a second conduit.

According to a further aspect, the at least one conduit is defined by the core.

In accordance with at least one embodiment disclosed herein, a strap of a headgear includes an inner core, at least one outer layer, and at least one reinforcement member.

According to a further aspect, the reinforcement member is embedded within the core.

According to a further aspect, the reinforcement member is configured to hold opposing outer layers or opposing sides of an outer layer apart from one another prior to the formation of the inner core.

In accordance with at least one embodiment disclosed herein, a strap of a headgear comprises an inner core, at least one outer layer, and at least one cushioning layer.

According to a further aspect, the cushioning layer surrounds the inner core.

According to a further aspect, a portion of the cushioning layer is externally exposed.

In accordance with at least one embodiment disclosed herein, a strap of a headgear comprises an inner core and an outer layer that at least partially surrounds the inner core, the outer layer comprising edges. The edges are embedded in the inner core.

According to a further aspect, the outer layer comprises more than one piece or more than two pieces.

According to a further aspect, a first piece of outer layer is located on one side of the strap and a second piece of the outer layer is located on an opposite side of the strap.

According to a further aspect, a third piece of the outer layer is located on one edge of the strap and a fourth piece of the outer layer is located on an opposite edge of the strap.

According to a further aspect, at least two pieces of the outer layer are located on one side of the strap.

In accordance with at least one embodiment disclosed herein, a strap of a headgear comprises an inner core and an outer layer, wherein the outer layer is textured.

According to a further aspect, the outer layer is ribbed or quilted.

According to a further aspect, the core is textured such that it imparts a texture to the outer layer.

In accordance with at least one embodiment disclosed herein, a headgear, strap or other portion thereof has one or more features as described herein or a method of making such a headgear, strap or other portion thereof.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 3 is a third angle orthographic view of one half of an injection moulding tool configured to mould a strap component similar to the headgear of the present disclosure and FIGS. 3A and 3B are cross-sectional views of the injection moulding tool of FIG. 3.

FIG. 8C is a perspective view of a first strap of an alternative size adjustment system.

FIG. 8D is a cross-sectional view of connected first and second straps of the size adjustment system of FIG. 8C.

FIG. 8E is a cross-sectional view of unconnected first and second straps of the size adjustment system of FIG. 8C.

FIG. 8F is a perspective exploded view of another alternative size adjustment system.

FIG. 8G is a close-up exploded view of the size adjustment system of FIG. 8F.

FIG. 8H is a top-down view of the first strap of the size adjustment system of FIG. 8F.

FIG. 8I is a cross-sectional view of the first strap of the size adjustment system along a line A-A in FIG. 8H.

FIG. 22A is a sectional view of the second strap and FIG. 22B is a sectional view of the first strap.

FIG. 22C is a sectional view of an alternative strap in which a core of the strap includes a recess configured to receive a seam of a cover layer of the strap.

FIG. 22D is a sectional view of another alternative strap in which the core has one or more recesses occupying a substantial portion of a width direction of the core and the seam of the cover layer is located within the recess.

FIG. 40A is a view of the first outer layer and FIG. 40B is a view of the second outer layer of the headgear of FIG. 38.

FIG. 41 is a sectional view of a headgear strap arrangement having a core and one or more outer layers.

FIG. 42 is a side view of the core of the headgear strap arrangement of FIG. 41.

FIG. 49 is a sectional view of a headgear strap arrangement having a core and one or more outer layers.

FIG. 50 is a side view of the core of the headgear strap arrangement of FIG. 49.

FIG. 51 is a sectional view of a headgear strap arrangement having a core and one or more outer layers.

FIG. 52 is a side view of the core of the headgear strap arrangement of FIG. 51.

FIG. 71 is a perspective view of a headgear having at least a first strap and a second strap.

FIG. 72 is an enlarged view of the headgear of FIG. 71 including a coupling arrangement that couples at least the first strap and the second strap.

FIG. 73 is a sectional view of a portion of the headgear of FIG. 71 taken through the coupling arrangement of FIG. 72.

FIG. 103 is a perspective view of a headgear strap having a core and a quilted outer layer, with a portion of the outer layer cut away to expose the core.

FIG. 104 is a sectional view of a headgear layer having a core and an outer layer, wherein the core imparts a textured shape to the outer layer.

FIG. 105 is a perspective view of a headgear having a first strap and a second strap.

FIG. 106 is a sectional view of the first strap of the headgear of FIG. 105.

FIG. 107 is a sectional view of the second strap of the headgear of FIG. 105.

FIG. 108 is a perspective view of a headgear having a first strap, a second strap and a connection between the first strap and the second strap.

FIG. 109 is an enlarged view of a portion of the headgear of FIG. 108 including the connection.

FIG. 110 is a sectional view of the connection of FIG. 109.

FIG. 111 is a perspective view of a headgear having a first strap, a second strap and a connection between the first strap and the second strap.

FIG. 112 is an enlarged view of the portion of the headgear of FIG. 111 including the connection.

FIG. 113 illustrated several possible sectional views of the straps within the connection.

FIG. 114 is a sectional view of the second strap of the headgear of FIG. 111.

Figure 115A:
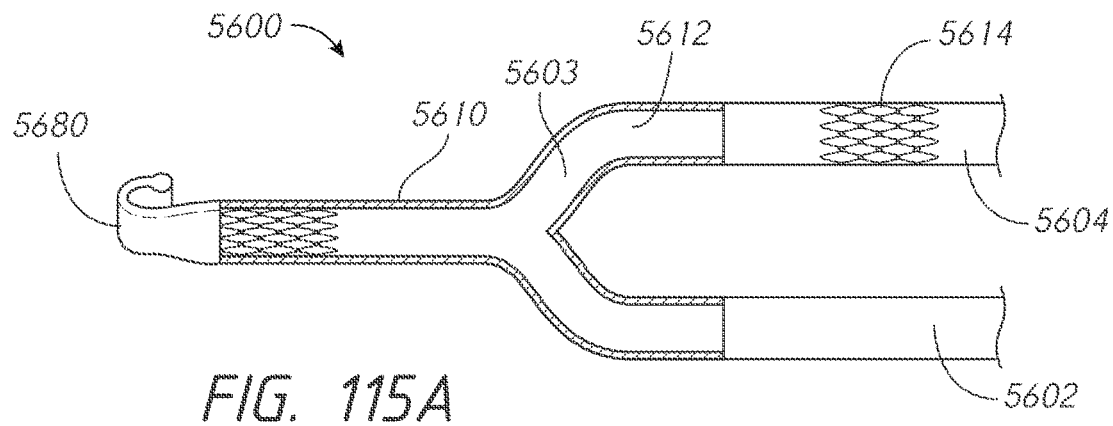

FIG. 115A is a top-down view of a front strap and bifurcated straps of an intra-moulded bifurcated headgear.

Figure 115B:
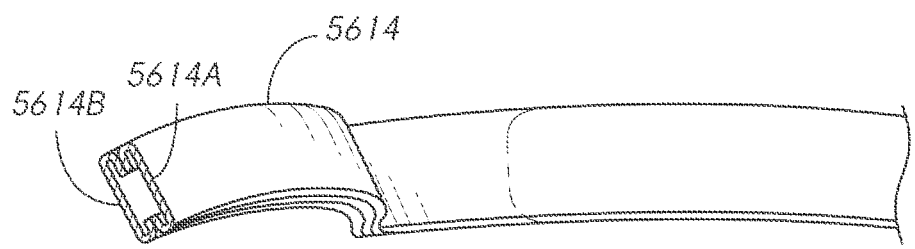

FIG. 115B is a perspective view of first and second cover layers joined together to form a strap of the intra-moulded bifurcated headgear of FIG. 115A.

Figure 115C:
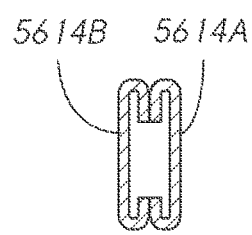

FIG. 115C is a cross-sectional view of first and second cover layers joined together to form a strap of the intra-moulded bifurcated headgear of FIG. 115A.

Figure 116:
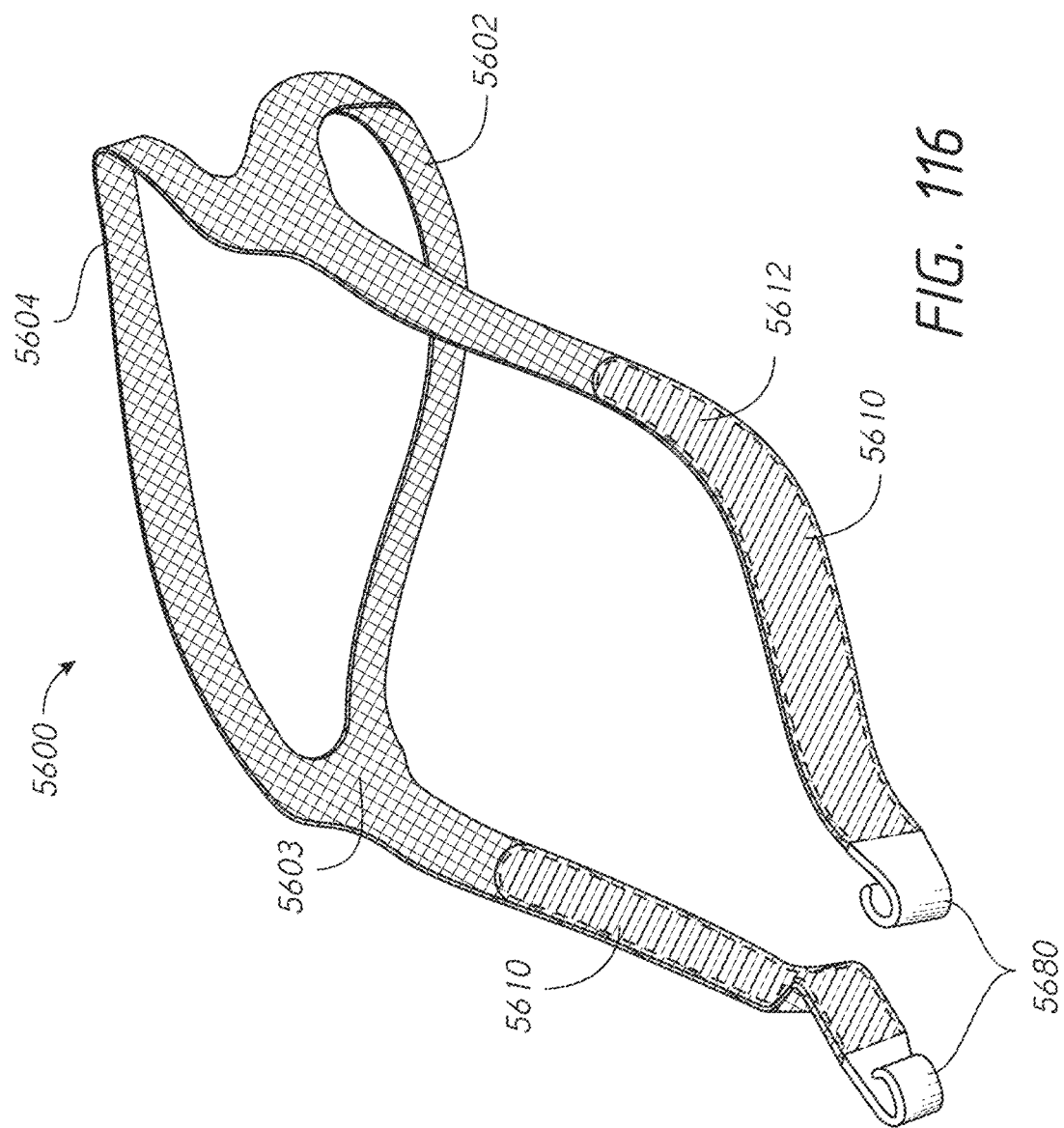

FIG. 116 is a perspective view of the intra-moulded bifurcated headgear of FIG. 115A having front straps that are partially rigid.

Figure 117:
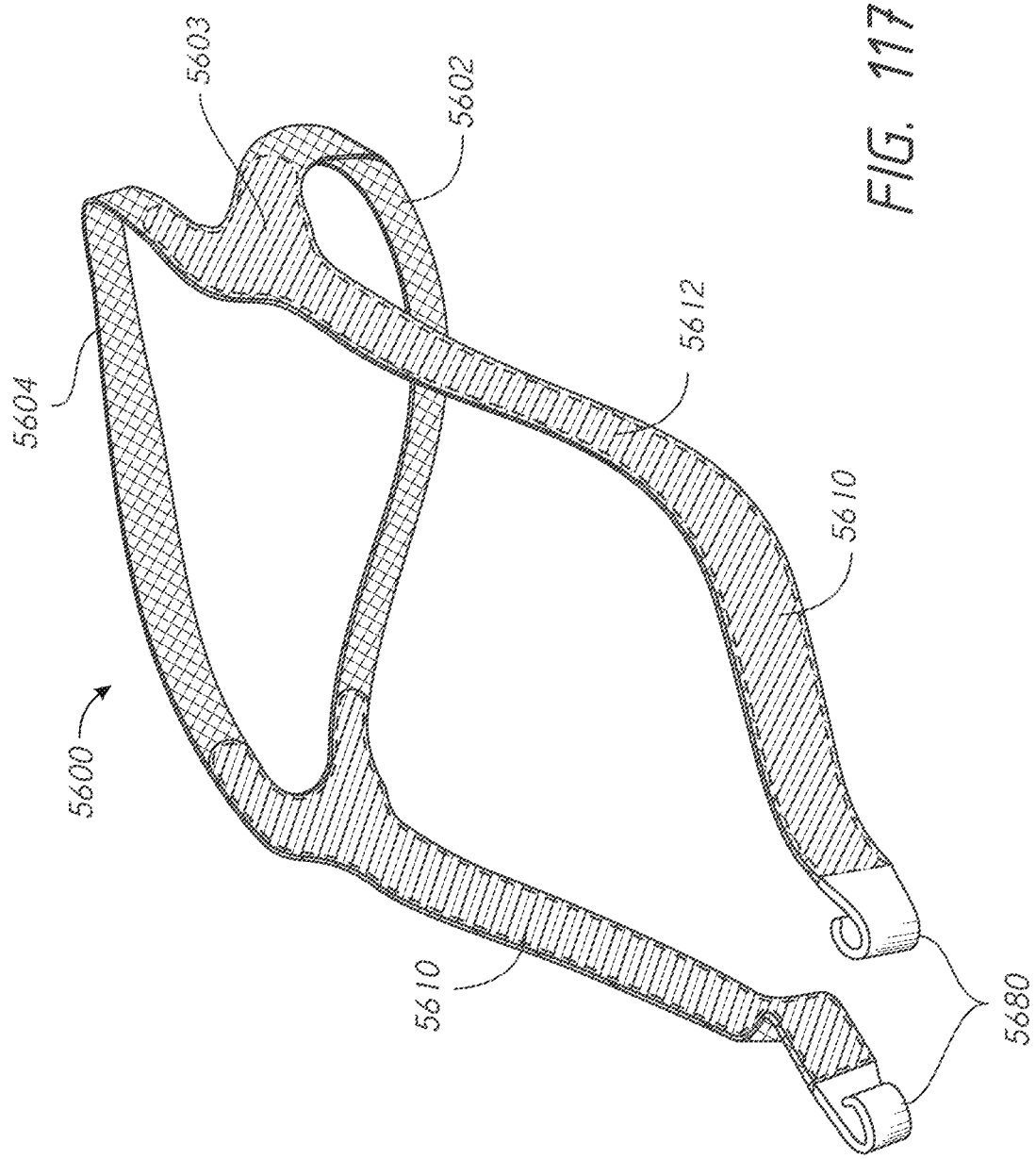

FIG. 117 is a perspective view of the intra-moulded bifurcated headgear of FIG. 115A having rigid front straps and partially rigid bifurcated straps.

Figure 118:
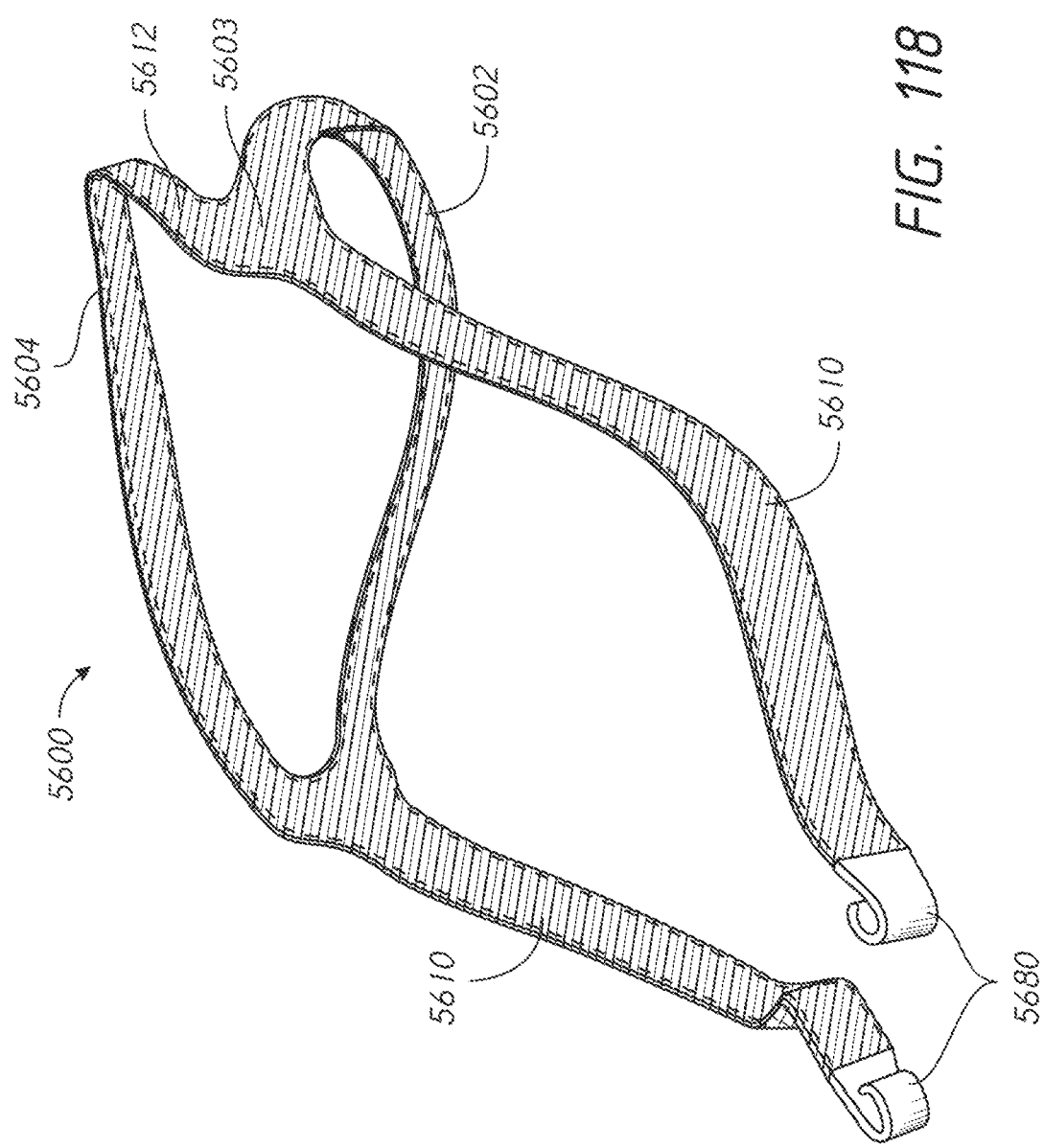

FIG. 118 is a perspective view of the intra-moulded bifurcated headgear of FIG. 115A having rigid front and bifurcated straps.

Figure 119A:
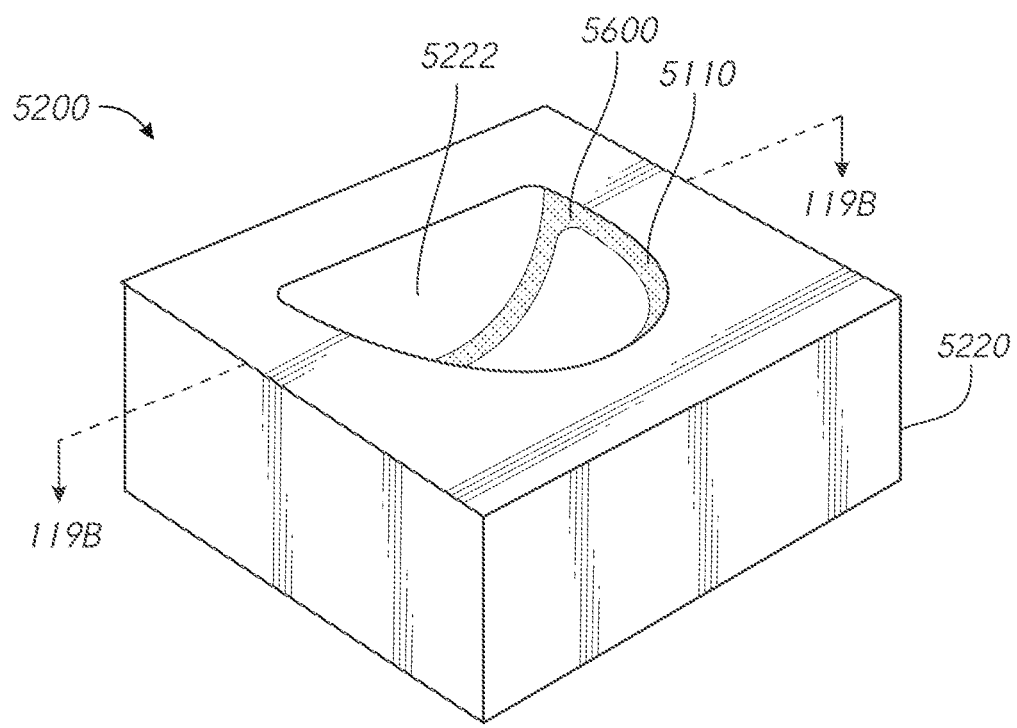

FIG. 119A is a perspective view of a mould tool configured to form the intra-moulded bifurcated headgear configuration of FIGS. 115A to 118.

Figure 119B:
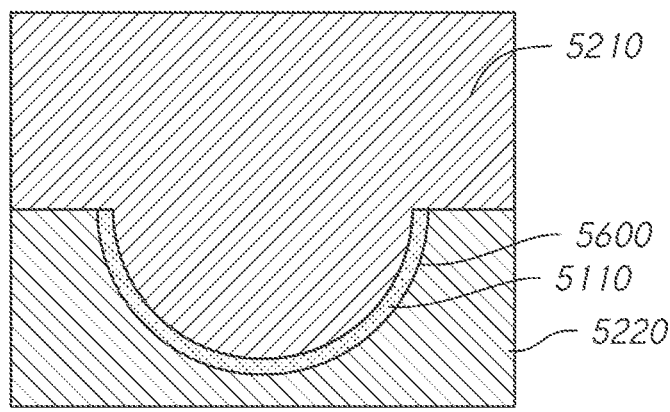

FIG. 119B is a cross-sectional view of the mould tool of FIG. 119A along a line A-A.

Figure 119C:
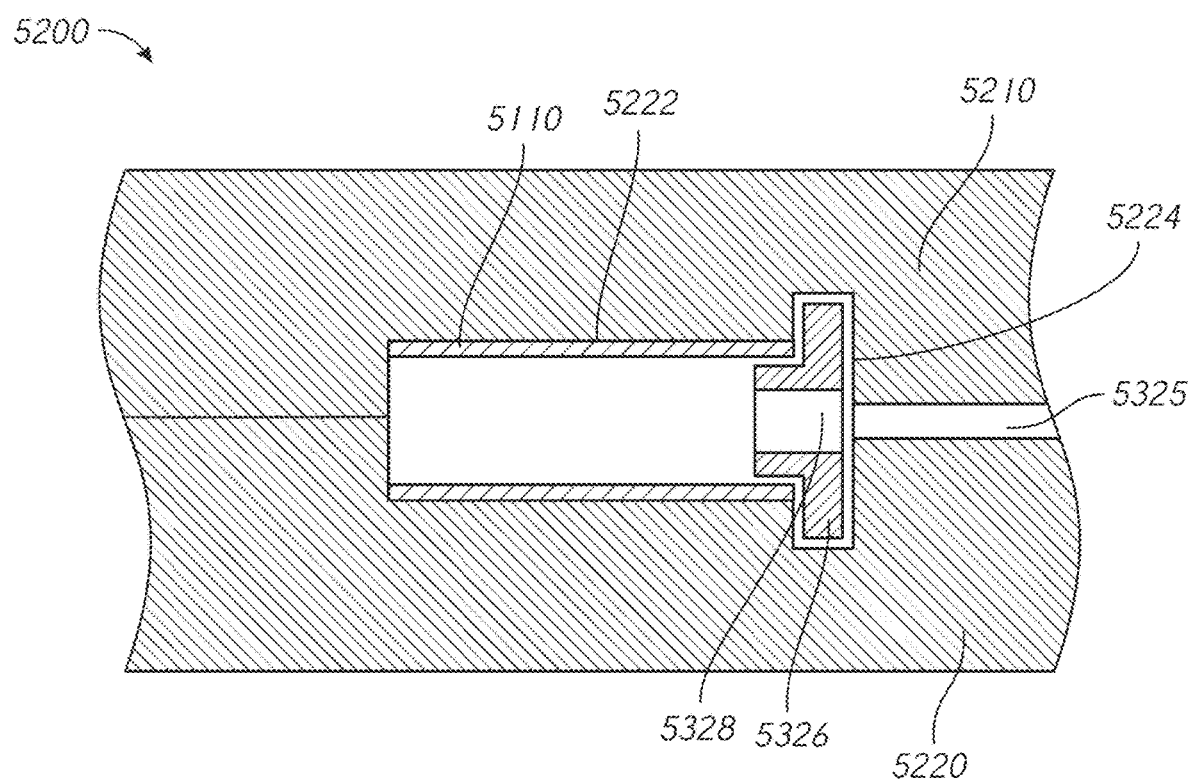

FIG. 119C is a cross-sectional view of a mould tool configured to secure in place a fabric casing within the mould tool.

Figure 119D:
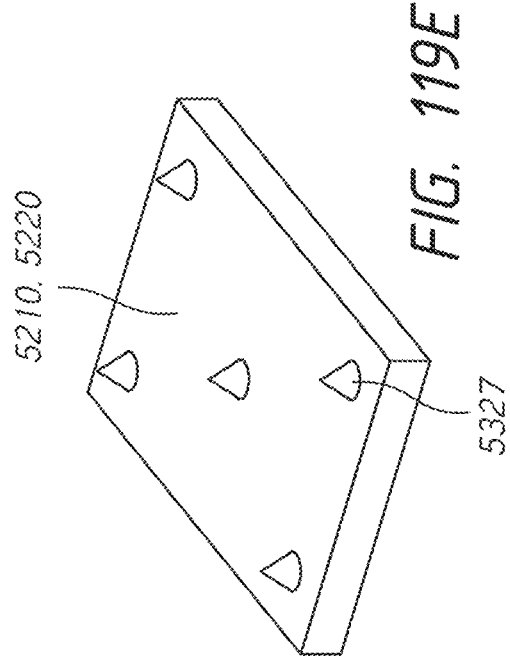

FIG. 119D is a cross-sectional view of a mould tool having retention spikes to secure in place a fabric casing within the mould tool.

Figure 119E:
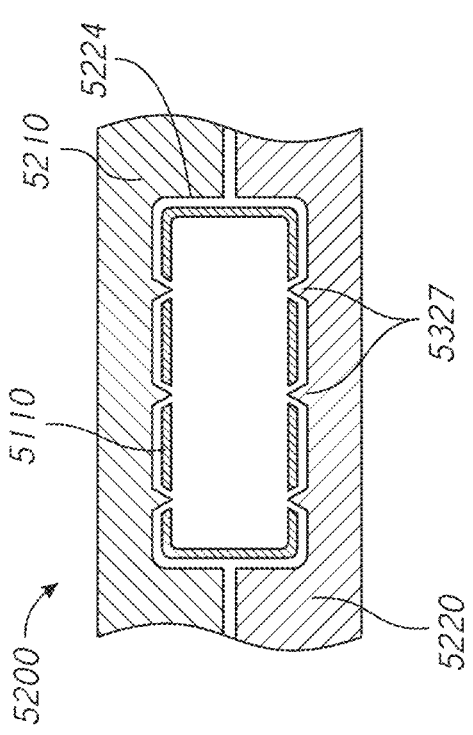

FIG. 119E is a partial perspective view of the mould tool of FIG. 119D showing retention spikes to secure in place a fabric casing within the mould tool.

Figure 119F:
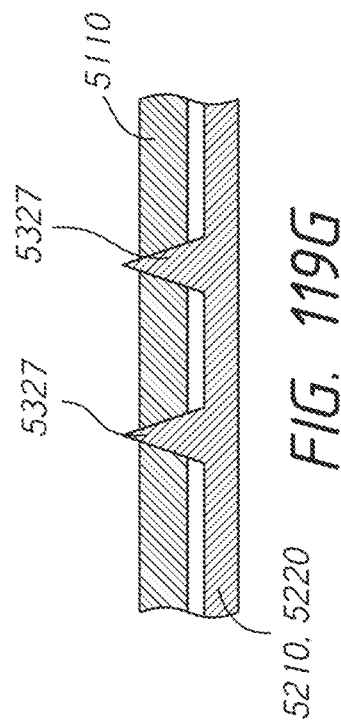

FIG. 119F is a cross-sectional view of the mould tool of FIG. 119D showing retention spikes piercing but not extending through the fabric casing.

Figure 119G:
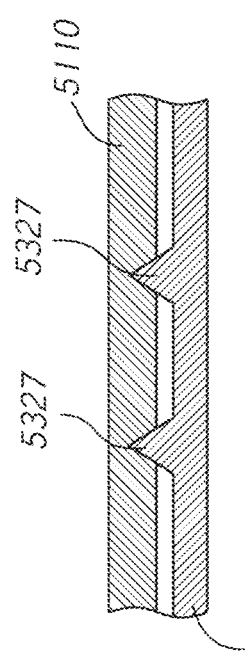

FIG. 119G is a cross-sectional view of the mould tool of FIG. 119D showing retention spikes piercing through the fabric casing.

Figure 120A:
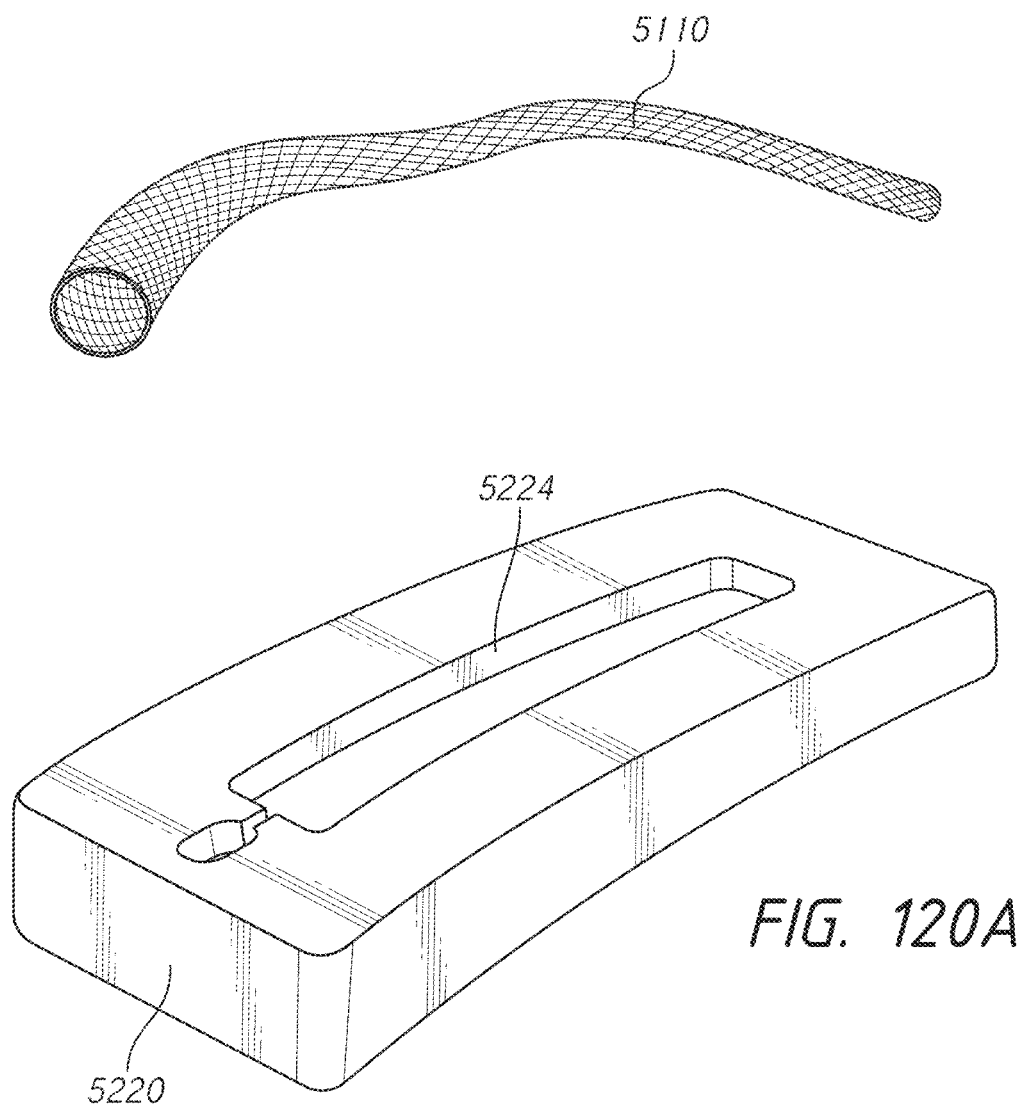

FIG. 120A is a perspective view of a mould tool for forming a headgear using a woven fabric casing.

Figure 120B:
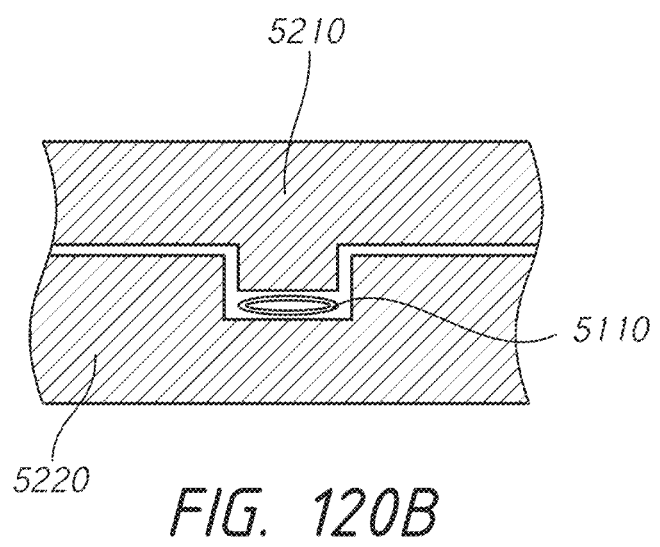

FIG. 120B is a cross-sectional view of the mould tool of FIG. 120A.

Figure 121:
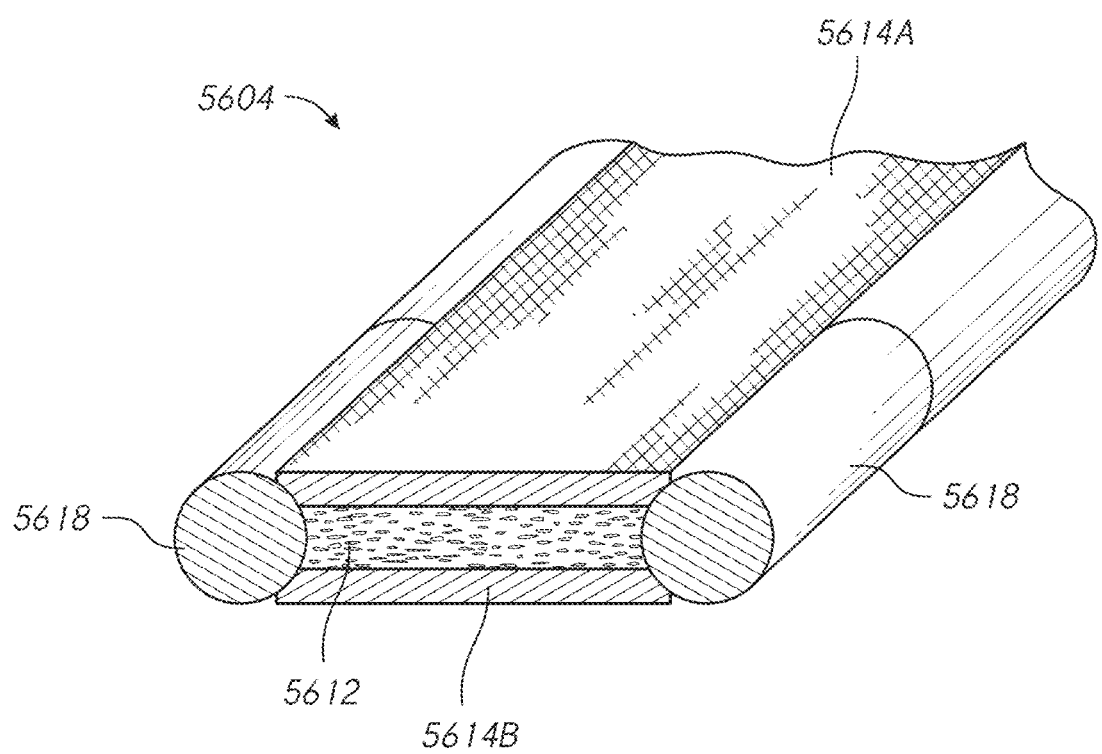

FIG. 121 is a perspective cross-sectional view of an alternative construction of an intra-moulded strap having a core, cover layers and rails.

FIG. 122A is a cross-sectional view of an alternative construction of an intra-moulded strap having an airpocket core, a cover layer and intra-moulded rails.

FIG. 122B is a perspective view of the intra-moulded strap of FIG. 122A.

FIG. 122C is a cross-sectional view of the intra-moulded strap of FIG. 122A when donned by the user.

Figure 123A:
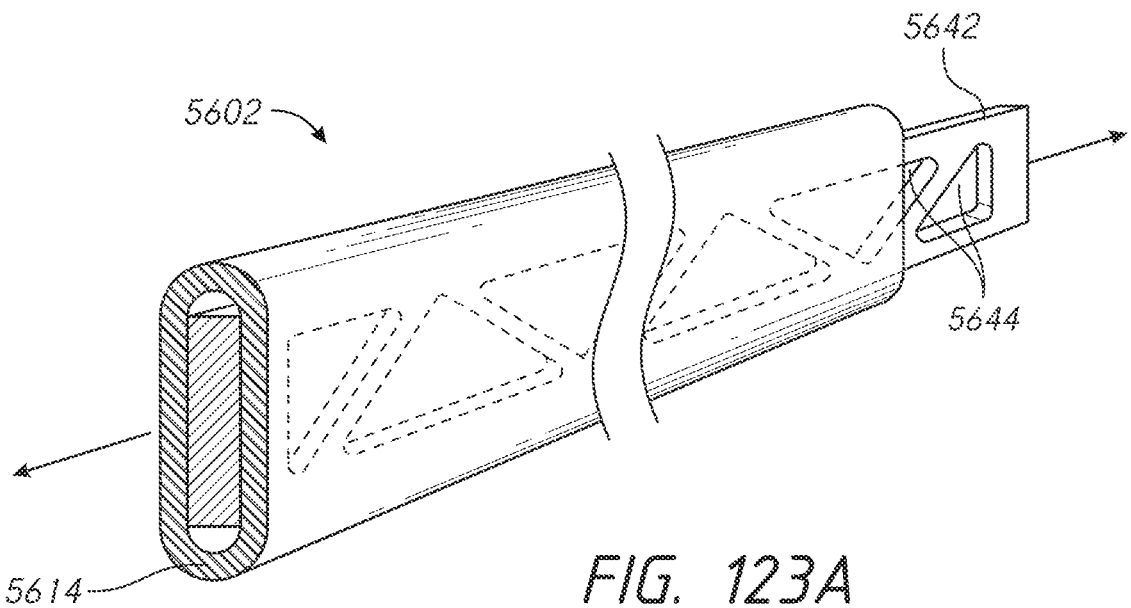

FIG. 123A is a perspective cross-sectional view of an alternative construction of an intra-moulded strap having a structured core.

Figure 123B:
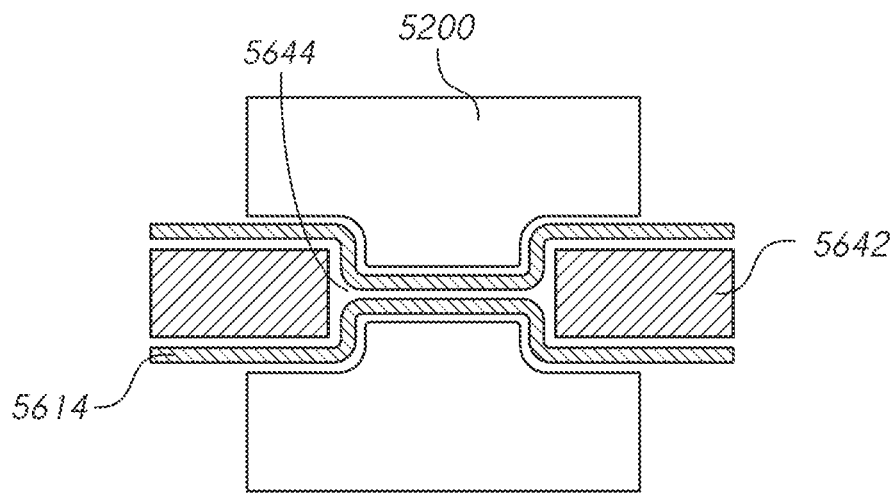

FIG. 123B is a cross-sectional view of a mould tool for constructing the structured core of the intra-moulded strap in FIG. 123A.

FIG. 124A is a perspective view of an alternative construction of an intra-moulded strap having a complex 3D shape with continuously variable geometry and cross-section along its length.

FIG. 124B is a cross-sectional view of the intra-moulded strap of FIG. 124A along a line A-A.

FIG. 124C is a cross-sectional view of the intra-moulded strap of FIG. 124A along a line B-B.

FIG. 125A is a perspective cross-sectional view of an alternative intra-moulded strap having embossed branding logos.

FIG. 125B is a perspective cross-sectional view of an alternative intra-moulded strap having laser cut branding logos.

FIG. 125C is a perspective cross-sectional view of the alternative intra-moulded strap of FIG. 125B.

FIG. 125D is a perspective cross-sectional view of an alternative intra-moulded strap having laser cut portion removed to expose core material.

Figure 125E:
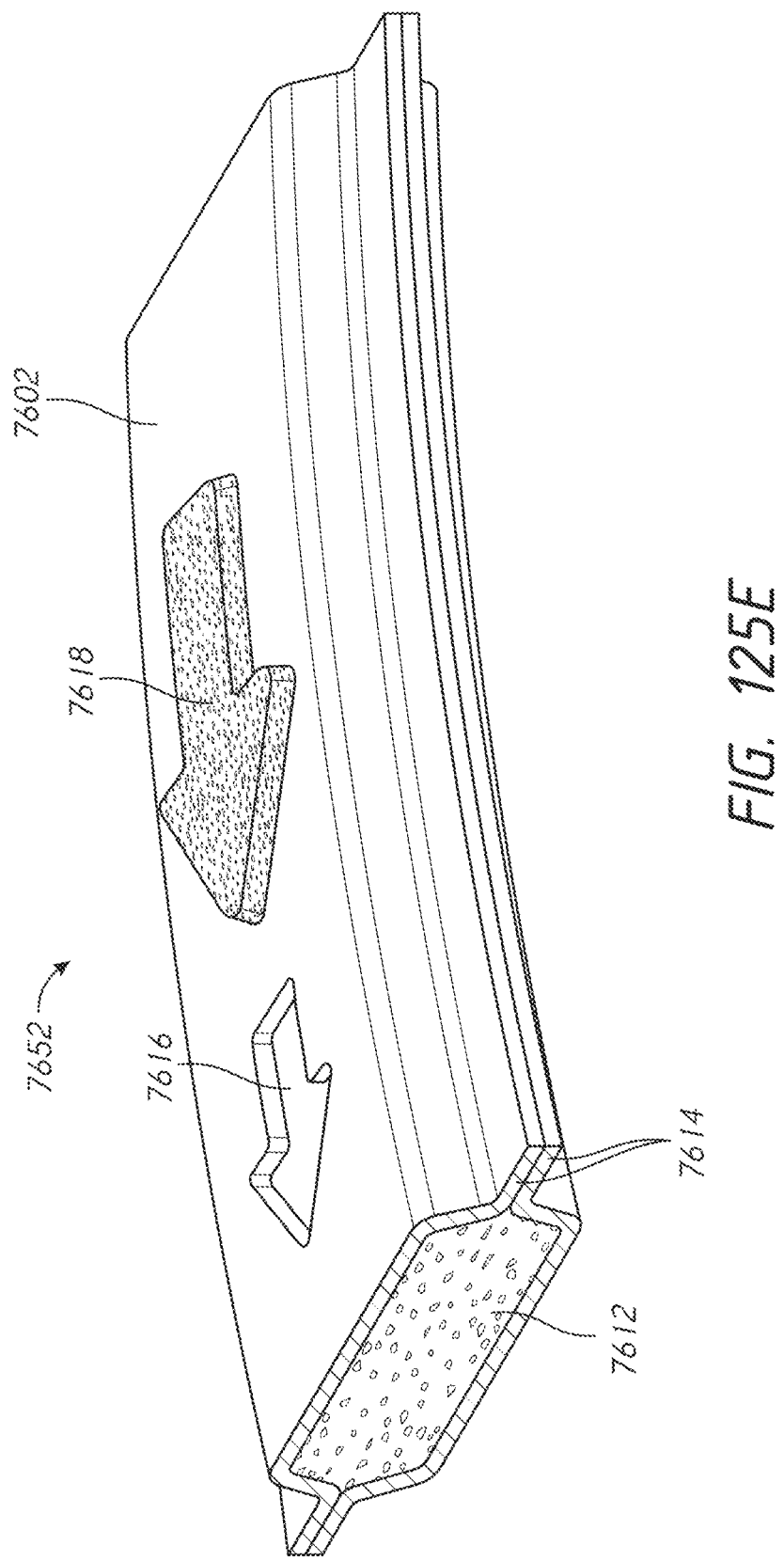

FIG. 125E is a perspective cross-sectional view of an alternative intra-moulded strap having an embossed indicator and a protruding indicator formed from exposed core material.

Figure 125G:
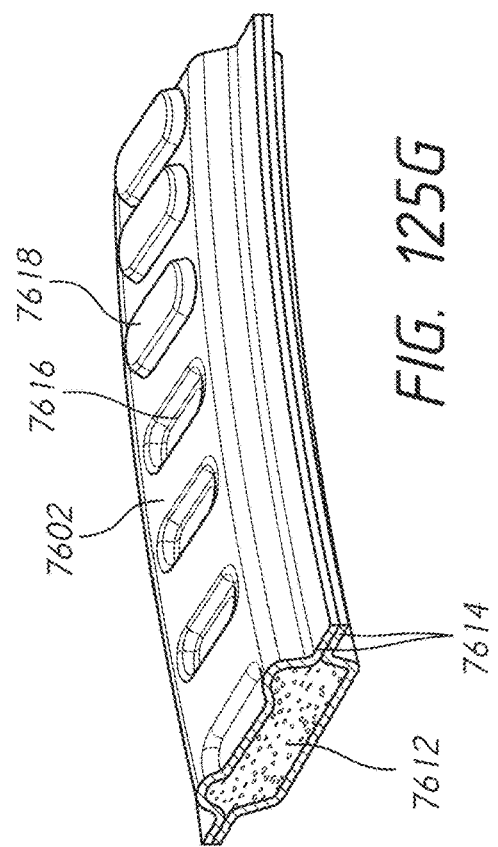
Figure 125F:
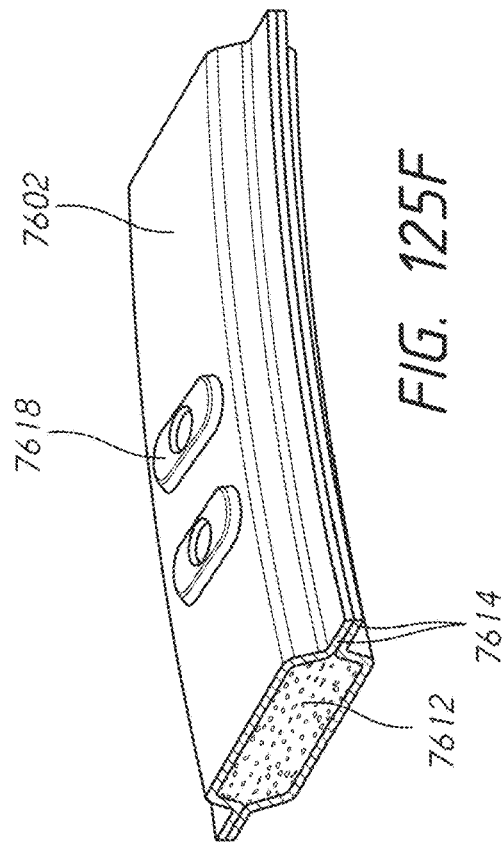

FIG. 125F is a perspective cross-sectional view of an alternative intra-moulded strap having protruding grip bumps with embossed features.

FIG. 125G is a perspective cross-sectional view of an alternative intra-moulded strap having embossed and protruding grip bumps.

FIG. 126A is a perspective cross-sectional view of an alternative intra-moulded strap having over-moulded branding logos.

FIG. 126B is a perspective cross-sectional view of an alternative intra-moulded strap having over-moulded grip bumps.

FIG. 126C is a cross-sectional view of the alternative intra-moulded strap having over-moulded grip bumps of FIG. 126B along a line A-A.

Figure 127A:
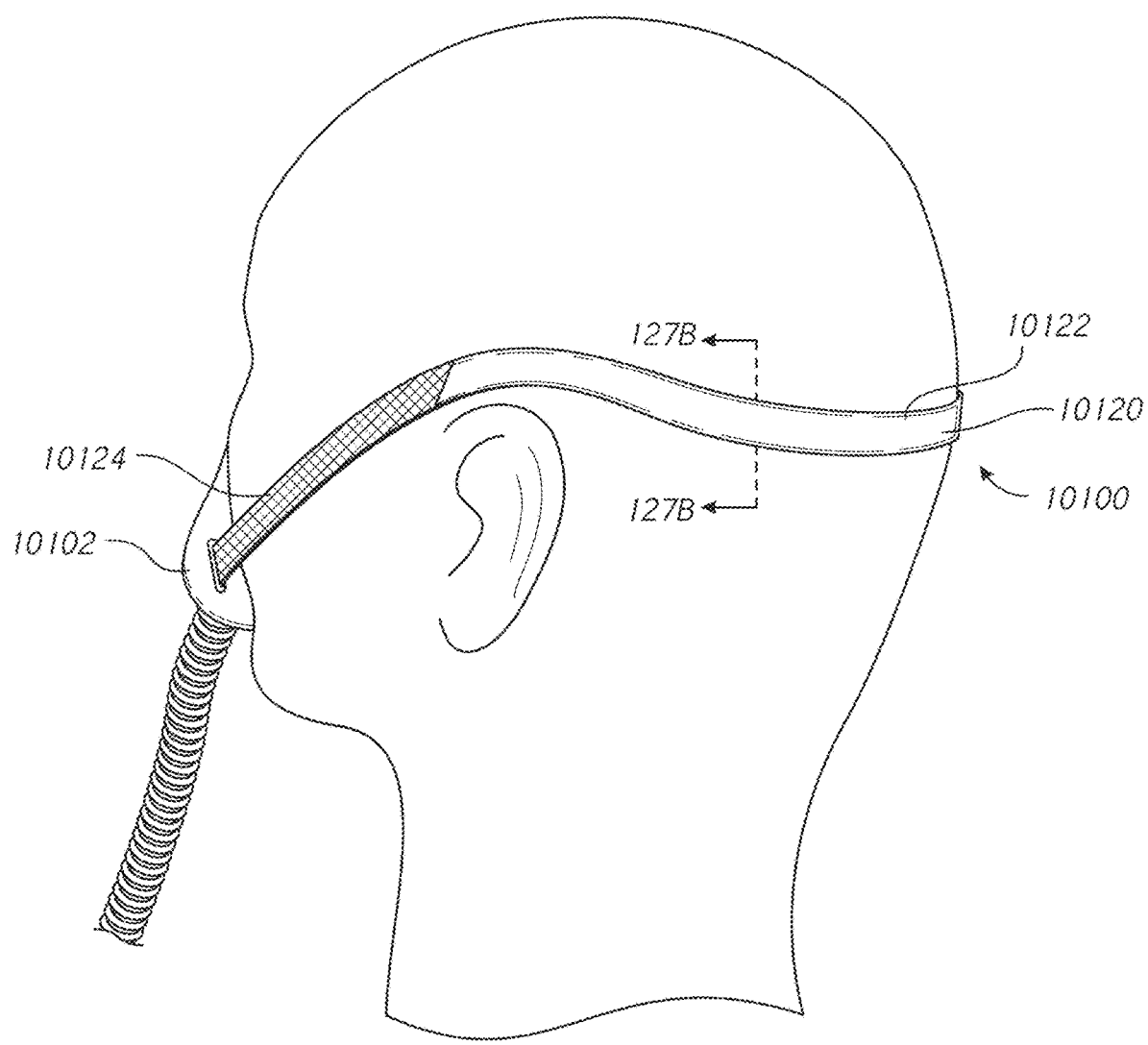

FIG. 127A is a rear perspective view of a moulded headgear configuration having a single back strap.

Figure 127B:
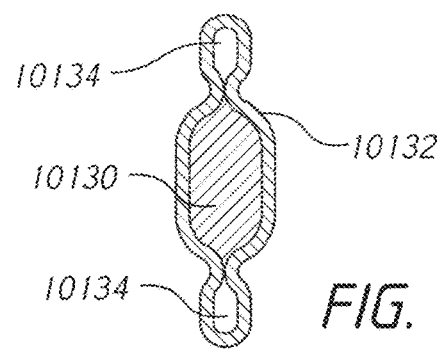

FIG. 127B is a cross-sectional view of the moulded headgear configuration of FIG. 127A along a line A-A.

Figure 128C:
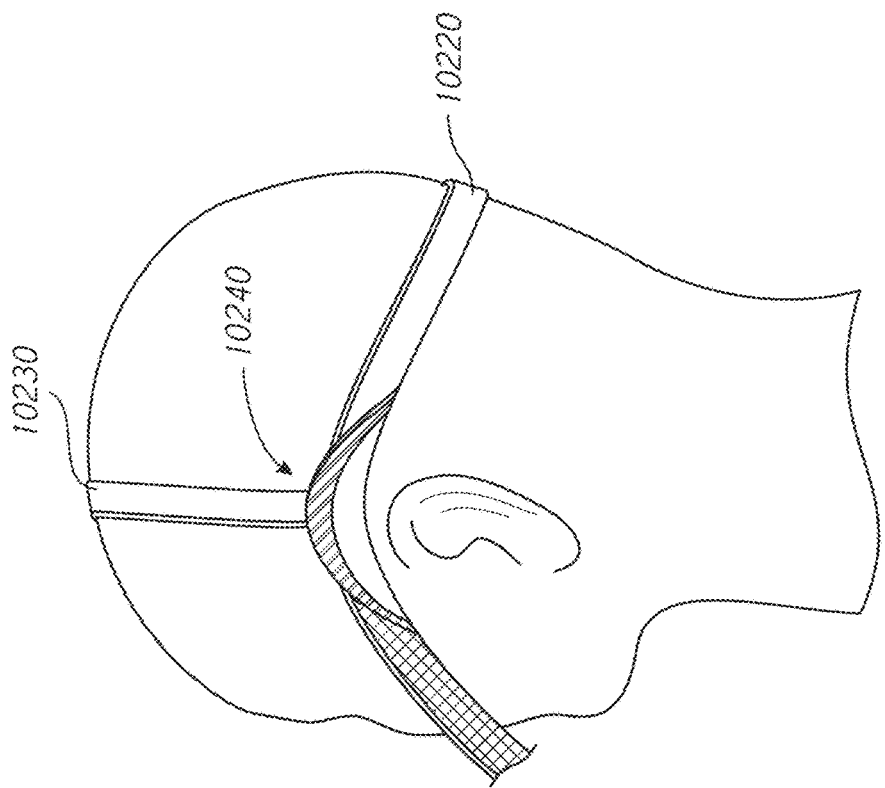
Figure 128A:
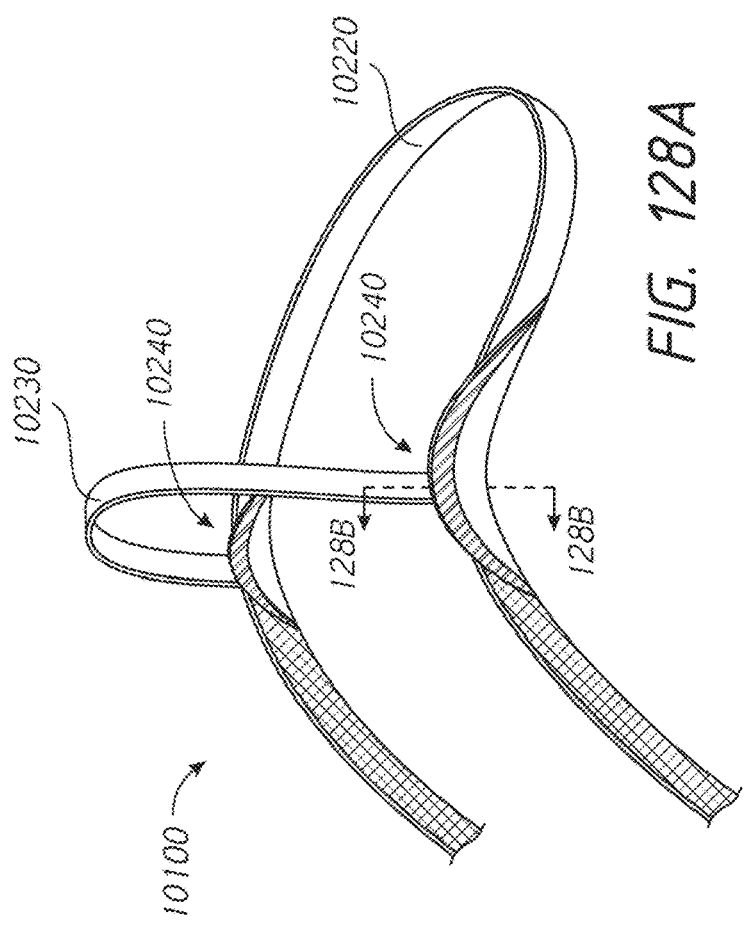

FIG. 128A is a side perspective view of a moulded headgear configuration having a lower strap connected to a crown strap by an arched connector.

Figure 128B:
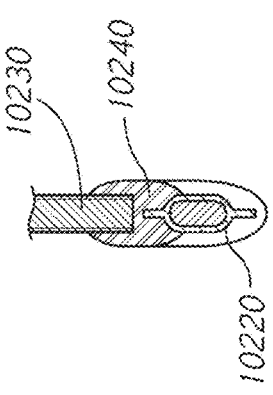

FIG. 128B is a cross-sectional view of the moulded headgear configuration of FIG. 128A along a line A-A.

FIG. 128C is a side view of the moulded headgear configuration of FIG. 128A.

Figure 129:
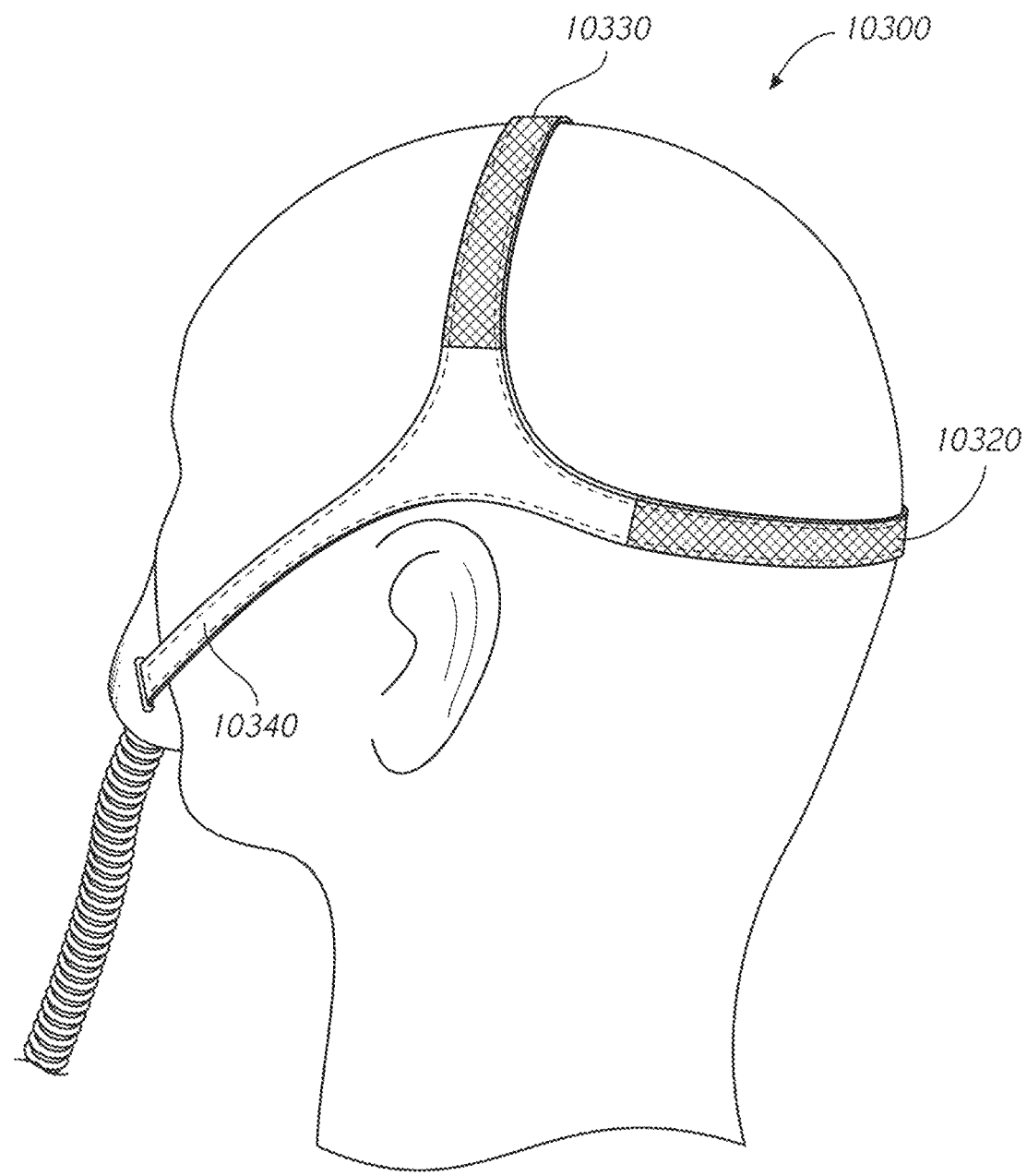

FIG. 129 is a rear perspective view of a moulded headgear configuration having a rigid front strap and elastic rear and crown straps.

FIG. 130A is a rear perspective view of a moulded bifurcating headgear configuration having a having a variable knit intra-mould.

FIG. 130B is a cross-sectional view of the moulded headgear configuration of FIG. 130A along a line A-A.

FIG. 130C is a cross-sectional view of the moulded headgear configuration of FIG. 130A along a line B-B.

FIG. 130D is a moulding tool for forming the moulded headgear configuration of FIG. 130A.

FIG. 131A is a side perspective view of a moulded headgear configuration having a fully integrated bifurcated rear strap and crown strap.

FIG. 131B is a partial exploded perspective view of the moulded headgear configuration of FIG. 131A.

FIG. 131C is a cross-sectional perspective view of the moulded headgear configuration of FIG. 131A along a line A-A.

Figure 132A:
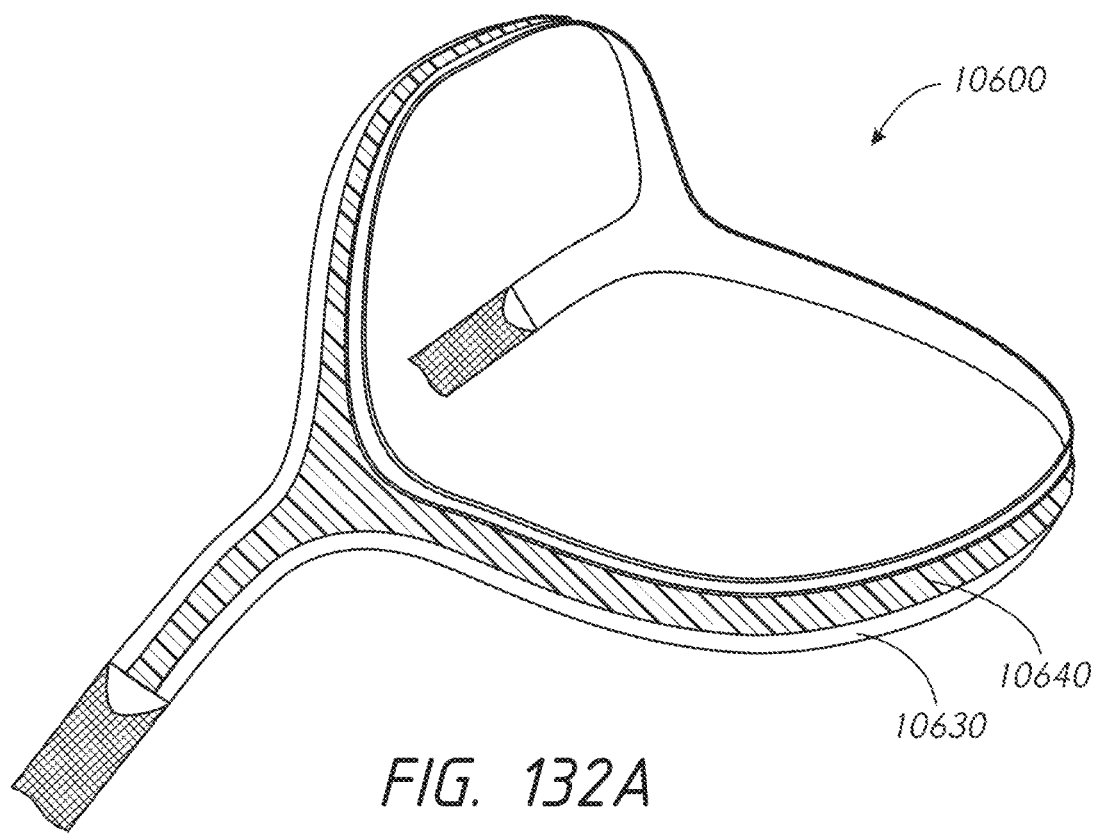

FIG. 132A is a side perspective view of a moulded headgear configuration having core material exposed and formed on the outside surface of the outer cover.

Figure 132B:
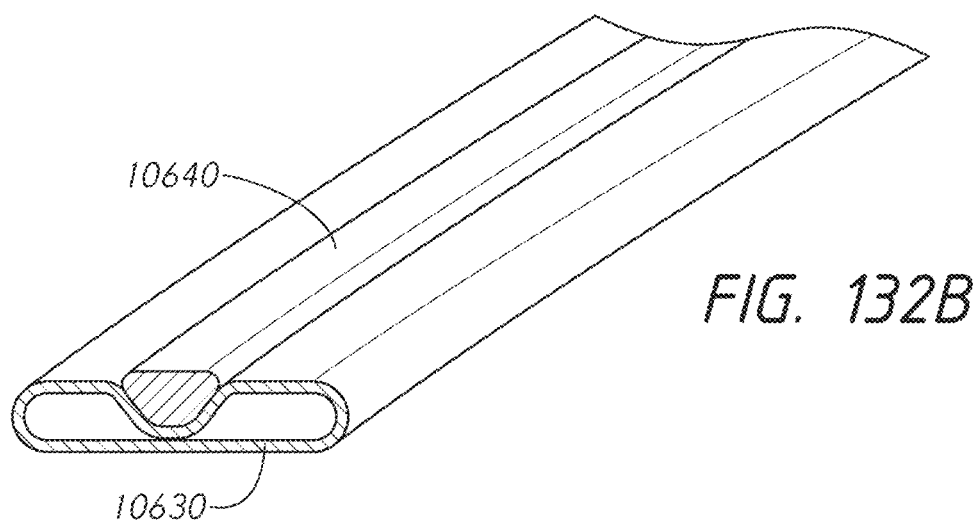

FIG. 132B is cross-sectional perspective view of the moulded headgear configuration of FIG. 131A having the core material recessed within the outer cover.

Figure 132C:
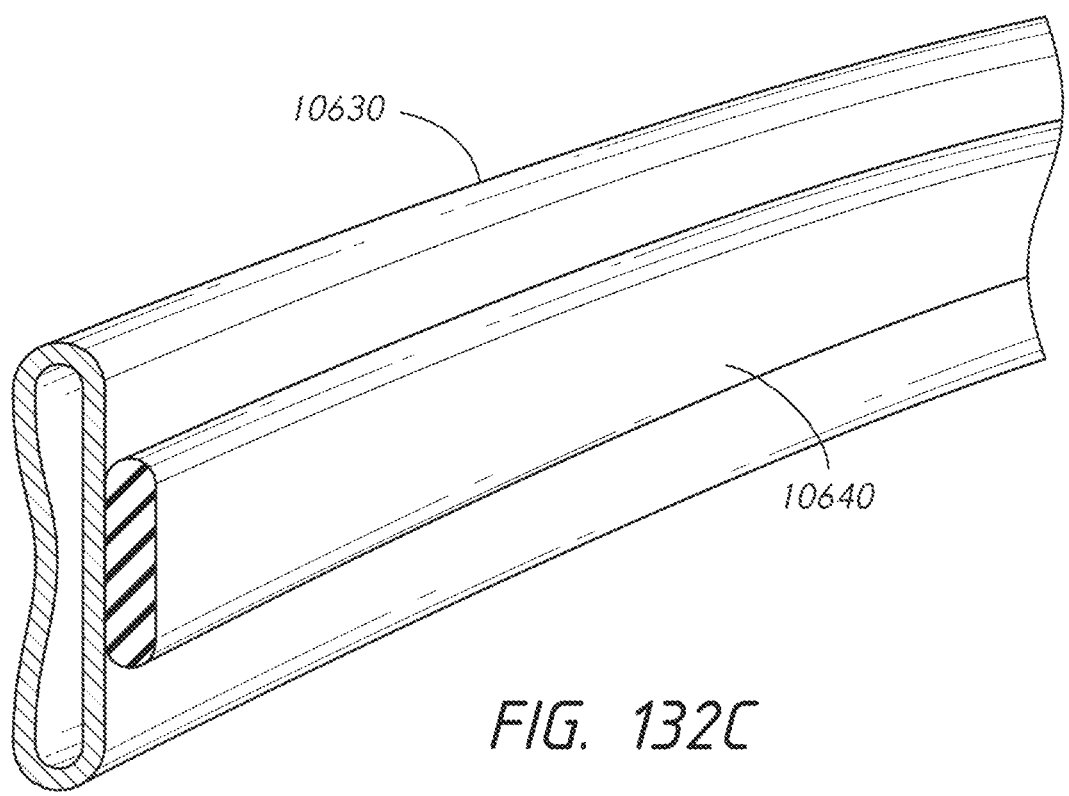

FIG. 132C is a cross-sectional perspective view illustrating an alternative construction of the moulded headgear configuration of FIG. 131A having core material positioned over the outer cover without recessing into the outer cover.

Figure 133:
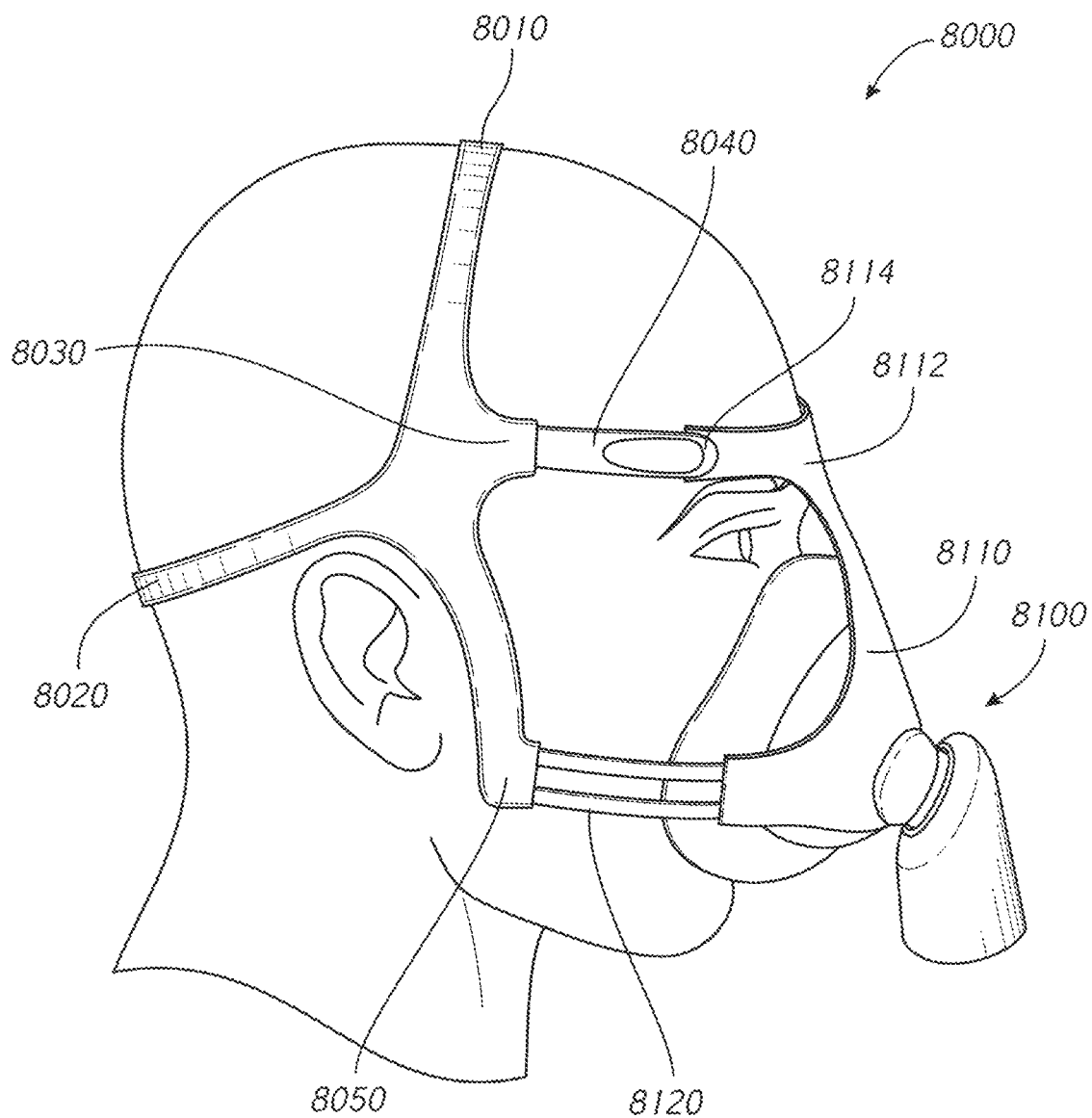

FIG. 133 is a side view of an exemplary intra-moulded headgear configuration for use in combination with a full-face mask.

Figure 134:
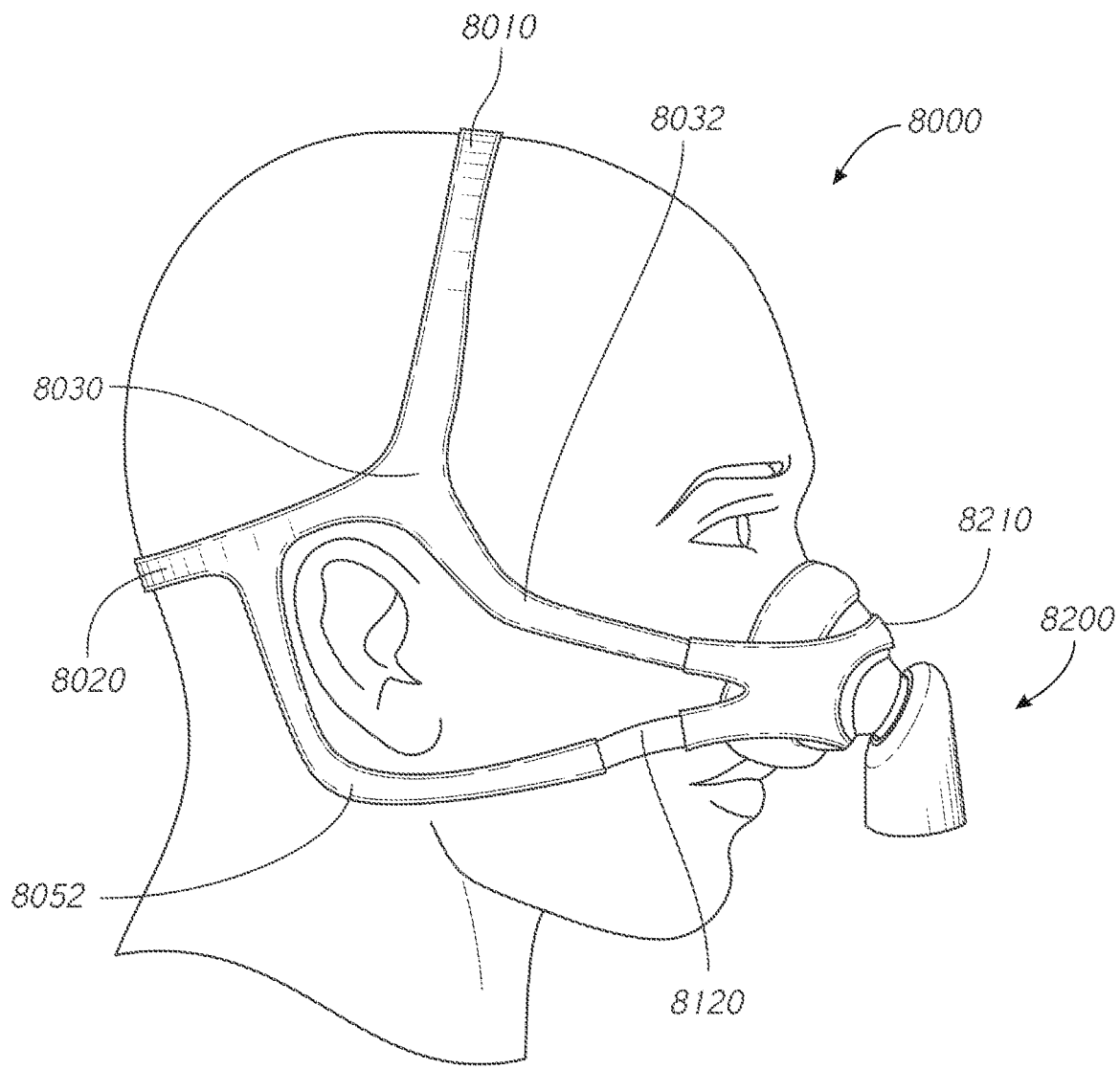

FIG. 134 is a side view of an exemplary intra-moulded headgear configuration having a below the ear lower strap for use in combination with a nasal mask.

Figure 135:
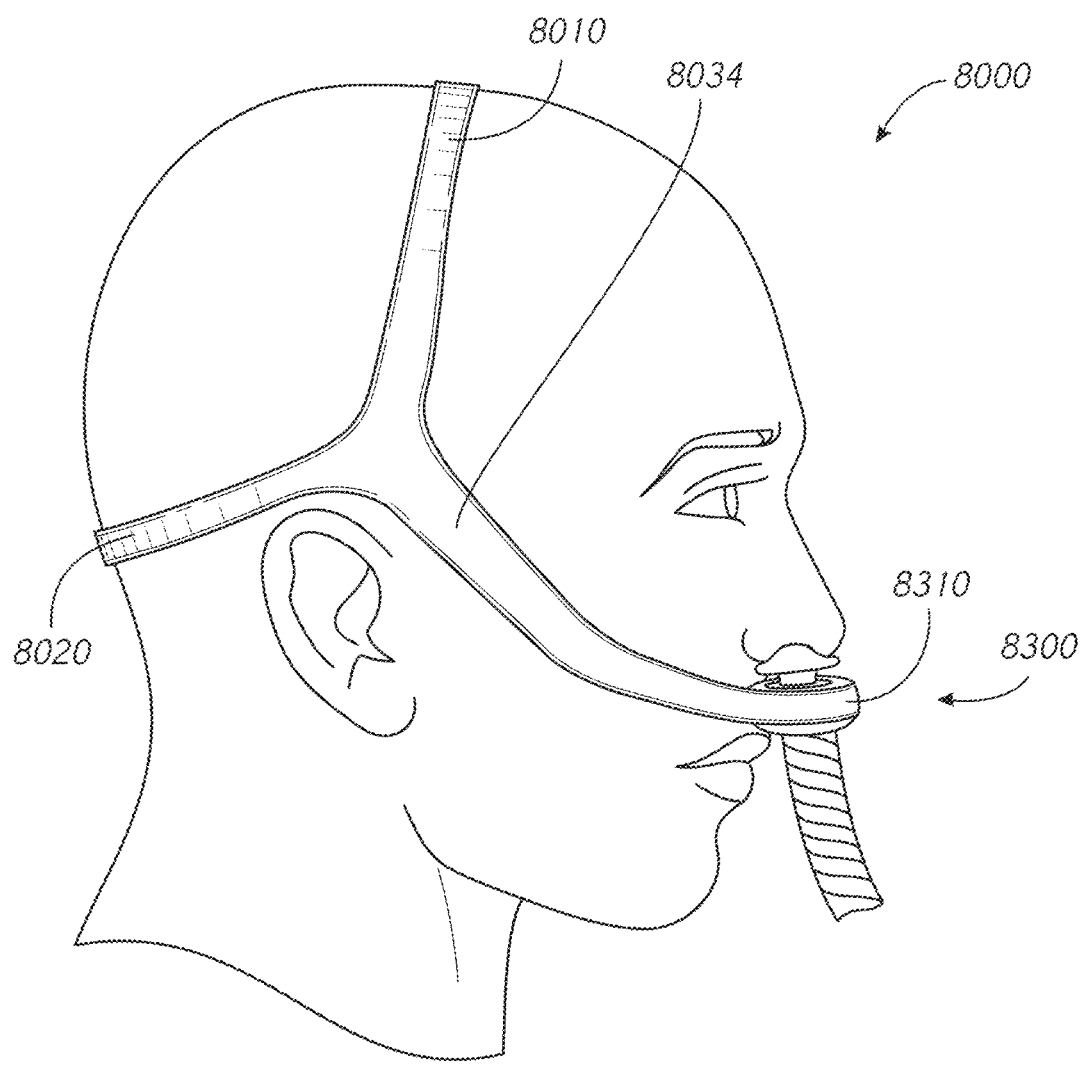

FIG. 135 is a side view of an exemplary intra-moulded headgear configuration for use in combination with a nasal pillows mask.

Figure 136:
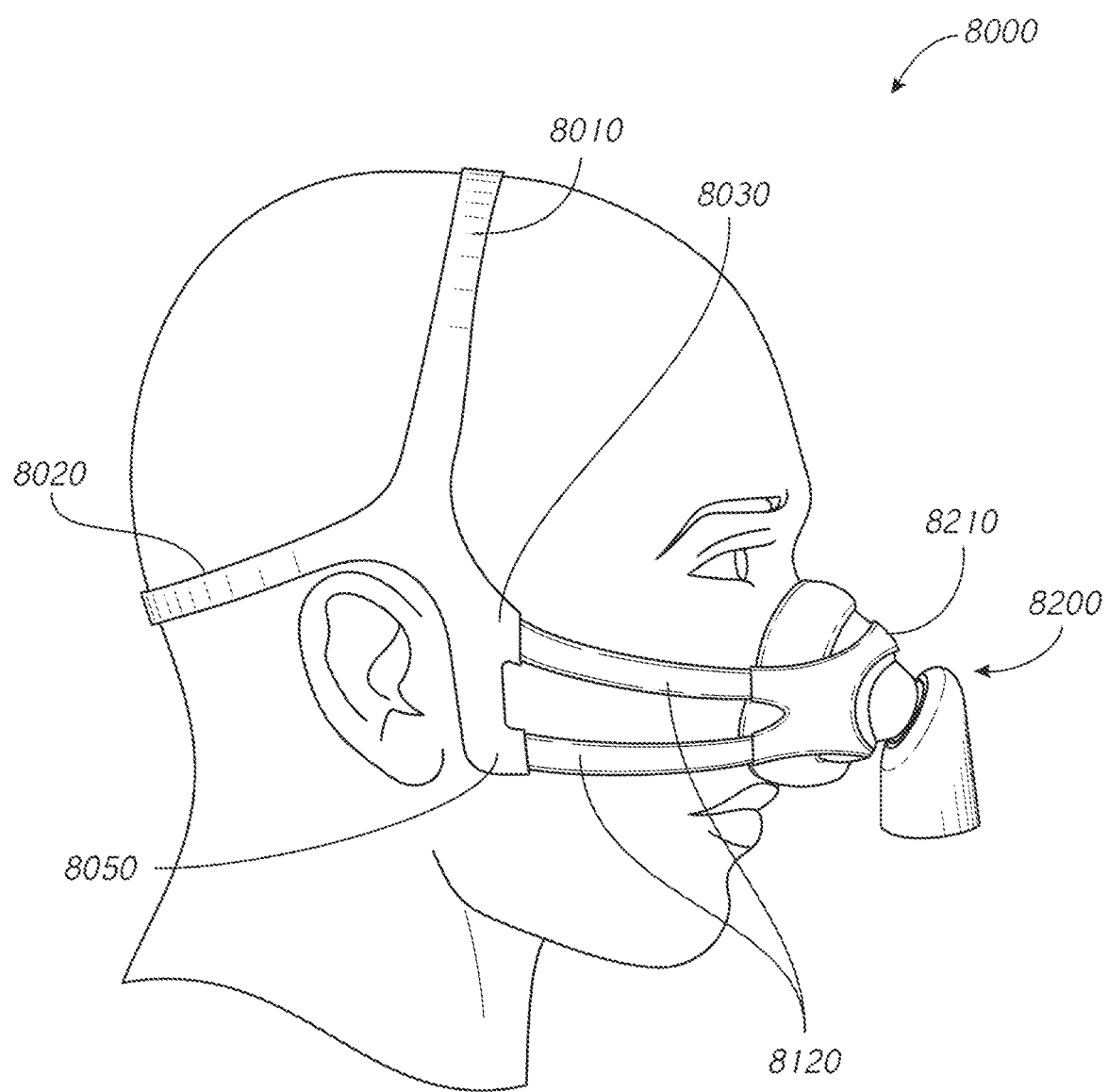

FIG. 136 is a side view of an exemplary intra-moulded headgear configuration for use in combination with a nasal mask.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

As used herein the term 'substantially inelastic' shall refer to the ability of a headgear or material to resist stretching relative to the loads to which it may be subjected. Thus, a headgear or material may be substantially inelastic in one direction and may be somewhat elastic in another direction. In some configurations, the headgear or material is configured to be substantially inelastic in a direction in which loads are applied by therapy with which the headgear or material is intended for use. A substantially inelastic headgear or material, for example, can resist stretching that would compromise a seal of a respiratory mask in a sealed system under normal or expected conditions. In an unsealed system, a substantially inelastic headgear or material, for example, can resist stretching that would compromise the appropriate placement of the respiratory interface in response to normal or expected conditions, such as hose pull forces or movement of the user. When the expected loading forces are relatively low, the headgear or material may have greater elasticity because the load will not be sufficient to cause stretching. Conversely, if it is expected that the headgear and/or material will be subjected to high loading forces, then greater inelasticity will be required to resist stretching.

Figure 1A:
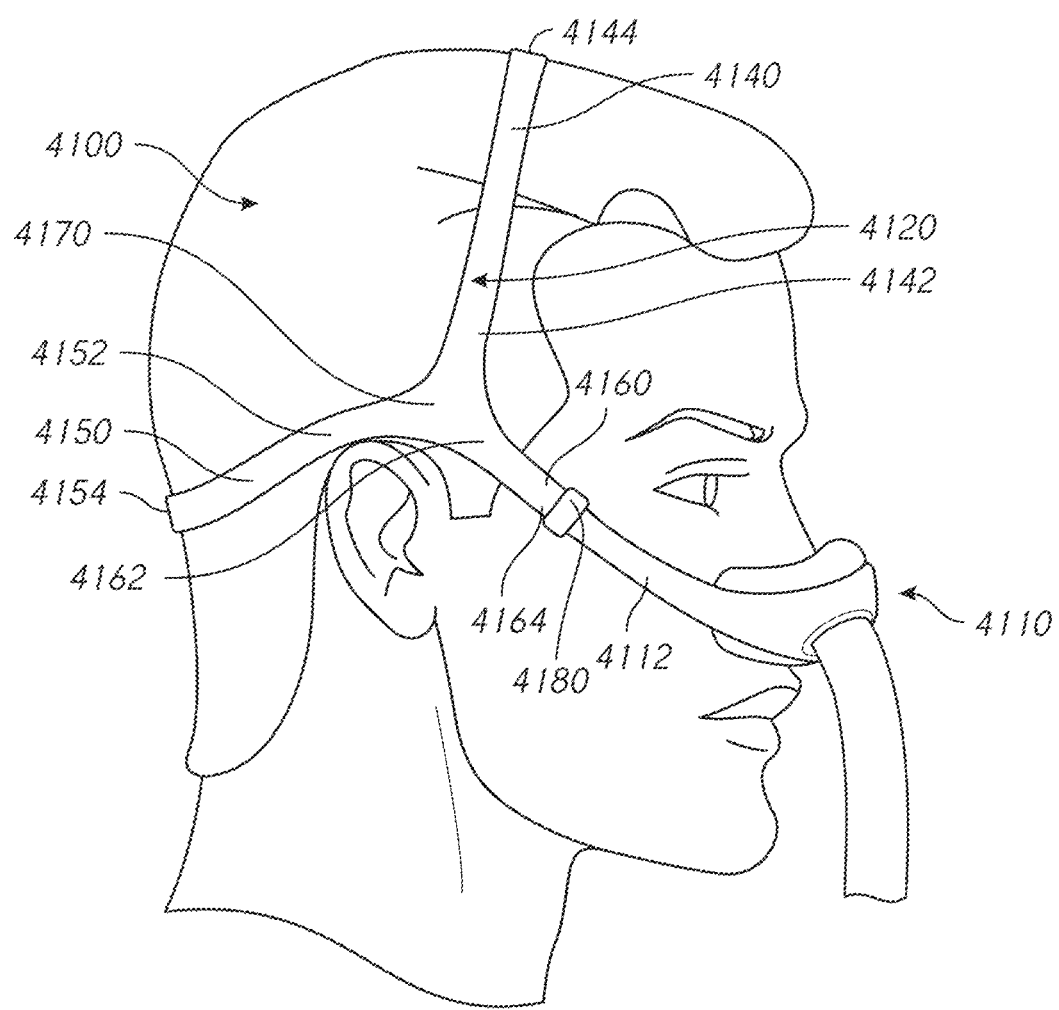
FIG. 1A is a side view of the headgear of the present disclosure being worn by a user.
Figure 1B:
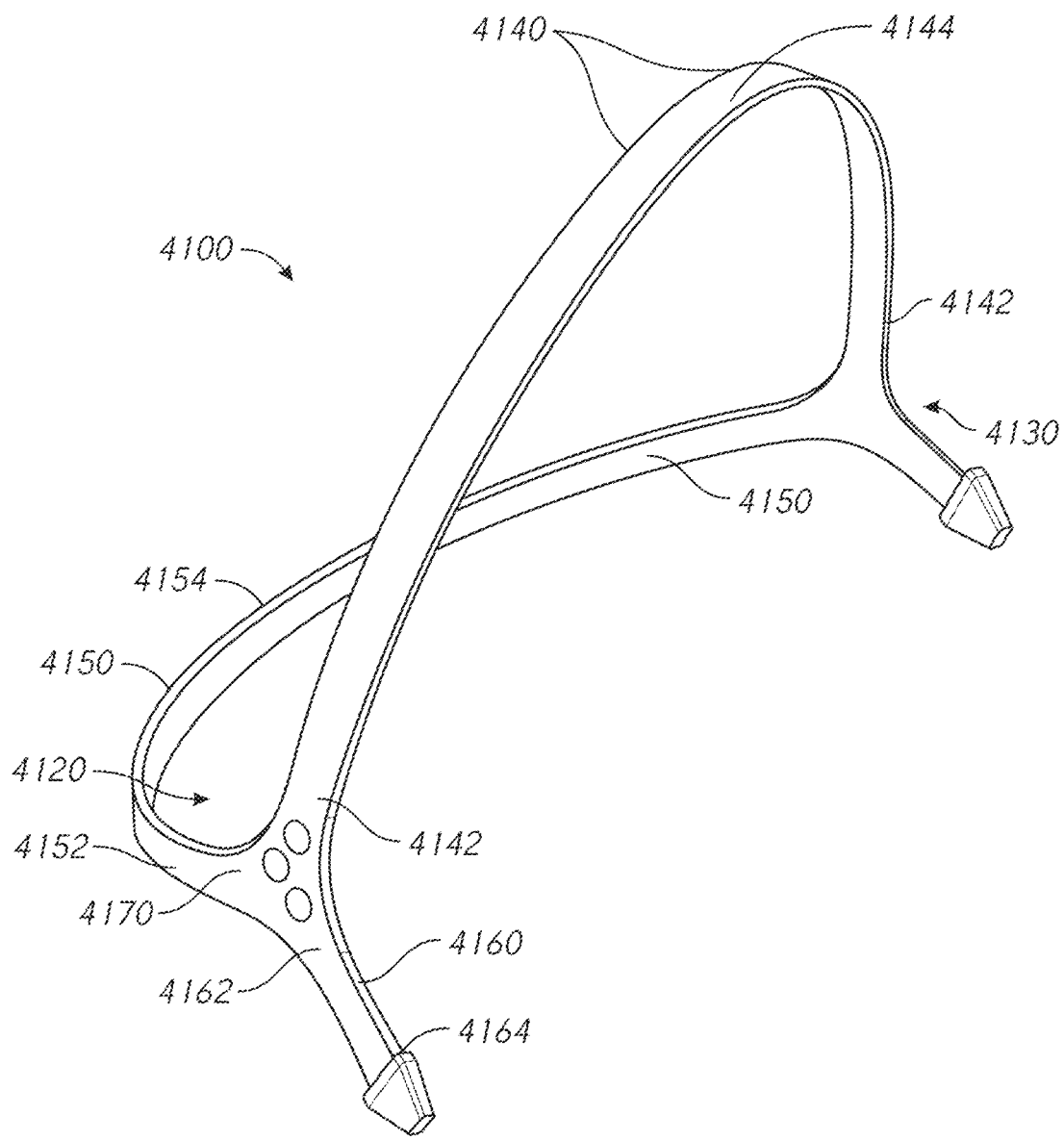
FIG. 1B is a perspective view of the headgear of the present disclosure.

Headgear:

FIG. 1A shows a non-limiting exemplary embodiment of headgear 4100 of the present disclosure in use in combination with a breathing apparatus 4110. FIGS. 1A and 1B show that the headgear 4100 is configured to be substantially inelastic and three dimensional (3D) in structure. As used herein, a three dimensional structure is one that doesn't lie in a single plane, but is shaped to extend in multiple planes. In other words, the three dimensional structure is not flat. The illustrated headgear 4100 comprises a right side 4120 and a left side 4130. Both the right and left sides 4120, 4130 comprise a top strap 4140, a rear strap 4150, a front strap 4160, a yoke 4170, and a connector 4180. The top straps 4140 comprise an elongate member having a top strap lateral end 4142 and a top strap central end 4144. The top strap 4140 is configured to extend upwardly from the lateral end 4142 at a location generally above each ear of the user and over the parietal or frontal region of a user's head before terminating at the top strap central end 4144. The top strap central end 4144 is configured to be positioned at or near a central point or location on the top of the user's head. The top strap central ends 4144 of the right and left sides 4120, 4130 are configured to be joined together. Each top strap lateral end 4142 is configured to directly or indirectly adjoin a yoke 4170.

The rear straps 4150 comprise an elongate member having a rear strap lateral end 4152 and a rear strap central end 4154. The rear strap 4150 is configured to extend rearward from the lateral end 4152 from a location generally above each ear of the user and around the occipital region of the user's head before terminating at the rear strap central end 4154. The rear strap central end 4154 is configured to be positioned at or near a central point or location on the rear of the user's head. The rear strap central ends 4154 of the right and left sides 4120, 4130 are configured to be joined together. Each rear strap lateral end 4152 is configured to directly or indirectly adjoin a yoke 4170.

The front straps 4160 comprise elongate members that are configured to directly or indirectly adjoin the yokes 4170 at a front strap lateral end 4162 and extend forward across the user's temples towards their nose. In some configurations, the front straps 4160 are shorter than one or both of the top straps 4140 or the rear straps 4150 and terminate at a front strap forward end 4164. The front strap forward ends 4164 are configured to comprise, or at least attach to, a connector 4180. The connector 4180 comprises a push fit, snap fit or other suitable connector that is configured to provide a detachable connection to a mask frame 4112 of the breathing apparatus 4110. In some embodiments, the connector 4180 may be configured to connect to an adjustment mechanism, wherein the adjustment mechanism provides a means of automatically or manually adjusting the size of the headgear 4100.

In some configurations, each of the yokes 4170 comprises a relatively triangular section that is configured to provide a lateral junction between the corresponding top straps 4140, rear straps 4150 and front straps 4160. Each of the top, rear and front straps 4140, 4150, 4160 is adjoined directly or indirectly to the yoke 4170 in a continuous manner such that the right and left sides 4120, 4130 are formed as unitary pieces. The thickness and/or shape of the yoke 4170 can be defined to restrict rotational movement about a lateral axis or axis extending in a thickness direction of the yoke 4170 of the top, rear and front straps 4140, 4150, 4160 relative to each other. Such an arrangement can provide the breathing apparatus with greater stability on the user's face.

The right and left sides 4120, 4130 are formed as substantially two dimensional (2D) pieces, i.e., they are formed in a flat structure. When the top straps 4140 and the rear straps 4150 of the right and left sides 4120, 4130 are joined together, a 3D bifurcated structure is formed (as shown in FIG. 1B). The top straps 4140 and the rear straps 4150 may be joined together by any appropriate method known in the art, including but not limited to sewing, welding, over-moulding or a mechanical connection, which can be permanent or removable/disconnectable. In some configurations, the composition of the headgear 4100 is such that the 3D-bifurcated structure is maintained at all times, at least when the right and left sides 4120, 4130 are connected. This 3D structure may improve the ease with which a user interacts with and fits or dons the headgear 4100 and the associated breathing apparatus 4110. Because the headgear 4100 holds its shape, the straps are less likely to get tangled and it should be easier for a user to grasp and orient the headgear 4100. In some configurations, the headgear 4100 at least maintains partial or complete separation of the sides 4120, 4130. In some configurations, the headgear 4100 at least maintains partial or complete separation of the yokes 4170 and/or front straps 4160 of the opposite sides 4120, 4130.

Figure 2:
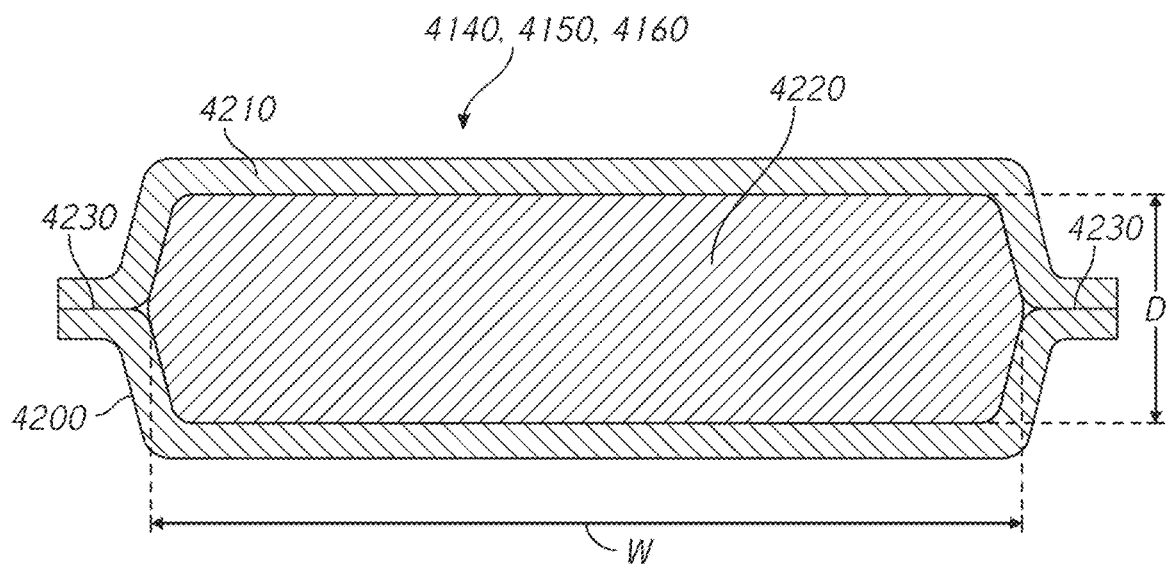
FIG. 2 is a cross-sectional view of a strap that forms part of the presently disclosed headgear.

A non-limiting exemplary embodiment of the composition of the headgear 4100 is shown in FIG. 2, which shows a cross-sectional view through any of the top strap 4140, the rear strap 4150 and/or the front strap 4160. In some configurations, the top, rear and front straps 4140, 4150, 4160 have a layered composition comprising a first portion or an inner casing 4200, a second portion or an outer casing 4210, a core 4220, and casing edges 4230. The inner casing 4200 and the outer casing 4210 comprise textile layers, wherein the inner casing is configured to contact the user's head and the outer casing 4210 is not and can be configured to face away from the user's head. The inner and outer casings 4200, 4210 may be made from the same or different textiles and can be configured to provide a soft and, in some embodiments, cushioned covering for the core 4220. However, in at least some preferred embodiments, the core 4220 forms the primary structure of the headgear 4100 and the casings 4200, 4210 are utilized to provide the headgear 4100 with a softer texture, improved moisture wicking properties and/or increased friction with the user's face relative to headgear constructed of the core 4220 without the casings 4200, 4210. Such an arrangement is in contrast to headgear arrangements constructed primarily of an elastic or flexible material that utilize localized rigidising structures.

In some configurations, the core 4220 comprises a relatively rectangular cross-section of a thermoform or thermoset plastic material that is configured to provide the headgear 4100 with the aforementioned 3D structure. The core 4220 provides the foundation for the overall structure of the headgear 4100. The plastic composition of the core 4220 offers the benefits of a resilient structure that is capable of maintaining a preformed shape while conforming somewhat to the individual cranial geometry of the user. The core 4220 has a width W and a depth D, wherein the width W is substantially greater than the depth D. The illustrated cross-sectional geometry in combination with the material selection allows the headgear 4100 to be flexible in a direction that is normal to the width W (the vertical direction in FIG. 2) and relatively inflexible in a direction that is normal to the depth D (the horizontal direction in FIG. 2). This flexibility in one direction allows the headgear 4100 to conform to a user's head while providing rigidity in a direction that stabilizes and minimizes dislodging of the breathing apparatus 4110 on a user's face.

In some configurations, the inner casing 4200 and the outer casing 4210 are configured to be permanently bonded to the core 4220 such that the core 4220 is completely encased and the headgear 4100 is formed from composite material. A casing edge 4230 can be formed where the inner and outer casings 4200, 4210 meet. The inner and outer casings 4200, 4210 are held together in close proximity by their bonds with the core 4220. In some configurations, the inner and outer casings 4200, 4210 are not directly connected to each other at the casing edge 4230. In the embodiment of FIG. 2, the casing edge 4230 is shown to be approximately at a midpoint of the depth D. In some embodiments, the casing edge 4230 may be skewed towards one or other of the inner and outer casings 4200, 4210. In other configurations, the casing edges 4230 can be coupled. In still other configurations, the casing edges 4230 can be separated from one another such that a portion of the core 4220 is left exposed.

The headgear 4100 can be configured to be substantially inelastic as a result of material selection, for example. One or more elements of the composite material may provide the headgear 4100 with substantially inelastic qualities. In the first non-limiting exemplary embodiment of this disclosure, the core 4220 is made from a substantially inelastic material, such as polypropylene or nylon, for example but without limitation. In embodiments where the headgear 4100 is expected be subjected to low loading forces, the core 4220 may be made of other materials, such as, but not limited to, thermoplastic elastomers (TPE) or silicone. In some embodiments, the core 4220 may have a degree of elasticity and one or both of the inner casing 4200 and/or the outer casing 4210 can be substantially inelastic. The inclusion of a substantially inelastic material in the headgear 4100 is advantageous because the material reduces or eliminates the likelihood of the headgear being stretched or pulled too far over the user's head. If the headgear 4100 is pulled too far over the user's head, the breathing apparatus may not be effectively positioned to provide therapy and uncomfortable forces may be applied to the user's head, which can result in reduced compliance with therapy.

The right and left sides 4120, 4130 can be formed by injection moulding the core 4220 onto a textile material, such as one or both of the inner casing 4200 and/or the outer casing 4230. With such a method, the molten plastic material can be applied onto or put into contact with the textile material and allowed to cool to form an integral structure without the use of adhesives. In some configurations, the right and left sides 4120, 4130 can be formed by injection moulding the core 4220 into a sleeve formed by the inner casing 4200 and the outer casing 4210. The casing edges 4230 can be held together under compression within an injection moulding tool. Such a structure forms a sealed sleeve that allows the plastic material of the core 4220 to be injected into, and to thereby fill, the inside of the sleeve without creating significant flash at the casing edges 4230. In some configurations, the casing edges 4230 may not create a sealed sleeve. In such arrangements, flash can be removed in a post-forming operation as is done with other molded components.

In some embodiments, there may be a textile casing on only one side of the headgear or the inner and outer casings 4200, 4210 may be made from differing materials. This may provide the headgear 4100 with varied physical properties in different regions.

Figure 3:
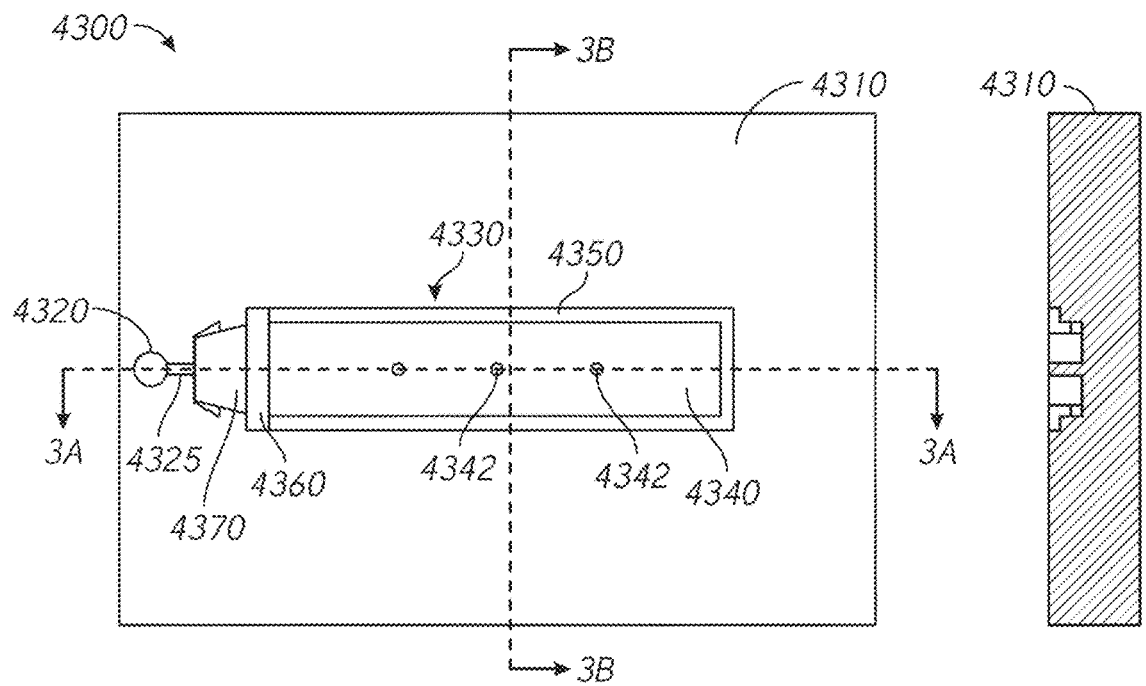
Figure 3A:
Figure 4:
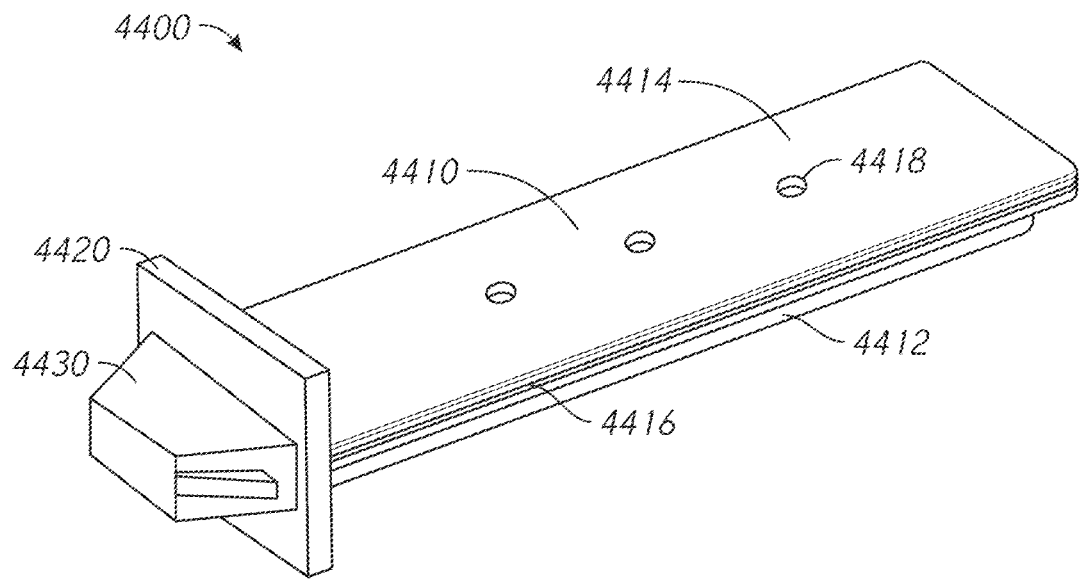
FIG. 4 is an isometric view of the strap component produced by the injection moulding tool of FIG. 3.

Mould Tool:

FIG. 3 shows a third angle orthographic view of one half of an injection moulding tool 4300 configured to form a strap 4400 (as shown in FIG. 4) that is similar to the front strap 4160 discussed above. A similar tool may be used to form any part of the headgear 4100. The strap 4400 comprises an elongate strap body 4410, a casing retainer 4420 and a connector 4430, wherein the casing retainer 4420 and the connector 4430 are located at one end of the strap body 4410. The strap body 4410 comprises an inner casing 4412, an outer casing 4414, a casing edge 4416 and a plurality of retention holes 4418. The inner and outer casings 4412, 4414 are made from a textile and, in the illustrated arrangement, are configured to substantially enclose and form a sleeve around an internal plastic core (not shown), thus forming the strap 4400 as a composite material structure.

The injection moulding tool 4300 is configured to have an opposing half that is substantially symmetrical about a parting surface 4310. Each half of the injection moulding tool 4300 comprises a sprue 4320, a gate 4325 and a mould cavity 4330. The sprue 4320 comprises a cylindrical recess, which forms the injection location for the tool 4300. The gate 4325 comprises a path through which the plastic material flows from the sprue 4320 into the mould cavity 4330. In some embodiments, the sprue 4320 and the gate 4325 may be provided on only one half of the injection moulding tool 4300. The mould cavity 4330 comprises a core cavity 4340, a casing clamp 4350, a casing slot 4360, and a connector cavity 4370 configured to form the composite material and geometry of the strap portion 4400.

The core cavity 4340 comprises a rectangular recess and, in some configurations, includes one or more retaining pins 4342. In the some embodiments, there are three retaining pins 4342, which comprise cylindrical posts that extend through a portion or the entire depth of the core cavity 4340. In some embodiments, there may be any suitable number of retaining pins 4342, which may have any appropriate cross-sectional geometry. The retaining pins 4342 are configured to form the retention holes 4418 in the strap 4400. The casing clamp 4350 comprises a relatively shallow recess that extends around three edges of the core cavity 4340 and is configured to form the casing edge 4416 of the strap 4400.

The casing clamp 4350 and the core cavity 4340 are terminated at one end by a casing slot 4360. The casing slot 4360 comprises a narrow rectangular slot that is deeper than the core cavity 4340. The casing slot 4360 is configured to have a width that is substantially the same as the combined width of the core cavity 4340 and the casing clamps 4350. The casing slot 4360 forms the casing retainer 4420. The connector cavity 4370 adjoins the casing slot 4360 on an opposite side from the core cavity and comprises a substantially trapezoidal recess. It is configured to be deeper than the core cavity 4340 and forms the connector 4430 of the strap 4400. In the illustrated arrangement, the gate 4325 connects to a central point on the short parallel wall of the connector cavity 4370.

Moulding Process:

A process of moulding the strap component 4400 using the injection moulding tool 4300 comprises the following steps: inserting textile layers that form the inner and outer casings 4410, 4420; closing the tool; injecting plastic; and opening the tool to release part. In some configurations, the steps are accomplished in this order; however, in other configurations the order may be changed and/or additional steps may be included. Such additional steps may be interposed within the above-identified steps.

Figure 5:
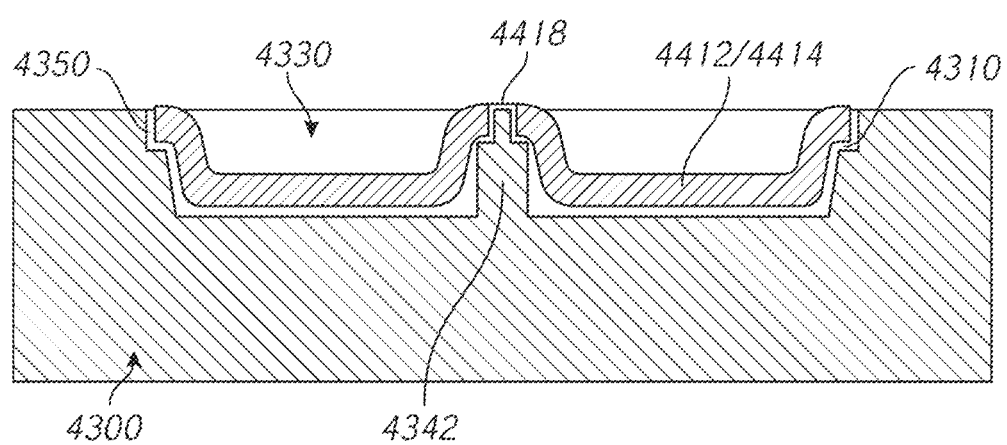
FIG. 5 is a cross-sectional view BB of the injection moulding tool of FIG. 3 with a textile casing placed inside.

With the two halves of the injection moulding tool 4300 separated (e.g., open), the pieces of textile that form the inner and outer casings 4412, 4414 are placed inside the mould cavity 4330, as shown in FIG. 5. The inner casing 4412 is placed inside one half of the injection moulding tool 4300 and the outer casing 4414 is placed inside the other half. The inner and outer casings 4412, 4414 can be cut to size such that they fit snuggly within the mould cavity 4330. Alternatively, uncut pieces of inner and outer casings 4412, 4414 may be placed in the mould cavity 4330 and then cut by the injection moulding tool 4300 before or after the inner and outer casings 4412, 4414 are joined together.

The inner or outer casing 4412, 4414 can be aligned and secured within the mould cavity 4330 by one or more components of the injection mould tool 4300, including any one or combination of the retaining pins 4342, the casing clamp 4350 and the casing slot 4360. The alignment and securement of the inner and outer casings 4412, 4414 reduces the likelihood of the casings 4412, 4414 moving during injection of the plastic material. Movement of the casings 4412, 4414 during injection of the plastic may result in the strap 4400 being incorrectly formed. The retaining pins 4342 can be configured to at least partially pass through the retainer holes 4418 such that the inner or outer casing 4412, 4414 is properly aligned and held in place against the walls within the mould cavity 4330.

The casing clamp 4350 can be configured to apply a compressive force to one, two or three (or more) edges of the inner and outer casing 4412, 4414 when the injection moulding tool 4300 is shut and when both halves of the injection moulding tool 4300 are together. The recesses can have a depth that is less than the thickness of the textile that forms the inner and/or the outer casings 4412, 4414 such that the casing sits proud of the parting surface 4310, as shown in FIG. 5. When the injection moulding tool 4300 is shut, the depth of the casing clamp 4340 results in the inner and outer casings 4412, 4414 being compressed together, temporarily sealing the edges, and forming the casing edge 4416 and a hollow sleeve-like structure.

Figure 6:
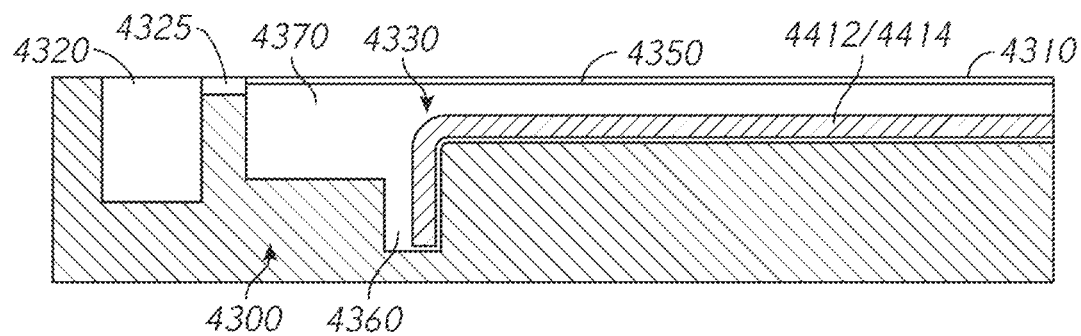
FIG. 6 is an enlarged view of the cross-section AA of the injection moulding tool of FIG. 3 with a textile casing placed inside.

The casing slot 4360 can be configured to secure the end of the inner or outer casing 4412, 4414, which is not secured by the casing clamp 4350. The end of the casing 4412, 4414 can be folded at an angle of approximately 90°, such that it ends proximate the deepest part of the casing slot 4360, as shown in FIG. 6. The deep narrow geometry of the casing slot 4360 retains the ends of the inner and outer casings 4412, 4414 in a separated position such that, when the both halves of the injection moulding tool 4300 are in a shut position, there is an opening between the inner and outer casings at the end of the core cavity 4340. This opening between the inner and outer casings 4412, 4414 provides a path through which plastic can be injected into the core cavity to form the core of the strap 4400. Injection through the opening results in the plastic core being formed on the inside of the inner and outer casings 4412, 4414.

Once the inner and outer casings 4412, 4414 are aligned and secured within each half of the injection moulding tool 4300, the tool 4300 is shut such that the mould cavity 4330 becomes fully enclosed and the casing edge 4416 is secured and sealed by compression. Thermoset or thermoform plastic is then injected into the mould cavity 4330 via the sprue 4320 and the gate 4325. Once the plastic has set, the injection moulding tool 4300 can be opened and the strap 4400 can be removed.

In some embodiments, the inner and outer casings 4412, 4414 can be held against the walls of the mould cavity 4330 by other appropriate means, including, but not limited to, temporary adhesives or in mould design (IMD) techniques.

Integrally Moulded Features:

Traditionally, labels, connections, and adjustment features, such as, but not limited to, buckles or buttons, can be formed as separate components that are attached to, or assembled to, a headgear in a secondary process. In some embodiments, the headgear of the present disclosure can include integrally moulded labels and/or connection or adjustment features that are configured to connect the headgear to a breathing apparatus or to adjust the size and/or fit of the headgear. The integral moulding of such features is beneficial in eliminating assembly steps within the manufacturing process and, thus, reducing costs. The integral moulding may also be beneficial in improving the strength of the connection of these features and the headgear.

Figure 7A:
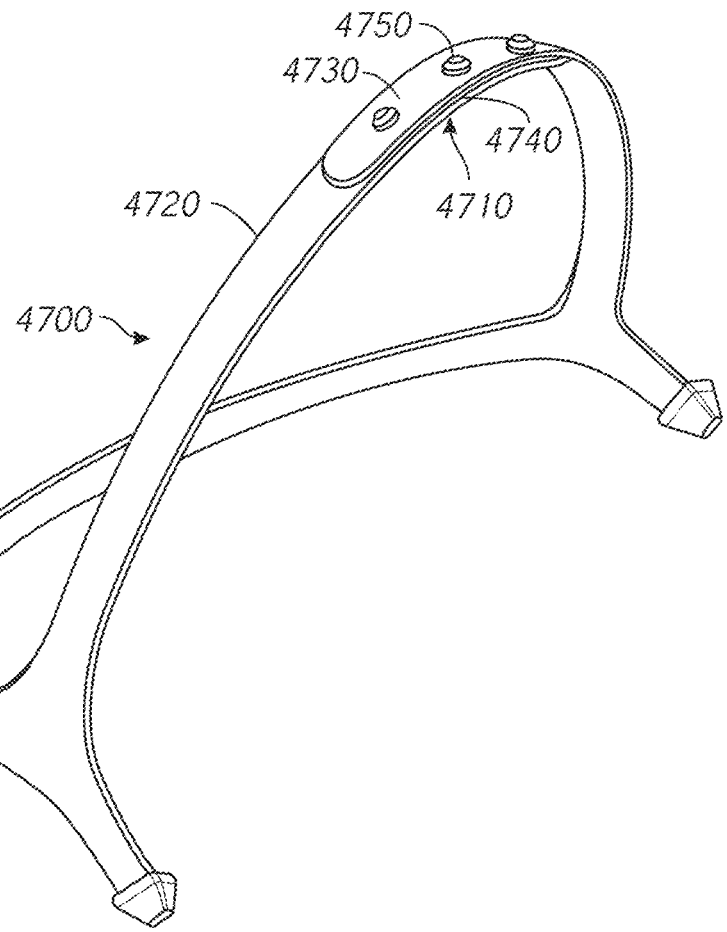
FIG. 7A is a perspective view of a second embodiment of the headgear of the present disclosure.

FIG. 7A shows another non-limiting exemplary embodiment of a headgear 700, wherein the headgear incorporates a button and hole size adjustment system 4710 within the top strap 4720. The size adjustment system 4710 can be similar to the 'snap fit' button and hole adjustment system, commonly used in baseball caps, but is moulded integrally as a part of the headgear 4700. The size adjustment system 4710 comprises an upper strap 4730 having a plurality of holes in it (not visible in FIG. 7A) and a lower strap 4740 having a plurality of buttons 4750 on its upper surface. With respect to features not specifically discussed, the headgear 4700 can be the same as or similar to other headgear disclosed herein, or can be of another suitable arrangement.

Figure 7B:
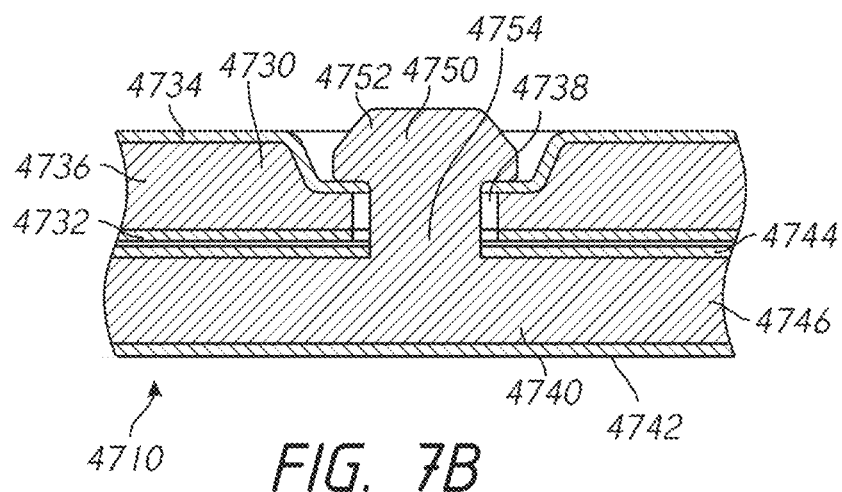
FIG. 7B is an enlarged cross-sectional view of a size adjustment system of the second embodiment of the headgear of the present disclosure.

As shown in the enlarged cross-sectional view of FIG. 7B, the upper strap 4730 comprises an upper inner casing 4732, an upper outer casing 4734, an upper core 4736 and one or more holes 4738. The buttons 4750 are configured to pass through the holes 4738 in the upper strap 4730 and to secure the upper and lower straps 4730, 4740 together. The lower strap comprises a lower inner casing 4742, a lower outer casing 4744, a lower core 4746 and one or more buttons 4750. The lower outer casing 4744 comprises one or more openings through which the lower core extends to form the one or more buttons 4750. The buttons 4750 comprise a mushroom shaped geometry that includes a head 4752 and stalk 4754. The buttons can have a substantially circular or elliptical profile as shown in FIG. 7A.

Figure 8A:
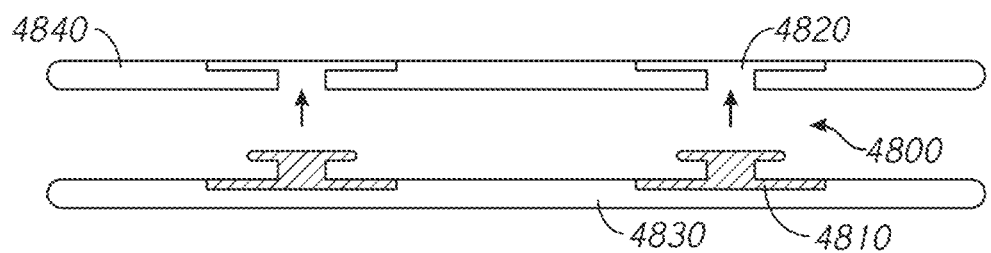
FIG. 8A is a cross-sectional view of a second embodiment of the size adjustment system of FIGS. 7A and 7B.
Figure 8B:
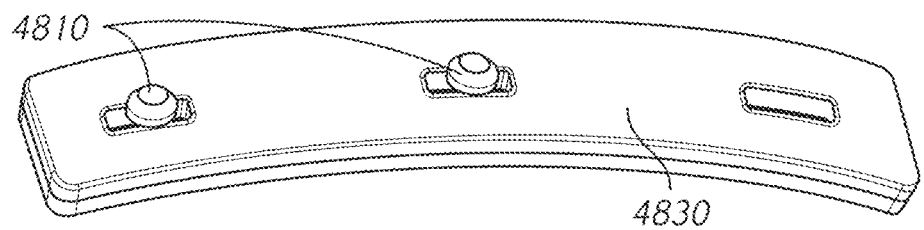
FIG. 8B is a plan view of the first strap of the size adjustment system of FIG. 8A.

FIGS. 8A and 8B show another non-limiting exemplary embodiment of a size adjustment system 4800 that is integrally moulded to a headgear structure. The size adjustment system 4800 comprises a 'snap fit' button 4810 and hole 4820 configuration. There are one or more buttons 4810 that are configured to be over-moulded directly onto a first strap 4830, such that the buttons are permanently bonded to the first strap. These buttons 4810 comprise a mushroom shaped geometry, which is configured to be received and retained within the one or more holes 4820. The holes 4820 comprise a plastic washer on one or both sides of the strap 4840 with a central opening that is configured to receive the buttons 4810. The holes 4820 are configured to be over-moulded through a second strap 4840, such that they are permanently bonded together.

In this embodiment, the first and second straps 4830, 4840 comprise an elongate member that is configured to be made from a single textile material, such as, but not limited to, Breath-o-Prene™. This configuration provides greater flexibility than the previous embodiment and, depending on material selection, can provide a cushioning element. However, in other configurations, the buttons 4810 and holes 4820 could be provided on a composite strap, such as the plastic/textile straps disclosed herein.

FIGS. 8C-8E shows another non-limiting exemplary embodiment of a size adjustment system 9800 that is integrally moulded to a headgear structure. The size adjustment system 9800 comprises a 'snap fit' button 9810 and hole 9820 configuration. In contrast to FIGS. 8A and 8B, the hole 9820 is not a through hole and does not extend through the entire thickness of the strap 9840. The button 9810 is configured to be molded into or over-moulded directly onto the first strap 9830, such that the buttons are permanently bonded to the first strap 9830. The button 9810 may comprise a single elongate button 9810 that extends along the length of the first strap 9830. In FIGS. 8C-8E, the button 9810 and the hole 9820 have a trapezoidal cross-sectional shape. However, the button 9810 and the hole 9820 may have any suitable shape to provide a releasable interference or snap-fit connection. In operation, the button 9810 is inserted into the hole 9820 to releasably connect the first strap 9830 and the second strap 9840.

FIGS. 8F-8I shows another non-limiting exemplary embodiment of a size adjustment system 9900 that is integrally moulded to a headgear structure. The size adjustment system 9900 comprises a 'snap fit' button 9910 and hole 9920 configuration. The button 9910 is configured to be molded into or over-moulded directly onto the first strap 9930, such that the buttons are permanently bonded to the first strap 9930. The button 9910 may comprise a single elongate button 9910 that extends along the length of the first strap 9930. Similar to the size adjustment system 9800 in FIGS. 8C-8E, the hole 9920 is not a through hole and does not extend through the entire thickness of the second trap 9940. However, in contrast to the size adjustment system 9800, the button 9910 has an interlocking hexagonal shape along the length of the first strap 9930. The hexagonal button 9910 prevents translational movement between the first strap 9930 and the second strap 9940.

Figure 9:
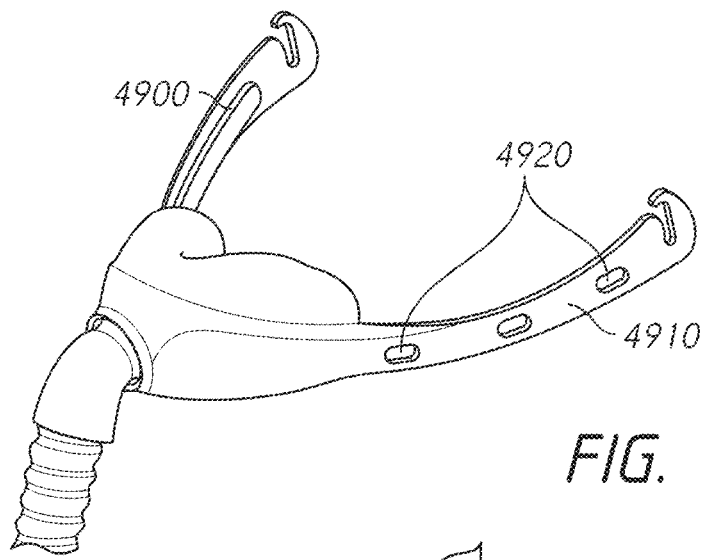
FIG. 9 is a perspective view of a breathing apparatus with cushion pads that are connected using the size adjustment systems of FIGS. 7A and 7B.
Figure 10A:
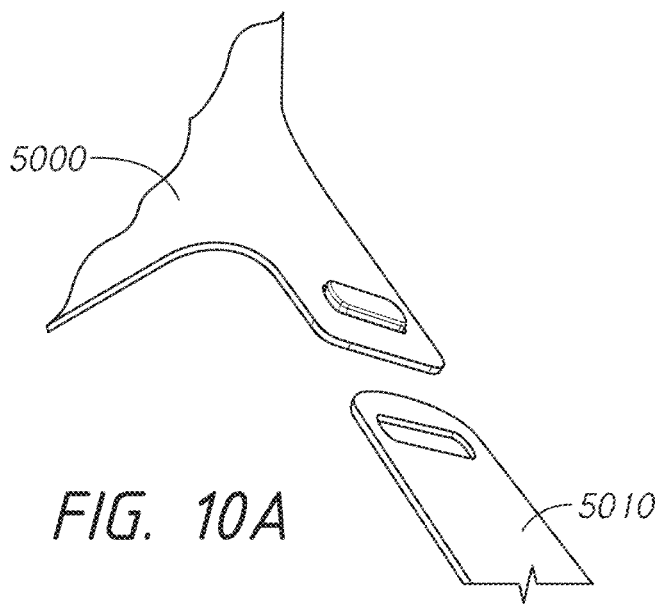
FIGS. 10A and 10B are plan views of a connection between breathing apparatus components.
Figure 10B:
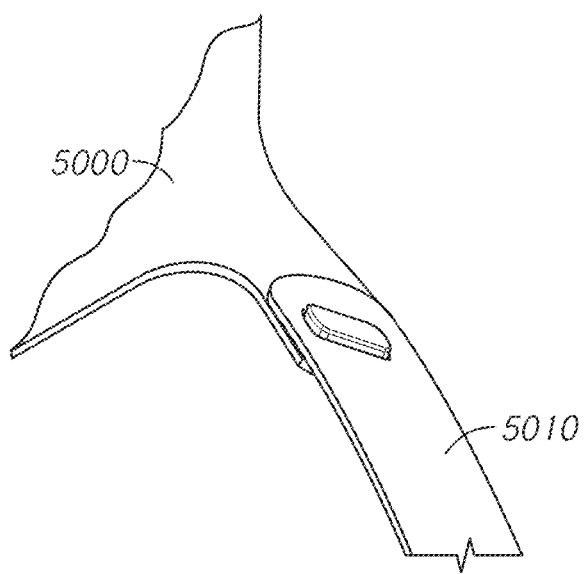

This approach of moulding various plastic features to a textile base can be applied to breathing apparatus components other than headgear. For example, FIG. 9 shows that textile cushioning pads 4900 may be attached to a substantially rigid mask frame 4910 via over-moulded buttons 4920, wherein the over-moulded buttons 4920 are the same as or similar to the buttons 4750, 4810 described in the previous embodiments. In yet another embodiment, a similar configuration can be used to provide a connection between two breathing apparatus components, such as, but not limited to, a flexible headgear 5000 and a substantially rigid mask frame 5010, as shown in FIGS. 10A and 10B.

Figure 11:
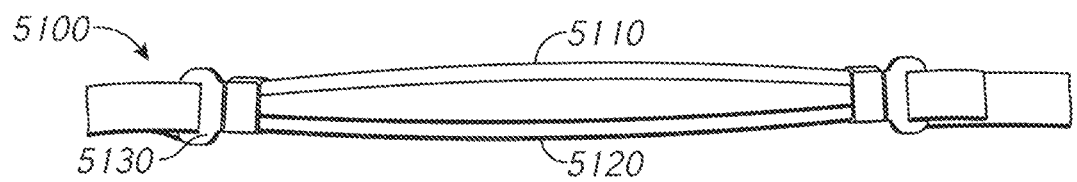
FIG. 11 is a plan view of a headgear component with a moulded grip.

FIG. 11 shows a headgear component 5100 comprising a textile strap 5110, a grip 5120 and two buckles 5130. The headgear component 5100 is configured to form a substantially non-slip rear portion of a headgear assembly. The textile strap 5110 comprises an elongate body that can be made of any suitable textile, including, but not limited to, micro-fiber fabrics. The grip 5120 comprises a raised silicone, TPE or thermoplastic polyurethane (TPU) bead that substantially follows an outline of the textile strap 5110. The grip 5120 is configured to provide a non-slip surface that, in use, grips the user's head or hair, such that the headgear is stable and less likely to slip down and displace the respiratory mask. In some embodiments, a grip bead, such as this may be applied to other regions of a headgear assembly.

Figure 12:
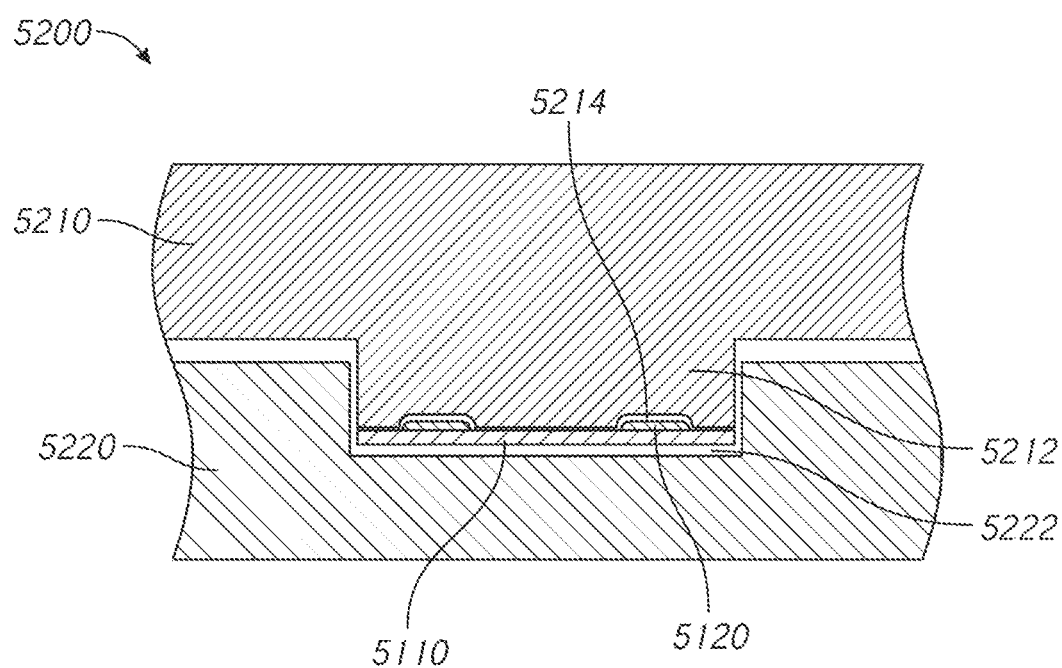
FIG. 12 is a cross-sectional view of a mould tool configured to form the headgear component of FIG. 11.

The grip 5120 may be applied to the textile strap by a moulding process similar to the one described in relation to the previous embodiments. FIG. 12 shows a cross-section schematic view of a mould tool 5200 configured to form the headgear component 5100. The mould tool 5200 comprises a first tool half 5210 and second tool half 5220. The first tool half 5210 comprises a strap insert 5212 and a grip cavity 5214. The second tool half comprises a strap cavity 5222. The strap cavity 5222 is configured to receive the textile strap 5110. In some configurations, the textile strap 5110 is cut to fit exactly within the strap cavity 5222, such that it is easily aligned within the open mould tool 5200. The strap cavity is also configured to receive the strap insert 5212, which has corresponding geometry. The strap insert 5212 is configured to apply a compression force to the textile strap 5110 during moulding, such that the textile strap is held in place and will not move when the material of the grip 5120 is injected. When the mould tool 5200 is in a closed position and the textile strap 5110 is secured in place, the material of the grip 5120 can be injected into the grip cavity 5214, via a gate and runner system (not shown), which in some configurations can be the same as or similar to that of FIG. 3. The grip cavity 5214 is configured to form the geometry of the grip 5120 onto the textile strap 5110. Injection moulding the grip 5120 directly onto the textile strap 5110 forms a chemical and/or mechanical bond between them.

Figure 13:
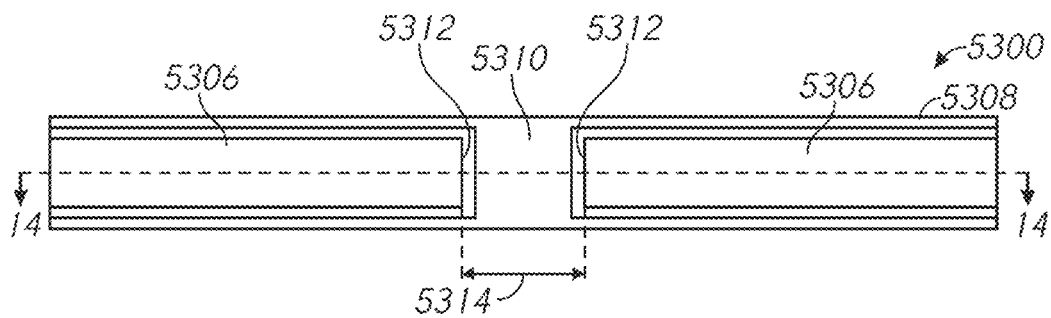
FIG. 13 is a side view of a headgear strap portion having a relatively inelastic core, a fabric casing on at least one surface of the core and a flexible joint between portions of the core.
Figure 14:
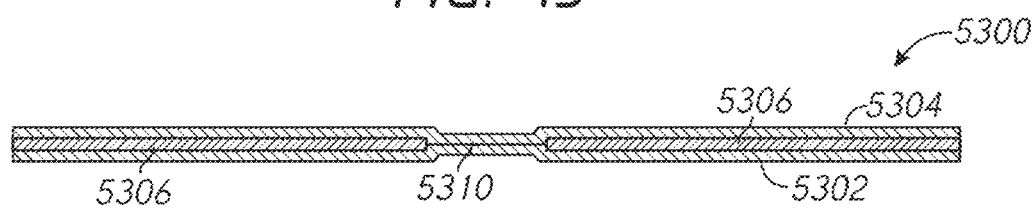
FIG. 14 is a sectional view of the headgear strap portion of FIG. 13 taken along line 14-14 of FIG. 13.

FIGS. 13 and 14 illustrate a strap 5300, which can be substantially similar to or the same as other straps disclosed herein, such as straps 4140, 4150, 4160, 4400, 4720, 4720, 4730, 4830, 4840. Similar to the arrangement illustrated in FIG. 2, the strap 5300 comprises an inner casing 5302, an outer casing 5304, a core 5306, and casing edges 5308. The inner casing 5302 and the outer casing 5304 comprise textile layers, wherein the inner casing 5302 is configured to face toward and/or contact the user's head and the outer casing 5304 is not. In the illustrated arrangement, the outer casing 5304 faces away from and/or doesn't contact the user's head.

However, in the illustrated arrangement, the strap 5300 comprises an interruption in the core 5306 along a length of the strap 5300. The interruption can form a flexible joint 5310 between two portions of the strap 5300. In some configurations, the flexible joint 5310 is formed in whole or in part by the inner casing 5302 and the outer casing 5304. Within the joint 5310, the casings 5302, 5304 can be secured to one another, such as with an adhesive, sewing, welding, or other suitable arrangements. In other configurations, the casings 5302, 5304 can be left separate within the joint 5310.

The core 5306 can be divided into two portions, each of which defines an end surface 5312 that face one another and are separated by a distance 5314. In some configurations, the distance 5314 is sufficient to allow the strap 5300 to fold to at least some extent at the location of the flexible joint 5310. In some configurations, the distance 5314 is sufficient to allow the strap 5300 to substantially fold in half at the joint 5310 such that the portions of the strap 5300 on each side of the joint 5310 are positioned one on top of the other. Such an arrangement can allow the strap 5300 to fold for storage or packaging. In some configurations, multiple straps 5300 of a headgear arrangement (e.g., top and rear straps) can include a flexible joint 5310 such that the entire headgear can collapse or fold in half for storage or packaging.

Preferably, however, the distance 5314 is not so great that the rigidity or the ability of the strap 5300 or associated headgear to accommodate external forces is compromised. In some configurations, the distance 5314 is no more than a small portion of an overall length of the strap 5300. In some configurations, the distance 5314 is equal to or less than 50 mm, 40 mm, 30 mm, 20 mm or 10 mm.

The joint 5310 can be located along the strap 5300 such that the flexible or foldable portion of the strap 5300 is located as desired within the overall form of the associated headgear. For example, the joint 5310 can be located within the strap 5300 such that the joint 5310 is located at or near a midline of the headgear in a lateral direction. Such an arrangement can allow the headgear to fold in half, as described above. In other configurations, the joint 5310 can be located elsewhere along the strap 5300 to provide flexibility in other locations.

Figure 15:
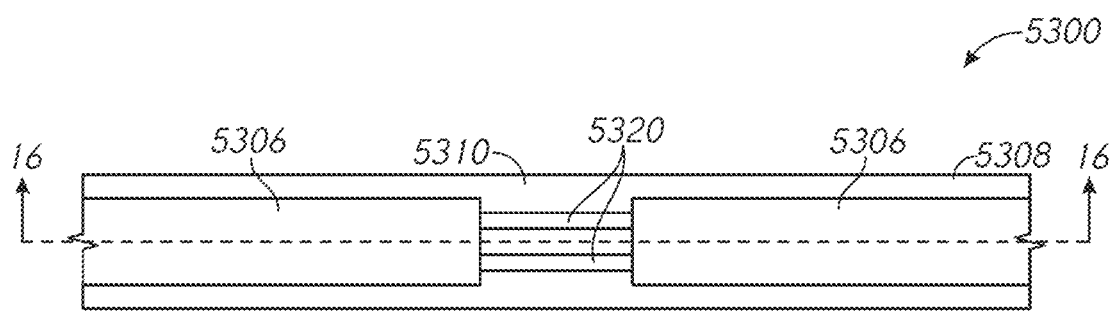
FIG. 15 is a side view of a headgear strap portion having a relatively inelastic core, a fabric casing on at least one surface of the core and a flexible joint between portions of the core, wherein the flexible joint comprises flexible bridge portions extending between the portion of the core.
Figure 16:
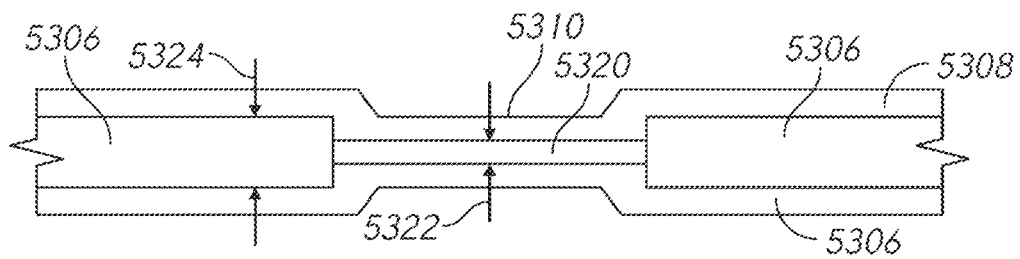
FIG. 16 is a cross sectional view of the headgear strap portion of FIG. 15 taken along line 16-16 of FIG. 15.

FIGS. 15 and 16 illustrate another strap 5300 having a flexible joint 5310. The strap 5300 can be substantially similar to or the same as the strap 5300 of FIGS. 13 and 14. However, the strap 5300 of FIGS. 15 and 16 includes connecting structures that connect the portions of the core 5306 on opposing sides of the joint 5310. In the illustrated arrangement, the connecting structure comprises a bridge portion 5320 extending between and connecting the portions of the core 5306 on opposing sides of the joint 5310. Any suitable number of bridge portions 5320 can be provided. In the illustrated arrangement, a pair of spaced-apart bridge portions 5320 is provided. The bridge portions 5320 are spaced inwardly from lateral edges of the core 5306 however, in other configurations, the lateral edges of the bridge portions 5320 can be aligned with the lateral edges of the core 5306.

The bridge portions 5320 preferably are configured to retain the flexible nature of the joint 5310 in at least one direction (e.g., bending in the thickness direction). Thus, the bridge portions 5320 can be constructed to provide a living hinge. However, the bridge portions 5320 can provide additional rigidity or support to the joint 5310, at least relative to the casing(s) 5302, 5304 alone, in other directions. For example, the bridge portion(s) 5320 can resist bending in the width direction, can resist lengthwise extension or compression and can resist twisting about a lengthwise axis.

In some configurations, the bridge portion(s) 5320 are constructed from the same material as the core 5306. The bridge portion(s) 5320 can be coupled to or unitarily-formed with the portions of the core 5306. In the illustrated arrangement, the bridge portions 5320 are unitarily-formed with the portions of the core 5306 and have a thickness 5322 that is less than a thickness 5324 of the portions of the core 5306. In some configurations, the thickness 5322 of the bridge portion(s) 5320 is less than one-half or less than one-third of the thickness 5324 of the core 5306. Other proportions are also possible and the thicknesses 5322, 5324 of the bridge portion(s) 5320 and core 5306 can be selected to provide traits desirable for the intended use.

In the illustrated arrangement, the bridge portions 5320 are elongate, linear structures extending substantially along or parallel to a longitudinal axis of the strap 5300. However, the bridge portion(s) 5320 could be angled relative to the longitudinal axis of the strap 5300. In some configurations, the bridge portion(s) 5320 are non-linear in shape.

FIGS. 17-20 illustrate additional assemblies, tools and related methods for constructing the straps and associated headgear disclosed herein. In particular, the arrangements of FIGS. 17-20 are configured to assist in locating and/or maintaining the fabric casings in position within the mould prior to formation of the core. In other respects, the moulding tools of FIGS. 17-20 can be similar to or the same as the moulding tool 5400 disclosed herein. In addition to the arrangements disclosed herein, other suitable arrangements or methods for securing the fabric casings within the mould can also be used.

Figure 17:
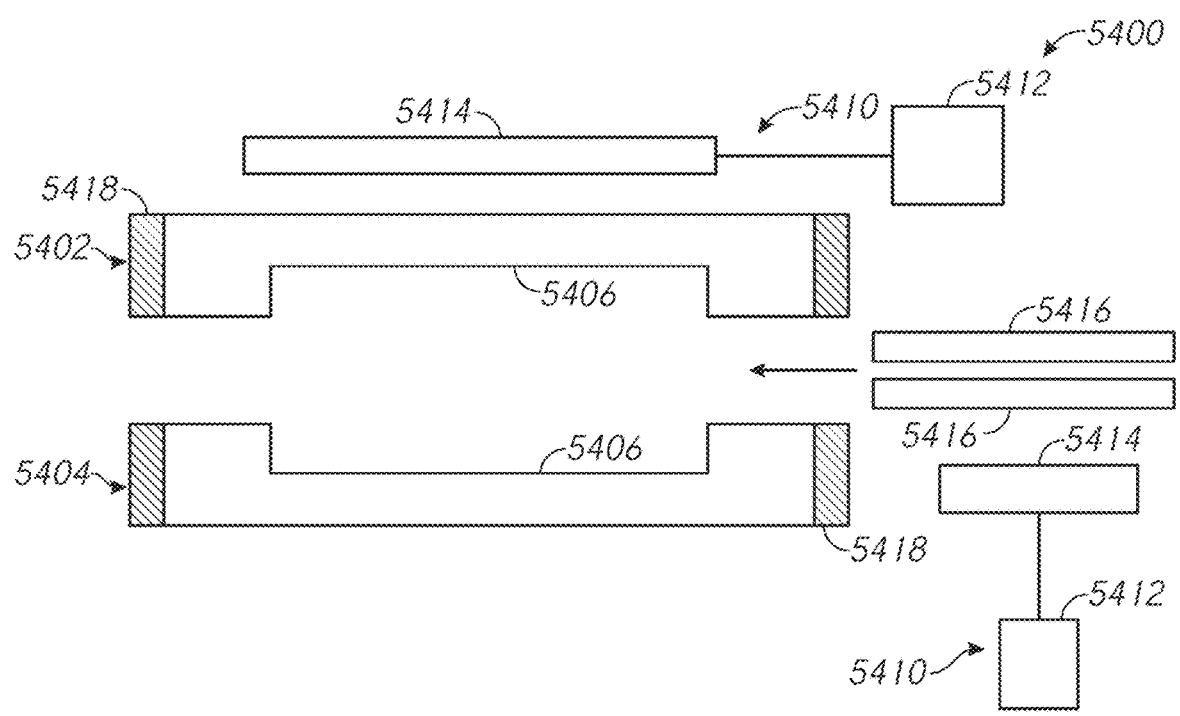
FIG. 17 illustrates a system for forming a headgear strap portion utilizing a static electrical charge to hold the fabric casing in place within a forming mould.

With reference to FIG. 17, a moulding tool 5400 is configured to form a strap and/or associated headgear, such as any of those disclosed herein. Preferably, one or more fabric casings are positioned within the moulding tool 5400 and then the core is formed adjacent to or between the fabric casings. The moulding tool 5400 is configured to secure the fabric casing(s) within the tool 5400 prior to formation of the core by utilizing an electrostatic force. Any suitable arrangement can be used to create an electrostatic charge within the fabric casing and/or the moulding tool 5400 suitable to attract the casing to the tool 5400. For example, the fabric casings and/or the moulding tool 5400 can be treated to create an electrostatic charge.

In some configurations, the moulding tool 5400 includes a first mould portion or half 5402 and a second mould portion or half 5404, each of which define a portion of a mould cavity 5406. The mould portions 5402, 5404 have mating surfaces that can be brought together and can be separated to close and open the mould cavity 5406. The illustrated moulding tool 5400 also comprises a static charging system 5410 comprising a charging generator 5412 and a charging applicator 5414. The charging generator 5412 is configured to create a static electrical charge, which can be applied to an object by the charging applicator 5414. The static charging system 5410 can be associated with the moulding tool 5400 or can be configured to apply a charge to the casings 5416 prior to the casings 5416 being positioned in the moulding tool 5400. If the static charging system 5410 is associated with the moulding tool 5400, the portions 5402, 5404 of the moulding tool 5400 can include an insulator 5418 to inhibit or prevent rapid dissipation of the charge applied thereto. Static charging systems suitable for industrial use can be employed, such as those manufactured by Simco-Ion of Hatfield, Pennsylvania, for example.

Figure 18:
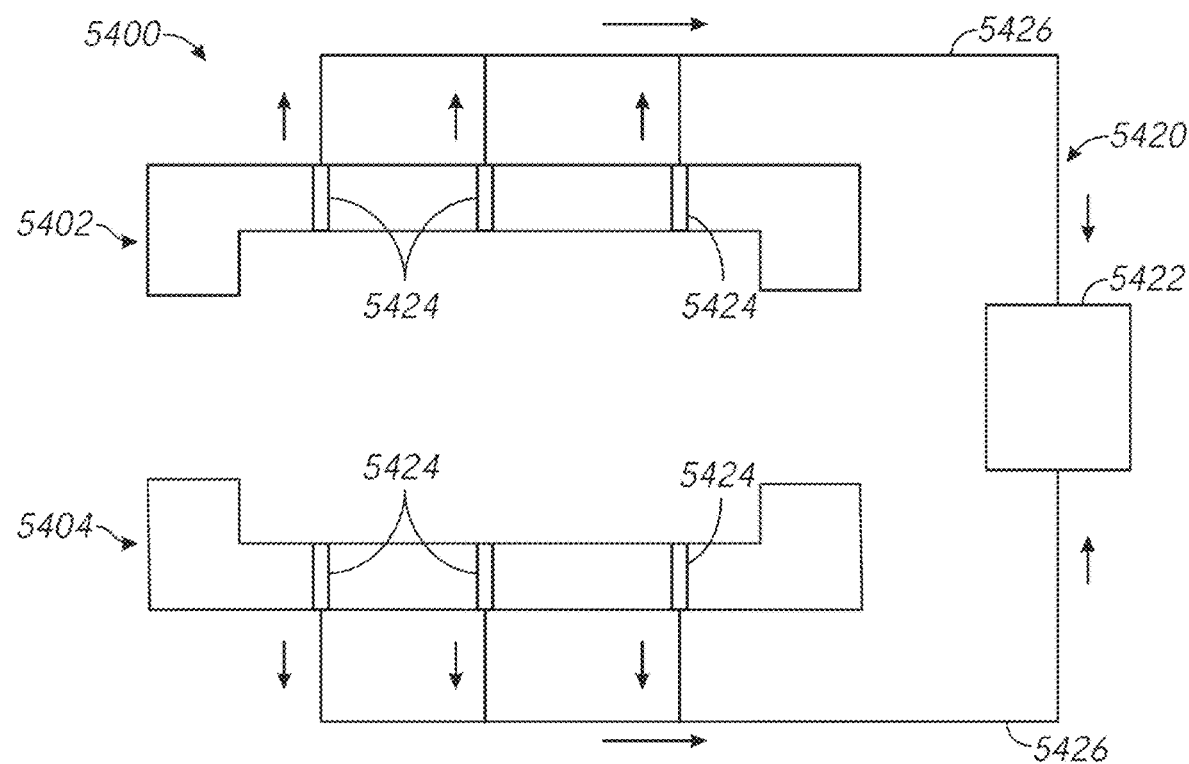
FIG. 18 illustrates a system for forming a headgear strap portion utilizing air pressure to hold the fabric casing in place within a forming mould.

With reference to FIG. 18, air pressure systems can be utilized to retain the casings within a moulding tool 5400. For example, an air pressure system can be configured to create a pressure differential between sides of the casing thereby creating a force tending to retain casing against a surface of the moulding tool 5400. The illustrated air pressure system 5420 is a vacuum system comprising a vacuum source 5422 connected to one or more vacuum ports 5424 in the moulding tool 5400 by suitable conduits 5426. However, in other configurations, positive pressure could be used to press the casings against a surface of the moulding tool 5400 at least until the mould portions 5402, 5404 close, at which point the casings can be pinched between the mould portions 5402, 5404.

In some configurations, the vacuum source 5422 comprises a pump that moves air from the vacuum ports 5424 toward the vacuum source 5422 through the conduits 5426. When positioned in the mould portions 5402, 5404, the casings block the vacuum ports 5424 to prevent or substantially impede the passage of air into the vacuum ports 5424. As a result, a vacuum or relative low pressure condition is created in the vacuum ports 5424 thereby holding the casings in place within the moulding tool 5400. Any suitable number of vacuum ports 5424 can be provided. For example, while multiple ports 5424 are illustrated in each mould portion 5402, 5404, in some configurations a single vacuum port 5424 can be provided in each mould portion 5402, 5404 into which a casing is to be placed prior to the moulding process.

Figure 19:
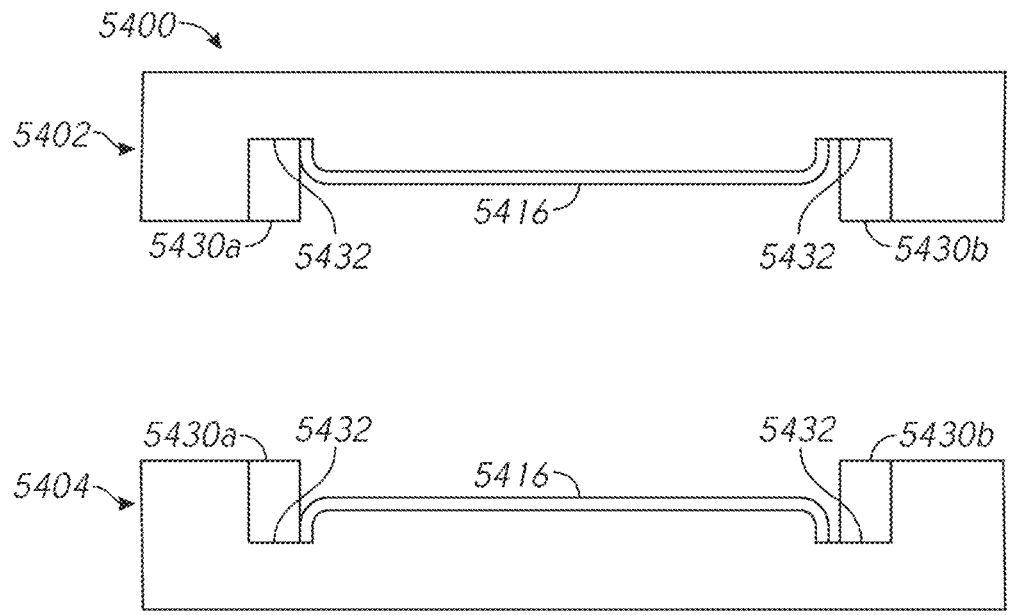
FIG. 19 illustrates a system for forming a headgear strap portion utilizing one or more components for holding the fabric casing in place within a forming mould.

With reference to FIG. 19, the casings 5416 can be secured within the moulding tool 5400 by a component 5430. For example, the component 5430 can mechanically secure the casing 5416 within the moulding tool 5400. One or more components (e.g., a pair of components 5430) can be utilized in each mould portion 5402, 5404 into which a casing 5416 is to be placed prior to the moulding process to retain the casing 5416 in place within the mould portion 5402, 5404. For example, in the illustrated arrangement, a first component 5430a can be utilized to secure the casing 5416 within the mould portion 5402, 5404 at a first location (e.g., a first end) and a second component 5430b can be utilized to secure the casing 5416 within the mould portion 5402, 5404 at a second location (e.g., a second end) spaced from the first location.

The component 5430 can be received within a receiving portion or retaining portion, such as a receptacle or cavity 5432, of the mould portion 5402, 5404. The cavity 5432 or other receiving portion can be configured to receive the component 5430 and a portion of the casing 5416 such that a portion of the casing 5416 is positioned or pinched between the component 5430 and a surface of the mould portion 5402, 5404. With such an arrangement, the component 5430 and the cavity 5432 can cooperate to form a structure similar to the casing slot 4360 shown in FIG. 6 and can secure the casing 5416 within the mould portion 5402, 5404 in a manner similar to that shown and described with reference to FIG. 6. In an alternative arrangement, the component(s) 5430 can be secured to the casing 5416 prior to the casing 5416 being positioned within the mould portion 5402, 5404. The combination of the component(s) 5430 and the casing 5416 can be secured within the mould portion 5402, 5404 by positioning the component(s) 5430 within the cavity 5432 or other receiving portion.

The component 5430 can have a relatively tight fit within the associated cavity 5432 or other receiving portion, along with the portion of the casing 5416, such that frictional forces retain the component(s) 5430 and, thus, the casing 5416 in place within the mould portion 5402, 5404. In some configurations, the component 5430 can have a slight interference fit with the associated cavity 5432 in one or more directions. Other suitable arrangements for securing the component 5430 at a desired location within the mould portion 5402, 5404 with enough retention force to retain the casing 5416 in place during the moulding process can be used.

The component 5430 can be any structure suitable for securing the casing 5416 within the mould portion 5402, 5404. The component 5430 can form a portion of the resulting strap or associated headgear. For example, the component 5430 can comprise a portion or an entirety of a connector and/or casing retainer, which can be the same as or similar to the connector 4430 and/or casing retainer 4420 shown and described in connection with FIG. 4. In such arrangements, the component(s) 5430 can be configured to fuse with the injected plastic that forms the core of the strap or headgear. Alternatively, the component 5430 can be a sacrificial component, which does not form a part of the final strap or headgear. In such arrangements, the component 5430 can comprise a material or can be coated or otherwise treated with a material that does not fuse with the injected plastic. Accordingly, once the strap or headgear is formed, the component(s) 5430 can be discarded. In some configurations, the component 5430 can comprise a material that breaks down when the plastic is introduced into the moulding tool 5400 such that the injected plastic fills a space that was occupied by the component 5430. In such an arrangement, vents may be provided to permit venting of the broken down material of the component 5430.

Figure 20:
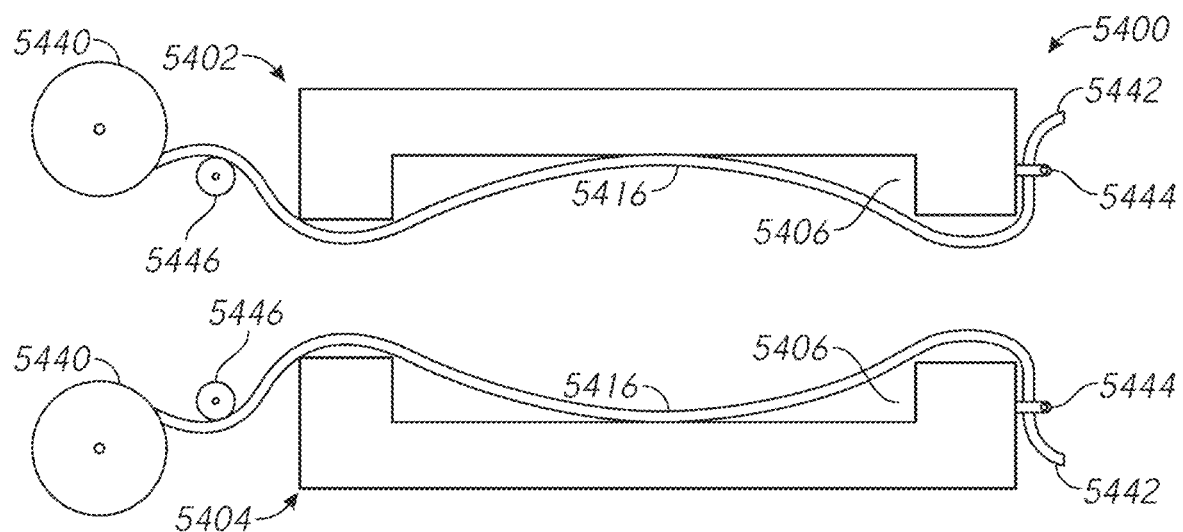
FIG. 20 illustrates a system for forming a headgear strap portion utilizing a roll of material for feeding the fabric casing into a forming mould.

With reference to FIG. 20, in some configurations the casings 5416 can be supported external of the cavities 5406 of the moulding tool 5400. In the illustrated arrangement, a bulk of material that forms the casings 5416 is supported for feeding into the mould portions 5402, 5404. The bulk of material can be, for example, a spool or roll 5440 of material that forms the casings 5416, which can be supported at one end of the moulding tool 5400. A loose or free end 5442 of the material or casing 5416 can be manually, automatically or otherwise passed through the space between the mould portions 5402, 5404 to the opposite end of the moulding tool 5400. Accordingly, a length of the material or casing 5416 is located adjacent to the moulding cavity 5406 of one or both of the moulding portions 5402, 5404. Once passed through the moulding tool 5400, the casings 5416 can be manually, automatically or otherwise positioned into the cavities 5406 of the mould portions 5402, 5404. For example, the operator can manually push the casings 5416 into the corners of the cavities 5406 or otherwise properly position the casings 5416 within the mould portions 5402, 5404. Once properly positioned, the plastic material can be injected onto the casing(s) 5416 within the moulding tool 5400. After the moulding process, excess material of the casing(s) 5416 can be trimmed.

In some configurations, the free ends 5442 of the casings 5416 can be secured relative to the mould portions 5402, 5404. For example, the free ends 5442 of the casings 5416 can be clipped or otherwise retained against or relative to the mould portions 5402, 5404 by clips or other suitable retention arrangements 5444 at locations outside of the cavities 5406 and away from the mating surfaces of the mould portions 5402, 5404. In other configurations, the free ends 5442 of the casings 5416 can be retained within the moulding tool 5400, such as within retention slots or utilizing retention holes in the casings 5416, for example. In some configurations, the rolls 5440 can provide some resistance to rotation to assist in keeping the casings 5416 relatively taut. If desired, tensioning rollers 5446 can be employed to assist in maintaining tension in the casings 5416.

FIGS. 21-40B illustrate several headgear configurations, which can be similar to other headgear disclosed herein and can by suitable for the same or similar applications. The headgear of FIGS. 21-40B can be connected to an interface by any suitable coupling arrangement, such as any of those disclosed herein. The headgear can be modified for used with other types of interfaces, such as those employing a forehead rest, for example. Accordingly, although the illustrated headgear has a single connection location on each side, other variations could include a pair of connection locations on each side. Other arrangements are also possible, such as a central, overhead strap, for example. In addition, features, components, materials or manufacturing methods of the headgear of FIGS. 21-40B can be interchanged with one another to create other headgear variations beyond those specifically disclosed. The illustrated headgears each comprise several straps, including a crown or top strap, a rear strap and a pair of front straps. Other variations can omit one or more of these straps and/or can include additional straps. Any of the straps can incorporate length or other adjustment mechanisms, as desired, including any of the adjustment mechanisms disclosed herein or other suitable arrangements.

Figure 21:
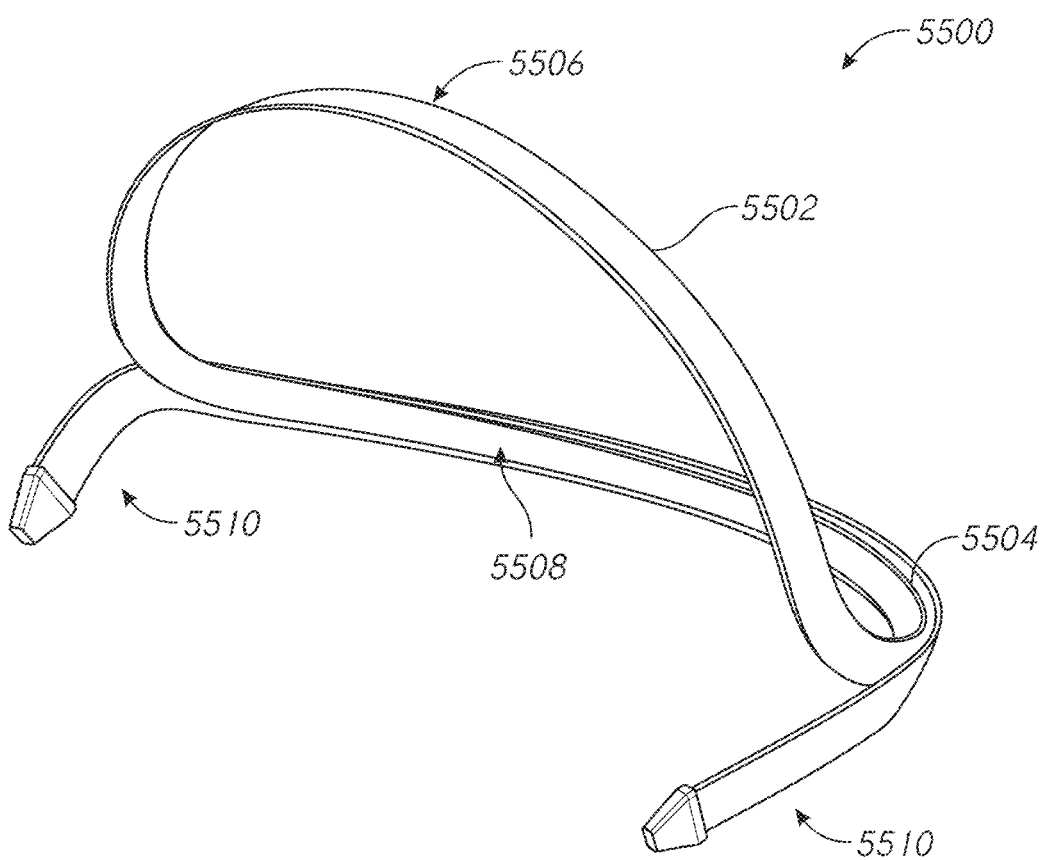
FIG. 21 illustrates a headgear having a first strap and a second strap.

FIGS. 21-23 illustrate a headgear 5500 have a first headgear portion or strap 5502 (a section of which is shown separately in FIG. 22B) and a second headgear portion or strap 5504 (a section of which is shown separately in FIG. 22A). The first strap 5502 can define a top strap or crown strap portion 5506 and the second strap 5504 can define a rear strap portion 5508. In the illustrated arrangement, the first strap 5502 and/or the second strap 5504 also define other portions of the headgear 5500. For example, the first strap 5502 also forms a portion of the rear strap portion 5508, such that the rear strap portion 5508 includes portions of both the first strap 5502 and the second strap 5504. In addition, the second strap 5504 defines front strap portions 5510 of the headgear 5500.

In some configurations, one or both of the first strap 5502 and the second strap 5504 have a composite structure. In the illustrated arrangement, each of the first strap 5502 and the second strap 5504 comprises a core 5512 and a cover layer 5514. The core 5512 can form a primarily structural element of the headgear 5500. In some configurations, the core 5512 can be constructed of a relatively rigid material, such as an injection-moulded or extruded plastic material. The cover layer 5514 can provide desirable characteristics for external surfaces of the headgear 5500. For example, the cover layer 5514 can be configured or selected to provide comfort for the user. In some configurations, the cover layer 5514 is a fabric or textile material. The cover layer 5514 surrounds a portion or an entirety of a periphery of the core 5512. An inelastic headgear can be desirable from a technical or performance standpoint because the headgear can retain an adjusted size (not stretch) in response to blow-off forces applied to the headgear by the mask. However, some elasticity may be desirable from a standpoint of user perception. In other words, a user may prefer a headgear that has some elasticity because the user perceives such a headgear as more comfortable. Thus, one or both of the core and cover layer in any of the headgear or portions thereof disclosed herein can be provided with some amount of elasticity or ability to stretch, such as in response to forces experienced during use and/or forces that could be manually applied by a user in evaluating the headgear or portions thereof. Furthermore, the cross-sectional dimensions (or other dimensions) of the headgear, straps or other headgear portions disclosed herein can be varied along a length of the headgear, strap or other portion. Such variations can be used to tune the performance of the headgear at particular locations or within particular sections. For example, regions around the user's ear may benefit from some additional structure, thus may be wider or thicker in order to provide the desired structure. In some configurations, it is preferable for the headgear to be wider at or around the user's ear, as increased thickness may lead to pressure points. Long strap lengths (e.g., along the top or rear of the user's head) typically need only be inelastic (or less elastic), but don't necessarily need to be rigid (e.g., could be flexible). Accordingly, these straps or strap portions may be thinner and/or narrower than other portions of the headgear. In other words, a width and/or thickness of a headgear, strap or strap portion can be tuned to customize stretch/elasticity and resistance to bending (i.e., rigidity). Additionally, the strap width may be increased towards the middle of the top or rear of the head. Such a configuration may be perceived as being more stable, yet allowing for narrow sections near, for example, the ears.

Figure 23A:
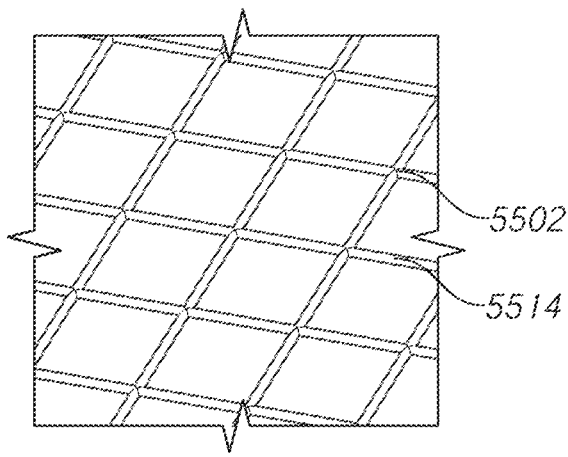
FIG. 23A is a view of an outer layer of the first strap and FIG. 23B is a view of an outer layer of the second strap.

In the illustrated arrangement, the core 5512 of the first strap 5502 is plastic and the cover layer 5514 is a stretch fabric, as illustrated in FIG. 23A, which provides the first strap 5502 with a visually and/or physically lighter structure. The material of the cover layer 5514 can be formed into a tubular structure by joining opposing edges of the material, such as by sewing or otherwise, to form a seam 5516. The seam 5516 can be positioned on any desired surface portion of the first strap 5502, such as along either side (width direction) or either end (thickness direction). In the illustrated arrangement, the seam 5516 is positioned on the user-facing or inner surface of the first strap 5502.

Figure 23B:
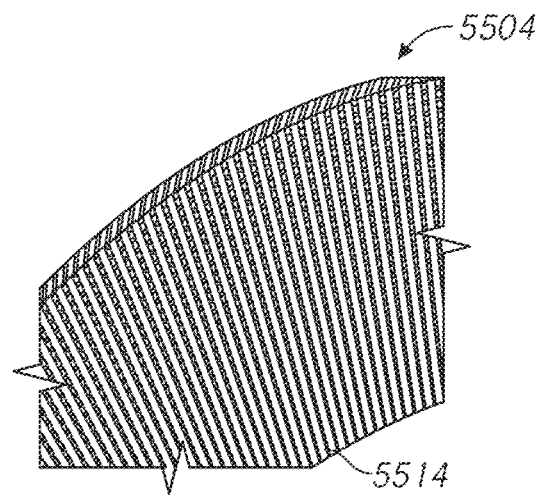

The core 5512 of the illustrated second strap 5504 is plastic and the cover layer 5514 is a knitted material formed into a tubular structure, as shown in FIG. 23B. Because the cover layer 5514 of the second strap 5504 is knitted, the cover layer 5514 does not have a seam. In other configurations, the cover layers 5514 can be reversed between the first strap 5502 and the second strap 5504, the cover layers 5514 could be the same material on each of the first strap 5502 and the second strap 5504, or different materials could be used.

The cover layers 5514 of each of the first strap 5502 and the second strap 5504 can be formed separately from the cores 5512 and can be assembled onto the cores 5512, such as by sliding the cover layer 5514 onto the core 5512. In some configurations, the cover layers 5514 can be loosely received on the cores 5512. In other words, the cover layers 5514 may not be affixed to the cores 5512 such that some relative movement is permitted between the cover layer 5514 and the respective core 5512. Such an arrangement may provide increased comfort. However, if desired, the cover layers 5514 could be affixed to the cores 5512, such as by an adhesive, for example.

In some configurations, the first strap 5502 and the second strap 5504 are joined to one another along a portion or an entirety of the rear strap portion 5508. In the illustrated arrangement, the first strap 5502 and the second strap 5504 are joined along a substantial entirety of the rear strap portion 5508. The first strap 5502 and the second strap 5504 separate at a junction between the top strap portion 5506, the rear strap portion 5508 and the front strap portions 5510. The first strap 5502 and the second strap 5504 can be secured to one another by any suitable arrangement, such as by a sewn joint or adhesive joint between the cover layers 5514 of the first strap 5502 and the second strap 5504. In the illustrated arrangement, the first strap 5502 is located inwardly of the second strap 5504 in the rear strap portion 5508 such that the first strap 5502 is closer to the user than the second strap 5504 in use. Thus, the first strap 5502 can define a portion or an entirety of a user-contacting surface of the rear strap portion 5508. In the illustrated arrangement, because the first strap 5502 also defines the top strap portion 5506, the first strap 5502 defines a user-contacting surface of both the top strap portion 5506 and the rear strap portion 5508 of the headgear 5500. However, this arrangement could also be reversed such that the second strap 5504 is positioned inwardly of the first strap 5502 in the rear strap portion 5508. In such an arrangement, the first strap 5502 can form a portion of a user-contacting surface of the headgear 5500 (e.g., the top strap portion 5506) and the second strap 5504 can form a portion of a user-contacting surface of the headgear 5500 (e.g., the rear strap portion 5508).

In some configurations, the first strap 5502 and the second strap 5504 can have a different color from one another. For example, in the illustrated arrangement, the first strap 5502 is a lighter color and the second strap 5504 is a darker color; however, this arrangement could also be reversed. The different colors between the first strap 5502 and the second strap 5504 can assist a user in orienting the headgear 5500. For example, the lighter (or darker) color of the first strap 5502 can indicate the user-contacting surfaces of the headgear 5500 to the user in those constructions in which the first strap 5502 is positioned inwardly of the second strap 5504 in the rear strap portion 5508. If the second strap 5504 is positioned inwardly of the first strap 5502 in the rear strap portion 5508, the lighter and darker colors can allow the user to differentiate between the top strap portion 5506 and the rear strap portion 5508, or vice versa. Similarly, different materials or textures can be useful, alone or in combination with different colors, to assist a user in distinguishing between different surfaces (e.g., inward-facing and outward-facing) or different portions (e.g., top strap portion 5506 and rear strap portions 5508) of the headgear 5500.

The first strap 5502 and the second strap 5504 can have different dimensions from one another. In the illustrated arrangement, the first strap 5502 has a width 5520 that is different than the width 5522 of the second strap 5504. In particular, the width 5520 of the first strap 5502 is less than the width 5522 of the second strap 5504. In some configurations, the width 5522 of the second strap 5504 is between 1.5-2 times the width 5520 of the first strap 5502. However, other relative proportions can also be used. The arrangement could also be reversed such that the first strap 5502 is wider than the second strap 5504.

The first strap 5502 can define a thickness 5524 and the second strap 5504 can define a thickness 5526. In some configurations, the thickness 5524 and the thickness 5526 can be the same or substantially the same. However, in other configurations, the thickness 5524 and the thickness 5526 can be different from one another. The dimensions of headgear straps discussed herein (including, but not limited to straps 5502, 5504) can include or omit the cover layers 5514. That is, in at least some configurations, the core 5512 is responsible for a majority or substantial entirety of the structural performance (e.g., load carrying capability) of the headgear 5500. Therefore, in order to compare performance properties between various configurations disclosed herein, the width and height dimensions can be taken at the core 5512. However, in other configurations, the focus may be on comfort or fit, to which the cover layers 5514 may make substantial contributions. Or, in some configurations, the cover layers 5514 can be relatively thick and can make up a significant portion of the overall width or thickness of the strap 5502, 5504. Under these or similar circumstances, the width and height dimensions can include the cover layer 5514.

In the illustrated configuration, the width 5520 of the first strap 5502 is between 4 mm-8 mm. For the sake of comparison with other straps and headgear portions disclosed herein, or other headgear configurations generally, such a strap width can be categorized as very narrow. In the illustrated configuration, the width 5522 of the second strap 5504 is between 8 mm-12 mm. Such a strap width can be categorized as narrow. In the illustrated configuration, the thickness 5524 of the first strap 5502 and the thickness 5526 of the second strap 5504 are between 1 mm-2 mm. Such strap thicknesses can be categorized as thin. The overall construction of the headgear 5500, including the thicknesses 5524 and 5526, provides flexibility of the headgear 5500 that can be characterized as very high for the purpose of comparison to other headgear configurations disclosed herein, or other headgear configurations generally.

Figure 22E:
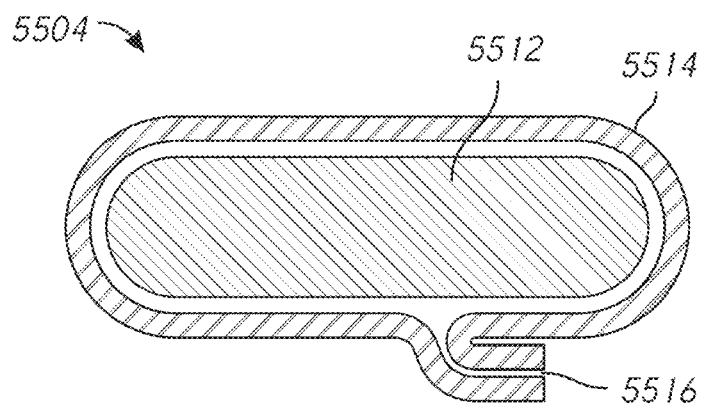
FIG. 22E is a sectional view of yet another alternative strap illustrating an alternative seam arrangement in which the seam of the cover layer is folded over onto the surface of the cover layer.

FIGS. 22C, 22D and 22E illustrate alternative arrangements for either one of the straps 5502, 5504. The arrangement of FIG. 22C illustrates a core 5512 having a relatively narrow channel or recess 5540 extending in a lengthwise direction and configured to receive the seam 5516 and/or edges of the cover layer 5514. As a result, the outer surface of the portion of the strap containing the seam 5516 can be relatively smooth or flat. In other words, the seam 5516 can be positioned within the recess 5540 and may not protrude outwardly or create a bump relative to adjacent or surrounding portions of the cover layer 5514 or strap. The recess 5540 can also function as an alignment feature for the cover layer 5514 relative to the core 5512. That is, the recess 5540 and seam 5516 can be aligned with one another to properly align the cover layer 5514 with the core 5512. In some configurations, such alignment can permit other features of the cover layer 5514 to also be properly aligned with the core 5512. The recess 5540 is illustrated on a width-defining surface (side) of the core 5512, but could be placed on thickness-defining surfaces (edge) or transitions therebetween in other configurations.

FIG. 22D illustrates a strap in which the core 5512 comprises one or more relatively large recesses 5542 or concave portions that accommodate the seam 5516 and limit or prevent the formation of a bump by the seam 5516. The illustrated core 5512 includes a recess 5542 defined on each side surface of the core 5512; however, the upper and/or lower edges could define concavities in addition or in the alternative. In the illustrated arrangement, the recesses 5542 occupy a relatively large portion of the side surfaces of the core 5512. In other words, the recesses 5542 extend along a substantial portion of a width of the core 5512. The recesses 5542 are illustrated as a gradual reduction in thickness of the core 5512 from the edges toward the center. However, in other configurations, the reduction in thickness can be more abrupt. The thicker upper and lower portions of the core 5512 provide for inelastic performance. The reduced thickness center can provide more flexibility for bending about an axis aligned with the width direction.

FIG. 22E illustrates a strap in which the seam 5516 is folded over or bent such that the seam 5516 contacts or is adjacent to the side surface (width direction) of the strap 5504. The headgear may be arranged such that the side of the strap 5504 having the seam 5516 is positioned away from the user. The seam 5516 may be positioned towards the middle of the strap 5504 and away from the rounded edges to position the seam 5516 away from areas of concentrated stress.

Figure 24:
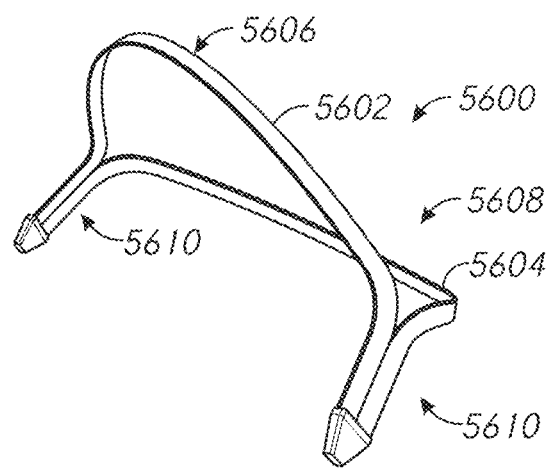
FIG. 24 illustrates a headgear having a first strap and a second strap.
Figure 25A:
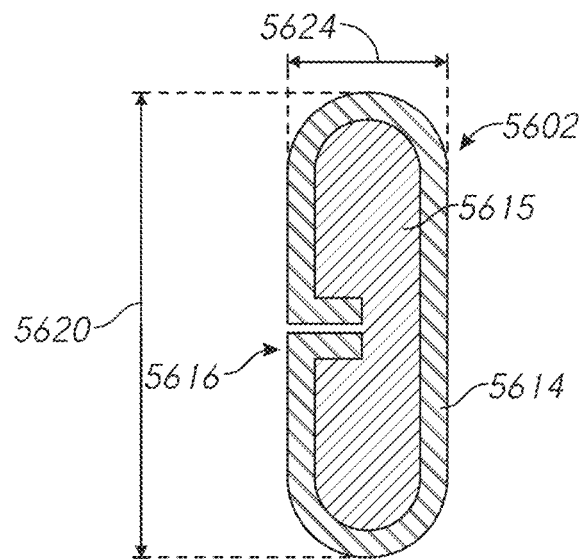
FIG. 25A is a sectional view of the first strap and FIG. 25B is a sectional view of the second strap.
Figure 25B:
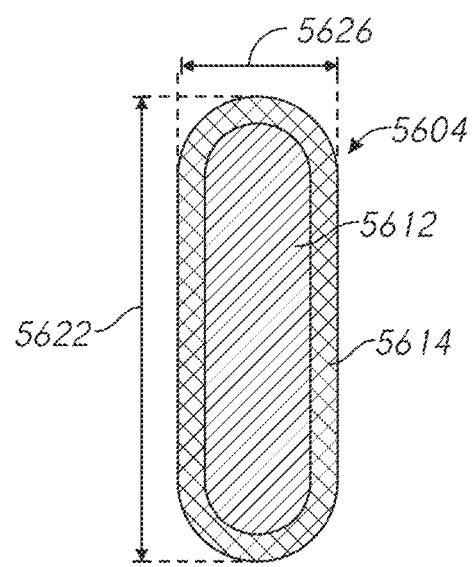

FIGS. 24-26 illustrate another configuration of a headgear 5600 having a first headgear portion or strap 5602 (a section of which is shown separately in FIG. 25A) and a second headgear portion or strap 5604 (a section of which is shown separately in FIG. 25B). The first strap 5602 can define a top strap or crown strap portion 5606 and the second strap 5604 can define a rear strap portion 5608. In the illustrated arrangement, the first strap 5602 and/or the second strap 5604 also define other portions of the headgear 5600. For example, the first strap 5602 and the second strap 5604 cooperate to define front strap portions 5610 of the headgear 5600. In the illustrated arrangement, the first strap 5602 is positioned above the second strap 5604 within the front strap portions 5610 such that a width of the front strap portions 5610 is equal to the combined widths of the first strap 5602 and the second strap 5604. The first strap 5602 and the second strap 5604 can be joined to one another within the front strap portions 5610 by any suitable arrangement, such as a by a sewn joint, adhesive joint or an over-moulded joint, for example.

The illustrated first strap 5602 and second strap 5604 comprise a composite structure having a core 5612 and a cover layer 5614. In some configurations, the core 5612 is constructed of a relatively rigid material, such as an injection-moulded plastic material. In some configurations, the cover layer 5614 is a fabric or textile material. The cover layer 5614 surrounds a portion or an entirety of a periphery of the core 5612.

Figure 26A:
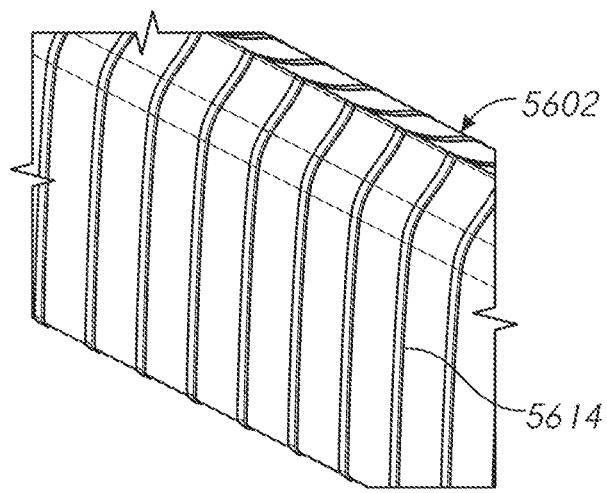
FIG. 26A is a view of an outer layer of the first strap and FIG. 26B is a view of an outer layer of the second strap.

In the illustrated arrangement, the core 5612 of the first strap 5602 is plastic and the cover layer 5614 is a ribbed textile material, as illustrated in FIG. 26A, which provides the first strap 5602 with tactile differentiation relative to the second strap 5604. The material of the cover layer 5614 can be formed into a tubular structure by joining opposing edges of the material, such as by sewing or otherwise, to form a seam 5616. The seam 5616 can be positioned on any desired surface portion of the first strap 5602, such as along either side (width direction) or either end (thickness direction). In the illustrated arrangement, the seam 5616 is positioned on the user-facing or inner surface of the first strap 5602.

Figure 26B:
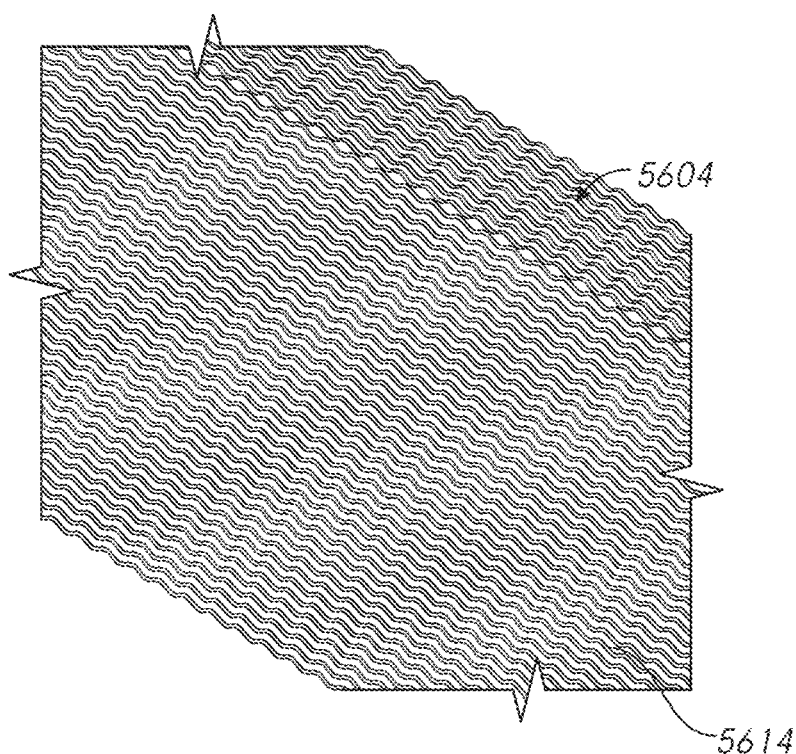
Figure 27:
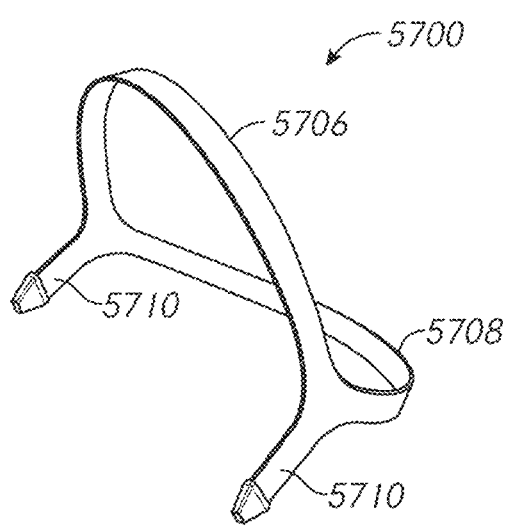
FIG. 27 illustrates a headgear having an inner core, a first outer layer and a second outer layer.
Figure 28:
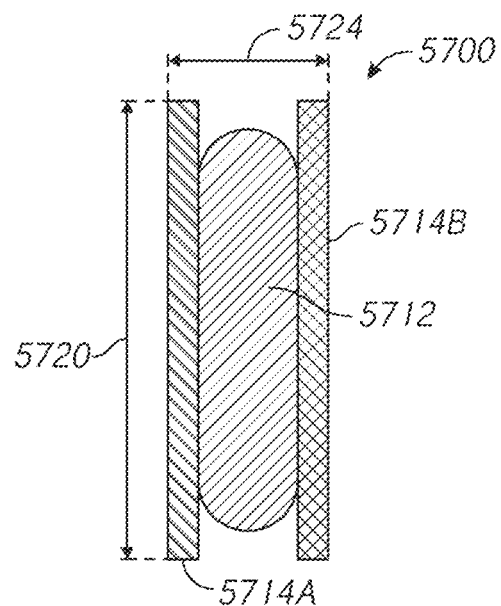
FIG. 28 is a sectional view of a portion of the headgear of FIG. 27.

The core 5612 of the illustrated second strap 5604 is plastic and the cover layer 5614 is a knitted material formed into a tubular structure, as shown in FIG. 26B. Because the cover layer 5614 of the second strap 5604 is knitted, the cover layer 5614 does not have a seam. In other configurations, the cover layers 5614 can be reversed between the first strap 5602 and the second strap 5604, the cover layers 5614 could be the same material on each of the first strap 5602 and the second strap 5604, or different materials could be used.

In the illustrated arrangement, the straps 5602, 5604 are formed by introducing molten plastic material into the cover layers 5614 and allowing the molten plastic material to cool to form the cores 5612 in accordance with any of the processes disclosed herein. As illustrated in FIG. 25A, the seam 5616 can be embedded in the core 5612. As a result, the seam 5616 is relatively flat or smooth relative to surrounding portions of the strap 5602. That is, the shape of the mold defines the overall shape of the strap 5602 and the seam 5616 does not protrude outwardly, unlike the seam 5516 of FIG. 22B. The seam 5616 may be visible. However, a patterned, textured, or soft/fluffy textile is used as the cover layer 5614, the seam 5616 may be obscured or may not be visible. Alternatively, the cover layers 5614 of each of the first strap 5602 and the second strap 5604 can be formed separately from the cores 5612 and can be assembled onto the cores 5612, such as by sliding the cover layer 5614 onto the core 5612. In some configurations, the cover layers 5614 may not be affixed to the cores 5612 such that some relative movement is permitted between the cover layer 5614 and the respective core 5612. However, if desired, the cover layers 5614 could be affixed to the cores 5612, such as by an adhesive, for example.

As described, the cover layers 5614 of the first strap 5602 and the second strap 5604 can have different textures to allow for differentiation of the straps 5602, 5604 from one another. In addition, the first strap 5602 and the second strap 5604 can have different colors to allow for differentiation between the straps 5602, 5604. If desired, inward-facing and outward-facing surfaces of the headgear 5600 can have different colors and/or textures to allow for differentiation between inward-facing and outward-facing surfaces.

In the illustrated arrangement, the first strap 5602 and the second strap 5604 have the same or substantially the same cross-sectional dimensions as one another. In the illustrated arrangement, the first strap 5602 has a width 5620 that is equal or substantially equal to the width 5622 of the second strap 5604. However, in other arrangements, the cross-sectional dimensions of the straps 5602, 5604 can be different from one another. The first strap 5602 can define a thickness 5624 and the second strap 5604 can define a thickness 5626. In some configurations, the thickness 5624 and the thickness 5626 can be the same or substantially the same. However, in other configurations, the thickness 5624 and the thickness 5626 can be different from one another.

In the illustrated configuration, the width 5620 of the first strap 5602 is between 4 mm-8 mm, or vary narrow. In the illustrated configuration, the width 5622 of the second strap 5604 is also between 4 mm-8 mm, or vary narrow. In the illustrated configuration, the thickness 5624 of the first strap 5602 and the thickness 5626 of the second strap 5604 are between 1 mm-2 mm. Such strap thicknesses can be categorized as thin. The overall construction of the headgear 5600, including the thicknesses 5624 and 5626, provides flexibility of the headgear 5600 that can be characterized as high for the purpose of comparison to other headgear configurations disclosed herein, or other headgear configurations generally.

FIGS. 27-29B illustrate another configuration of a headgear 5700 having a top strap or crown strap portion 5706, a rear strap portion 5708 and a pair of front strap portions 5710. The headgear 5700 can comprise a composite structure having a core 5712 and a cover, which comprises an inner cover layer 5714a and an outer cover layer 5714b. In some configurations, the core 5712 is constructed of a relatively rigid material, such as an injection-moulded plastic material. In some configurations, the cover layers 5714a, 5714b are constructed from a fabric or textile material. The cover layers 5714a, 5714b surround a portion or an entirety of a periphery of the core 5712. Edges of the cover layers 5714a, 5714b may or may not contact or be secured to one another. In the illustrated arrangement, the headgear 5700 is formed by introducing molten plastic material into the cover layers 5714a, 5714b and allowing the molten plastic material to cool to form the cores 5712 in accordance with any of the processes disclosed herein. Alternatively, the cover layers 5714a, 5714b can be formed separately from the cores 5712 and can be assembled onto the cores 5712 and secured, such as by adhesives, sewing, RF welding or another suitable process.

Figure 29A:
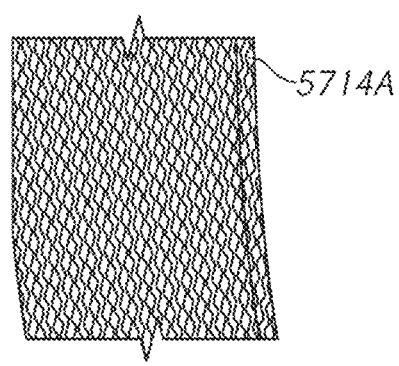
FIG. 29A is a view of the first outer layer and FIG. 29B is a view of the second outer layer of the headgear of FIG. 27.
Figure 29B:
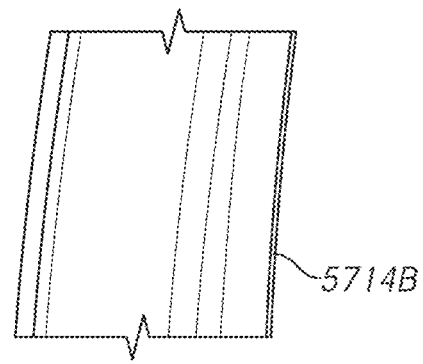

In the illustrated arrangement, the cover layer 5714a is a patterned polyester material, as illustrated in FIG. 29a, which provides the user-contacting or inward-facing (inner) surface with tactile and visual differentiation relative to the cover layer 5714b that defines the outward-facing (outer) surface, as illustrated in FIG. 29b. The patterned cover layer 5714a also indicates softness and comfort to the user, as well as hiding details resulting from the process used to create the headgear 5700, such as the edges of the core 5712. The illustrated cover layer 5714b is a polyurethane (imitation leather) material, which provides high slip to allow the headgear 5700 to slide along other objects (e.g., pillows) and a premium finish. As a result of such a construction, the cover layers 5714a, 5714b can have different textures to allow for differentiation of the inner and outer surfaces from one another. In addition, the layers 5714a, 5714b can have different colors to allow for differentiation between the inner and outer surfaces. In other configurations, the cover layers 5714a, 5714b can be reversed between the inner surface and the outer surface, the cover layers 5714a, 5714b could be the same material on each of the inner surface and the outer surface, or different materials from those shown could be used.

In the illustrated arrangement, the top strap portion 5706, the rear strap portion 5708 and the front strap portions 5710 have the same or substantially the same cross-sectional dimensions as one another. However, in other arrangements, the cross-sectional dimensions of the strap portions 5706, 5708, 5710 can be different from one another. In the illustrated arrangement, the strap portions 5706, 5708, 5710 each have a width 5720 that is the same or substantially the same. In addition, the strap portions 5706, 5708, 5710 can each define a thickness 5724 that is the same or substantially the same.

In the illustrated configuration, the width 5720 of each of the strap portions 5706, 5708, 5710 is between 12 mm-16 mm, or categorized as a medium width. In the illustrated configuration, the thickness 5724 of each of the strap portions 5706, 5708, 5710 is between 2 mm-3 mm. Such strap thicknesses can be categorized as medium. The overall construction of the headgear 5700, including the thicknesses 5724, provides flexibility of the headgear 5700 that can be characterized as medium for the purpose of comparison to other headgear configurations disclosed herein, or other headgear configurations generally.

Figure 30:
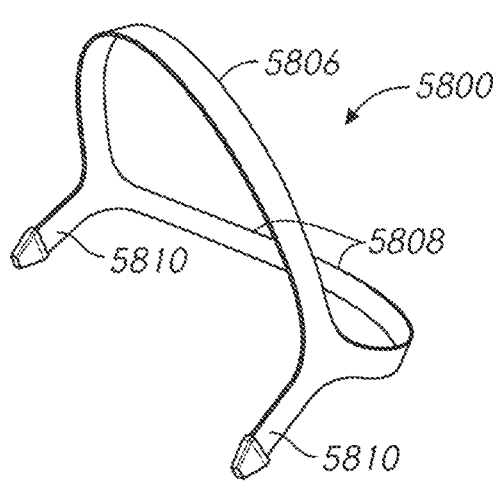
FIG. 30 illustrates a headgear having an inner core, a first outer layer and a second outer layer.
Figure 31:
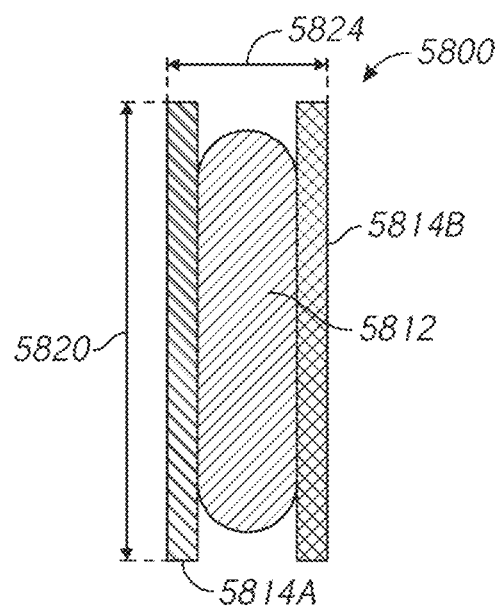
FIG. 31 is a sectional view of a portion of the headgear of FIG. 30.

FIGS. 30-32 illustrate another configuration of a headgear 5800 having a top strap or crown strap portion 5806, a rear strap portion 5808 and a pair of front strap portions 5810. The headgear 5800 can comprise a composite structure having a core 5812 and a cover, which comprises an inner cover layer 5814a and an outer cover layer 5814b. In some configurations, the core 5812 is constructed of a relatively rigid material, such as an injection-moulded plastic material. In some configurations, the cover layers 5814a, 5814b are constructed from a fabric or textile material. The cover layers 5814a, 5814b surround a portion or an entirety of a periphery of the core 5812. Edges of the cover layers 5814a, 5814b may or may not contact or be secured to one another. In the illustrated arrangement, the headgear 5800 is formed by introducing molten plastic material into the cover layers 5814a, 5814b and allowing the molten plastic material to cool to form the cores 5812 in accordance with any of the processes disclosed herein. Alternatively, the cover layers 5814a, 5814b can be formed separately from the cores 5812 and can be assembled onto the cores 5812 and secured, such as by adhesives, sewing, RF welding or another suitable process.

Figure 32A:
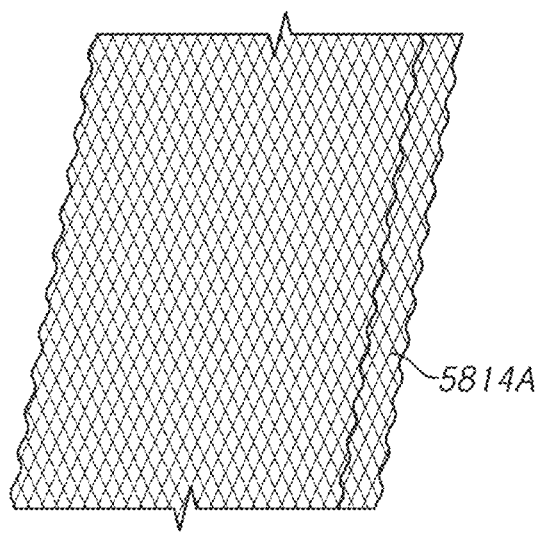
FIG. 32A is a view of the first outer layer and FIG. 32B is a view of the second outer layer of the headgear of FIG. 30.
Figure 32B:
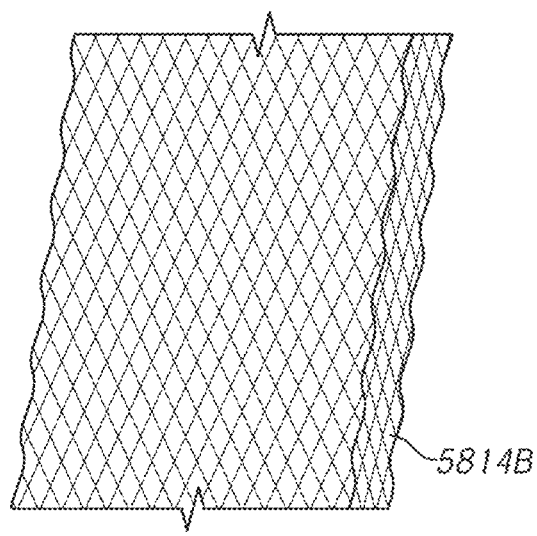

In the illustrated arrangement, the cover layer 5814a is a wool (e.g., Merino wool) material with a mesh knit, as illustrated in FIG. 32a, which provides the user-contacting or inward-facing (inner) surface with tactile and visual differentiation relative to the cover layer 5814b that defines the outward-facing (outer) surface, as illustrated in FIG. 32b. The patterned cover layer 5814a also conveys softness, comfort and performance to the user. The illustrated cover layer 5814b is a patterned polyester material, which conveys softness and comfort to the user, as well as hiding details resulting from the process used to create the headgear 5800, such as the edges of the core 5812. As a result of such a construction, the cover layers 5814a, 5814b can have different textures and/or colors to allow for differentiation of the inner and outer surfaces from one another. In other configurations, the cover layers 5814a, 5814b can be reversed between the inner surface and the outer surface, the cover layers 5814a, 5814b could be the same material on each of the inner surface and the outer surface, or different materials from those shown could be used.

In the illustrated arrangement, the top strap portion 5806, the rear strap portion 5808 and the front strap portions 5810 have the same or substantially the same cross-sectional dimensions as one another. However, in other arrangements, the cross-sectional dimensions of the strap portions 5806, 5808, 5810 can be different from one another. In the illustrated arrangement, the strap portions 5806, 5808, 5810 each have a width 5820 that is the same or substantially the same. In addition, the strap portions 5806, 5808, 5810 can each define a thickness 5824 that is the same or substantially the same.

In the illustrated configuration, the width 5820 of each of the strap portions 5806, 5808, 5810 is between 12 mm-16 mm, or categorized as a medium width. In the illustrated configuration, the thickness 5824 of each of the strap portions 5806, 5808, 5810 is between 2 mm-3 mm. Such strap thicknesses can be categorized as medium. The overall construction of the headgear 5800, including the thicknesses 5824, provides flexibility of the headgear 5800 that can be characterized as medium for the purpose of comparison to other headgear configurations disclosed herein, or other headgear configurations generally.

Figure 33:
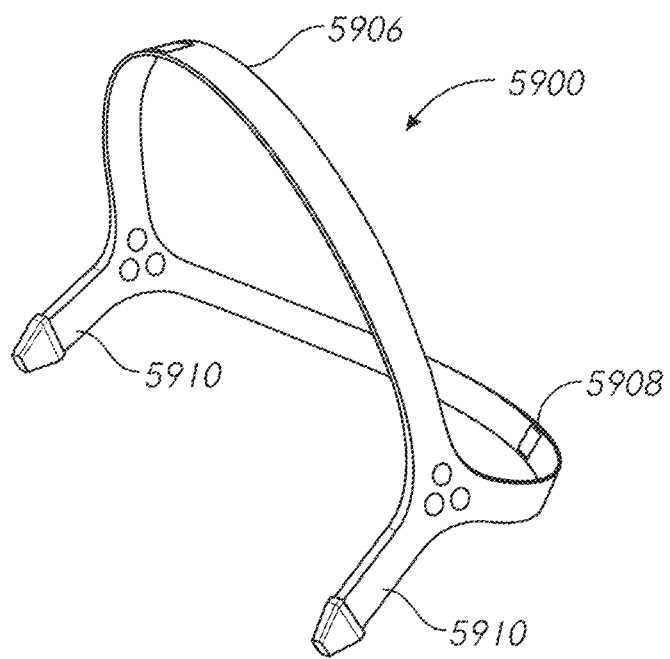
FIG. 33 illustrates a headgear having an inner core, a first outer layer and a second outer layer.
Figure 34:
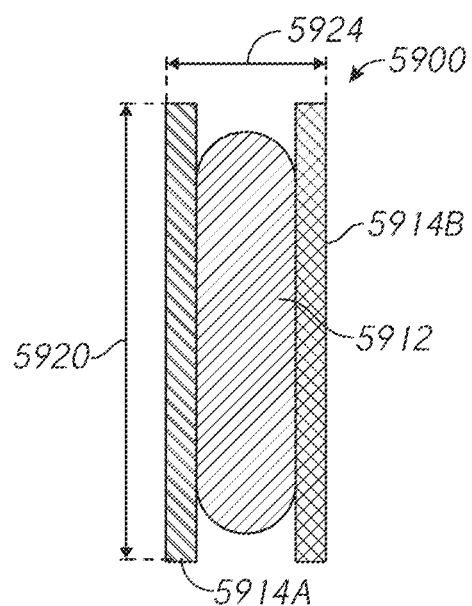
FIG. 34 is a sectional view of a portion of the headgear of FIG. 33.

FIGS. 33-35 illustrate another configuration of a headgear 5900 having a top strap or crown strap portion 5906, a rear strap portion 5908 and a pair of front strap portions 5910. The headgear 5900 can comprise a composite structure having a core 5912 and a cover, which comprises an inner cover layer 5914a and an outer cover layer 5914b. In some configurations, the core 5912 is constructed of a relatively rigid material, such as an injection-moulded plastic material. In some configurations, the cover layers 5914a, 5914b are constructed from a fabric or textile material. The cover layers 5914a, 5914b surround a portion or an entirety of a periphery of the core 5912. Edges of the cover layers 5914a, 5914b may or may not contact or be secured to one another. In the illustrated arrangement, the headgear 5900 is formed by introducing molten plastic material into the cover layers 5914a, 5914b and allowing the molten plastic material to cool to form the cores 5912 in accordance with any of the processes disclosed herein. Alternatively, the cover layers 5914a, 5914b can be formed separately from the cores 5912 and can be assembled onto the cores 5912 and secured, such as by adhesives, sewing, RF welding or another suitable process.

Figure 35A:
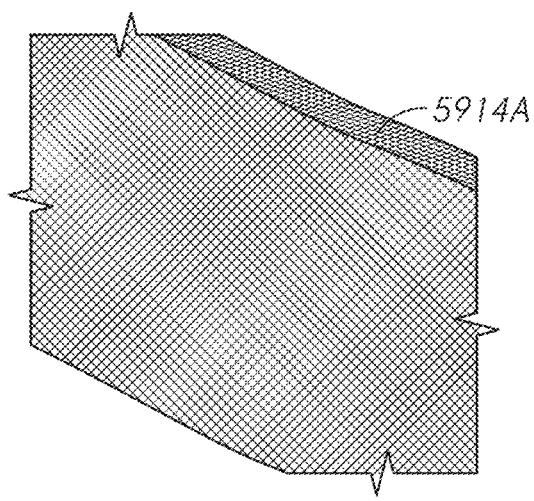
FIG. 35A is a view of the first outer layer and FIG. 35B is a view of the second outer layer of the headgear of FIG. 33.
Figure 35B:
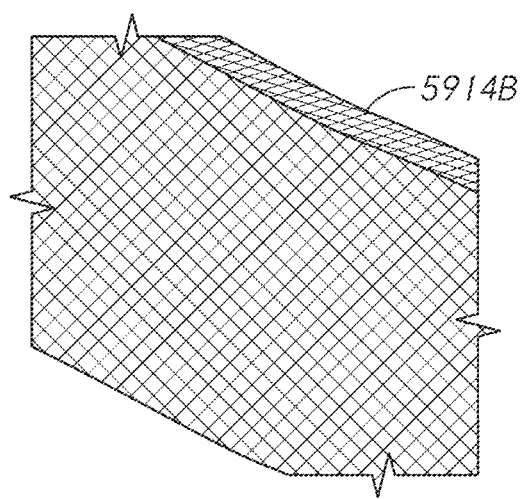

In the illustrated arrangement, each of the cover layers 5914a, 5914b is a UBL (unbroken loop) material, as illustrated in FIGS. 35a and 35b, respectively. In such an arrangement, if desired, different colors can be used to provide the user-contacting or inward-facing (inner) surface with tactile and visual differentiation relative to the cover layer 5914*b* that defines the outward-facing (outer) surface. The UBL material conveys softness and comfort to the user. In addition, the UBL material can be connected to a hook portion of a hook and loop fastener. In other configurations, different materials from those shown could be used.

In the illustrated arrangement, the top strap portion 5906, the ear strap portion 5908 and the front strap portions 5910 have the same or substantially the same cross-sectional dimensions as one another. However, in other arrangements, the cross-sectional dimensions of the strap portions 5906, 5908, 5910 can be different from one another. In the illustrated arrangement, the strap portions 5906, 5908, 5910 each have a width 5920 that is the same or substantially the same. In addition, the strap portions 5906, 5908, 5910 can each define a thickness 5924 that is the same or substantially the same.

In the illustrated configuration, the width 5920 of each of the strap portions 5906, 5908, 5910 is between 12 mm-16 mm, or categorized as a medium width. In the illustrated configuration, the thickness 5924 of each of the strap portions 5906, 5908, 5910 is between 2 mm-3 mm. Such strap thicknesses can be categorized as medium. The overall construction of the headgear 5900, including the thicknesses 5924, provides flexibility of the headgear 5900 that can be characterized as medium for the purpose of comparison to other headgear configurations disclosed herein, or other headgear configurations generally.

Figure 36:
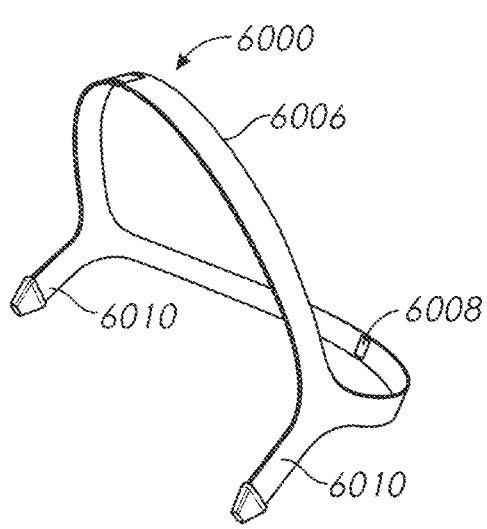
FIG. 36 illustrates a headgear having an inner core, a first outer layer and a second outer layer.
Figure 37:
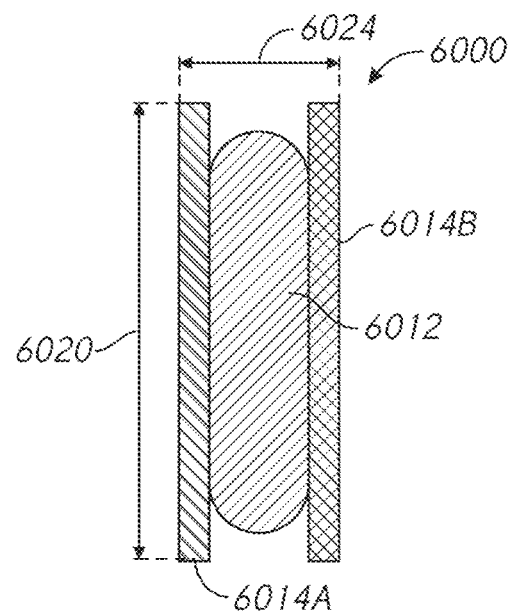
FIG. 37 is a sectional view of a portion of the headgear of FIG. 36.

FIGS. 36 and 37 illustrate another configuration of a headgear 6000 having a top strap or crown strap portion 6006, a rear strap portion 6008 and a pair of front strap portions 6010. The headgear 6000 can comprise a composite structure having a core 6012 and a cover, which comprises an inner cover layer 6014*a* and an outer cover layer 6014*b*. In some configurations, the core 6012 is constructed of a relatively rigid material, such as an injection-moulded plastic material. In some configurations, the cover layers 6014*a*, 6014*b* are constructed from a plastic sheet material. The cover layers 6014*a*, 6014*b* surround a portion or an entirety of a periphery of the core 6012. Edges of the cover layers 6014*a*, 6014*b* may or may not contact or be secured to one another. The headgear 6000 can be formed by any suitable process. In some configurations, the cover layers 6014*a*, 6014*b* are formed separately from the cores 6012 and can be assembled onto the cores 6012 and secured by RF welding. However, other securing processes or arrangements can also be used, such as adhesives, sewing, or other suitable methods.

In the illustrated arrangement, each of the cover layers 6014*a*, 6014*b* is a thin nylon sheet material. In such an arrangement, if desired, different colors can be used to provide the user-contacting or inward-facing (inner) surface with tactile and visual differentiation relative to the cover layer 6014*b* that defines the outward-facing (outer) surface. The nylon material provides high slip, is resistant to water and sweat and can be easily cleaned. In other configurations, different materials from those shown could be used.

In the illustrated arrangement, the top strap portion 6006, the rear strap portion 6008 and the front strap portions 6010 have the same or substantially the same cross-sectional dimensions as one another. However, in other arrangements, the cross-sectional dimensions of the strap portions 6006, 6008, 6010 can be different from one another. In the illustrated arrangement, the strap portions 6006, 6008, 6010 each have a width 6020 that is the same or substantially the same. In addition, the strap portions 6006, 6008, 6010 can each define a thickness 6024 that is the same or substantially the same.

In the illustrated configuration, the width 6020 of each of the strap portions 6006, 6008, 6010 is between 12 mm-16 mm, or categorized as a medium width. In the illustrated configuration, the thickness 6024 of each of the strap portions 6006, 6008, 6010 is between 2 mm-3 mm. Such strap thicknesses can be categorized as medium. The overall construction of the headgear 6000, including the thicknesses 6024, provides flexibility of the headgear 6000 that can be characterized as medium for the purpose of comparison to other headgear configurations disclosed herein, or other headgear configurations generally.

Figure 38:
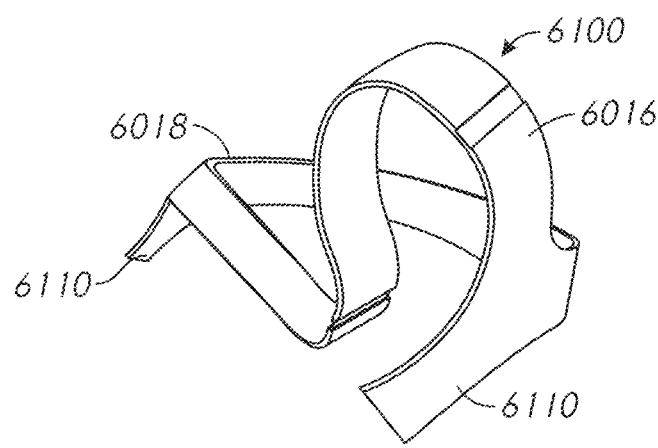
FIG. 38 illustrates a headgear having an inner core, a first outer layer and a second outer layer.
Figure 39:
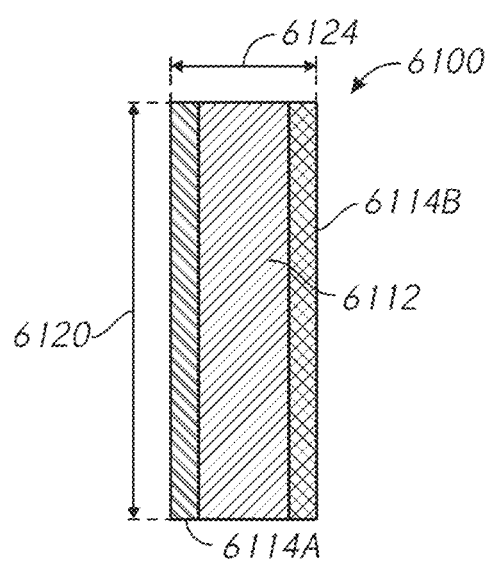
FIG. 39 is a sectional view of a portion of the headgear of FIG. 38.

FIGS. 38-40 illustrate another configuration of a headgear 6100 having a top strap or crown strap portion 6106, a rear strap portion 6108 and a pair of front strap portions 6110. The headgear 6100 can comprise a composite structure having a core 6112 and a cover, which comprises an inner cover layer 6114*a* and an outer cover layer 6114*b*. In some configurations, the core 6112 is constructed of a relatively soft and flexible material, such as a foam or neoprene material. In the illustrated configuration, the cover layer 6114*a* is constructed from a soft fabric material, such as nylon. In the illustrated configuration, the cover layer 6114*b* is constructed from a soft fabric material, such as a UBL (unbroken loop) material so that the cover layer 6114*b* can cooperate with a hook portion of a hook and loop fastener. The cover layers 6114*a*, 6114*b* surround a portion or an entirety of a periphery of the core 6112. Edges of the cover layers 6114*a*, 6114*b* may or may not contact or be secured to one another. The headgear 6100 can be formed by any suitable process. In some configurations, a composite work piece (e.g., a sheet) of the core 6112, and the cover layers 6114*a*, 6114*b* are formed by any suitable arrangement or process, such as RF welding. However, other securing processes or arrangements can also be used, such as adhesives, or other suitable methods. The headgear 6100 can then be cut (e.g., die cut) from the composite work piece.

If desired, a first color can be used for the cover layer 6114*a* and a different color used for cover layer 6114*b* to provide the user-contacting or inward-facing (inner) surface with tactile and visual differentiation relative to the outward-facing (outer) surface. In other configurations, different materials from those shown could be used.

In the illustrated arrangement, the top strap portion 6106, the rear strap portion 6108 and the front strap portions 6110 have the same or substantially the same cross-sectional dimensions as one another. However, in other arrangements, the cross-sectional dimensions of the strap portions 6106, 6108, 6110 can be different from one another. In the illustrated arrangement, the strap portions 6106, 6108, 6110 each have a width 6120 that is the same or substantially the same. In addition, the strap portions 6106, 6108, 6110 can each define a thickness 6124 that is the same or substantially the same.

In the illustrated configuration, the width 6120 of each of the strap portions 6106, 6108, 6110 is between 16 mm-20 mm, or categorized as a wide. In the illustrated configuration, the thickness 6124 of each of the strap portions 6106, 6108, 6110 is between 3 mm-4 mm. Such strap thicknesses can be categorized as thick. The overall construction of the headgear 6100, including the thicknesses 6124, provides flexibility of the headgear 6100 that can be characterized as very high for the purpose of comparison to other headgear configurations disclosed herein, or other headgear configurations generally.

FIGS. 41-56 illustrate several strap configurations, which can form a portion or an entirety of a headgear, such as any of the headgear disclosed herein. For example, the illustrated strap configurations can form a portion or an entirety of a crown or top strap, a rear strap or a front strap of a headgear, such as those headgear disclosed herein. In other arrangements, the strap configurations could form a portion or an entirety of upper straps used to connect to a forehead rest of an interface. Features of other headgear arrangements disclosed herein can be applied to the strap configurations of FIGS. 41-56, such as color and/or tactile differentiation between the inner and outer (or other) surfaces of the strap, for example.

FIGS. 41 and 42 illustrate a strap 6200 comprising a core 6212 and a cover, which comprises a first cover layer 6214a and a second cover layer 6214b. In the illustrated arrangement, edges of the cover layers 6214a, 6214b are not connected to one another. Accordingly, edges of the core 6212 are exposed between the cover layers 6214a, 6214b. The core 6212 can be constructed of a relatively rigid material, such as a plastic. In some configurations, the core 6212 is formed by an injection molding process, which allows the edges of the core 6212 to be shaped (e.g., rounded). The cover layers 6214a, 6214b can be constructed of a relatively soft fabric or textile material. In the illustrated configuration, each of the cover layers 6214a, 6214b is constructed from a UBL (unbroken loop) material. The cover layers 6214a, 6214b can be secured to the core 6212 by any suitable arrangement or method, such as RF welding, for example. Other suitable arrangements or methods could also be used, such as adhesives, for example.

As noted, the edges of the cover layers 6214a, 6214b are not connected to one another such that the edges of the core 6212 are exposed. The edges of the core 6212 are rounded to avoid sharp edges that could be uncomfortable or could be perceived as uncomfortable by a user. The rounded edges can include rounded corners or a rounding of the entire thickness of the core 6212. In some configurations, the edges of the cover layers 6214a, 6214b extend beyond or overhang from the core 6212, or at least the beyond the point that the edges of the core 6212 starts to round. Such an arrangement can disguise the rigid plastic core 6212 and provide an appearance that softens the hard edge of the core 6212.

The illustrated strap 6200 defines a width 6220 and a thickness 6224. A length of the strap 6200 can vary depending on the particular application. Accordingly, FIGS. 41-56 illustrate strap segments having a length of 80 mm. In the illustrated configuration, the width 6220 of the strap 6200 is 12 mm and the thickness 6224 of the strap 6200 is 2 mm. However, such dimensions are for the sake of example and comparison between the strap configurations of FIGS. 41-56 and other suitable strap dimensions can be used, such as those disclosed herein, for example.

Figure 43:
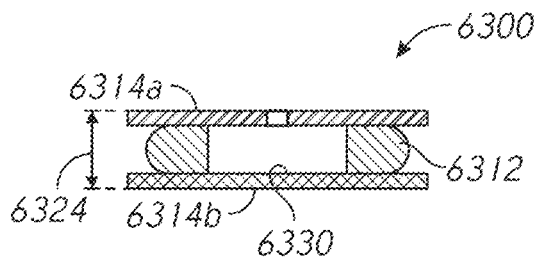
FIG. 43 is a sectional view of a headgear strap arrangement having a core and one or more outer layers.
Figure 44:
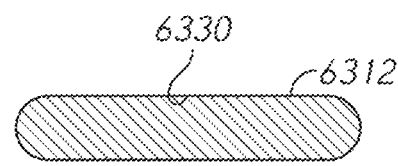
FIG. 44 is a side view of the core of the headgear strap arrangement of FIG. 43.

FIGS. 43 and 44 illustrate a strap 6300 comprising a core 6312 and a cover, which comprises a first cover layer 6314a and a second cover layer 6314b. In the illustrated arrangement, edges of the cover layers 6314a, 6314b are not connected to one another. Accordingly, edges of the core 6312 are exposed between the cover layers 6314a, 6314b. The core 6312 can be constructed of a relatively rigid material, such as a plastic. In some configurations, the core 6312 is formed by an injection molding process, which allows the edges of the core 6312 to be shaped (e.g., rounded). The cover layers 6314a, 6314b can be constructed of a relatively soft fabric or textile material. In the illustrated configuration, each of the cover layers 6314a, 6314b is constructed from a UBL (unbroken loop) material. The cover layers 6314a, 6314b can be secured to the core 6312 by any suitable arrangement or method, such as RF welding, for example. Other suitable arrangements or methods could also be used, such as adhesives, for example.

In some configurations, the core 6312 can include a recess or cut-out along a portion of the core 6312. The illustrated core 6312 includes a cut-out 6330 of a central portion of the core 6312 in a width direction that extends through the entire thickness of the core 6312. The cut-out 6330 can be sized and shaped as desired, such as dependent on the overall shape of the strap 6300 or associate headgear. Such an arrangement may help disguise the rigidity of the strap 6300 by creating compressibility in the width direction. Because the edges of the cover layers 6314a, 6314b are not connected to one another, the edges of the core 6312 are exposed. The edges of the core 6312 are rounded to avoid sharp edges that could be uncomfortable or could be perceived as uncomfortable by a user. The rounded edges can include rounded corners or a rounding of the entire thickness of the core 6312. In some configurations, the edges of the cover layers 6314a, 6314b extend beyond or overhang from the core 6312, or at least the beyond the point that the edges of the core 6312 starts to round. Such an arrangement can disguise the rigid plastic core 6312 and provide an appearance that softens the hard edge of the core 6312.

The illustrated strap 6300 defines a width 6320 and a thickness 6324. In the illustrated configuration, the width 6320 of the strap 6300 is 12 mm and the thickness 6324 of the strap 6300 is 2 mm. However, such dimensions are for the sake of example and comparison between the strap configurations of FIGS. 41-56 and other suitable strap dimensions can be used, such as those disclosed herein, for example.

Figure 45:
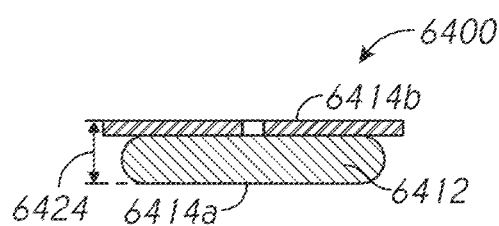
FIG. 45 is a sectional view of a headgear strap arrangement having a core and one or more outer layers.
Figure 46:
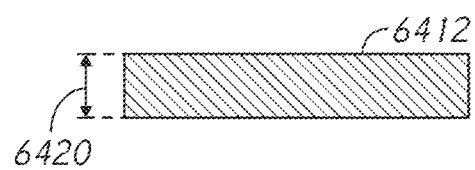
FIG. 46 is a side view of the core of the headgear strap arrangement of FIG. 45.

FIGS. 45 and 46 illustrate a strap 6400 comprising a core 6412 and a cover 6414, which comprises a first cover portion 6414a and a second cover portion 6414b. In the illustrated arrangement, the first cover portion 6414a is wrapped around the core 6412 such that the first cover portion 6414a surrounds at least one side and two edges of the core 6412. Accordingly, opposing edges of the first cover portion 6414a are located on a side of the core 6412 opposite the side that is covered by the first cover portion 6414a. The edges of the first cover portion 6414a can be spaced apart or can meet. Accordingly, edges of the core 6412 are covered by the first cover portion 6414a. The second cover portion 6414b is positioned on the side of the core 6412 on which the edges of the first cover portion 6414a are located and cover the edges of the first cover portion 6414a. The second cover portion 6414b can cover a portion or an entirety of the associated side of the core 6412.

The core 6412 can be constructed of a relatively rigid material, such as a plastic. In some configurations, the core 6412 is formed by an injection molding process, which allows the edges of the core 6412 to be shaped (e.g., rounded). The cover portions 6414a, 6414b can be constructed of a relatively soft fabric or textile material. In the illustrated configuration, each of the cover portions 6414a, 6414b is constructed from a UBL (unbroken loop) material. The cover portions 6414a, 6414b can be secured to the core 6412 by any suitable arrangement or method, such as RF welding, for example. Other suitable arrangements or methods could also be used, such as adhesives, for example.

The edges of the core 6412 can be rounded to avoid sharp edges that could be uncomfortable or could be perceived as uncomfortable by a user. The rounded edges can include rounded corners or a rounding of the entire thickness of the core 6412. The wrapping of the core 6412 by the first cover portion 6414a can disguise the rigid plastic core 6412 and provide an appearance that softens the hard edge of the core 6412. The second cover portion 6414b can provide additional comfort or perceived comfort if used as the inner surface and can enable wrapping of curved headgear geometry.

The illustrated strap 6400 defines a width 6420 and a thickness 6424. In the illustrated configuration, the width 6420 of the strap 6400 is 12 mm and the thickness 6424 of the strap 6400 is 2.5 mm. However, such dimensions are for the sake of example and comparison between the strap configurations of FIGS. 41-56 and other suitable strap dimensions can be used, such as those disclosed herein, for example.

Figure 47:
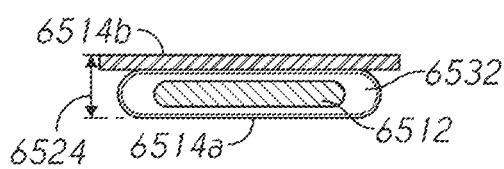
FIG. 47 is a sectional view of a headgear strap arrangement having a core and one or more outer layers.
Figure 48:
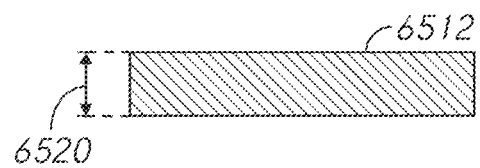
FIG. 48 is a side view of the core of the headgear strap arrangement of FIG. 47.

FIGS. 47 and 48 illustrate a strap 6500 that is similar to the strap 6400 of FIGS. 45 and 46. The strap 6500 of FIGS. 47 and 48 comprises a core 6512 and a cover 6514, which comprises a first cover portion 6514a and a second cover portion 6514b. In the illustrated arrangement, the first cover portion 6514a is wrapped around the core 6512 such that the first cover portion 6514a surrounds at least one side and two edges of the core 6512. Accordingly, opposing edges of the first cover portion 6514a are located on a side of the core 6512 opposite the side that is covered by the first cover portion 6514a. However, the first cover portion 6514a is not tightly wrapped on the core 6512 such that an air gap 6532 is provided adjacent one or both edges of the core 6512 between the core 6512 and the first cover portion 6514a. The edges of the first cover portion 6514a can be spaced apart or can meet. Accordingly, edges of the core 6512 are covered by the first cover portion 6514a, but with intervening air gaps 6532 on one or both edges. The second cover portion 6514b is positioned on the side of the core 6512 on which the edges of the first cover portion 6514a are located and cover the edges of the first cover portion 6514a. The second cover portion 6514b can cover a portion or an entirety of the associated side of the core 6512.

The core 6512 can be constructed of a relatively rigid material, such as a plastic. In some configurations, the core 6512 is formed by an injection molding process, which allows the edges of the core 6512 to be shaped (e.g., rounded). The cover portions 6514a, 6514b can be constructed of a relatively soft fabric or textile material. In the illustrated configuration, each of the cover portions 6514a, 6514b is constructed from a UBL (unbroken loop) material. The cover portions 6514a, 6514b can be secured to the core 6512 by any suitable arrangement or method, such as RF welding, for example. Other suitable arrangements or methods could also be used, such as adhesives, for example.

The edges of the core 6512 can be rounded to avoid sharp edges that could be uncomfortable or could be perceived as uncomfortable by a user. The rounded edges can include rounded corners or a rounding of the entire thickness of the core 6512. The wrapping of the core 6512 by the first cover portion 6514a and provision of the air gap(s) 6532 can disguise the rigid plastic core 6512 and provide an appearance that softens the hard edge of the core 6512. The second cover portion 6514b can provide additional comfort or perceived comfort if used as the inner surface and can enable wrapping of curved headgear geometry.

The illustrated strap 6500 defines a width 6520 and a thickness 6524. In the illustrated configuration, the width 6520 of the strap 6500 is 12 mm and the thickness 6524 of the strap 6500 is 2.5 mm. However, such dimensions are for the sake of example and comparison between the strap configurations of FIGS. 41-56 and other suitable strap dimensions can be used, such as those disclosed herein, for example.

FIGS. 49 and 50 illustrate a strap 6600 comprising a core 6612 and a cover, which comprises a first cover layer 6614a and a second cover layer 6614b. As used herein, the term "layer" can refer to a construction having a single material or multiple materials (e.g., a composite material), unless otherwise indicated. In the illustrated arrangement, edges of the cover layers 6614a, 6614b are not connected to one another. Accordingly, edges of the core 6612 are exposed between the cover layers 6614a, 6614b. The core 6612 can be constructed of a relatively rigid material, such as a plastic. In some configurations, the core 6612 is formed by an injection molding process, which allows the edges of the core 6612 to be shaped (e.g., rounded). The cover layers 6614a, 6614b can be constructed of a composite of multiple materials, such as relatively soft fabric or textile materials. In the illustrated configuration, each of the cover layers 6614a, 6614b is constructed from a UBL (unbroken loop) material with a spacer fabric material on top. That is, in some configurations, the UBL material is closer to the core 6612 and the spacer fabric is further away from the core 6612. The cover layers 6614a, 6614b can be secured to the core 6612 by any suitable arrangement or method, such as RF welding, for example. Other suitable arrangements or methods could also be used, such as adhesives, for example.

Because the edges of the cover layers 6614a, 6614b are not connected to one another, the edges of the core 6612 are exposed. The edges of the core 6612 are rounded to avoid sharp edges that could be uncomfortable or could be perceived as uncomfortable by a user. The rounded edges can include rounded corners or a rounding of the entire thickness of the core 6612. In some configurations, the edges of the cover layers 6614a, 6614b extend beyond or overhang from the core 6612, or at least the beyond the point that the edges of the core 6612 starts to round. Such an arrangement can disguise the rigid plastic core 6612 and provide an appearance that softens the hard edge of the core 6612. In addition, the spacer fabric provides additional compressibility in the thickness direction (the vertical direction in the illustrated orientation) to further disguise rigidity and provide cushioning for sensitive areas (e.g., a user's cheeks).

The illustrated strap 6600 defines a width 6620 and a thickness 6624. In the illustrated configuration, the width 6620 of the strap 6600 is 12 mm and the thickness 6624 of the strap 6600 is 8 mm. However, such dimensions are for the sake of example and comparison between the strap configurations of FIGS. 41-56 and other suitable strap dimensions can be used, such as those disclosed herein, for example.

FIGS. 51 and 52 illustrate a strap 6700 comprising a core 6712 and a cover, which comprises a first cover layer 6714a and a second cover layer 6714b. In the illustrated arrangement, edges of the cover layers 6714a, 6714b are not connected to one another. Accordingly, edges of the core 6712 are exposed between the cover layers 6714a, 6714b. The core 6712 can be constructed of a relatively rigid material, such as a plastic. In some configurations, the core 6712 is formed by an injection molding process, which allows the edges of the core 6712 to be shaped (e.g., rounded). The cover layers 6714a, 6714b can be constructed of a composite of multiple materials, such as relatively soft fabric or textile and foam or similar cushioning materials. In the illustrated configuration, each of the cover layers 6714a, 6714b is constructed from a UBL (unbroken loop) material with a breath-o-prene material on top. That is, in some configurations, the UBL material is closer to the core 6712 and the breath-o-prene material is further away from the core 6712. The cover layers 6714a, 6714b can be secured to the core 6712 by any suitable arrangement or method, such as RF welding, for example. Other suitable arrangements or methods could also be used, such as adhesives, for example.

Because the edges of the cover layers 6714a, 6714b are not connected to one another, the edges of the core 6712 are exposed. The edges of the core 6712 are rounded to avoid sharp edges that could be uncomfortable or could be perceived as uncomfortable by a user. The rounded edges can include rounded corners or a rounding of the entire thickness of the core 6712. In some configurations, the edges of the cover layers 6714a, 6714b extend beyond or overhang from the core 6712, or at least the beyond the point that the edges of the core 6712 starts to round. Such an arrangement can disguise the rigid plastic core 6712 and provide an appearance that softens the hard edge of the core 6712. In addition, the breath-o-prene material provides additional compressibility in the thickness direction (the vertical direction in the illustrated orientation) to further disguise rigidity and provide cushioning for sensitive areas (e.g., a user's cheeks).

The illustrated strap 6700 defines a width 6720 and a thickness 6724. In the illustrated configuration, the width 6720 of the strap 6700 is 12 mm and the thickness 6724 of the strap 6700 is 8 mm. However, such dimensions are for the sake of example and comparison between the strap configurations of FIGS. 41-56 and other suitable strap dimensions can be used, such as those disclosed herein, for example.

Figure 53:
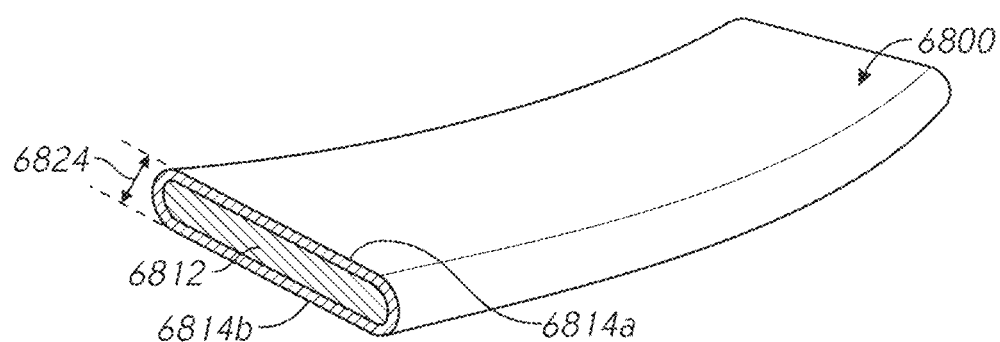
FIG. 53 is a sectional view of a headgear strap arrangement having a core and one or more outer layers.
Figure 54:
FIG. 54 is a side view of the core of the headgear strap arrangement of FIG. 53.

FIGS. 53 and 54 illustrate a strap 6800 comprising a core 6812 and a cover, which comprises a first cover layer 6814a and a second cover layer 6814b. In the illustrated arrangement, edges of the cover layers 6814a, 6814b are not connected to one another. Accordingly, edges of the core 6812 are exposed between the cover layers 6814a, 6814b. The core 6812 can be constructed of a relatively rigid material, such as a plastic. In some configurations, the core 6812 is formed by an injection molding process. The cover layers 6814a, 6814b can be constructed of a relatively soft fabric or textile material. In the illustrated configuration, each of the cover layers 6814a, 6814b is constructed from a UBL (unbroken loop) material. The cover layers 6814a, 6814b can be secured to the core 6812 by any suitable arrangement or method. In the illustrated arrangement, the molten material of the core 6812 is injected between the cover layers 6814a, 6814b, such as by a method disclosed herein. However, other suitable arrangements or methods could also be used, such as adhesives or RF welding, for example.

Because the edges of the cover layers 6814a, 6814b are not connected to one another, the edges of the core 6812 are exposed. The edges of the core 6812 can be square or sharp, but in other configurations could be rounded to avoid sharp edges that could be uncomfortable or could be perceived as uncomfortable by a user. In some configurations, the edges of the cover layers 6814a, 6814b extend beyond or overhang from the core 6812. Such an arrangement can disguise the rigid plastic core 6812 and provide an appearance that softens the hard edge of the core 6812.

The illustrated strap 6800 defines a width 6820 and a thickness 6824. In the illustrated configuration, the width 6820 of the strap 6800 is 10 mm and the thickness 6824 of the strap 6800 is 2 mm. However, such dimensions are for the sake of example and comparison between the strap configurations of FIGS. 41-56 and other suitable strap dimensions can be used, such as those disclosed herein, for example.

Figure 55:
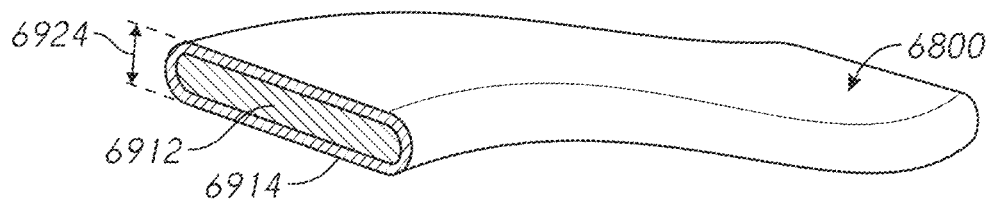
FIG. 55 is a sectional view of a headgear strap arrangement having a core and one or more outer layers.
Figure 56:
FIG. 56 is a side view of the core of the headgear strap arrangement of FIG. 55.

FIGS. 55 and 56 illustrate a strap 6900 comprising a core 6912 and a cover 6914, which is wrapped around the core 6912. In the illustrated arrangement, edges of the cover layer 6914 are embedded within the core 6912. The core 6912 can be constructed of a relatively rigid material, such as a plastic. In some configurations, the core 6912 is formed by an injection molding process. The cover layer 6914 can be constructed of a relatively soft fabric or textile material. In the illustrated configuration, the cover layer 6914 is constructed from a UBL (unbroken loop) material. The cover layer 6914 can be secured to the core 6912 by any suitable arrangement or method. In the illustrated arrangement, the cover layer 6914 is constructed as a tubular structure, such as by sewing of opposing edges of a flat piece of material. The molten material of the core 6912 is injected into a center of the tubular cover layer 6914, such as by a method disclosed herein. However, other suitable arrangements or methods could also be used, such as adhesives or RF welding, for example.

The edges of the core 6912 can be rounded to avoid sharp edges that could be uncomfortable or could be perceived as uncomfortable by a user. In addition, the cover layer 6914 preferably is wrapped around the edges of the core 6912. Such an arrangement can disguise the rigid plastic core 6912 and provide an appearance that softens the hard edge of the core 6912.

The illustrated strap 6900 defines a width 6920 and a thickness 6924. In the illustrated configuration, the width 6920 of the strap 6900 is 10 mm and the thickness 6924 of the strap 6900 is 2 mm. However, such dimensions are for the sake of example and comparison between the strap configurations of FIGS. 41-56 and other suitable strap dimensions can be used, such as those disclosed herein, for example.

Figure 57:
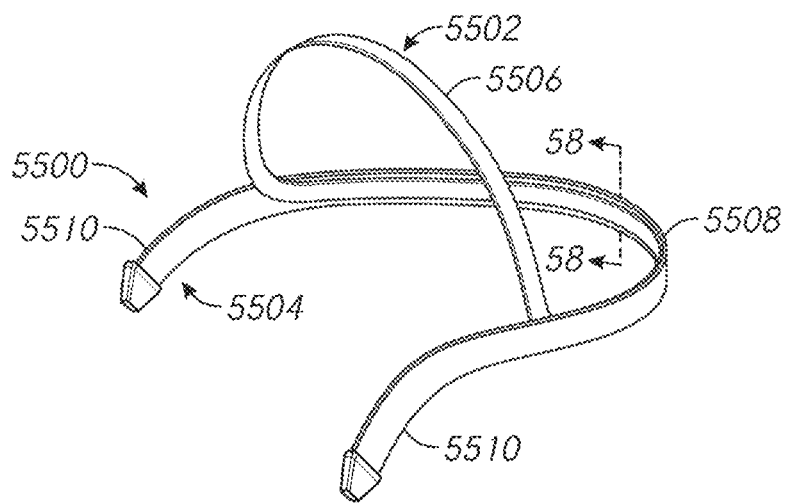
FIG. 57 is a perspective view of a headgear having a first strap and a second strap.
Figure 58A:
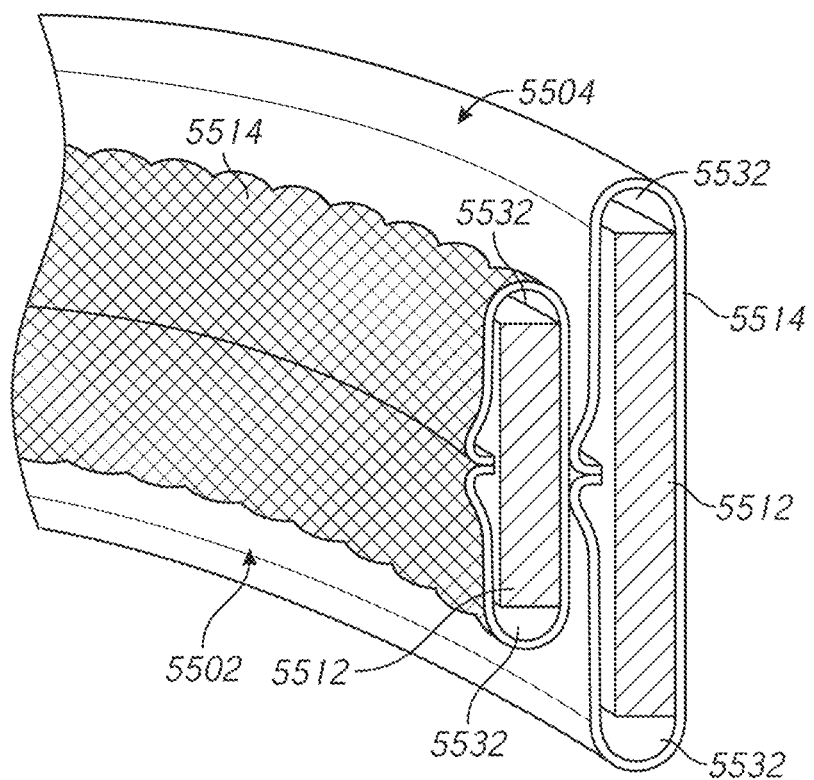
FIG. 58A is a sectional view of a portion of the headgear of FIG. 57.

FIGS. 57 and 58A illustrated a headgear 5500 that is similar to the headgear 5500 of FIGS. 21 and 22. Accordingly, the same reference numbers are used to indicate the same or similar features. In addition, any details not discussed in connection with FIGS. 57 and 58A can be the same as or similar to the corresponding features or components of FIGS. 21 and 22, or can be of another suitable arrangement. The headgear 5500 has a first headgear portion or strap 5502 and a second headgear portion or strap 5504. The first strap 5502 defines a top strap or crown strap portion 5506 and the second strap 5504 defines a rear strap portion 5508. In the illustrated arrangement, the first strap 5502 also forms a portion of the rear strap portion 5508, such that the rear strap portion 5508 includes portions of both the first strap 5502 and the second strap 5504. In addition, the second strap 5504 defines front strap portions 5510 of the headgear 5500.

In the illustrated arrangement, each of the first strap 5502 and the second strap 5504 comprises a core 5512 and a cover layer 5514. In some configurations, the core 5512 can be constructed of a relatively rigid material, such as an injection-moulded plastic material. In some configurations, the cover layer 5514 is a fabric or textile material. The cover layer 5514 surrounds a portion or an entirety of a periphery of the core 5512. In the illustrated arrangement, the core 5512 of the first strap 5502 is plastic and the cover layer 5514 is a soft, quilted fabric material. The material of the cover layer 5514 can be formed into a tubular structure by joining opposing edges of the material, such as by sewing or otherwise, to form a seam 5516. The seam 5516 can be positioned on any desired surface portion of the first strap

5502, such as along either side (width direction) or either end (thickness direction). In the illustrated arrangement, the seam 5516 is positioned on the user-facing or inner surface of the first strap 5502.

The core 5512 of the illustrated second strap 5504 is plastic and the cover layer 5514 is a relatively durable and slippery material formed into a tubular structure. The material of the cover layer 5514 can be formed into a tubular structure by joining opposing edges of the material, such as by sewing or otherwise, to form a seam 5516. The cover layers 5514 of each of the first strap 5502 and the second strap 5504 can be formed separately from the cores 5512 and can be assembled onto the cores 5512, such as by sliding the cover layer 5514 onto the core 5512. In some configurations, the cover layers 5514 can be loosely received on the cores 5512. In other words, the cover layers 5514 may not be affixed to the cores 5512 such that some relative movement is permitted between the cover layer 5514 and the respective core 5512. In some configurations, air gaps 5532 can be provided between edges of the cores 5512 and edges of the cover layers 5514. Such an arrangement may provide increased comfort. However, if desired, the cover layers 5514 could be tightly affixed to the cores 5512, such as by molding within the cover layers 5514, as described herein, or by adhesives, for example.

In the illustrated arrangement, the first strap 5502 and the second strap 5504 are joined along a substantial entirety of the rear strap portion 5508. The first strap 5502 and the second strap 5504 separate at a junction between the top strap portion 5506, the rear strap portion 5508 and the front strap portions 5510. The first strap 5502 and the second strap 5504 can be secured to one another by any suitable arrangement, such as by a sewn joint or adhesive joint between the cover layers 5514 of the first strap 5502 and the second strap 5504. RF welding or Ultrasonic welding could also be used. If desired, the straps 5502, 5504 could be secured to one another during a molding process in which the molten material of the cores 5512 is introduced into the cover layers 5514.

In the illustrated arrangement, the first strap 5502 is located inwardly of the second strap 5504 in the rear strap portion 5508 such that the first strap 5502 is closer to the user than the second strap 5504 in use. Thus, the first strap 5502 can define a portion or an entirety of a user-contacting surface of the rear strap portion 5508. In the illustrated arrangement, because the first strap 5502 also defines the top strap portion 5506, the first strap 5502 defines a user-contacting surface of both the top strap portion 5506 and the rear strap portion 5508 of the headgear 5500. The quilted material of the first strap 5502 can provide and/or convey softness and comfort to the user. The material of the second strap can provide durability and good pillow slide properties.

Figure 58C:
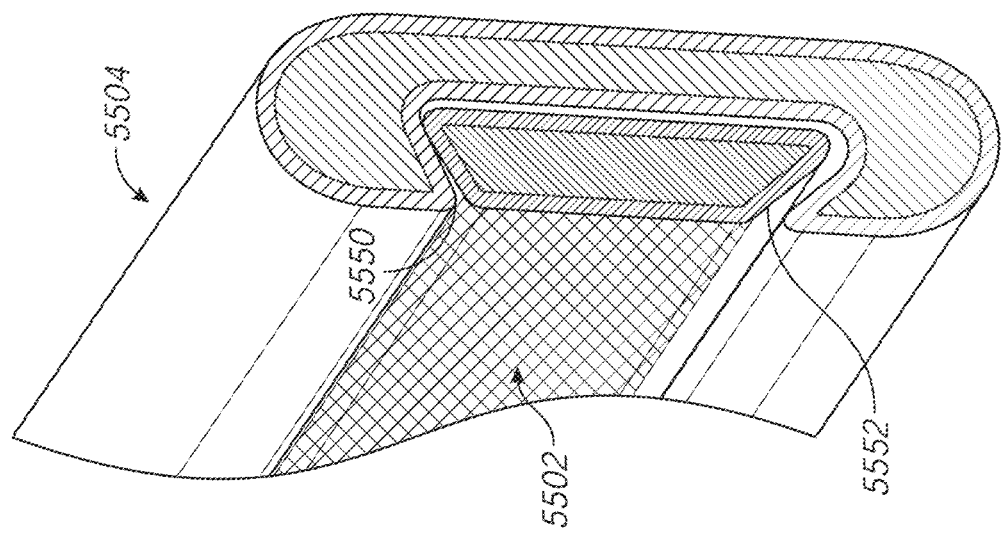
FIG. 58C is a sectional view of another alternative arrangement of the straps of the headgear of FIG. 57.
Figure 58B:
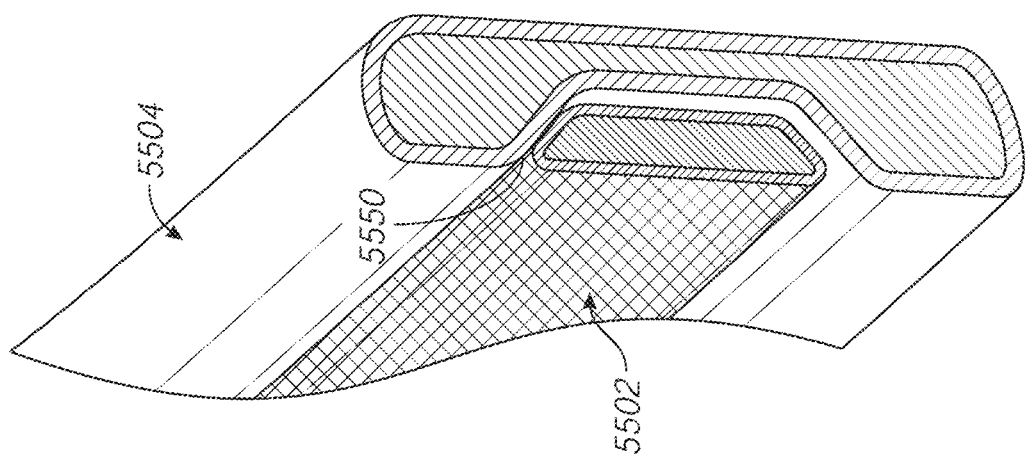
FIG. 58B is a sectional view of an alternative arrangement of the straps of the headgear of FIG. 57.

FIGS. 58B and 58C illustrate an alternative arrangement of the straps 5502, 5504 of the headgear 5500 of FIG. 57. Both designs of FIGS. 58B and 58C provide for a reduced thickness stack up in contrast with the arrangement of FIG. 58A, in which the rear portion 5508 has the combined thickness of both straps 5502, 5504. With reference to FIG. 58B, a recess 5550 is provided in a lengthwise direction along the strap 5504. The recess 5550 is configured to receive a portion or an entirety of the strap 5502. In the illustrated arrangement, at least a substantial entirety of the strap 5502 is accommodated within the recess 5550 such that the inner surfaces of the straps 5502, 5504 are substantially aligned to provide comfort to the user. In at least some embodiments, the strap 5504 is a higher load bearing strap than strap 5502 such that the strap 5504 holds the associated mask in sealing engagement with the user's face. In at least some embodiments, the strap 5502 is a lower load bearing strap compared to strap 5504. The top strap 5506 (defined by strap 5502 alone in the illustrated arrangement) typically maintains a vertical force vector, which keeps the headgear assembly 5500 above the ears. The force required to achieve this may be a lower force that the mask blow-off force. Thus, the top strap 5506 can be smaller and/or lighter than the strap 5504. The recess 5550 can extend upwardly at its ends to allow the strap 5502 to transition from the rear strap portion 5508 to the top strap portion 5506 of the headgear 5500. The illustrated strap 5504 includes upper and lower ends or edges that are relatively thick, which allows the strap 5504 to accommodate a relatively high tensile force. That is, the middle region can define the recess 5550 without compromising inelastic performance of strap 5504. The strap 5502 may be narrow as shown in FIG. 58B throughout its entire length or a substantial entirety of its length, as discussed above. In other embodiments, the strap 5502 may vary in width along its length. For example, the strap 5502 may be the same width as strap 5504 in the top strap portion 5506 and transition to a reduced width where positioned within the recess 5550 of strap 5504. If desired, various suitable attachment mechanisms could be employed (e.g., adhesive, overmoulding, stitching, etc.) to secure the straps 5502, 5504 to one another. In some configurations, a baseball cap-style snap fits (e.g., a plurality of protrusions on one of strap 5502 or 5504 and corresponding snap-in receptacles on the other strap 5502 or 5504). The cover layers 5514 could include access openings for each, several or an entirety of the protrusions or receptacles, or other interlocking features. The illustrated arrangement could also be reversed and strap 5504 could be received within strap 5502 such that the recess 5550 is on the non-patient contacting side of the headgear 5500. FIG. 58C illustrates an arrangement similar to that of FIG. 58B; however, in the arrangement of FIG. 58C the straps 5502, 5504 are interlocked with one another. In particular, the recess 5550 has an opening 5552 that is narrower than the internal portion of the recess 5550 such that the strap 5502 cannot pass through the opening 5552. The illustrated recess 5550 has a trapezoid cross-sectional shape and the strap 5502 has a corresponding shape. The strap 5502 does not necessarily have to fill the entire recess 5550. The strap 5502 could be shaped to limit contact surface with the strap 5504 to ease assembly. However other shapes that have a narrow opening could also be used or other suitable interlocking arrangements, as well. The illustrated shapes work together to form a mechanical interlock, which in at least some configurations does not require any other attachment mechanisms. However, if desired, suitable attachment mechanisms, such as those described above, could be employed.

FIGS. 59-76 illustrate several headgear configurations 5600 similar to the headgear 5600 of FIGS. 24-26. Accordingly, the same reference numbers are used to indicate the same or similar features. In addition, any details not discussed in connection with FIGS. 59-76 can be the same as or similar to the corresponding features or components of FIGS. 24-26, or can be of another suitable arrangement. Each headgear 5600 has a first headgear portion or strap 5602 and a second headgear portion or strap 5604. The first strap 5602 defines a top strap or crown strap portion 5606 and the second strap 5604 defines a rear strap portion 5608.

The first strap 5602 and the second strap 5604 cooperate to define front strap portions 5610 in each headgear 5600. The first strap 5602 is positioned above the second strap 5604 within the front strap portions 5610 such that a width of the front strap portions 5610 is equal to the combined widths of the first strap 5602 and the second strap 5604. The first strap 5602 and the second strap 5604 are joined to one another within the front strap portions 5610 by a coupling arrangement, coupler or connector 5650. In the illustrated arrangements, the coupling arrangement 5650 also joins the first strap 5602 and the second strap 5604 to a front strap connector or extension strap 5652, which can be coupled to an interface by any suitable arrangement. The extension strap 5652 can be of any suitable arrangement, such as any of the strap arrangements disclosed herein or otherwise known. In some configurations, the coupling arrangement 5650 is over-moulded onto the first strap 5602 and the second strap 5604 to join the straps 5602, 5604. The coupling arrangement 5650 can also be over-moulded onto the extension strap 5652. In some configurations, the coupling arrangement 5650 is not over-moulded onto the extension strap 5652 and the extension strap 5652 is coupled to the coupling arrangement 5650 by another suitable, coupling arrangement, such as a snap-fit connection, for example. The coupling arrangement 5650 can surround the first and second straps 5602, 5604 (and, in some configurations, the extension strap 5652) such that a portion of the coupling arrangement 5650 is positioned on opposing sides (e.g., inner and outer and/or upper and lower) of the straps 5602, 5604. In some configurations, the coupling arrangement 5650 could be otherwise assembled to the straps 5602, 5604, 5652, such as a clamshell or snap-together arrangement, for example.

In the illustrated arrangements, the first strap 5602 and second strap 5604 comprise a composite structure having a core 5612 and a cover layer 5614. In some configurations, the core 5612 is constructed of a relatively rigid material, such as an injection-moulded plastic material. In some configurations, the cover layer 5614 is a fabric or textile material. The cover layer 5614 surrounds a portion or an entirety of a periphery of the core 5612. Any suitable materials or combinations of materials can be used, such as those disclosed herein.

In the illustrated arrangements, the straps 5602, 5604 are formed by introducing molten plastic material into the cover layers 5614 and allowing the molten plastic material to cool to form the cores 5612 in accordance with any of the processes disclosed herein. The cover layers 5614 can be separate layers, a knitted tubular structure or can be a sewn tube having a seam, which can be embedded in the core 5612. Alternatively, the cover layers 5614 of each of the first strap 5602 and the second strap 5604 can be formed separately from the cores 5612 and can be secured to the cores 5612, such as by adhesives or other suitable arrangements.

As disclosed herein, the cover layers 5614 of the first strap 5602 and the second strap 5604 can have different textures to allow for differentiation of the straps 5602, 5604 from one another. In addition or in the alternative, the first strap 5602 and the second strap 5604 can have different colors to allow for differentiation between the straps 5602, 5604. If desired, inward-facing and outward-facing surfaces of the headgear 5600 can have different colors and/or textures to allow for differentiation between inward-facing and outward-facing surfaces.

Figure 59:
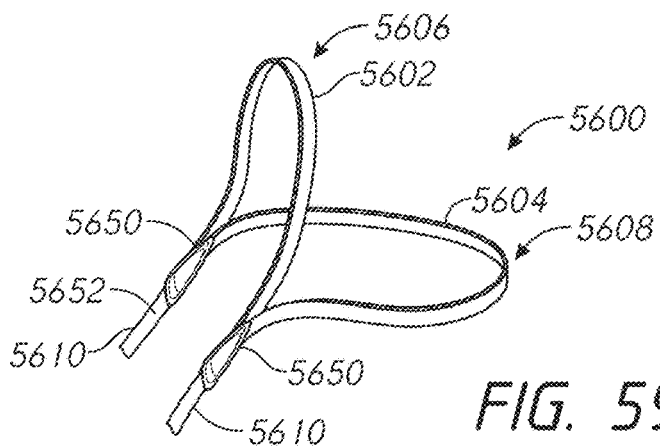
FIG. 59 is a perspective view of a headgear having at least a first strap and a second strap.
Figure 60:
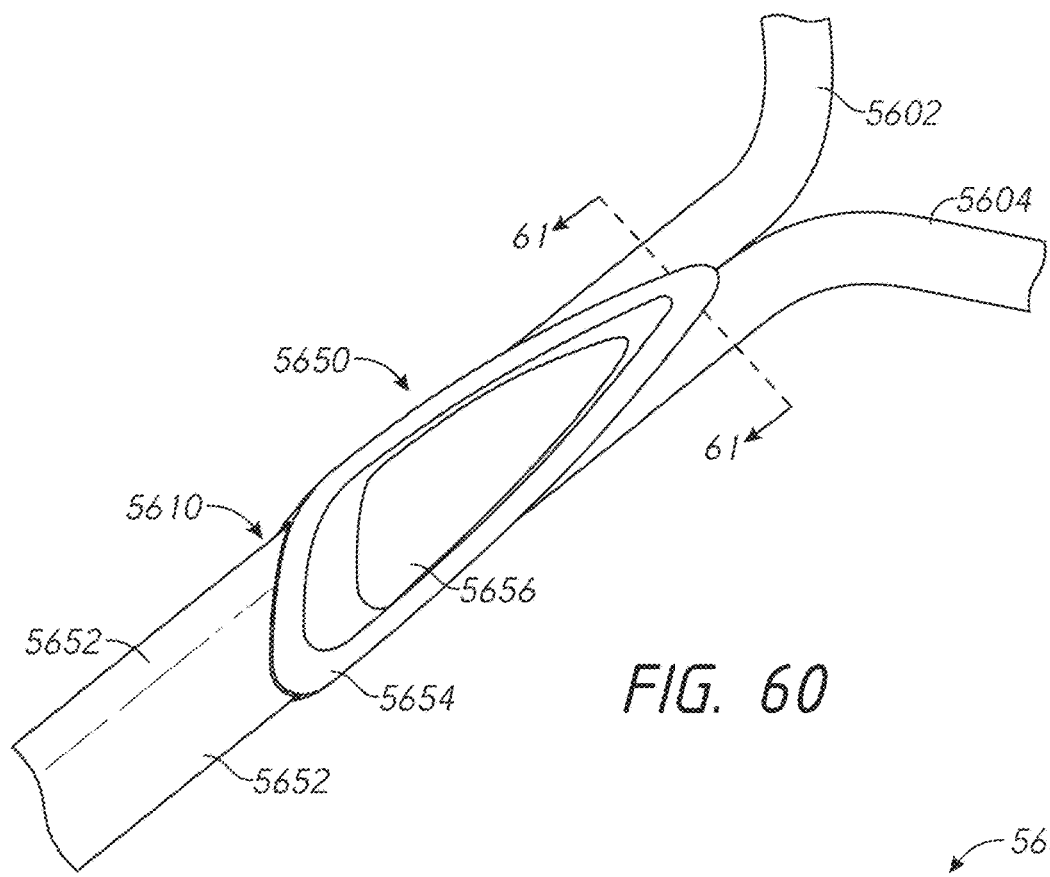
FIG. 60 is an enlarged view of the headgear of FIG. 59 including a coupling arrangement that couples at least the first strap and the second strap.
Figure 61:
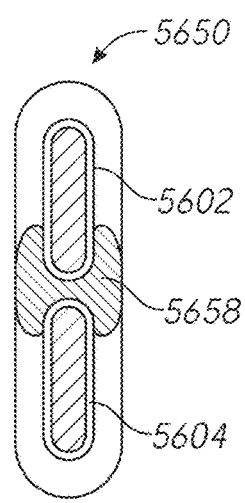
FIG. 61 is a sectional view of a portion of the headgear of FIG. 59 taken through the coupling arrangement of FIG. 60.

The headgear arrangements of FIGS. 59-76 differ in the coupling arrangement 5650 that couples the first strap 5602 and the second strap 5604 to one another and, if desired, to the extension strap 5652. The different coupling arrangements 5650 of FIGS. 59-76 are described in turn. The coupling arrangement 5650 of FIGS. 59-61 is generally triangular in shape when viewed from the side with rounded corners. The coupling arrangement 5650 increases in size in a width direction of the straps 5602, 5604 from a rearward position toward a forward position relative to the orientation of the headgear 5600, or in a direction from the straps 5602, 5604 toward the extension strap 5652.

The coupling arrangement 5650 includes a relatively thick perimeter portion 5654 and a relatively thinner interior portion 5656, which can define a recessed portion of the coupling arrangement 5650. The coupling arrangement 5650 can have the same configuration or appearance on the opposite surface (the inner surface), or it can have a relatively planar surface facing the user. In the illustrated arrangement, a portion 5658 of the coupling arrangement 5650 extends between the first strap 5602 and the second strap 5604 to assist in joining the straps 5602, 5604 to one another.

Figure 62:
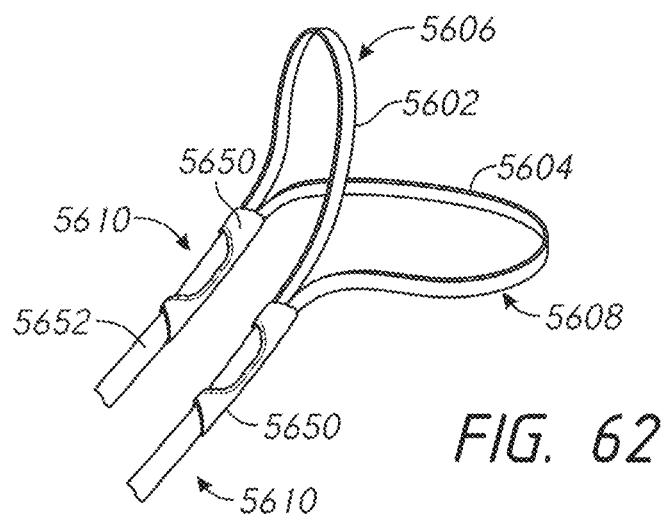
FIG. 62 is a perspective view of a headgear having at least a first strap and a second strap.
Figure 63:
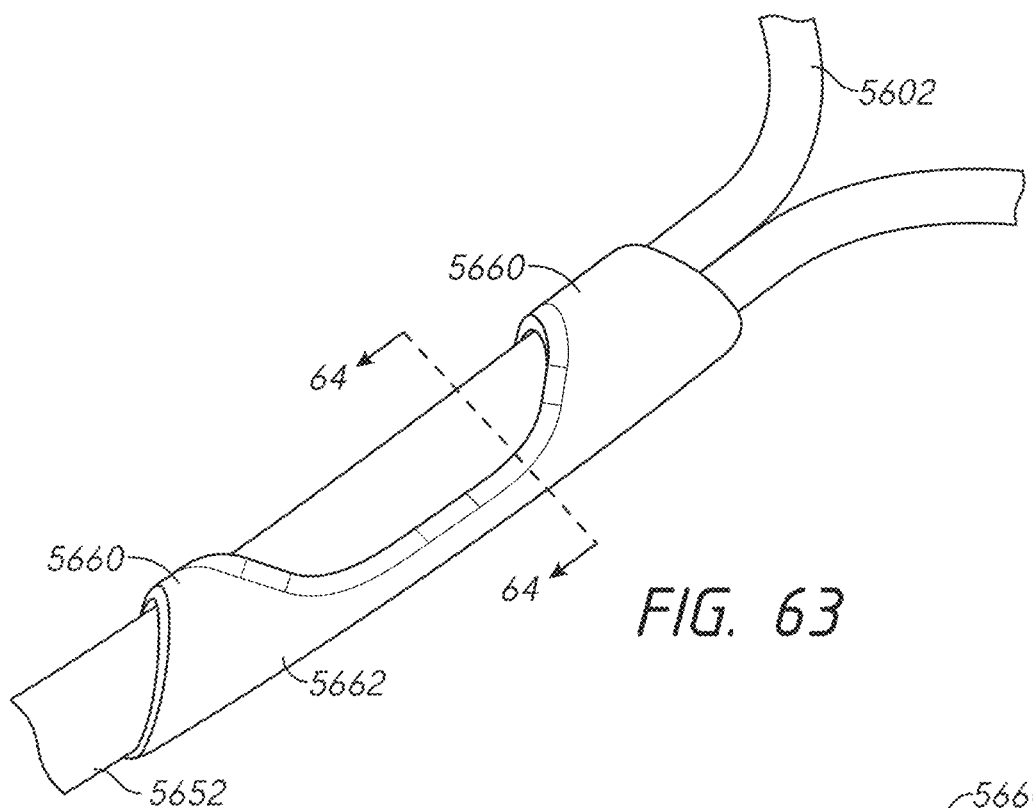
FIG. 63 is an enlarged view of the headgear of FIG. 62 including a coupling arrangement that couples at least the first strap and the second strap.
Figure 64:
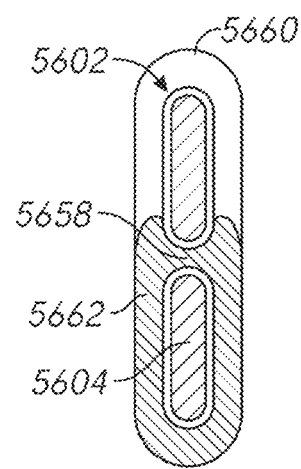
FIG. 64 is a sectional view of a portion of the headgear of FIG. 62 taken through the coupling arrangement of FIG. 63.

FIGS. 62-64 illustrate a coupling arrangement 5650 having a band portion 5660 at each end, which completely encircles the straps. The rear band portion 5660 can encircle only the straps 5602, 5604. The front band portion 5660 can encircle the straps 5602, 5604, as well as the extension strap 5652, or can encircle just the extension strap 5652. A bridge portion 5662 can extend between the band portions 5660. The bridge portion 5662 can encircle only one of the straps 5602, 5604. In the illustrated arrangement, the bridge portion 5662 surrounds the second strap 5604 or lower strap; however, in other configurations, the bridge portion 5662 can surround the first strap 5602 or upper strap. A portion 5658 of the bridge portion 5662 and/or the band portions 5660 can be positioned between the straps 5602, 5604. That is, the portion 5658 between the straps 5602, 5604 can extend between the straps 5602, 5604 along some or all of the portions of the straps 5602, 5604 within the coupling arrangement 5650.

Figure 65:
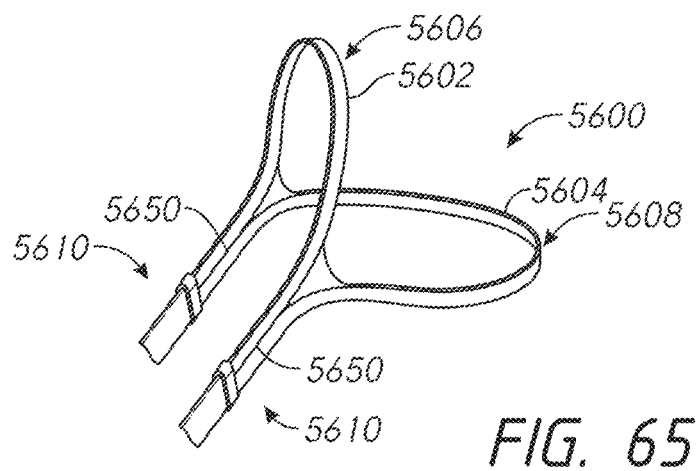
FIG. 65 is a perspective view of a headgear having at least a first strap and a second strap.
Figure 66:
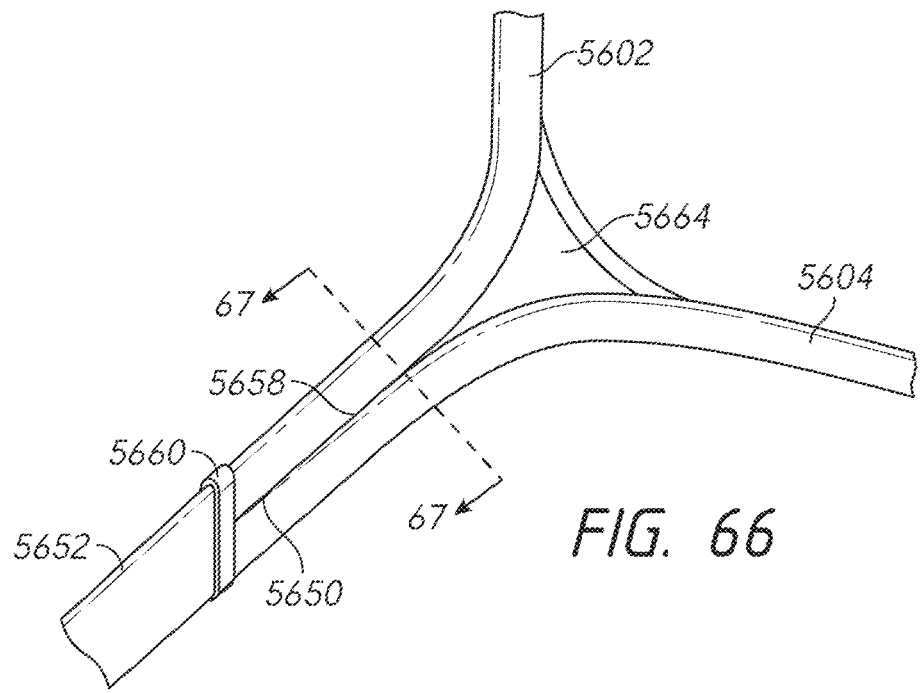
FIG. 66 is an enlarged view of the headgear of FIG. 65 including a coupling arrangement that couples at least the first strap and the second strap.
Figure 67:
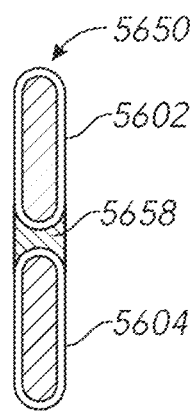
FIG. 67 is a sectional view of a portion of the headgear of FIG. 65 taken through the coupling arrangement of FIG. 66.

The coupling arrangement 5650 of FIGS. 65-67 omits material along one or both sides of the first strap 5602 and the second strap 5604 such that the sides of the straps 5602, 5604 are left exposed. The coupling arrangement 5650 includes the portion 5658 between the straps 5602, 5604, which can extend along a portion or an entirety of the coupling arrangement 5650. In some configurations, the coupling arrangement 5650 comprises a front band 5660 that surrounds the straps 5602, 5604 and, in some configurations, the extension strap 5652. The band 5660 could be configured to otherwise connect to the extension strap 5652. In some configurations, the coupling arrangement 5650 comprises a web or gusset 5664 at a rearward end. The gusset 5664 can be generally triangular in shape and can reinforce a rearward end of the connection between the straps 5602, 5604 to inhibit or prevent the straps 5602, 5604 from separating. The gusset 5664 can also hold the straps 5602, 5604 at a desired angle to properly position the top strap 5606 and the rear strap 5608.

Figure 68:
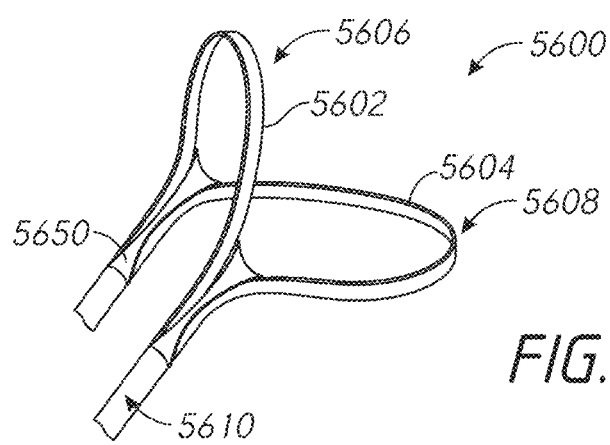
FIG. 68 is a perspective view of a headgear having at least a first strap and a second strap.
Figure 69:
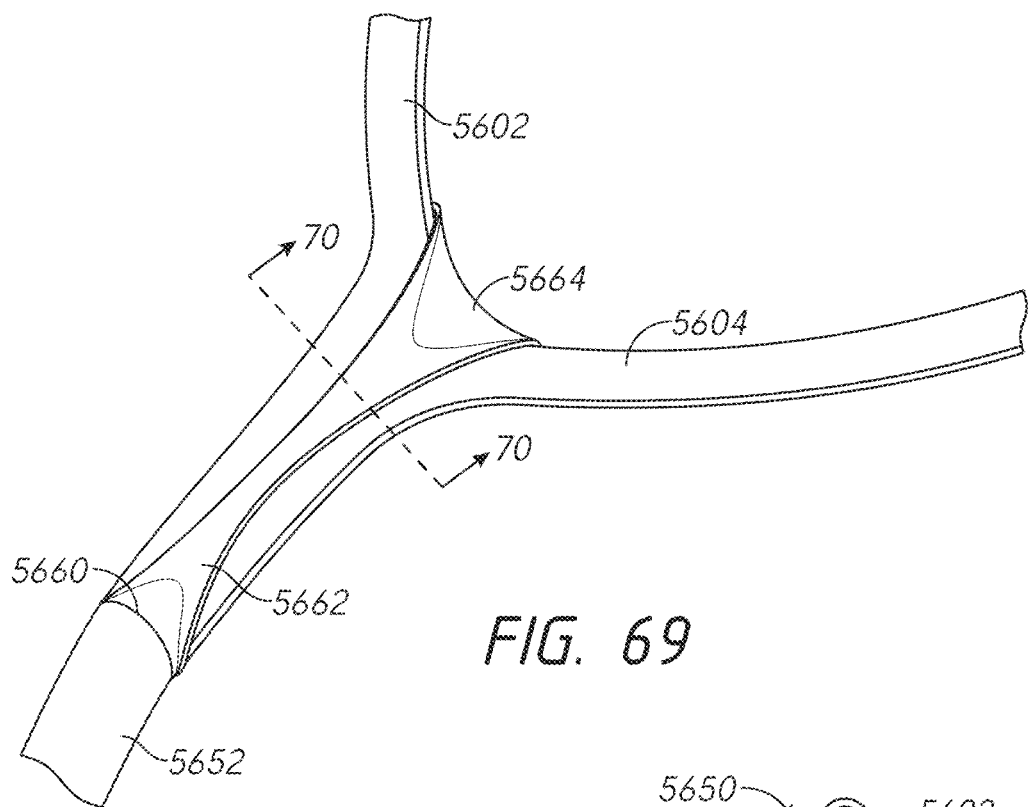
FIG. 69 is an enlarged view of the headgear of FIG. 68 including a coupling arrangement that couples at least the first strap and the second strap.
Figure 70:
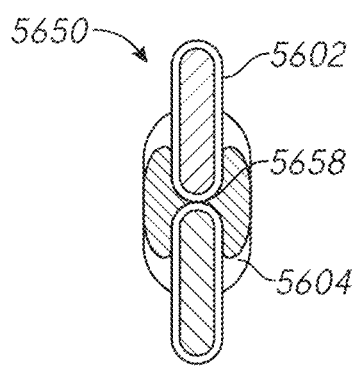
FIG. 70 is a sectional view of a portion of the headgear of FIG. 68 taken through the coupling arrangement of FIG. 69.

The coupling arrangement 5650 of FIGS. 68-70 is similar to the coupling arrangement 5650 of FIGS. 65-67. However, the coupling arrangement 5650 of FIGS. 68-70 extends onto or covers a portion of one or both of the inner side and outer side surfaces of the straps 5602, 5604. The coupling arrangement 5650 includes a front band 5660, a rear gusset 5664 and bridge portion 5662 that extends between the front band 5660 and the rear gusset 5664. The bridge portion 5662 includes the portion 5658 positioned between the straps 5602, 5604 as well as portions that extend along a portion of the side surfaces of the one or both of the straps 5602, 5604 in a width direction. From a side view, the coupling arrangement 5650 can taper from each end toward the center.

The coupling arrangement 5650 of FIGS. 71-73 includes only the portion 5658 that is positioned between the straps 5602, 5604. In the illustrated arrangement, the portion 5658 does not extend completely through the front straps 5610 in a thickness direction of the straps 5602, 5604 such that the portion 5658 includes a pair of distinct portions on each of the inner and outer sides of the front straps 5610. However, in other arrangements, the portion 5658 could extend completely through the front strap 5610 in a thickness direction of the straps 5602, 5604. The portion 5658 can extend along an entirety of, or could be intermittent along, the coupling arrangement 5650.

Figure 74:
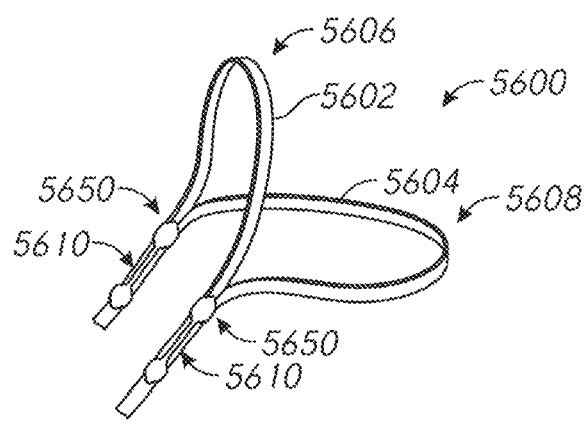
FIG. 74 is a perspective view of a headgear having at least a first strap and a second strap.
Figure 75:
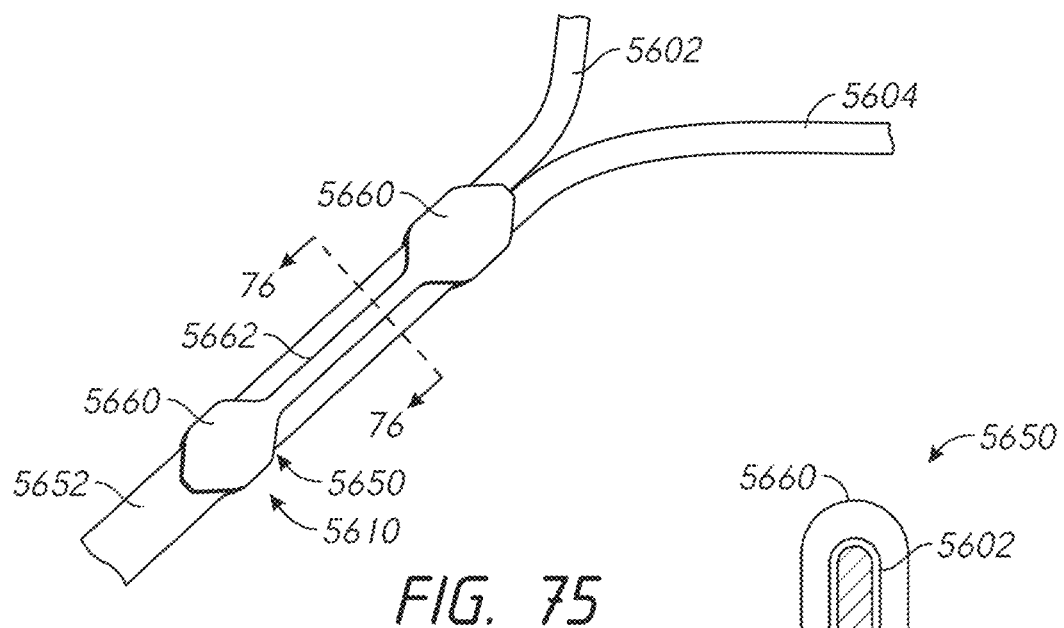
FIG. 75 is an enlarged view of the headgear of FIG. 74 including a coupling arrangement that couples at least the first strap and the second strap.
Figure 76:
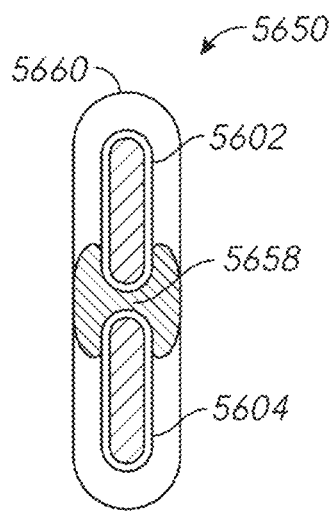
FIG. 76 is a sectional view of a portion of the headgear of FIG. 74 taken through the coupling arrangement of FIG. 75.

The coupling arrangement 5650 of FIGS. 74-76 is similar to the coupling arrangement 5650 of FIGS. 62-64 except the bridge portion 5662 is centrally-located relative to the combination of the straps 5602, 5604, similar to the bridge portion 5662 of FIGS. 68-70. The coupling arrangement 5650 of FIGS. 74-76 includes a front band portion 5660, a rear band portion 5660 and the bridge portion 5662 extending between the band portions 5660. The bridge portion 5662 can be a relatively thin member that comprises the portion 5658 between the straps 5602, 5604, as well as portions that extend along one or both of the inner and outer sides of one or both of the straps 5602, 5604 in a width direction of the straps 5602, 5604.

FIGS. 77-104 illustrate variations of strap portions suitable for use in headgear, portions of headgear or headgear. The arrangements disclosed in FIGS. 77-104 can be constructed by introducing a molten plastic material into a void or space defined by a layer or layers of one or more materials in accordance with any of the processes or methods disclosed herein. The arrangements disclosed in FIGS. 77-104 could be constructed by other suitable processes or methods, as well. The arrangements generally comprise a relatively rigid or semi-rigid core 7012 and an outer layer or layers 7014. The core 7012 can be constructed from a plastic material, any other materials disclosed herein or any other suitable material. The outer layer or layers 7014 can be constructed from a fabric or textile material, any other materials disclosed herein or any other suitable material. The cover layers 7014 can comprise knitted, woven or braided materials and can be elastic or inelastic.

Figure 77:
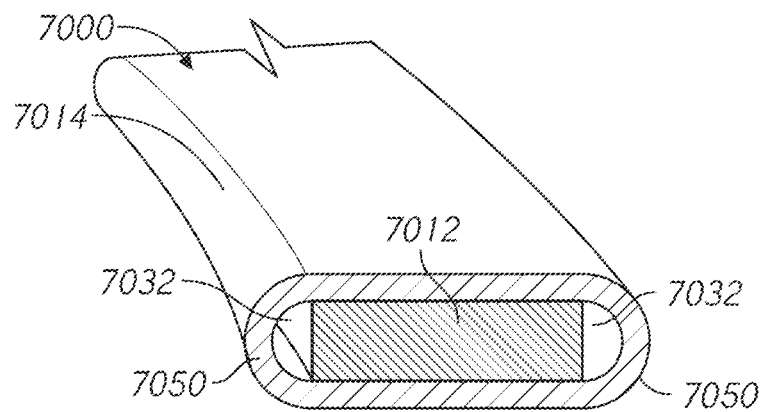
FIG. 77 is a sectional view of a headgear strap having a core and an outer layer with one or more air gaps or voids between the outer layer and the core.

FIG. 77 illustrates a strap 7000 having a core 7012 and an outer layer 7014. The outer layer 7014 is secured to the long sides of the core 7012 and is spaced from the short sides or edges of the core 7012 to create voids or air gaps 7032 on each lateral edge 7050 of the strap 7000. With such an arrangement, the lateral edges 7050 of the outer layer 7014 can compress toward the plastic core 7012 to provide some ability of the lateral edges 7050 to deform or provide some cushioning in a width and/or thickness direction of the strap 7000. The cushioning provided by the voids 7032 can improve comfort by reducing or eliminating contact between a hard edge of the core 7012 and the user's head and, in particular, the ears. In a width direction of the strap 7000, the voids 7032 could each have a dimension of, for example, 3 mm and the core 7012 could have a dimension of, for example, 3 mm for a total of 9 mm of width. As a result, each of the voids 7032 and the core 7012 could occupy about one-third of the width dimension of the strap 7000. Such an arrangement provides relatively high flexibility due to the relatively small dimensions of the core 7012, which may be desirable to some users from a perception standpoint, as described above. The user can manually apply a force to the strap 7000 and detect some stretch. However, in use, headgear incorporating the strap 7000 can perform substantially as an inelastic headgear due to friction between the user's head and the strap 7000. Alternatively, the voids 7032 could each have a dimension of, for example, 2 mm and the core 7012 could have a dimension of, for example, 5 mm in a width direction of the strap 7000 for a total of 9 mm of width. Such an arrangement (e.g., a medium width core 7012) can provide good flexibility and less elasticity than a strap 7000 having a smaller core 7012. Other suitable relative dimensions could also be used depending on the desired amounts of flexibility and cushioning or compressibility provided by the voids 7032. Such arrangements, including the dimensions or proportions described, can also be applied to other straps or headgear disclosed herein, such as those shown in FIGS. 21 and 57, for example. For example, in the headgear 5500 of FIG. 21, the strap 5502 could have 3 mm voids and a 3 mm core 5512 and the strap 5504 could have 2 mm voids and a 5 mm core 5512. This can provide the top strap 5506 with greater elasticity than the rear strap 5508.

Figure 78:
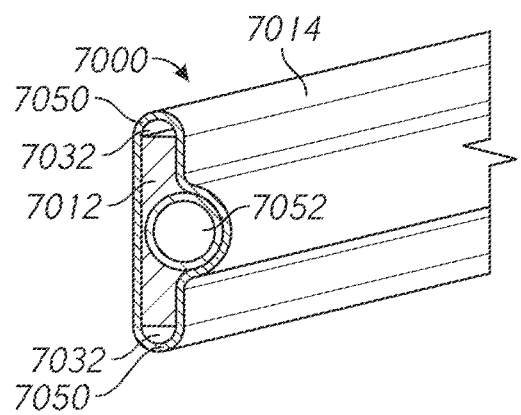
FIG. 78 is a sectional view of a headgear strap having a core and an outer layer with one or more conduits between the outer layer and the core.
Figure 79:
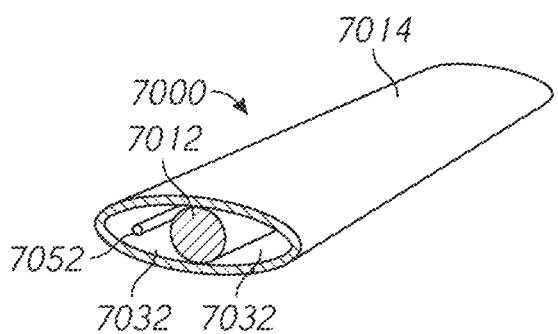
FIG. 79 is a sectional view of another headgear strap having a core and an outer layer with one or more conduits between the outer layer and the core.

FIGS. 78 and 79 illustrate straps 7000 similar to the strap 7000 of FIG. 77 including a core 7012, an outer layer 7014 and voids 7032 at the lateral edges 7050 thereof. However, the straps 7000 of FIGS. 78 and 79 each include a conduit 7052 extending in a lengthwise direction along the strap 7000 within an interior of the cover layer 7014. FIG. 78 illustrates a relatively large conduit 7052 relative to a cross-sectional size of the strap 7000 and that is partially recessed into the generally rectangular core 7012. FIG. 79 illustrates a relatively small conduit 7052 positioned within one of the voids 7032 and a rounded core 7012. In other configurations, additional conduits 7032 could be provided in one or both of the voids 7032. The conduits 7052 can be utilized as an air supply, for use in an adjustment mechanism (e.g., containing a locking filament), electrical wiring or any other purpose.

Figure 80:
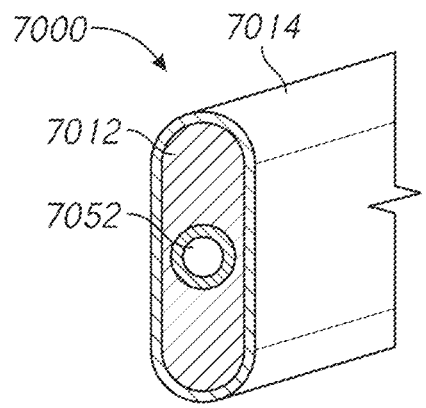
FIG. 80 is a sectional view of a headgear strap having a core and an outer layer with one or more conduits at least partially surrounded by the core.
Figure 81:
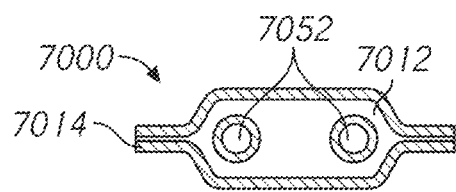
FIG. 81 is a sectional view of another headgear strap having a core and an outer layer with one or more conduits at least partially surrounded by the core.
Figure 82:
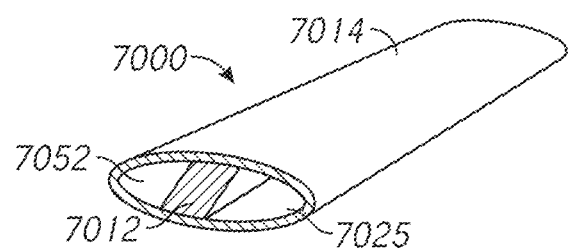
FIG. 82 a sectional view of a headgear strap having a core and an outer layer with a pair of conduits defined by the core.

FIGS. 80-82 illustrate straps 7000 similar to the straps 7000 of FIGS. 78 and 79 except the straps 7000 of FIGS. 80-82 omit voids 7032. The strap 7000 of FIG. 80 includes a conduit 7052 encased within a center of the rectangular core 7012. In other configurations, the conduit 7052 could be off-center and/or additional conduits 7052 could be included. FIG. 81 illustrates a strap 7000 having a pair of conduits 7052 encased within a generally rectangular core 7012. The outer casing comprises a pair of outer layers 7014, the edges of which may or may not be secured to one another. FIG. 82 illustrates a strap 7000 having a pair of conduits 7052 defined by a core 7012 that has an elliptical cross-sectional shape. In some configurations, the core 7012 can be constructed from a somewhat flexible material (e.g., TPE) so that the conduits 7052 are compressible and provide cushioning.

Figure 83:
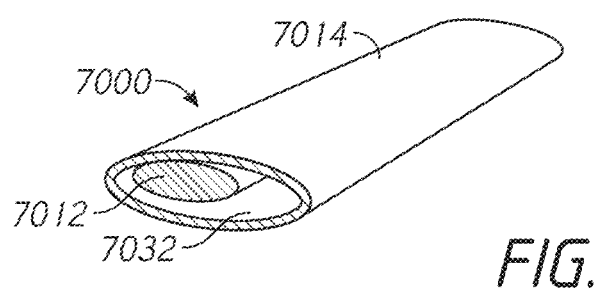
FIG. 83 is a sectional view of a headgear strap having a core and an outer layer with an air gap between the outer layer and the core.
Figure 84A:
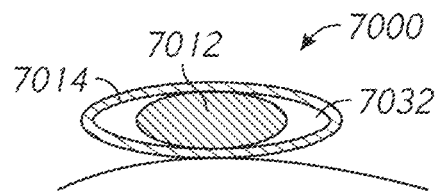
FIG. 84A is a sectional view of the headgear strap of FIG. 83 in a first position against a surface.
Figure 84B:
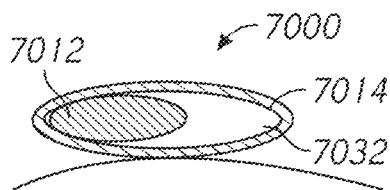
FIG. 84B is a sectional view of the headgear strap of FIG. 83 in a second position against the surface.
Figure 85:
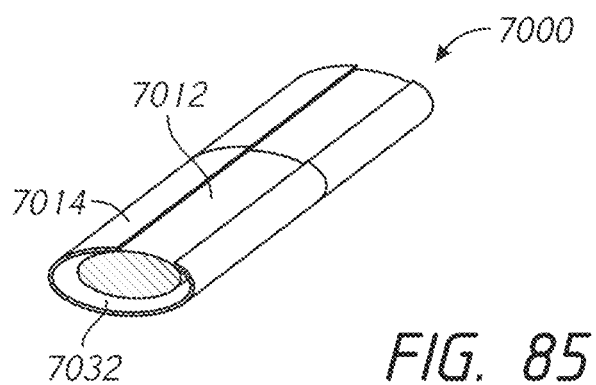
FIG. 85 is a sectional view of a headgear strap having a core and an outer layer with an air gap between the outer layer and the core, wherein a portion of the core is externally exposed.
Figure 86:
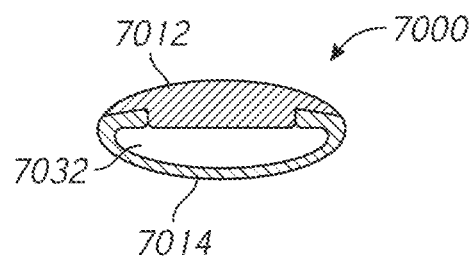
FIG. 86 is a sectional view of another headgear strap having a core and an outer layer with an air gap between the outer layer and the core, wherein a portion of the core is externally exposed.

FIGS. 83-86 illustrate straps 7000 that include at least one air gap 7032. The air gap 7032 of the straps 7000 of FIGS. 83-86 may be larger than the voids 7032 of FIGS. 77-79 and/or may be located (or capable of being located) on more than one side or edge of the core 7012. For example, FIG. 83 illustrates a strap 7000 having an air gap 7032 that, under at least some circumstances, is positioned on one side and both lateral edges of the core 7012. The outer layer 7014 can be attached to the side of the core 7012 opposite the air gap 7032. In some configurations, the air gap 7032 can be located on the inner or user-contacting side of the strap 7000. FIGS. 84a and 84b illustrate how the strap 7000 can permit decoupled movement of the core 7012 and outer layer 7014. Thus, the core 7012 can move without corresponding movement of the outer layer 7014 on the user's skin. FIG. 85 illustrates a similar strap 7000 except a portion of core 7012 is externally exposed. For example, the non-user side of the core 7012 can be exposed and the outer layer 7014 does not completely encircle the core 7012, but only partially surrounds the core 7012. FIG. 86 illustrates a strap 7000 in which the lateral edges of the outer layer 7014 are not exposed, but are overlapped by a portion of the core 7012. The core 7012 can define pockets or recesses configured to receive the lateral edges of the outer layer 7014. The overall arrangement of the core 7012 and outer layer 7014 can provide the strap 7000 with an elliptical cross-sectional shape.

Figure 87:
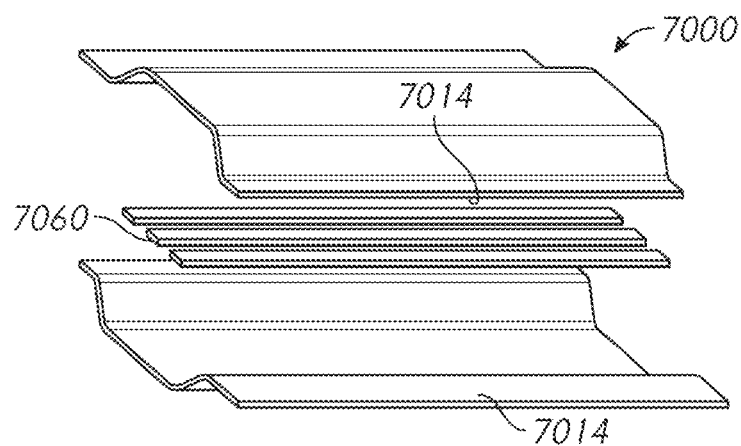
FIG. 87 is an exploded view of an outer layer and reinforcement members of a headgear strap.
Figure 88:
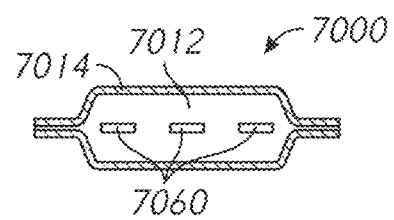
FIG. 88 is a sectional view of a headgear strap incorporating the outer layer and reinforcement members of FIG. 87.
Figure 89:
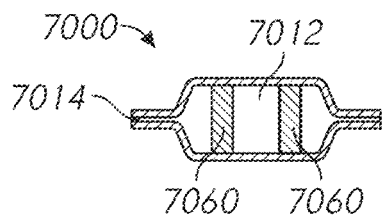
FIG. 89 is a sectional view of a headgear strap having a core, a first outer layer, a second outer layer and one or more reinforcement or separating members that separate the outer layers prior to the introduction of the core material.
Figure 90:
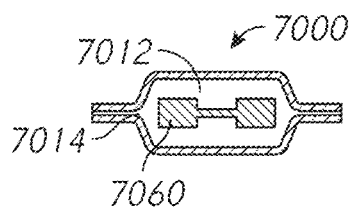
FIG. 90 is a sectional view of a headgear strap having a core, a first outer layer, a second outer layer and a reinforcement member encapsulated in the core.

FIGS. 87-90 illustrate straps 7000 having one or more reinforcement members 7060 within the outer layer 7014. In particular, the illustrated embodiments include one or more reinforcement members 7060 at least partially contained within or surrounded by the core 7012. The reinforcement members 7060 can be fibers or strands of reinforcement materials, such as inelastic thread or carbon fiber, a preformed structural component (e.g., plastic or metal) or a malleable element (e.g., metal wire) that can be deformed and retain the strap 7000 in the deformed state to permit customization of the shape of the strap 7000. The reinforcement members 7060 can modify the properties of the strap 7000 by provided additional or localized rigidity or inelasticity. Thus, the reinforcement members 7060 can extend along a portion or an entirety of the strap 7000 or associated headgear. FIGS. 87 and 88 illustrate a strap 7000 having multiple, elongate reinforcement members 7060 having a generally rectangular cross-sectional shape encapsulated within the core 7012. FIG. 87 illustrates the cover layer 7014 and reinforcement members 7060 prior to the formation of the core 7012. FIG. 89 illustrates a strap 7000 having reinforcement members 7060 that extend partially, a substantial entirely or entirely through the thickness of the core 7012. Such reinforcement members 7060 can assist in maintaining the cover layers 7014 or opposing sides of a tubular cover member separated from one another prior to the formation of the core 7012. In such an arrangement, the members 7060 could be made from the same material of the core 7012 and, thus, may not provide reinforcement to the core 7012, but may simply be cover retention members 7060. FIG. 90 illustrates a strap 7000 having a reinforcement member 7060 having a generally I-shaped cross-section similar to an I-beam. The reinforcement member 7060 has two thickened portions or flanges separated by a thin portion or web.

Figure 91:
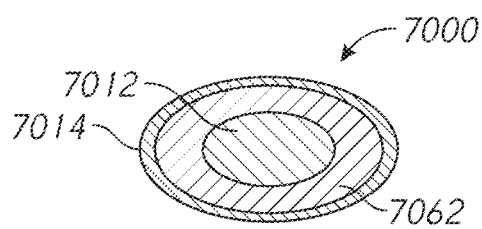
FIG. 91 is a sectional view of a headgear strap having a core, a cushioning layer and an outer layer.
Figure 92:
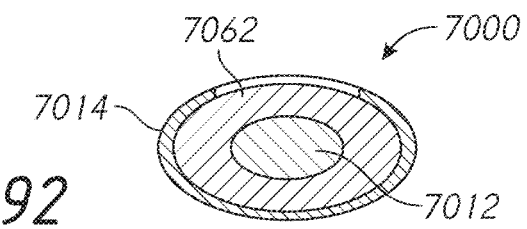
FIG. 92 is a sectional view of another headgear strap having a core, a cushioning layer and an outer layer, wherein a portion of the cushioning layer is externally exposed.

FIGS. 91 and 92 illustrate straps 7000 having a plastic core 7012, an outer layer or layers 7014 and an additional cushioning layer 7062 within the outer layer 7014. In the illustrated arrangements, the cushioning layer 7062 is positioned partially or completely around the core 7012. In FIG. 91, the cushioning layer 7062 is completely enclosed by the outer layer 7014. In FIG. 92, the outer layer 7014 only partially surrounds the cushioning layer 7062 such that a portion of the cushioning layer 7062 is externally exposed. The cushioning layer 7062 can be constructed from any suitable material, such as a soft TPE, foamed plastic or other plastic material that provides a desired amount of cushioning. In some configurations, the cushioning layer 7062 has a hardness of 0-40 on the shore hardness 00 scale. The cushioning layer 7062 can be co-molded with the core 7012, or can be otherwise formed. The illustrated arrangements provide the structure of a semi-rigid headgear with the comfort of a cushioning layer 7062 around it. The cushioning layer 7062 can be deformable so that is can conform to a certain extent to the user, such as above the ears, which can improve comfort. The protrusion of the cushioning layer 7062, as illustrated in FIG. 92, can act as an alignment indicator or provide a region that grips the user's head in use. The outer layer 7014 and the cushioning layer 7062 can be different colors to facilitate recognition of the alignment indicator.

Figure 93:
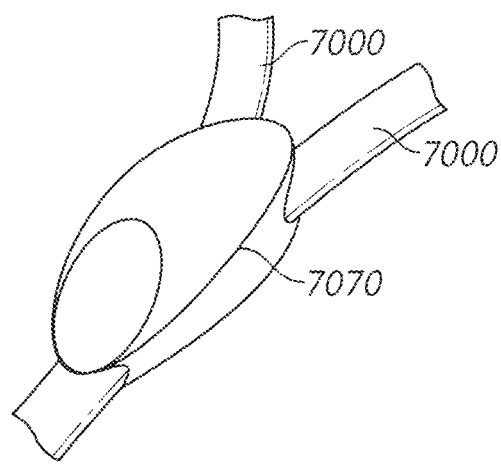
FIG. 93 is a side view of a portion of a headgear having several straps and a connector that connects two or more of the straps.
Figure 94:
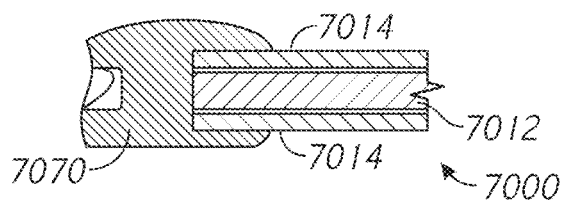
FIG. 94 is a sectional view of the connector and one of the straps of FIG. 93.

FIGS. 93 and 94 illustrate a headgear having multiple straps, some or all of which can be straps 7000 having a core 7012 and an outer layer 7012, possibly among other features disclosed herein. The headgear of FIGS. 93 and 94 comprises a coupling arrangement 7070 that can secure multiple straps 7000 together and/or in a desired position relative to one another. The coupling arrangement 7070 can be similar to the coupling arrangements of 5650 of FIGS. 59-76. The illustrated coupling arrangement 7070 is in the form of an over-moulded joint between multiple straps 7000. FIG. 94 illustrates a cross-sectional view of a connection between the coupling arrangement 7070 and one of the straps 7000. A portion of the coupling arrangement 7070 covers a portion of each side of the outer layer 7014 of the strap 7000 and can be adhered or attached to the cover 7014 via the over-moulding process. In the illustrated arrangement, the coupling arrangement 7070 is separate from the core 7012 (although it could be adhered or attached via the over-molding process); however, in other arrangements, the coupling arrangement 7070 could be formed at the same time as the core 7012. The coupling arrangement 7070 can be rigid or flexible (e.g., TPE). The coupling arrangement 7070 can be substantially flat or shaped, such as shaped to correspond to facial geometry and/or to orient the straps 7000 in three dimensions. Such an arrangement can provide a tidy appearance and prevent fraying or rough edges.

FIGS. 95-101 illustrate straps 7000 that either have no seam in the cover layer(s) 7014 or encapsulate the lateral edges of the outer layer(s) 7014 in the core 7012. Such an arrangement avoids external fabric edges that require finishing in a post processing step. The straps 7000 can include a core 7012, one or more outer layers 7014 and, in some configurations, one or more voids 7032. The core 7012 can have any suitable cross-sectional shape and, if desired, can have a three dimensional curvature. The outer layer 7012 can be any suitable material, such as natural or synthetic fibers, and can be elastic or inelastic.

Figure 95:
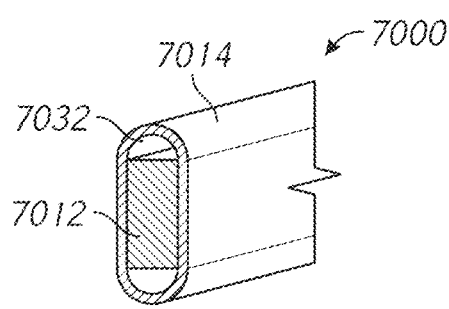
FIG. 95 is a sectional view of a headgear strap having a core and a single piece, seamless outer layer.
Figure 96:
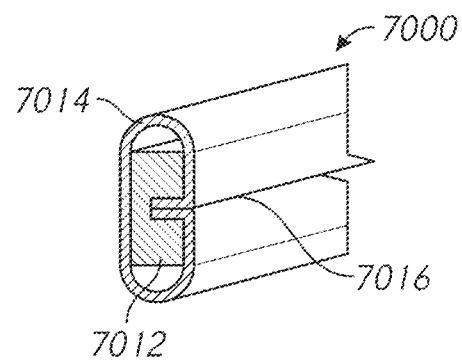
FIG. 96 is a sectional view of a headgear strap having a core and a single piece outer layer having a seam, with edges of the outer layer embedded within the core.
Figure 97:
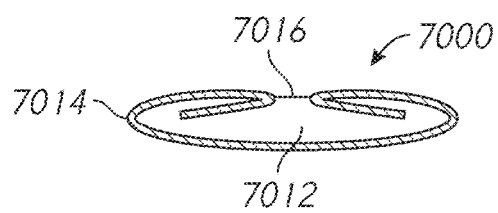
FIG. 97 is a sectional view of another headgear strap having a core and a single piece outer layer having a seam, with edges of the outer layer embedded within the core.

FIGS. 95-97 illustrate straps 7000 having a single piece outer layer 7014. FIG. 95 illustrates a strap 7000 having a seamless, tubular outer layer 7014. The illustrated strap 7000 includes voids 7032 at each lateral edge of the strap 7000 between the core 7012 and the outer layer 7014, which could be omitted. FIG. 96 illustrates a strap 7000 in which the lateral edges of the outer layer 7014 a encapsulated within the core 7012. The illustrated arrangement includes voids 7032, which could be omitted. FIG. 97 illustrates a strap 7000 having an outer layer 7014 with a seam 7016. The seam 7016 can be a sewn, welded, bonded or other type of seam created by another joining method. The lateral edges of the outer layer 7014 can be encapsulated in the core 7012. The seam 7016 is positioned on a side of the strap 7000, which could be the outer side, but could be otherwise positioned, as well.

Figure 98:
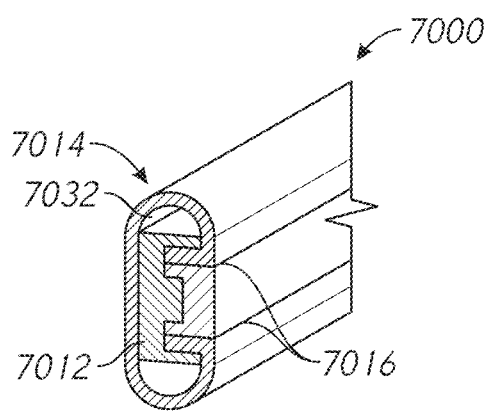
FIG. 98 is a sectional view of a headgear strap having a core and a two piece outer layer having a pair of seams, with edges of the outer layer pieces embedded within the core.
Figure 99A:
FIG. 99A is a sectional view of a two piece outer layer without the core and FIG. 99B is a sectional view of the two piece outer layer after the core has been formed.
Figure 99B:
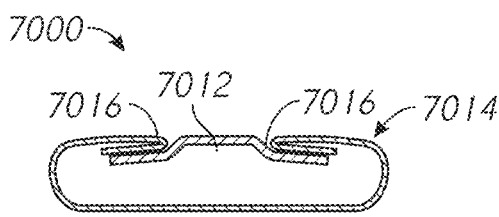

FIGS. 98 and 99 illustrate straps 7000 having multi-piece outer layers 7014. The illustrated straps 7000 have two-piece outer layers 7014. FIG. 98 illustrates a two-piece outer layer 7014 having two seams 7016 positioned on one side of the strap 7000 (e.g., an outer side of the strap 7000). The illustrated arrangement includes voids 7032, which could be omitted, if desired. FIGS. 99a and 99b illustrate a strap 7000 having a two-piece outer layer 7014 in which one or both of the pieces are preformed that are configured to align and temporarily interlock together before the core 7012 is formed. One of the pieces surrounds, overlaps and retains the other piece. When the core material is injected, one piece is pushed toward the other piece and both are bonded to the core 7012. The edges of both pieces are turned inwardly and are encapsulated in the core 7012. FIG. 99a illustrates the two pieces of the outer layer 7014 prior to the formation of the core 7012 and FIG. 99b illustrates the strap 7000 after formation of the core 7012.

Figure 100:
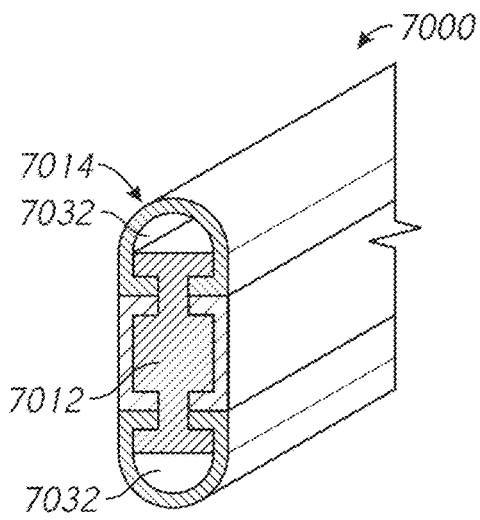
FIG. 100 is a sectional view of a headgear strap having a core and a four piece outer layer having four seams, with edges of the outer layer pieces embedded within the core.
Figure 101:
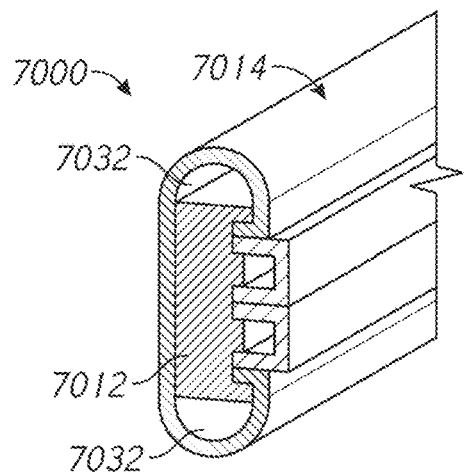
FIG. 101 is a sectional view of another headgear strap having a core and a three piece outer layer having three seams, with edges of the outer layer pieces embedded within the core.

FIGS. 100 and 101 illustrate straps 7000 having multi-piece outer layers 7014 comprising more than two pieces. In FIG. 100, the outer layer 7014 comprises four pieces, which one on each side and one on each end. The pieces are joined by seams 7016, with the edges of the pieces encapsulated in the core 7012. The illustrated strap 7000 includes voids 7032, which could be omitted. FIG. 101 illustrates a strap 7000 having an outer layer 7014 with three pieces. Two of the pieces are on one side, with one piece on the other side and both ends. The pieces are joined at seams 7016, with the edges of the pieces encapsulated in the core 7012. The illustrated strap 7000 includes voids 7032, which could be omitted.

Figure 102:
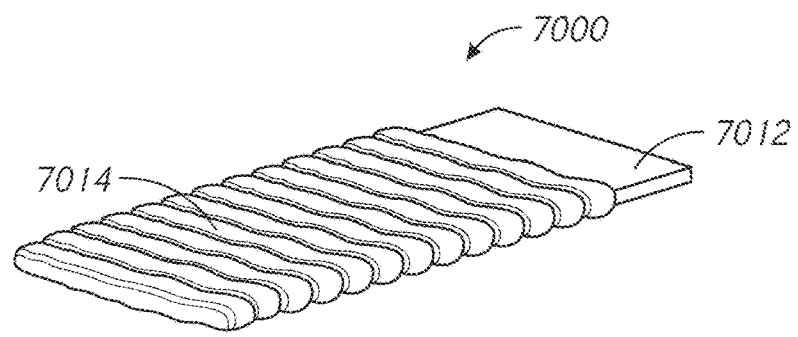
FIG. 102 is a perspective view of a headgear strap having a core and a textured outer layer, with a portion of the outer layer cut away to expose the core.
Figure 103:
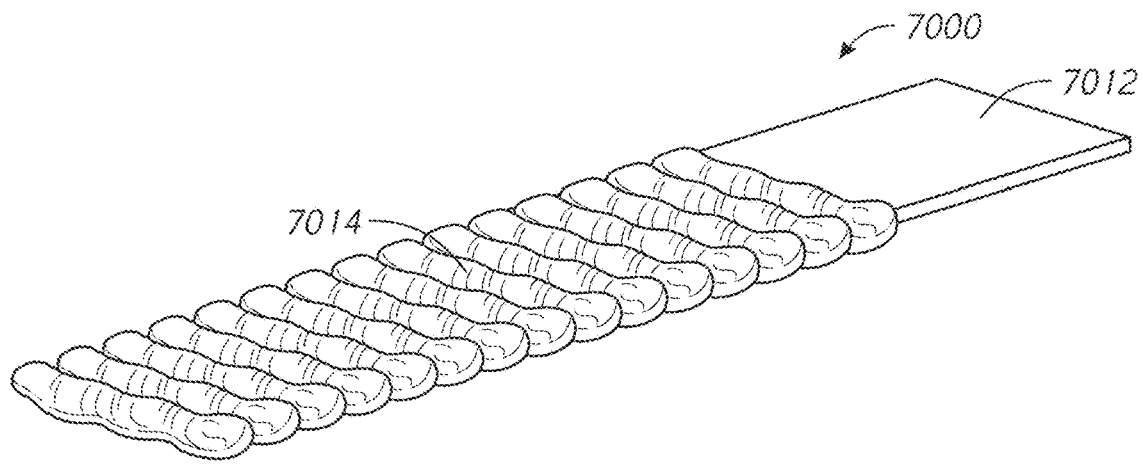

FIGS. 102-104 illustrate straps 7000 having shaped or textured fabric outer layers 7014. FIG. 102 illustrates a strap 7000 having a core 7012 and a ribbed cover layer 7014. FIG. 103 illustrates a strap 7000 having core 7012 and a quilted cover layer 7014. FIG. 104 illustrates a strap 7000 having a shaped core 7012 that provides shaping or texture to the outer layer 7014. For example, the core material can be injected into a space defined by or between one or more outer layers 7014 within a mold having a three dimensional textured surface, which results in the outer layer 7014 being pushed into the texture of the mold and the final strap 7000 having a textured surface. In some configurations, the core 7012 is a relatively soft material, such as TPE. Such arrangements provide visual indication that the strap 7000 is soft and/or cushioned.

FIGS. 105-107 illustrate a headgear configuration 5600 similar to the headgear 5600 of FIGS. 24-26 and FIGS. 59-76. Accordingly, the same reference numbers are used to indicate corresponding or similar features. The straps 5602, 5604 can be constructed in a manner similar to that described with reference to FIG. 77 to include voids, air gaps or air pockets 5632 on each lateral edge of the strap 5602, 5604. In the illustrated arrangement, in a width direction, each of the voids 5632 and the core 5612 could each make up about one-third of the overall width of the strap 5602. In some configurations, the voids 5632 could each have a dimension of, for example, 3 mm and the core 5612 could have a dimension of, for example, 3 mm for a total of 9 mm of width. Such an arrangement provides relatively high flexibility due to the relatively small dimensions of the core 5612, which may be desirable to some users from a perception standpoint, as described above. The user can manually apply a force to the strap 5602 and detect some stretch. However, in use, headgear incorporating the strap 5602 can perform substantially as an inelastic headgear due to friction between the user's head and the strap 5602. In the strap 5604, each of the voids 5632 can make up about one-sixth of the overall width of the strap 5604 and the core 5612 can make up the other two-thirds of the width. The voids 5632 could each have a dimension of, for example, 1.5 mm and the core 5612 could have a dimension of, for example, 6 mm in a width direction of the strap 5604 for a total of 9 mm of width. Such an arrangement can provide good flexibility and less elasticity than a strap having a smaller core 5612. Other suitable relative dimensions could also be used depending on the desired amounts of flexibility and cushioning or compressibility provided by the voids 5632. In the illustrated arrangements, the cover layers 5614 wrap at least partially around the core 5612 to create folds 5334 between the portion of the strap 5602, 5604 having the core 5612 and the portions having the air pockets 5632. These folds can appear as stripes extending lengthwise along the straps 5602, 5604 to provide a nice aesthetic look to the strap 5602, 5604 and associated headgear 5600.

Figure 108:
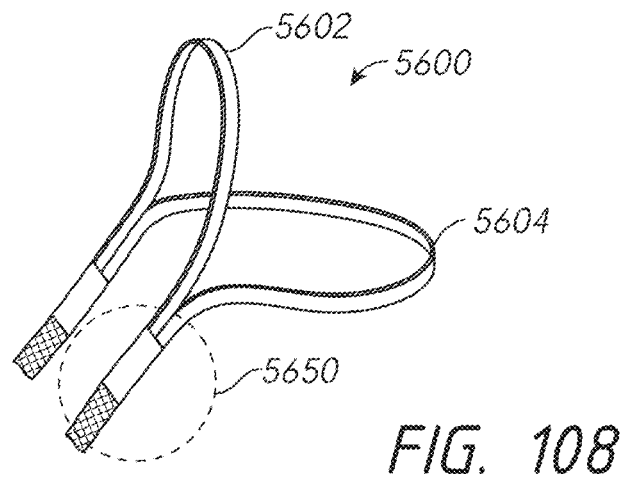
Figure 109:
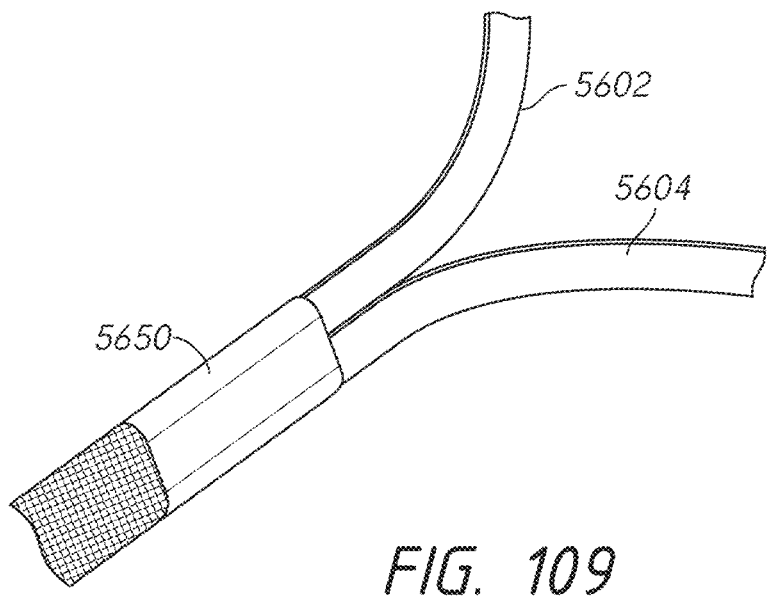
Figure 110:
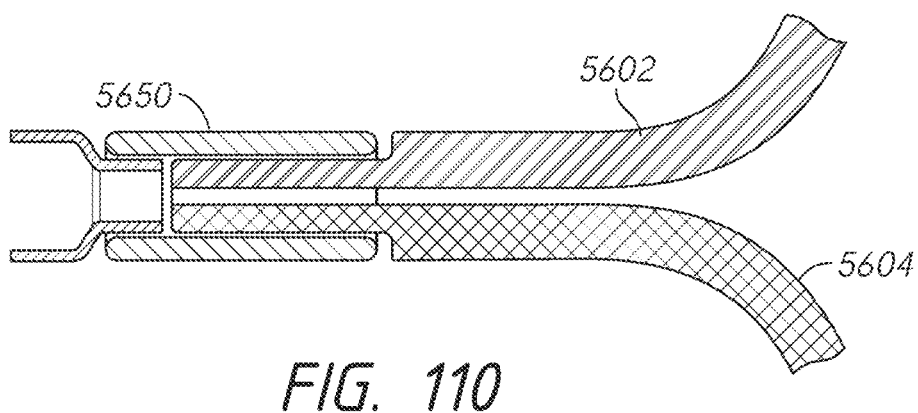

FIGS. 108-110 illustrate a headgear configuration 5600 similar to the headgear 5600 of FIGS. 24-26 and FIGS. 59-76. Accordingly, the same reference numbers are used to indicate corresponding or similar features. However, the straps 5602, 5604 can neck down or have a reduced thickness in at least the portions that are connected by the connector 5650 such that the combined thickness of the connected portion of the straps 5602, 5604 are less than twice the thickness of the strap 5602, 5604 outside of the connected portion. In some configurations, the thicknesses of the individual straps 5602, 5604 in the connected portion is about one-half of the thicknesses outside the connected portion such that the connected portion has a thickness approximately equal to the thickness of each strap 5602, 5604 outside of the connected portions. In other arrangements, the top strap 5602 can be narrower than the rear strap 5604 and the rear strap 5604 narrows at the connection 5650 to the top strap 5602. In such an arrangement, the rear strap 5604 can narrow by an amount that is approximately the width of the top strap 5602. Other combinations of variable or tapering thicknesses between the connection portion and portions outside of the connection portion can also be employed. Similarly, the straps 5602, 5604 could be overlapped in a thickness direction and the thicknesses of the individual straps 5602, 5604 could be reduced in the connected portion compared to portions outside of the connected portion.

FIGS. 111-114 illustrate a headgear configuration 5600 similar to the headgear 5600 of FIGS. 24-26 and FIGS. 59-76. Accordingly, the same reference numbers are used to indicate corresponding or similar features. In some configurations, the straps 5602, 5604 can be reduced in the portion connected by the connector 5650 compared to portions outside of the connected portion. As described above, in at least some configurations, the combined width of the straps 5602, 5604 in the connected portion is substantially equal to the thickness of one or both of the straps 5602, 5604 outside of the connected portion.

FIG. 113 illustrates several arrangements of connecting the straps 5602, 5604. For example, the straps 5602, 5604 can each be substantially L-shaped in cross-section. The L-shape can be defined by both the core 5612 and the cover layer 5614 or by just the cover layer 5614, for example. The cover layer 5614 can be formed into the L-shape by the mold tool by a process as described herein or by a post-molding step, for example. The cover layer 5614 can have a loose fabric portion or edge that can be shaped during the molding process or afterwards. The L-shaped cover layers 5614 of the straps 5602, 5604 could be reversed so that the fit together and the connector 5650 can be overmolded onto or between the straps 5602, 5604. Alternatively, the straps 5602, 5604 could include a convex edge and a concave edge that complement one another. The connector 5650 can be overmolded onto or between the straps 5602, 5604. As described above, the cross-sectional shape can be defined by the core 5612 and cover 5614 or by the cover 5614 alone. In some configurations, the straps 5602, 5604 both have concave edges that cooperate to define a relatively large space therebetween. The connector 5650 can be overmolded onto or between the straps 5602, 5604, such as within the space defined by the concave edges. As described above, the cross-sectional shape can be defined by the core 5612 and cover 5614 or by the cover 5614 alone. At least the second or rear strap 5604 can include air gaps on one or both lateral ends, as disclosed herein and shown in FIG. 114.

FIGS. 115A-118 illustrate an intra-moulded bifurcated headgear configuration 5600 similar to the headgear 5600 of FIGS. 24-26 and FIGS. 59-76. Accordingly, the same reference numbers are used to indicate corresponding or similar features. As shown in FIGS. 116-118, the arrangements generally comprise a front strap 5610 connected to bifurcated straps 5602, 5604. Providing bifurcated straps 5602, 5604 stabilizes the headgear 5600 on the user's head. The front strap 5610 can be connected to an attachment clip 5680 for attaching to a mask. The bifurcated straps 5602, 5604 of the headgear 5600 are positioned around the ears of the user for improved comfort.

As illustrated in FIGS. 115A-C, the straps 5602, 5604, 5610 have a cover layer 5614. The cover layer 5614 can be a fabric casing constructed from natural or synthetic fabric or textile material, any other materials disclosed herein or any other suitable material. The cover layer 5614 can comprise knitted, woven or braided materials and can be elastic. Preferably, the cover layer 5614 has a texture that is soft to the touch and in appearance. The cover layer 5614 may be circular, tubular and hollow in cross-section. As illustrated in FIGS. 115B-C, the cover layer 5614 may be formed by joining first and second cover layers 5614A, 5614B. Alternatively, the cover layer 5614 may be formed or knitted into an integrally woven fabric tube. That is, the cover layer 5614 may be woven and preformed into a woven fabric tube that includes the front strap and the bifurcated straps 5602, 5604.

As illustrated in FIGS. 115A-118, portions of the front strap 5610 and/or the bifurcated straps 5602, 5604 may be filled with a relatively rigid or semi-rigid intra-moulded core 5612. In other words, core material may be injected into the hollow cover layer 5614 to allow specific portions of the headgear 5600 to be relatively rigid or semi-rigid while allowing other portions of the headgear to be elastic. As shown in FIG. 115A, only the front strap 5610 and the junction 5603 of the bifurcated straps 5602, 5604 may be filled with the intra-moulded core 5612. As such, the front strap 5610 and the junction 5603 may be substantially rigid or inelastic while the portion of the bifurcated straps 5602, 5604 beyond the junction 5603 remains elastic. Similarly, in FIG. 116, only the front straps 5610 include the intra-moulded core 5612. As such, the semi-rigid front region stabilizes the mask on the user's face while the elastic portions allow the headgear to be easily fitted onto the user. Further, the elastic portions allow the rear of the headgear to fit a range of head sizes. In FIG. 117, the front straps 5610 and portions of the bifurcated straps 5602, 5604 may be filled with the intra-moulded core 5612. Accordingly, the front straps 5610 and the bifurcated region of the bifurcated straps 5602, 5604 are rigid while the rear portions of the bifurcated straps 5602, 5604 are elastic. In FIG. 118, the front straps 5610 and the bifurcated straps 5602, 5604 may be filled with the intra-moulded core 5612 to form a headgear 5600 that is substantially rigid throughout.

The intra-moulded core 5612 may be a plastic material or any other suitable material. Further, the intra-moulded core 5612 may be fused and permanently bonded with the cover layer 5614 to produce a substantially rigid or inelastic structure. As illustrated in FIG. 115A, the attachment clips 5680 may be integrally formed and molded with the intra-moulded core 5612.

FIGS. 119A-B show a mould tool 5200 configured to form the intra-moulded bifurcated headgear configuration 5600. The mould tool 5200 comprises a first tool half 5210 and second tool half 5220. The first and second tool halves 5210, 5220 are joined together to form a strap cavity 5222. The strap cavity 5222 is configured to receive the fabric casing 5110. In some configurations, the fabric casing 5110 may be cut or preformed to fit exactly within the fabric casing 5110, such that the fabric casing 5110 is easily aligned within the strap cavity 5222. When the mould tool 5200 is in a closed position and the fabric casing 5110 is secured in place, the core material can be injected into the fabric casing 5110, via a gate and runner system (not shown), which in some configurations can be the same as or similar to that of FIG. 3. Accordingly, the headgear 5600 may be easily molded in a single manufacturing process.

FIG. 119C shows a cross-section schematic view of a mould tool 5200 configured to secure the fabric casing 5110 in place within the mould tool 5200 during forming process. The mould tool 5200 comprises a first tool half 5210 and second tool half 5220. The first and second tool halves 5210, 5220 are joined together to form a fabric casing cavity 5222, a mould insert cavity 5224 and a gate 5325. An insert 5326 is inserted into an open end of the fabric casing 5110 and the mould insert 5326 and the fabric casing 5110 are both positioned within the mould insert cavity 5224 and the fabric casing cavity 5222, respectively. When using a fabric casing 5110 to form the straps of a headgear, the fabric casing 5110 must be held open in order to allow the plastic core to be injected within the fabric casing 5110. Accordingly, the mould insert 5326 prevents the open end of the fabric casing 5110 from closing. The mould insert 5326 comprises a pre-made component that fits inside the open end of the fabric casing 5110 and pushes the opening of the fabric casing 5110 outwards towards the walls of the fabric casing cavity 5222 in the first and second tool halves 5210, 5220. The mould insert 5326 has a central opening 5328 that is aligned with the gate 5325 through which a direct flow path is provided for core material to be injected into the fabric casing 5110. The mould insert 5326 may be made of plastic or metal. If made of plastic, the mould insert 5326 may be made of the same plastic as that of the core so that a chemical bond can be formed between the mould insert 5326 and the core material during the intra-moulding process. Further, the insert 5326 may be formed in a shape that can have additional function as a connector between headgear components, adjustment mechanisms or between the headgear and mask (e.g., attachment clips 5680).

FIGS. 119D-G illustrate a mould tool arrangement 5200 configured to retain the fabric casing 5110 in a fixed position so that it does not move under the injection forces of the core material. FIG. 119D shows a cross-sectional schematic view of a mould tool 5200 configured to retain the fabric casing 5110. The mould tool 5200 comprises a first tool half 5210 and second tool half 5220. The first and second tool halves 5210, 5220 are joined together to form a mould tool cavity 5224. The surface of first and second tool halves 5210, 5220 include a plurality of retention spikes 5327 that protrude from the surface of first and second tool halves 5210, 5220 and extend in a direction towards the fabric casing 5110. As shown in FIG. 119E, the retention spikes 5327 may be spaced equidistant apart and across the surfaces of the tool halves 5210, 5220 that are perpendicular to the opening/closing directions of the first and second tool halves 5210,

5220. As shown in FIGS. 119F and 119G, the retention spikes 5327 are configured to prevent movement between the fabric casing 5110 and the walls of the mould tool cavity 5224. The spikes 5327 can have a sharp tip that penetrates the surface of the fabric casing. The retaining spikes 5327 may have a height such that the retention spikes 5327 are either submerged in the fabric casing 5110 such that they do not pierce through the entire thickness of the fabric casing 5110 (see FIG. 119F) or pierce through the entire thickness of the fabric casing 5110 (FIG. 119G). Accordingly, prior to the plastic core being injected, retaining spikes 5327 may secure and hold open the fabric casing 5110 within the mould tool cavity 5224.

In contrast to fabric casings constructed from bonded layers, woven fabric tubes have a tendency to remain open outside of forces being applied to the woven fabric tube. As such, the moulding tool may not need separate structures to hold an open end of the woven fabric tube open in order for core material to have a path into the woven fabric tube. FIGS. 120A and 120B show a mould tool 5200 configured to form a fabric casing comprising of a woven fabric tube 5110. The mould tool 5200 comprises a first tool half 5210 and second tool half 5220. The woven fabric tube 5110 may be positioned within the mould tool cavity 5224 and the first and second tool halves 5210, 5220 are joined together. As illustrated in FIG. 120B, the end of the woven fabric tube remains open despite the closing of the tool cavity. Accordingly, the core material has a path into the woven fabric tube 5110.

FIG. 121 illustrates an alternative construction of an intra-moulded strap 5604 comprising a core 5612 and a cover layer, which comprises a first cover layer 5614A and a second cover layer 5614B and rails 5618. The cover layers 5614A, 5614B can be constructed from a composite of multiple materials, such as relatively soft fabric or textile and foam or similar cushioning materials. The first and second cover layers 5614A, 5614B and the rails 5618 define a cavity for receiving an intra-moulded core 5612 that comprises a relatively rigid material, such as a plastic. In the illustrated arrangement, edges of the cover layers 5614A, 5614B are covered by the rails 5618. The rails 5618 may be formed from a soft silicone or plastic material to provide the strap with a soft and rounded edge and finish. The soft and rounded edge of the rails 5618 improves comfort and reduces irritation caused by the strap when rubbed against the skin. Further, the soft and compliant texture of the rails 5618 provides the perception that the strap 5604 is soft or has a soft construction despite the actual rigidity of the strap 5604 created by the intra-moulded core 5612. That is, the rails 5618 may partially mask or conceal the rigid construction of the strap 5604, which may affect user perception. Moreover, the soft silicone rails 5618 may reduce wear and improve the usable life of the strap 5604.

FIG. 122A-C illustrates an alternative construction of an intra-moulded tubular strap head strap 5602 comprising an airpocket core 5632, a cover layer 5614 and intra-moulded rails 5618. The cover layer 5614 covers the intra-moulded rails 5618 and defines the airpocket core 5632. The cover layer 5614 may be constructed from a fabric that is airtight such that the airpocket core 5632 is sealed and remains inflated.

The intra-moulded rails 5618 combined with the airpocket core 5632 provide a head strap 5602 that is rigid in structure but also lightweight. Further, the airpocket core 5632 of the head strap 5602 provides cushioning and padding to improve user comfort. Further, the cover layer 5614 may be arranged such that the air pocket core 5632 is formed closer to one side of the strap 5604 than the other. Accordingly, as shown in FIG. 120C, the air pocket core 5632 may extend in a direction towards the user's face and prevent the harder and more rigid intra-moulded rails 5618 from contacting the user's skin.

FIG. 123A illustrates an alternative construction of an intra-moulded tubular strap 5602 comprising a cover layer 5614 surrounding a structured core 5642 having internal structure. The cover layer 5614 may be constructed from a composite of multiple materials, such as relatively soft fabric or textile and foam or similar cushioning materials. The core 5642 may be formed by injection molding a semi-rigid plastic into the cavity within the hollow center within the cover layer 5614. The core 5642 may be substantially rectangular in cross-section. The core 5642 has a pattern of apertures 5644 that extend through the thickness of the core 5642. The apertures 5644 allow the strap 5602 to be flexible along the length of the strap 5602 while retaining stiffness in other directions. That is, the strap 5602 may be stretched or compressed in a direction parallel to the lengthwise direction of the strap 5602 while still being rigid in other directions. As such, the apertures 5644 may partially mask or conceal the rigid construction of the strap 5602, which may affect user perception. Moreover, the apertures 5644 provide for a lighter weight and breathable strap that may improve user comfort. The apertures 5644 may be positioned at specific areas of the strap 5602 where elasticity is desired. Alternatively, the apertures 5644 may be positioned throughout the entire length of the strap 5602.

FIG. 123B illustrates the construction of the strap 5602 by using a mould tool 5200. Initially, the semi-rigid plastic is injected into the hollow center of the cover layer 5614. Then, the apertures 5644 within the core 5642 are then formed by compressing layers of the fabric cover layer 5614 together, by a mould tool shut-off, such that the molten plastic of the core 5642 cannot flow between the layers of the fabric cover layer 5614 in the regions where an aperture 5644 is to be formed, as shown in FIG. 123B.

FIG. 124A illustrates an alternative construction for an intra-moulded tubular head strap 5602 having a complex 3D shape with continuously variable geometry and cross-section along its length. In other words, the head strap 5602 may have varying width, thickness, edge radii, surface curvature (concave/convex) along its length, as shown along cross-sectional line A-A in FIG. 124B and cross-sectional line B-B in FIG. 124C. The varying curvature along the length of the head strap 5602 provides customised performance and structure to specific regions of the headgear. For example, the curved surface 5646 of the head strap 5602 along cross-sectional line A-A in FIG. 124B may be shaped to conform to the head geometry closer to the mask and the face of the user (e.g., cheek bones). In contrast, the head strap 5602 along cross-sectional line B-B in FIG. 124C may be shaped to have minimal size/volume such that the head strap 5602 may fit closely above, behind, under and/or around the user's ear.

The cover layer 5614 may be knitted or woven and the core 5642 may be formed by injection molding a semi-rigid plastic into the cavity within the hollow center within the woven cover layer 5614. It should be noted that the complex 3D shape of the strap 5602 cannot be achieved by sliding a knitted strap over a continuous curvature plastic core because the knitted strap has to be large enough to pass over the largest cross-section of the core, thus the knitted strap will be over sized and bulky in some regions. Further, injection moulding allows branding or orientation indicators to be moulded into the continuous curvature head strap 5602 in a single manufacturing process.

FIGS. 125A-G and 126A-C illustrate straps 7602, 7702 having permanently formed features 7652, 7752 such as branding logos (FIG. 125A-C), indicators (FIG. 125E), grip bumps (FIGS. 125F-G and 126B-C), etc. FIGS. 125A-125G illustrate a strap 7602 with features 7652 permanently and integrally formed into the strap by intra-moulding. FIGS. 126A-C illustrate a strap 7702 with features 7752 permanently and integrally formed onto the strap by over-moulding. Accordingly, the features 7652, 7752 are integral with the strap 7652, 7752 and cannot be removed such that the features are always visible and identifiable (i.e., logos, branding, indicators). Further, the features 7652, 7752 may be positioned anywhere on the strap 7602, 7702 to vary the texture of the strap 7602, 7702 to increase tactile grip (i.e., grips) which improves handling of the headgear.

FIGS. 125A-G illustrates an intra-moulded strap 7602 with the features 7652 embossed on the strap 7602. Similar to intra-moulded straps previously described, the strap 7602 may comprise a semi-rigid plastic core 7612 that is covered by a fabric skin 7614. The features 7652 may be embossed during the intra-moulding process such that the features 7652 may be integrally applied to the headgear without a separate manufacturing step or process (i.e., reduces manufacturing steps and cost).

As illustrated in FIG. 125A, the features 7652 may be embossed into the strap 7602 in a thickness direction of the strap 7602. In other words, the features 7652 may be recessed into the strap 7602 to form a depression 7616 in both the core 7612 and the fabric skin 7614. Alternatively, the features 7652 may extend or protrude above and beyond the fabric skin 7614 to form a protrusion 7618, as shown in FIGS. 125E-G. That is, the features 7652 may be formed on a thicker region of the core 7612 that is still covered by the fabric skin 7614.

In some configurations, openings 7618 may be formed through the fabric skin 7614 such that the core 7612 is exposed, as shown in FIGS. 125B and 125E. The openings 7618 may be formed by any variety of techniques, such as but not limited to, laser-cutting. The exposed portions of the core 7612 may protrude through the openings 7618 of the fabric skin 7614 (FIGS. 125C and 125E), be flush with the fabric skin 7614 (FIG. 125D), or be recessed below the fabric skin 7614 (FIGS. 125B and 125C).

FIGS. 126A-C illustrate a strap 7702 having features 7752 overmoulded onto the strap 7702. The strap 7702 comprises a single layer of fabric such as, but not limited to, Breath-o-Prene™. The logo 7752 can be a flexible plastic such as a TPE or a silicone, to provide a soft touch that does not interfere with the functionality of the strap. The features 7702 may be overmoulded onto the strap 7702 and positioned anywhere along the length of the strap 7702.

FIGS. 127A-136 illustrate various moulded headgear configurations, which can be similar to other headgear disclosed herein and can by suitable for the same or similar applications. The headgear of FIGS. 127A-136 can be connected to an interface by any suitable coupling arrangement, such as any of those disclosed herein. The headgear can be modified for use with other types of interfaces, such as those employing a forehead rest, for example. Similarly, the headgear can be connected to an interface at single or multiple connections at various locations, for example, by using side, central or overhead straps. In addition, features, components, materials or manufacturing methods of the headgear of FIGS. 127A-136 can be interchanged with one another to create other headgear variations beyond those specifically disclosed. The illustrated headgears each comprise several straps, including a crown or top strap, a rear strap and at least one front strap. Other variations can omit one or more of these straps and/or can include additional straps. Any of the straps can incorporate length or other adjustment mechanisms, as desired, including any of the strap adjustment mechanisms disclosed herein or other suitable arrangements.

FIGS. 127A-B illustrate a headgear configuration 10100 having a single back strap 10120 (i.e., without a crown strap). The back strap 10120 may include a rear portion 10122 and a frontal portion 10124. When donned by the user, the frontal portion 10124 of the single rear strap 10120 is positioned across the user's cheeks just below the eyes and rearward towards the user's ears. As illustrated in FIG. 127A, the frontal portion 10124 is connected with the rear portion 10122 above and slightly forward of the user's ear. The rear portion 122 extends above the user's ears before extending downward towards the lower rear portion (i.e., occipital bone) of user's head. The rear and frontal portions 10122, 10124 may have different constructions. In other words, the rear portion 10122 may be more rigid than the frontal portion 10124. Accordingly, the frontal portion 10124 stretches to provide a retention force to the mask 10102 and allows the headgear 10100 to stretch such that the headgear may be donned on the user's face. The headgear configuration 10100 having the single back strap 10120 provides a headgear arrangement that is low in cost, easily manufactured and easily fitted to a user.

FIG. 127B illustrates a cross-sectional view of the rear portion 10122 along a line A-A in FIG. 127A. The rear portion 10122 includes a core 10130 that is covered by a cover layer 10132. The core 10130 may be a plastic material or any other suitable material, as previously disclosed herein. Similarly, the cover layer 10132 may be constructed from a composite of multiple materials, such as relatively soft fabric or textile and foam or similar cushioning materials. Also, as shown in FIG. 127B, the strap 10120 can be constructed in a manner similar to that described with reference to FIG. 77 to include voids, air gaps or air pockets 10134 on each lateral edge of the strap 10120. The air pockets 10134 provide flexibility and cushioning or compressibility. The frontal portion 10124 may be constructed from elastic knitted, woven or braided materials. In some configurations, the frontal portion 10124 may also include an intra-moulded core. In an alternative configuration (not shown), the same core material may be used in both the rear and front portions 10122, 10124 to provide a headgear arrangement having substantially the same modulus of elasticity throughout.

FIGS. 128A-C illustrates a headgear configuration 10200 having a lower strap 10220 connected to a crown strap 10230 by an arched connector 10240. The lower strap 10220 may be similar in construction as the single rear strap 10120 in FIGS. 127A-B. Therefore, duplicative discussion is omitted. The crown strap 10230 may be constructed from relatively soft fabric, textile, foam or similar cushioning materials, as previously disclosed herein. The arched connector 10240 may be constructed from plastic that is overmolded onto both the lower strap 10220 and the crown strap 10230. The arched connector 10240 is positioned above the user's ear and has a curved shape that is contoured similar to the curvature of the lower strap 10220. Overmolding the arched connector 10240 allows the lower strap 10220 and the crown strap 10230 to be easily joined. Further, the arched connector 10240 provides a relatively low profile connector that is substantially the same width and thickness as the lower strap 10220.

FIG. 129 illustrates a headgear configuration 10300 having a rear strap 10320, a crown strap 10330, and a front strap 10340. The front strap 10340 may have a different construction than the rear and crown straps 10320, 10330. In other words, the front strap 10340 may be substantially more rigid than the rear and crown straps 10320, 10330. The front strap 10340 may have a core formed from a relatively rigid material while the rear and crown straps 10320, 10330 have a core formed from a more flexible core material. In some configurations, the rear and crown straps 10320, 10330 are not filled with a core material. The rear and crown straps 10320, 10330 have a cover layer formed from elastic knitted, woven or braided materials. The rear and crown straps 10320, 10330 are flexible in construction such that the rear and crown straps 10320, 10330 may stretch to fit a wide range of head sizes as well as providing a retention force for the mask 10310. Further, the rear and crown straps 10320, 10330 relocate the retention force portions of the headgear away from the sensitive parts of the head (i.e., the face).

FIGS. 130A-D illustrates a bifurcating headgear configuration 10400 having a variable knit intra-mould. The bifurcating headgear configuration 10400 is similar in construction as the headgear configuration 10100 with the single rear strap 10120 in FIGS. 127A-B. However, the rear portion of the bifurcating headgear configuration 10400 is bifurcated into a lower rear portion 10422 and an upper rear portion 10424. The headgear 10400 may have an outer cover 10430 that is formed entirely from an elastic woven material, as previously described herein. The outer cover 10430 may span between the lower and upper rear portions 10422, 10424. FIG. 130B illustrates a cross-section of the headgear 10400 along a line A-A in FIG. 130A. FIG. 130C illustrates a cross-section of the headgear 10400 along a line B-B in FIG. 130A. As illustrated, the outer covering 10430 is tightly knitted or woven over the lower and upper rear portions 10422, 10424 while the portion of the outer covering 10430 between the lower and upper rear portions 10422, 10424 does not include core material. Accordingly, the portion of the outer covering 10430 between the lower and upper rear portions 10422, 10424 stretches to control movement and provide a retention force on the mask 10402. As shown in FIG. 130D, the headgear 10400 may be constructed as a single piece within a mould tool 10450. In other words, the headgear 10400 may be easily molded in a single manufacturing process.

FIGS. 131A-C illustrate a construction of a headgear configuration 10500 having a fully integrated bifurcated rear strap 10520 and crown strap 10530. As shown in FIG. 131B, two layers of outer cover 10540 may be joined together by sewing, adhesives, or any bonding techniques. The outer cover 10540 may be the same material or different materials. As shown in FIG. 131C, a core material 10550 may be positioned between the outer covers 10540. Voids, air gaps or air pockets 10534 on each lateral edge of the straps. The air pockets 10534 provide flexibility and cushioning or compressibility. Further, the seams 10536 may be positioned within the air pockets 10534 to provide a seamless aesthetic appearance.

FIGS. 132A-C illustrate an alternate configuration having a headgear 10600 with the core material 10640 exposed and formed on the outside surface of the outer cover 10630. The exposed core material 10640 allows the straps of the headgear 10600 to be easily moulded and formed into complex shapes. Further, the exposed core material 10640 allows the headgear 10600 to be easily cleaned. Even further, the plastic core material 10640 provides low friction such that the headgear 10600 easily slides against other objects, such as a pillow. In FIG. 132B, the core material 10640 is recessed into the outer cover 10630 such that the core material 10640 is substantially flush with the outer cover 10630. In contrast, FIG. 132C illustrates the core material 10640 positioned over the outer cover 10630 without being recessed into the outer cover 10630.

FIG. 133 illustrates a headgear 8000 for use in combination with a full-face mask 8100. The full-face mask 8100 has a mask frame 8110 with a T-piece 8112. The headgear 8000 is not limited to use with only a full-face mask breathing apparatus 8100 and may be used in combination with a nasal mask with a T-piece. The headgear 8000 has a bifurcated top strap 8010 and rear strap 8020. The top strap 8010 and rear strap 8020 are connected near an upper connection point 8030 that is located at the sides of the user's forehead. A fabric strap 8040 extends from the upper connection point 8030 and loops through an opening 8114 of the T-piece 8112 of the mask frame 8110. The end of the fabric strap 8040 may include a hook pads or patches that can be secured to complementary loop surfaces on the fabric strap 8040. The fabric strap 8040 allows the user to adjust the tightness between the top portion of the headgear 8000 and the T-piece 8112. The fabric strap 8040 may be attached to the T-piece 8112 by any variety of releasable mechanical fastening arrangements, such as, but not limited to, clips, push or snap connectors, etc. A lower connection point 8050 is positioned below the upper connection point 8030 and located forward of the user's ear and approximately in line with the user's mouth. The lower connection point 8050 may be connected to the mask frame 8110 by one or more adjustment mechanisms 8120. The adjustment mechanisms 8120 may include one of a variety of adjustment mechanism configurations, such as but not limited to, a one-way friction mechanism or any other appropriate locking mechanism.

FIG. 134 illustrates a headgear 8000 in use in combination with a nasal mask 8200. The nasal mask 8200 has a mask frame 8210. Similar to FIG. 133, the headgear 8000 has a bifurcated top strap 8010 and rear strap 8020. The headgear 8000 is not limited to use with only a nasal mask and may be used in combination with a full-face mask with or without a T-piece or a respiratory mask having an under-nose sealing region. The headgear 8000 has an upper strap 8032 that is connected to the top strap 8010 and the rear strap 8012. The headgear 8000 is located on the side portion of the user's forehead that extends across the cheek between the user's ear and eye. The upper strap 8032 can be connected directly to the mask frame 8210. Alternatively, there may be an adjustment mechanism positioned between the upper strap 8032 and the mask frame 8210. A lower strap 8052 is connected to the rear strap at a position behind the user's ear and extends substantially downward to a position below the user's ear and forward towards the mask frame 8210. In other words, the lower strap 8052 is connected to the rear strap 8012 and extends downward around the user's ear and extends across the user's cheek. The lower strap 8052 is connected to the mask frame 8210 by one or more adjustment mechanisms 8120. The adjustment mechanisms 8120 may include one of a variety of adjustment mechanism configurations, such as but not limited to, a one-way friction mechanism or any other appropriate locking mechanism.

FIG. 135 illustrates a headgear 8000 in use in combination with a nasal pillows (direct nasal) mask 8300. Similar to FIGS. 133 and 134, the headgear 8000 has a bifurcated top strap 8010 and rear strap 8020. The headgear 8000 has a front strap 8034 that is connected to the top strap 8010 and the rear strap 8012. The front strap 8034 extends between the ear and eye of the user and towards the bottom of the nose. The front strap 8034 also extends across the front of the mask 8300 to form a portion of the frame 8310. In alternative embodiments the front strap 8034 may terminate before the mask 8300 and connect to a separate mask frame 8310. Further, in some configurations, an adjustment mechanism (not shown) may be positioned between the front strap 8034 and mask frame 8310.

FIG. 136 illustrates a headgear 8000 in use in combination with a nasal mask 8200. The nasal mask 8200 has a mask frame 8210. The headgear 8000 is not limited to use with only a full-face mask breathing apparatus 8100 and may be used in combination with a nasal mask without a T-piece or a respiratory mask having an under-nose sealing region. The headgear 8000 has a bifurcated top strap 8010 and rear strap 8020. The top strap 8010 and rear strap 8020 are connected near an upper connection point 8030 that is located at the sides of the user's forehead and in line with the user's eye. The upper connection point 8030 is connected to the mask frame 8210 by an adjustment mechanism 8120. The adjustment mechanisms 8120 may include one of a variety of adjustment mechanism configurations, such as but not limited to, a one-way friction mechanism or any other appropriate locking mechanism. The adjustment mechanism 8120 extends towards the mask frame 8210 across the user's cheeks just below the eyes. A lower connection point 8050 is connected to the headgear 8000 below the upper connection point 8030 and is positioned approximately in line with the bottom of the user's nose. The lower connection point 8050 is also connected to the mask frame 8210 by an adjustment mechanism 8120, which extends towards the mask frame 8210 across the user's cheeks just below the eyes.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An elongate strap for a headgear, comprising:
   a textile outer layer;
   a plastic core having a cross-sectional shape comprising two long sides and two short sides,
   wherein the textile outer layer is secured to the two long sides of the plastic core to form an integral structure,
   wherein the textile outer layer is spaced from each of the two short sides of the plastic core to create voids on each lateral edge of the elongate strap, and
   wherein the textile outer layer wraps at least partially around the two short sides of the plastic core to create folds between a portion of the elongate strap having the plastic core and portions of the elongate strap having the voids.

2. The elongate strap of claim 1, wherein the textile outer layer is secured to the two long sides of the plastic core by a mechanical bond created by injection of molten plastic within the textile outer layer.

3. The elongate strap of claim 1, wherein the voids occupy about one-third, about half, or about two-thirds of a width dimension of the elongate strap.

4. The elongate strap of claim 1, wherein the textile outer layer surrounds the plastic core completely.

5. The elongate strap of claim 1, wherein the textile outer layer is a seamless tubular outer layer.

6. The elongate strap of claim 1, wherein lateral edges of the textile outer layer are configured to compress toward the plastic core such that the lateral edges of the textile outer layer are configured to deform or provide cushioning in a width or thickness direction of the elongate strap.

7. The elongate strap of claim 1, wherein the elongate strap includes a conduit extending in a lengthwise direction along the elongate strap within each of the voids.

8. The elongate strap according to claim 1, wherein edges of the textile outer layer are embedded in the plastic core.

9. The elongate strap of claim 1, wherein the textile outer layer is knitted or woven.

10. The elongate strap of claim 1, wherein the elongate strap comprises an interruption in the plastic core along a length of the elongate strap, wherein the interruption forms a flexible joint between two portions of the elongate strap.

11. An elongate strap for a headgear, comprising:
    a textile outer layer comprising a first portion, a second portion, and a third portion; and
    a plastic core,
    wherein the first portion of the textile outer layer surrounds the plastic core, wherein the first portion is secured to the plastic core to form an integral structure,
    wherein the second portion of the textile outer layer is spaced away from the plastic core to create a first void on a first lateral edge of the elongate strap, and
    wherein the third portion of the textile outer layer is spaced away from the plastic core to create a second void on a second lateral edge of the elongate strap.

12. The elongate strap of claim 11, wherein the first portion of the textile outer layer is secured to the plastic core by a mechanical bond created by injection of molten plastic within the first portion of the textile outer layer.

13. The elongate strap of claim 11, wherein the first void and the second void occupy about one-third, about half, or about two-thirds of a width dimension of the elongate strap.

14. The elongate strap of claim 11, wherein the first portion of the textile outer layer surrounds the plastic core completely.

15. The elongate strap of claim 11, wherein the first void defines a first conduit extending in a lengthwise direction along the first lateral edge of the elongate strap, wherein the second void defines a second conduit extending in the lengthwise direction along the second lateral edge of the elongate strap.

16. An elongate strap for a headgear, comprising:
    a seamless textile tube, the seamless textile tube comprising:
        a first fold on a first lateral side of the elongate strap; and
        a second fold on a second lateral side of the elongate strap,
        wherein a first lateral cavity, a second lateral cavity, and a central cavity are formed within the seamless textile tube,
        wherein the central cavity comprises a plastic core bonded to the seamless textile tube to form an integral structure.

17. The elongate strap of claim 16, wherein the plastic core is bonded to the seamless textile tube by a mechanical bond created by injection of molten plastic within the central cavity.

18. The elongate strap of claim 16, wherein the central cavity of the seamless textile tube surrounds the plastic core completely.

19. The elongate strap of claim 16, wherein the first lateral cavity defines a first conduit extending in a lengthwise direction along the first lateral side of the elongate strap, wherein the second lateral cavity defines a second conduit extending in the lengthwise direction along the second lateral side of the elongate strap.

* * * * *